US012606819B2

(12) United States Patent
Zhao et al.

(10) Patent No.: US 12,606,819 B2
(45) Date of Patent: Apr. 21, 2026

(54) PCR-FREE LIBRARY PREPARATION USING DOUBLE-STRANDED SPLINT ADAPTORS AND METHODS OF USE

(71) Applicant: Element Biosciences, Inc., San Diego, CA (US)

(72) Inventors: Junhua Zhao, San Diego, CA (US); Xiaodong Qi, San Diego, CA (US); Shawn Levy, San Diego, CA (US)

(73) Assignee: Element Biosciences, Inc., San Diego, CA (US)

( * ) Notice: Subject to any disclaimer, the term of this patent is extended or adjusted under 35 U.S.C. 154(b) by 0 days.

(21) Appl. No.: 18/347,440

(22) Filed: Jul. 5, 2023

(65) Prior Publication Data

US 2024/0011022 A1      Jan. 11, 2024

Related U.S. Application Data

(60) Provisional application No. 63/508,833, filed on Jun. 16, 2023, provisional application No. 63/358,491, filed on Jul. 5, 2022.

(51) Int. Cl.
*C12N 15/10*          (2006.01)
(52) U.S. Cl.
CPC ............................... *C12N 15/1065* (2013.01)
(58) Field of Classification Search
CPC .............. C12N 15/1065; C12Q 1/6855; C12Q 2525/155; C12Q 2525/191; C12Q 2531/125; C12Q 2535/122
See application file for complete search history.

(56) References Cited

U.S. PATENT DOCUMENTS 5,558,991 A    9/1996  Trainor
5,576,448 A    11/1996  Van Daele et al.
(Continued)

FOREIGN PATENT DOCUMENTS

CN        108203847 B      1/2022
EP          2423325 B1      4/2019
(Continued)

OTHER PUBLICATIONS

Illumina Adapter Sequences guide (Year: 2015).*
(Continued)

*Primary Examiner* — Jeremy C Flinders
(74) *Attorney, Agent, or Firm* — Fenwick & West LLP; Heidi A. Erlacher; Jessica D. Cande

(57)          ABSTRACT

The present disclosure provides compositions comprising nucleic acid double-stranded splint adaptors, including kits, and methods that employ the double-stranded splint adaptors, e.g., PCR-free workflows. The double-stranded splint adaptors (200) can be used in a one-pot, multi-enzyme reaction to introduce one or more new adaptor sequences into a library molecule. The double-stranded splint adaptor (200) comprises a first splint strand (long splint strand (300)) and a second splint strand (short splint strand (400)), where the first and second splint strands are hybridized together to form the double-stranded splint adaptor (200) having a double-stranded region and two flanking single-stranded regions. The second splint strand (400) carries the new adaptor sequence(s) to be introduced, such as for example a universal binding sequence and/or an index sequence.

30 Claims, 28 Drawing Sheets

Specification includes a Sequence Listing.

(56) References Cited

U.S. PATENT DOCUMENTS

| | | | |
|---|---|---|---|
| 5,700,642 A | 12/1997 | Monforte et al. | |
| 5,750,341 A | 5/1998 | Macevicz | |
| 5,854,033 A | 12/1998 | Lizardi | |
| 5,871,921 A | 2/1999 | Landegren et al. | |
| 6,284,497 B1 | 9/2001 | Sabanayagam et al. | |
| 6,576,448 B2 | 6/2003 | Weissman et al. | |
| 6,977,153 B2 | 12/2005 | Kumar et al. | |
| 7,170,050 B2 | 1/2007 | Turner et al. | |
| 7,195,872 B2 | 3/2007 | Agrawal et al. | |
| 7,302,146 B2 | 11/2007 | Turner et al. | |
| 7,405,281 B2 | 7/2008 | Xu et al. | |
| 7,432,048 B2 | 10/2008 | Neri et al. | |
| 7,709,197 B2 | 5/2010 | Drmanac | |
| 7,741,463 B2 | 6/2010 | Gormley et al. | |
| 7,820,387 B2 | 10/2010 | Neri et al. | |
| 7,862,999 B2 | 1/2011 | Zheng et al. | |
| 7,910,302 B2 | 3/2011 | Drmanac et al. | |
| 7,910,354 B2 | 3/2011 | Drmanac et al. | |
| 7,968,702 B2 | 6/2011 | Wegener et al. | |
| 7,989,166 B2 | 8/2011 | Koch et al. | |
| 8,053,192 B2 | 11/2011 | Bignell et al. | |
| 8,182,989 B2 | 5/2012 | Bignell et al. | |
| 8,252,910 B2 | 8/2012 | Korlach et al. | |
| 8,445,196 B2 | 5/2013 | Drmanac et al. | |
| 8,476,022 B2 | 7/2013 | Ronaghi et al. | |
| 8,563,477 B2 | 10/2013 | Smith et al. | |
| 8,563,478 B2 | 10/2013 | Gormley et al. | |
| 8,637,650 B2 | 1/2014 | Cherkasov et al. | |
| 8,715,966 B2 | 5/2014 | Xiaohai et al. | |
| 8,716,190 B2 | 5/2014 | Fu et al. | |
| 8,822,150 B2 | 9/2014 | Bignell et al. | |
| 8,906,612 B2 | 12/2014 | Shen et al. | |
| 8,927,212 B2 | 1/2015 | Kong et al. | |
| 8,932,994 B2 | 1/2015 | Gormley et al. | |
| 8,969,258 B2 | 3/2015 | Smith et al. | |
| 8,980,563 B2 | 3/2015 | Zheng et al. | |
| 9,029,103 B2 | 5/2015 | Rigatti et al. | |
| 9,085,802 B2 | 7/2015 | Liu et al. | |
| 9,228,228 B2 | 1/2016 | Drmanac et al. | |
| 9,328,378 B2 | 5/2016 | Earnshaw et al. | |
| 9,388,457 B2 | 7/2016 | Fu et al. | |
| 9,416,415 B2 | 8/2016 | Ronaghi et al. | |
| 9,493,818 B2 | 11/2016 | Kazakov et al. | |
| 9,498,763 B2 | 11/2016 | Liu et al. | |
| 9,512,478 B2 | 12/2016 | Bignell et al. | |
| 9,650,673 B2 | 5/2017 | Drmanac et al. | |
| 9,777,326 B2 | 10/2017 | Ronaghi et al. | |
| 9,822,408 B2 | 11/2017 | Amorese et al. | |
| 9,879,312 B2 | 1/2018 | Steemers et al. | |
| 9,889,422 B2 | 2/2018 | Smith et al. | |
| 9,896,709 B2 | 2/2018 | Makarov et al. | |
| 9,902,994 B2 | 2/2018 | Gormley et al. | |
| 9,944,984 B2 | 4/2018 | Drmanac et al. | |
| 9,957,291 B2 | 5/2018 | Sebo et al. | |
| 9,982,293 B2 | 5/2018 | Fu et al. | |
| 9,999,866 B2 | 6/2018 | Liu et al. | |
| 10,072,260 B2 | 9/2018 | Happe et al. | |
| 10,155,980 B2 | 12/2018 | Weng et al. | |
| 10,184,122 B2 | 1/2019 | Grunenwald et al. | |
| 10,246,744 B2 | 4/2019 | Vijayan et al. | |
| 10,287,574 B2 | 5/2019 | Goryshin et al. | |
| 10,329,600 B2 | 6/2019 | Fu et al. | |
| 10,351,909 B2 | 7/2019 | Drmanac et al. | |
| 10,407,722 B2 * | 9/2019 | Barany | C12Q 1/6809 |
| 10,525,437 B2 | 1/2020 | Smith et al. | |
| 10,590,464 B2 | 3/2020 | Boutell et al. | |
| 10,669,299 B2 | 6/2020 | Sebo et al. | |
| 10,710,046 B2 | 7/2020 | Liu et al. | |
| 10,731,141 B2 | 8/2020 | Iyidogan | |
| 10,731,194 B2 | 8/2020 | Makarov et al. | |
| 10,768,173 B1 | 9/2020 | Arslan et al. | |
| 10,781,483 B2 | 9/2020 | Sebo et al. | |
| 10,920,269 B2 | 2/2021 | Fu et al. | |
| 10,953,379 B2 | 3/2021 | Smith et al. | |
| 11,028,435 B2 | 6/2021 | Kelley et al. | |
| 11,028,436 B2 | 6/2021 | Singer et al. | |
| 11,028,438 B2 | 6/2021 | Rearick et al. | |
| 11,118,207 B2 | 9/2021 | Makarov et al. | |
| 11,124,829 B2 | 9/2021 | Fisher et al. | |
| 11,168,360 B2 | 11/2021 | George et al. | |
| 11,180,749 B2 | 11/2021 | Dambacher et al. | |
| 11,198,121 B1 | 12/2021 | Guo et al. | |
| 11,220,707 B1 | 1/2022 | Arslan et al. | |
| 11,230,731 B2 | 1/2022 | Sekedat et al. | |
| 11,236,388 B1 | 2/2022 | Arslan et al. | |
| 11,255,847 B2 | 2/2022 | Schnall-Levin | |
| 11,279,975 B2 | 3/2022 | Rigatti et al. | |
| 11,408,094 B2 | 8/2022 | Fu et al. | |
| 11,427,855 B1 | 8/2022 | Arslan et al. | |
| 11,434,538 B2 | 9/2022 | Babic et al. | |
| 11,535,892 B1 | 12/2022 | Arslan et al. | |
| 11,578,320 B2 | 2/2023 | Glezer et al. | |
| 11,634,765 B2 | 4/2023 | Boutell et al. | |
| 11,649,452 B2 | 5/2023 | Glezer et al. | |
| 11,654,411 B2 | 5/2023 | Smith et al. | |
| 11,781,185 B2 | 10/2023 | Arslan et al. | |
| 11,821,030 B2 | 11/2023 | Zheng et al. | |
| 11,859,241 B2 | 1/2024 | Arslan et al. | |
| 11,891,651 B2 | 2/2024 | Arslan et al. | |
| 11,905,553 B2 | 2/2024 | Gawad et al. | |
| 12,104,194 B2 | 10/2024 | Makarov et al. | |
| 12,359,193 B2 | 7/2025 | Light et al. | |
| 12,365,892 B2 | 7/2025 | Zhao et al. | |
| 12,371,743 B2 | 7/2025 | Light et al. | |
| 12,421,545 B2 | 9/2025 | Arslan et al. | |
| 2002/0076716 A1 | 6/2002 | Sabanayagam et al. | |
| 2004/0110153 A1 | 6/2004 | Dong et al. | |
| 2009/0018024 A1 | 1/2009 | Church et al. | |
| 2009/0186343 A1 | 7/2009 | Wang et al. | |
| 2010/0035252 A1 | 2/2010 | Rothberg et al. | |
| 2010/0035454 A1 | 2/2010 | Morgan et al. | |
| 2010/0121582 A1 | 5/2010 | Pan et al. | |
| 2012/0196279 A1 * | 8/2012 | Underwood | C12P 19/34 |
| | | | 435/91.51 |
| 2017/0022553 A1 | 1/2017 | Vijayan et al. | |
| 2018/0044668 A1 | 2/2018 | Jiang et al. | |
| 2019/0119742 A1 | 4/2019 | Zhang et al. | |
| 2019/0194737 A1 | 6/2019 | Ach et al. | |
| 2020/0149095 A1 | 5/2020 | Arslan et al. | |
| 2020/0216891 A1 | 7/2020 | Francais et al. | |
| 2020/0224244 A1 | 7/2020 | Nilsson et al. | |
| 2020/0308576 A1 | 10/2020 | Badenhorst et al. | |
| 2020/0347443 A1 | 11/2020 | Arslan et al. | |
| 2021/0387184 A1 | 12/2021 | Guo et al. | |
| 2022/0042082 A1 | 2/2022 | Fu et al. | |
| 2022/0356519 A1 | 11/2022 | Shen et al. | |
| 2022/0403351 A1 | 12/2022 | Ambroso et al. | |
| 2022/0403352 A1 | 12/2022 | Ambroso et al. | |
| 2022/0403353 A1 | 12/2022 | Ambroso et al. | |
| 2022/0403445 A1 | 12/2022 | Arslan et al. | |
| 2022/0403463 A1 | 12/2022 | Arslan et al. | |
| 2023/0065693 A1 | 3/2023 | Arslan et al. | |
| 2023/0193354 A1 | 6/2023 | Arslan et al. | |
| 2023/0203564 A1 | 6/2023 | Arslan et al. | |
| 2023/0235392 A1 | 7/2023 | Arslan et al. | |
| 2023/0265400 A1 | 8/2023 | Hentshcel et al. | |
| 2023/0265401 A1 | 8/2023 | Hentshcel et al. | |
| 2023/0265402 A1 | 8/2023 | Hentshcel et al. | |
| 2023/0279382 A1 | 9/2023 | Light et al. | |
| 2023/0279483 A1 | 9/2023 | Light et al. | |
| 2023/0295692 A1 | 9/2023 | Berti et al. | |
| 2023/0392144 A1 | 12/2023 | Price et al. | |
| 2023/0392201 A1 | 12/2023 | Stapleton et al. | |
| 2024/0052398 A1 | 2/2024 | Previte et al. | |
| 2024/0084380 A1 | 3/2024 | Arslan et al. | |
| 2024/0191225 A1 | 6/2024 | Zhao et al. | |
| 2024/0191278 A1 | 6/2024 | Arslan et al. | |
| 2025/0236903 A1 | 7/2025 | Arslan et al. | |
| 2025/0333787 A1 | 10/2025 | Arslan et al. | |

FOREIGN PATENT DOCUMENTS

| | | | |
|---|---|---|---|
| EP | | 1954818 B2 | 1/2021 |
| WO | WO-2005111236 A1 | | 11/2005 |

(56)           References Cited

FOREIGN PATENT DOCUMENTS

| WO | WO-2005111240 A2 | 11/2005 |
| WO | WO-2009006907 A1 | 1/2009 |
| WO | WO-2012003374 A2 | 1/2012 |
| WO | WO-2014196863 A1 | 12/2014 |
| WO | WO-2015154028 A1 | 10/2015 |
| WO | WO-2016058517 A1 | 4/2016 |
| WO | WO-2018175258 A1 | 9/2018 |
| WO | WO-2019068797 A1 | 4/2019 |
| WO | WO-2019149958 A1 | 8/2019 |
| WO | WO-2020102594 A1 | 5/2020 |
| WO | WO-2021061841 A1 | 4/2021 |
| WO | WO-2021178467 A1 | 9/2021 |
| WO | WO-2021236792 A1 | 11/2021 |
| WO | WO-2022026891 A1 | 2/2022 |
| WO | WO-2022266462 A2 | 12/2022 |
| WO | WO-2022266470 A1 | 12/2022 |
| WO | WO-2023114392 A1 | 6/2023 |
| WO | WO-2023168443 A1 | 9/2023 |
| WO | WO-2023168444 A1 | 9/2023 |
| WO | WO-2024011145 | 1/2024 |
| WO | WO-2024040058 A1 | 2/2024 |
| WO | WO-2024040068 A1 | 2/2024 |
| WO | WO-2024059550 A1 | 3/2024 |
| WO | WO-2025024465 A1 | 1/2025 |
| WO | WO 2025/163526 A1 | 8/2025 |
| WO | WO 2025/191535 A1 | 9/2025 |
| WO | WO 2025/212654 A1 | 10/2025 |
| WO | WO 2025/212655 A1 | 10/2025 |

OTHER PUBLICATIONS

MacConaill et al. (BMC Genomics, 2018, 19:30) (Year: 2018).*

Co-pending U.S. Appl. No. 18/544,085, inventors Sinan Arslan; et al., filed Dec. 18, 2023.

Ohtsubo, Y., et al.; "Efficient N-tailing of blunt DNA ends by Moloney murine leukemia virus reverse transcriptase," Sci Rep.; 7:41769; pp. 1-10; doi: 10.1038/srep41769 (2017).

Ohtsubo, Y., et al.; "Optimization of single strand DNA incorporation reaction by Moloney murine leukaemia virus reverse transcriptase," DNA Res.; 25(5):477-487 (2018).

Anderson, J.P. et al.; Fluorescent Structural DNA Nanoballs Functionalized with Phosphate-Linked Nucleotide Triphosphates. Nano Letters 10(3):788-792 (2010).

Balakrishnan, L., et al.; "Flap Endonuclease 1," Annual Review Biochemistry 82:119-138 (2013).

Chen, X., et al.; "Efficient in situ barcode sequencing using padlock probe-based BaristaSeq," Nucleic Acids Research; 46(4):e22 pp. 1-10 (2018).

Ericsson, O., et al.; "A dual-tag microarray platform for high-performance nucleic acid and protein analyses," Nucleic Acids Research, 36(8):e45, pp. 1-9 (2008).

Friedrich-Heineken, E., et al.; "The Fen1 extrahelical 3'-flap pocket is conserved from archaea to human and regulates DNA substrate specificity," Nucleic Acids Research, 32(8):2520-2528 (2004).

Gao, H., et al.; "Rolling circle amplification for single cell analysis and in situ sequencing," TrAC Trends in Analytical Chemistry; 121:115700; pp. 1-13 (2019).

GenBank Accession AAB52611.1; "DNA polymerase I [Geobacillus stearothermophilus]," Apr. 21, 1997; [retrieved online Sep. 23, 2024] URL: www.ncbi.nlm.nih.gov/protein/AAB52611.1, 2 pages.

GenBank Accession KUO42443.1; "MAG: hypothetical protein APZ16_03045 [Candidatus Hadarchaeum yellowstonense]," Jan. 14, 2016; [retrieved online Sep. 23, 2024], URL: www.ncbi.nlm.nih.gov/protein/KUO42443.1, 2 pages.

GenBank Accession MBC7218772.1; "MAG: DNA polymerase [Hadesarchaea archaeon]," Sep. 1, 2020; [retrieved online Sep. 23, 2024] URL: www.ncbi.nlm.nih.gov/protein/mbc7218772.1, 2 pages.

GenBank Accession NOZ58130.1; "MAG: DNA polymerase [Euryarchaeota archaeon]," Mar. 17, 2023 [retrieved online Sep. 23, 2024] URL: www.ncbi.nlm.nih.gov/protein/NOZ58130, 2 pages.

GenBank Accession NOZ77387.1; "MAG: DNA polymerase, partial [Euryarchaeota archaeon]," Mar. 17, 2023 [retrieved online Sep. 23, 2024] URL: www.ncbi.nlm.nih.gov/protein/NOZ77387.1, 2 pages.

GenBank Accession RLF78286.1; "MAG: DNA polymerase [Thermococci archaeon]," Oct. 15, 2018; URL: www.ncbi.nlm.nih.gov/protein/RLF78286.1, 2 pages.

GenBank Accession RLF89458.1; "MAG: DNA polymerase [Thermococci archaeon]," Oct. 15, 2018; [retrieved online Sep. 23, 2024] URL: www.ncbi.nlm.nih.gov/protein/RLF89458.1, 2 pages.

GenBank Accession RLI89578.1; "MAG: DNA polymerase [Candidatus Altiarchaeales archaeon]," Oct. 15, 2018; [retrieved online Sep. 23, 2024] URL: www.ncbi.nlm.nih.gov/protein/RLI89578.1, 2 pages.

GenBank Accession RMF90817.1; "MAG: DNA polymerase [Euryarchaeota archaeon]," Oct. 29, 2018; [retrieved online Sep. 23, 2024] URL: www.ncbi.nlm.nih.gov/protein/RMF90817.1, 2 pages.

Greenough, L., et al.; "Adapting capillary gel electrophoresis as a sensitive, high-throughput method to accelerate characterization of nucleic acid metabolic enzymes," Nucleic Acids Research, 44(2):e15, pp. 1-11 (2016).

Hatch, A., et al.; "Rolling circle amplification of DNA immobilized on solid surfaces and its application to multiplex mutation detection," Genetic Analysis: Biomolecular Engineering, 15(2):35-40 (1999).

Hu, T., et al.; "Next-generation sequencing technologies: An overview," Hum Immunol.; 82(11):801-811 (2021).

Illumina "Overview of Illumina Sequencing by Synthesis Workflow," Oct. 5, 2016 (Oct. 5, 2016) [retrieved online Oct. 9, 2024] https://www.youtube.com/watch?v=fCd6B5HRaZ8, 2 pages.

Kao, H-I, et al.; "Cleavage specificity of Saccharomyces cerevisiae flap endonuclease 1 suggests a double-flap structure as the cellular substrate," Journal of Biological Chemistry, 277(17):14379-14389 (2002).

Konry, T., et al.; "Microsphere-based rolling circle amplification microarray for the detection of DNA and proteins in a single assay," Analytical Chemistry, 81(14):5777-5782 (2009).

Lee, B-I., et al.; "The RAD2 domain of human exonuclease 1 exhibits 5' to 3' exonuclease and flap structure-specific endonuclease activities," Journal of Biological Chemistry, 274(53):37763-37769 (1999).

Lee, J., et al.; "Diffractometric detection of proteins using microbead-based rolling circle amplification," Analytical Chemistry, 82(1):197-202 (2010).

Lin, T., et al.; "Biochemical characterization and mutational analysis of a novel flap endonuclease 1 from Thermococcus barophilus Ch5," International Journal of Biochemistry and Cell Biology, 143:106154, pp. 1-11 (2022).

Lu, M., et al.; "A surface invasive cleavage assay for highly parallel SNP analysis," Human Mutation, 19(4):416-422 (2002).

Mignardi, M., et al.; "Fourth-generation sequencing in the cell and the clinic," Genome Med.; 6(4):31; pp. 1-4 (2014).

NCBI Reference Sequence: NP_041963.1; Accession NC_001604.1; "DNA ligase [Escherichia phage T7]," Jan. 7, 2023; [retrieved online Sep. 23, 2024] URL: www.ncbi.nlm.nih.gov/protein/9627435, 3 pages.

NCBI Reference Sequence: NP_049813.1; Accession NC_000866.4; "DNA ligase [Escherichia phage T4]," Jan. 11, 2023; [retrieved online Sep. 23, 2024] URL: www.ncbi.nlm.nih.gov/protein/9632609, 2 pages.

NCBI Reference Sequence: NP_523305.1; Accession NC_003298.1; "DNA ligase [Enterobacteria phage T3]," Jan. 7, 2023; [retrieved online Sep. 23, 2024] URL: www.ncbi.nlm.nih.gov/protein/17570796, 2 pages.

NCBI Reference Sequence: WP_042693257.1; Accession WP_042693257; "ATP-dependent DNA ligase [Thermococcus nautili]," Jun. 2, 2024; [retrieved online Sep. 23, 2024] URL: www.ncbi.nlm.nih.gov/protein/757139009, 1 page.

NCBI Reference Sequence: WP_175059460.1; Accession WP_175059460; "DNA-directed DNA polymerase [Thermococcus sp. 2319x1]," May 21, 2021; [retrieved online Sep. 23, 2024] URL: www.ncbi.nlm.nih.gov/protein/WP_175059460.1, 1 page.

Pettersson, E., et al.; "Generations of sequencing technologies," Genomics 93(2):105-111 (2009).

(56) References Cited

OTHER PUBLICATIONS

Russell, C., et al.; "Gold nanowire based electrical DNA detection using rolling circle amplification," ACS Nano, 8(2):1147-1153 (2014).

Schlecht, U., et al.; "ConcatSeq: A method for increasing through-put of single molecule sequencing by concatenating short DNA fragments," Sci Rep; 7(1):5252; pp. 1-10 (2017).

Stougaard, M., et al.; "In situ detection of non-polyadenylated RNA molecules using Turtle Probes and target primed rolling circle PRINS," BMC Biotechnology, 7:69, pp. 1-10 (2007).

Tsutakawa, S.E., et al.; "Human flap endonuclease structures, DNA double-base flipping, and a unified understanding of the FEN1 superfamily," Cell., 145(2):198-211, with supplemental pp. S1-S7, 21 pages (2011).

Tsutakawa, S.E., et al.; "Phosphate steering by Flap Endonuclease 1 promotes 5'-flap specificity and incision to prevent genome instability," Nature Communications, 8:15855, pp. 1-15 (2017).

Ulahannan, N., et al.; "Nanopore sequencing of DNA concatemers reveals higher-order features of chromatin structure," bioRxiv, Nov. 7, 2019 [retrieved on Oct. 9, 2024] https://www.biorxiv.org/content/10.1101/833590v1.full.pdf, 19 pages.

UniProtKB: P0CL77—DPOL_PYRAB; "DNA polymerase 1," Last Updated: Apr. 5, 2011; [retrieved online Sep. 23, 2024] URL: www.uniprot.org/uniprotkb/P0CL77/entry, 5 pages.

UniProtKB: P30317—DPOL_THELI; "DNA polymerase," Last Updated: Apr. 1, 1993 [retrieved online Sep. 23, 2024] URL: www.uniprot.org/uniprotkb/P30317/entry, 6 pages.

UniProtKB: P61875—DPOL_PYRFU; "DNA polymerase," Last Updated: Jun. 7, 2004 [retrieved online Sep. 23, 2024] URL: www.uniprot.org/uniprotkb/P61875/entry, 6 pages.

UniProtKB: Q38087—DPOL_BPR69; "DNA-directed DNA polymerase," Last Updated: Nov. 1, 1996 [retrieved online Sep. 23, 2024] URL: www.uniprot.org/uniprotkb/Q38087/entry, 6 pages.

UniProtKB: Q51334—DPOL_PYRSD; "DNA polymerase," Last Updated: Nov. 1, 1996 [retrieved online Sep. 23, 2024] URL: www.uniprot.org/uniprotkb/Q51334/entry, 6 pages.

UniProtKB: Q56366—DPOL_THES9; "DNA polymerase," Last Updated: Nov. 1, 1996 [retrieved online Sep. 23, 2024] URL: www.uniprot.org/uniprotkb/Q56366/entry, 7 pages.

UniProtKB/Swiss-Prot: P03680.1—DPOL_BPPH2; "DNA polymerase," Last Updated: Jul. 21, 1986; [retrieved online Sep. 23, 2024] URL: www.uniprot.org/uniprotkb/P03680/entry, 7 pages.

UniProtKB/Swiss-Prot: Q9HH07.1; "RecName: Full=DNA ligase; AltName: Full=Polydeoxyribonucleotide synthase [ATP/NAD(+)]," Date updated: Mar. 1, 2001; [retrieved online Sep. 20, 2024] URL: www.ncbi.nlm.nih.gov/protein/Q9HH07, 2 pages.

U.S. Appl. No. 18/824,527, filed Sep. 4, 2024, by Sinan Arslan, et al.

U.S. Appl. No. 19/240,104, filed Jun. 17, 2025, Inventors William Light, et al.

U.S. Appl. No. 19/241,620, filed Jun. 18, 2025, Inventors Junhua Zhao, et al.

U.S. Appl. No. 19/244,055, filed Jun. 20, 2025, Inventors William Light, et al.

MGI Techco., Ltd. "BGISEQ/MGISEQ Oligos." MGI: Tech. Support Centre, Jan. 22, 2021, pp. 1-5.

U.S. Appl. No. 19/306,603, filed Aug. 21, 2025, Inventors Sinan Arslan, et al.

U.S. Appl. No. 18/465,687, inventors Zhao; Junhua et al., filed Sep. 12, 2023.

Lindahl, T. Nyberg, B., "Heat-induced deamination of cytosine residues in deoxyribonucleic acid," Biochemistry (Jul. 1974); 13(16):3405-3410.

Obi, P., et al., "The design and synthesis of circular RNAs," Methods. (2021); 196:85-103.

Wang, F. et al., "TEQUILA-seq: a versatile and low-cost method for targeted long-read RNA sequencing," Nat Commun., (2023); 14(1):4760, pp. 1-15.

Wang, R.Y.-H. et al., "Heat- and alkali-induced deamination of 5-methylcytosine and cytosine residues in DNA," Biochim Biophys Acta, (Jun. 1982); 697(3):371-377.

Diegelman et al., "Chemical and Enzymatic Methods for Preparing Circular Single-Stranded DNAs" Curr Protoc Nucleic Acid Chem, May 2001, Chapter 5:Unit 5.2, 27 pages.

Eschenmoser, "Chemical Etiology of Nucleic Acid Structure," Science, Jun. 25, 1999, 284:2118-2124.

Ferrero, et al., "Biocatalytic Selective Modifications of Conventional Nucleosides, Carbocyclic Nucleosides, and C-Nucleosides," Chem. Rev., 2000, 100:4319-4347.

Fire et, al., "Rolling replication of short DNA circles" Proc Natl Acad Sci USA, May 9, 1995, 92(10):4641-4645.

Floyd et, al., "Single-particle kinetics of influenza virus membrane fusion" PNAS, Oct. 7, 2008, 105(40):15382-15387.

Harris T.D., et al., "Single-Molecule DNA Sequencing of a Viral Genome," Science, Apr. 4, 2008, 320(5872):106-109.

International Search Report and Written Opinion for International Application No. PCT/US2023/063734, mailed on Jul. 17, 2023, 14 pages.

International Search Report and Written Opinion for International Application No. PCT/US2023/063736, mailed on Aug. 21, 2023, 19 pages.

Joeng, et al., "Structure-Activity Relationships of β-D-(2S,5R)- and α-D-(2S,5S)-1,3-Oxathiolanyl Nucleosides as Potential Anti-HIV Agents," J. Med. Chem., 1993, 36:2627-2638.

Joneja et al. "Linear nicking endonuclease-mediated strand-displacement DNA amplification." Anal Biochem., Jul. 1, 2011, 414(1):58-69, Epub Feb. 20, 2011 (26 pages total).

Kim, et al., "1,3-Dioxolanylpurine Nucleosides (2R,4R) and (2R,4S) with Selective Anti-HIV-1 Activity in Human Lymphocytes," J. Med. Chem., 1993, 36:30-37.

Korostin D., "Comparative analysis of novel MGISEQ-2000 sequencing platform vs Illumina HiSeq 2500 for whole-genome sequencing", PLOS ONE, Mar. 16, 2020, 15(3):e0230301, 13 pages, Retrieved from the Internet: URL: https://journals.plos.org/plosone/article?id=10.1371/journal.pone.0230301.

Lizardi et al., "Mutation detection and single-molecule counting using isothermal rolling-circle amplification" Nature Genetics, Jul. 1998, 19(3):225-232.

Martinez, et al., "Acyclic Nucleoside Triphosphate Analogs as Terminators in Biocatalytic DNA Replication," Bioorganic & Medicinal Chemistry Letters, 1997, 7(23):3013-3016.

Martinez, et al., "An allylic/acyclic adenosine nucleoside triphosphate for termination of DNA synthesis by DNA template-dependent polymerases," Nucleic Acids Research, 1999, 27(5):1271-1274.

McNaughton et al. "Illumina and Nanopore methods for whole genome sequencing of hepatitis B virus (HBV)." Scientific Reports, May 8, 2019, 9(7081), retrieved from internet at https://doi.org/10.1038/s41598-019-43524-9, 14 pages.

Ruparel, et al., "Design and synthesis of a 3'-O-allyl photocleavable fluorescent nucleotide as a reversible terminator for DNA sequencing by synthesis," Proceedings of the National Academy of Sciences of the United States of America, Apr. 26, 2005, 102(17):5932-5937.

* cited by examiner

Sample index with no NNN spacer          linker          nucleotide unit core
attachment
moiety Spacer:

Linkers:

11 atom Linker:

16 atom Linker:

23 atom Linker:

N3 Linker:

FIG. 27

Linker 1:    Linker 2:

Linker 3:    Linker 4:

Linker 5:    Linker 6:

Molecular Weight: 352.35

Linker 7:    Linker 8:

Molecular Weight: 449.42    Molecular Weight: 518.57

Linker 9:

Molecular Weight: 615.64 dNTP-PA-NH₂:

dNTP-PA-11 Atom Linker-NH₂:

dNTP-PA-16 Atom Linker-NH₂:

dNTP-PA-23 Atom Linker-NH₂:

dNTP-PA-N3 Linker-NH₂:

dNTP-PA-Linker 1-NH₂:

dNTP-PA-Linker 2-NH₂:

FIG. 30 dNTP-PA-Linker 3-NH₂:

5- pyrimidine; 7- purine base 1- pyrimidine; 9- purine

OH dNTP-PA-Linker 4-NH₂:

5- pyrimidine; 7- purine base 1- pyrimidine; 9- purine

OH dNTP-PA-N3 Linker-NH₂:

5- pyrimidine; 7- purine base 1- pyrimidine; 9- purine

PCR-FREE LIBRARY PREPARATION USING DOUBLE-STRANDED SPLINT ADAPTORS AND METHODS OF USE

CROSS-REFERENCE TO RELATED APPLICATIONS

This application claims priority to, and the benefit of, U.S. Provisional Patent Application No. 63/358,491, filed Jul. 5, 2022, and U.S. Provisional Patent Application No. 63/508, 833, filed Jun. 16, 2023, the contents of each of which are incorporated by reference herein in their entireties.

REFERENCE TO AN ELECTRONIC SEQUENCE LISTING

The contents of the electronic sequence listing (ELEM-013_001US_SeqListing_ST26.xml; Size 63,088 bytes; and Date of Creation: Jun. 21, 2024) are herein incorporated by reference in their entireties.

TECHNICAL FIELD

The present disclosure provides compositions comprising nucleic acid double-stranded splint adaptors, and methods for preparing nucleic acid libraries using the double-stranded splint adaptors. The double-stranded splint adaptors can hybridize to portions of library molecules to form library-splint complexes having nicks, where the nicks can be ligated to form covalently closed circular molecules which can be subjected to downstream amplification and sequencing workflows.

BACKGROUND

The transition from traditional Sanger-style sequencing methods to next-generation sequencing methods has lowered the cost of sequencing, yet significant limitations of next-generation sequencing methods remain. In one respect, available sequencing platforms generate sequencing reads that, while numerous, are relatively short and can require computational reassembly into full sequences of interest. Available assembly methods can be slow, laborious, expensive, computationally demanding, and/or unsuitable for populations of similar individuals (e.g., viruses). This is especially true for sequencing of complex genomes. Assembly is challenging, in part due to the ever-swelling sequencing datasets associated with assembly of short reads. Such datasets can place a large strain on computer clusters. For example, de novo assembly can require that sequencing reads (or k-mers derived from them) be stored in random access memory (RAM) simultaneously. For large datasets this requirement is not trivial. Moreover, even when assembly is possible, crucial haplotype information often cannot be recovered. Indeed, inherent limitations of available technologies obstruct improvements to overcoming the shortcomings of status quo sequencing technologies. Thus, there exists a need for improved sequencing methods and associated assembly techniques that reduce the time and/or computational requirements necessary to obtain accurate sequences.

SUMMARY

The present disclosure provides a method for forming a plurality of library-splint complexes (500) comprising: providing a plurality of double-stranded splint adaptors (200), wherein individual double-stranded splint adaptors (200) in the plurality comprise a first splint strand (300) hybridized to a second splint strand (400), wherein the double-stranded splint adaptor includes a double-stranded region and two flanking single-stranded regions, wherein the first splint strand comprises a first region (320), an internal region (310), and a second region (330), and wherein the internal region of the first splint strand (310) is hybridized to the second splint strand (400); and hybridizing the plurality of double-stranded splint adaptors with a plurality of single-stranded nucleic acid library molecules (100), wherein individual library molecules comprise a sequence of interest (110) flanked on a first side by a universal adaptor sequence for a forward sequencing primer binding site (120) and flanked on a second side by a universal adaptor sequence for a reverse sequencing primer binding site (130), thereby circularizing the plurality of library molecules to form a plurality of library-splint complexes (500) each having two nicks.

In some embodiments, the method further comprises: (c) contacting the plurality of library-splint complexes (500) with a ligase to generate a plurality of covalently closed circular library molecules (600).

In some embodiments, the hybridizing is conducted under a condition suitable for hybridizing the first region of the first splint strand (320) to the universal adaptor sequence for a forward sequencing primer binding site (120) of the library molecule. In some embodiments, the condition is suitable for hybridizing the second region of the first splint strand (330) to the universal adaptor sequence for a reverse sequencing primer binding site (130) of the library molecule.

In some embodiments, the internal region (310) of the first splint strand (300) comprises at least three sub-regions. In some embodiments, the at least three sub-regions comprise sub-region (311), sub-region (312) and sub-region (313). In some embodiments, the sub-region (311) comprises a universal adaptor sequence for a surface capture primer binding site, a universal adaptor sequence for a surface pinning primer binding site, a sample index sequence, a short random sequence (NNN) and/or a unique molecule index (UMI). In some embodiments, the sub-region (312) comprises a universal adaptor sequence for a surface capture primer binding site, a universal adaptor sequence for a surface pinning primer binding site, a sample index sequence, a short random sequence (NNN) and/or a unique molecule index (UMI). In some embodiments, the sub-region (313) comprises a universal adaptor sequence for a surface capture primer binding site, a universal adaptor sequence for a surface pinning primer binding site, a sample index sequence, a short random sequence (NNN) and/or a unique molecule index (UMI).

In some embodiments, the sub-region (311), (312) or (313) comprises a sample index sequence, and wherein the sample index sequence comprises: a sample index sequence lacking a short random sequence (NNN); a sample index sequence and a short random sequence (NNN); a sample index flanked on both sides with nucleotide base that can be converted to an abasic base; at least one nucleotide base that can be converted to an abasic base; at least one deoxyinosine; an 18-carbon spacer; and/or an 18-carbon spacer and at least one deoxyinosine.

In some embodiments, the method further comprises: distributing the plurality of covalently closed circular library molecules (600) onto a support having a plurality of the surface capture primers immobilized to the support, under a condition suitable for hybridizing individual covalently closed circular library molecules (600) to individual immobilized surface capture primers thereby immobilizing the plurality of covalently closed circular library molecules (600) to the support. In some embodiments, the support further comprises a plurality of surface pinning primers immobilized to the support.

In some embodiments, the method further comprises: contacting the plurality of immobilized covalently closed circular library molecules (600) with a plurality of strand-displacing polymerases and a plurality of nucleotides, under a condition suitable to conduct a rolling circle amplification reaction on the support using the plurality of surface capture primers as immobilized amplification primers and the plurality of covalently closed circular library molecules (600) as template molecules, thereby generating a plurality of nucleic acid concatemer molecules immobilized to the surface capture primers.

In some embodiments, the method further comprises: iii) sequencing the plurality of nucleic acid concatemer molecules immobilized to the surface capture primers, wherein the sequencing comprises (i) sequencing the sample indexes and (ii) sequencing the sequence of interest (110).

In some embodiments, the method further comprises: iv) sequencing the plurality of nucleic acid concatemer molecules immobilized to the surface capture primers, wherein the sequencing comprises (A) sequencing one or more short random sequences NNN, (B) sequencing one or more sample indexes, and (C) sequencing the sequence of interest (110).

In some embodiments, the internal region (310) of the first splint strand (300) comprises one sample index.

In some embodiments, the internal region (310) of the first splint strand (300) comprises one sample index and a short random sequence (NNN).

In some embodiments, the library molecule (100) comprises one or more nucleotide sequences selected from Table 1.

In some embodiments, the first splint strand (300) comprises one or more nucleotide sequences selected from Table 2.

In some embodiments, the second splint strand (400) comprises one or more nucleotide sequences selected from Table 3.

DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 8A is a schematic of double-stranded adaptor carrying a full-length sequence of a universal adaptor sequence for a forward sequencing primer binding site (120). FIG. 8B is a schematic of double-stranded adaptor carrying a truncated sequence of a universal adaptor sequence for a forward sequencing primer binding site (120). FIG. 8C is a schematic of double-stranded adaptor having a 5' overhang end, where one of the adaptor strands is carrying a full-length sequence of a universal adaptor sequence for a forward sequencing primer binding site (120) and the other adaptor strand is carrying a truncated sequence of a universal adaptor sequence for a forward sequencing primer binding site (120). FIG. 8D is a schematic of double-stranded adaptor having a 3' overhang end where one of the adaptor strands is carrying a truncated sequence of a universal adaptor sequence for a forward sequencing primer binding site (120), and the other adaptor strand is carrying a full-length sequence of a universal adaptor sequence for a forward sequencing primer binding site (120).

FIG. 9A is a schematic of double-stranded adaptor carrying a full-length sequence of a universal adaptor sequence for a reverse sequencing primer binding site (130).

FIG. 9B is a schematic of double-stranded adaptor carrying a truncated sequence of a universal adaptor sequence for a reverse sequencing primer binding site (130). FIG. 9C is a schematic of double-stranded adaptor having a 5' overhang end where one of the adaptor strands is carrying a full-length sequence of a universal adaptor sequence for a reverse sequencing primer binding site (130) and the other adaptor strand is carrying a truncated sequence of a universal adaptor sequence for a reverse sequencing primer binding site (130). FIG. 9D is a schematic of double-stranded adaptor having a 3' overhang end where one of the adaptor strands is carrying a truncated sequence of a universal adaptor sequence for a reverse sequencing primer binding site (130), and the other adaptor strand is carrying a full-length sequence of a universal adaptor sequence for a reverse sequencing primer binding site (130).

FIG. 10A is a schematic of a Y-shaped adaptor comprising a first oligonucleotide carrying a full-length sequence of a universal adaptor sequence for a forward sequencing primer binding site (120), and a second oligonucleotide carrying a full-length sequence of a universal adaptor sequence for a reverse sequencing primer binding site (130). FIG. 10B is a schematic of a Y-shaped adaptor comprising a first oligonucleotide carrying a truncated sequence of a universal adaptor sequence for a forward sequencing primer binding site (120), and a second oligonucleotide carrying a truncated sequence of a universal adaptor sequence for a reverse sequencing primer binding site (130).

FIG. 10C is a schematic of a Y-shaped adaptor comprising a first oligonucleotide carrying a full-length sequence of a universal adaptor sequence for a forward sequencing primer binding site (120), and a second oligonucleotide carrying a truncated sequence of a universal adaptor sequence for a reverse sequencing primer binding site (130). FIG. 10D is a schematic of a Y-shaped adaptor comprising a first oligonucleotide carrying a truncated sequence of a universal adaptor sequence for a forward sequencing primer binding site (120), and a second oligonucleotide carrying a full-length sequence of a universal adaptor sequence for a reverse sequencing primer binding site (130).

FIG. 11A is a schematic of two transpososomes in which the first transpososome (top) comprises a transposase bound to a double-stranded polynucleotide comprising a transposon end sequence and universal adaptor sequence for a forward sequencing primer binding site (120). The transposon end sequence specifically binds the transposase. The second transpososome (bottom) comprises a transposase bound to a double-stranded polynucleotide comprising a transposon end sequence and universal adaptor sequence for a reverse sequencing primer binding site (130). The transposon end sequence specifically binds the transposase. FIG. 11B is a schematic of an exemplary transpososome comprising a transposase bound to a first double-stranded polynucleotide comprising a transposon end sequence and universal adaptor sequence for a forward sequencing primer binding site (120), and the transposase is bound to a second double-stranded polynucleotide comprising a transposon end sequence and universal adaptor sequence for a reverse sequencing primer binding site (130). The transposon end sequence specifically binds the transposase.

Figure 27:
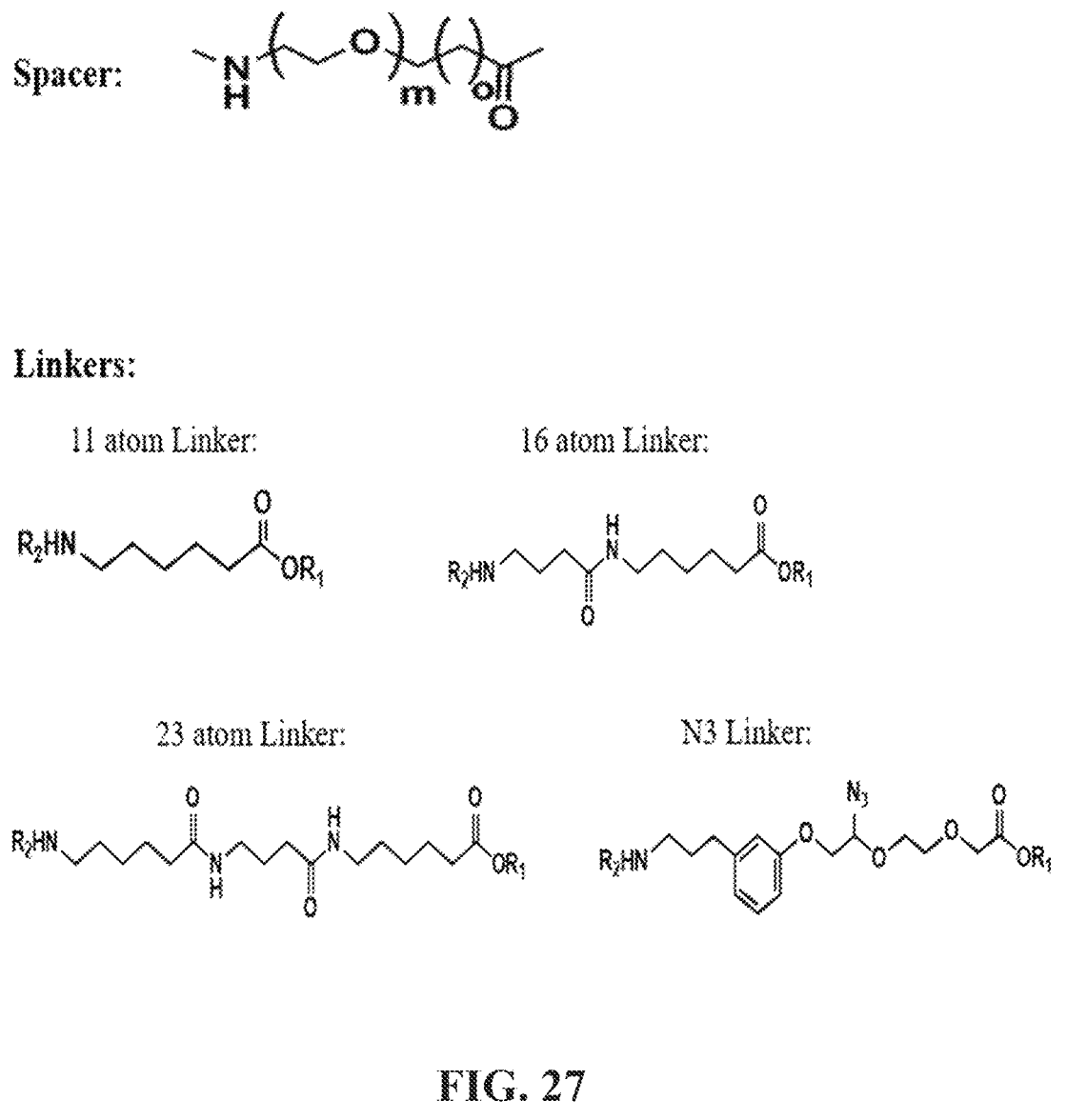

FIG. 27 shows the chemical structure of an exemplary spacer (top), and the chemical structures of various exemplary linkers, including an 11-atom Linker, 16-atom Linker, 23-atom Linker, and an N3 Linker (bottom).

Figure 30:
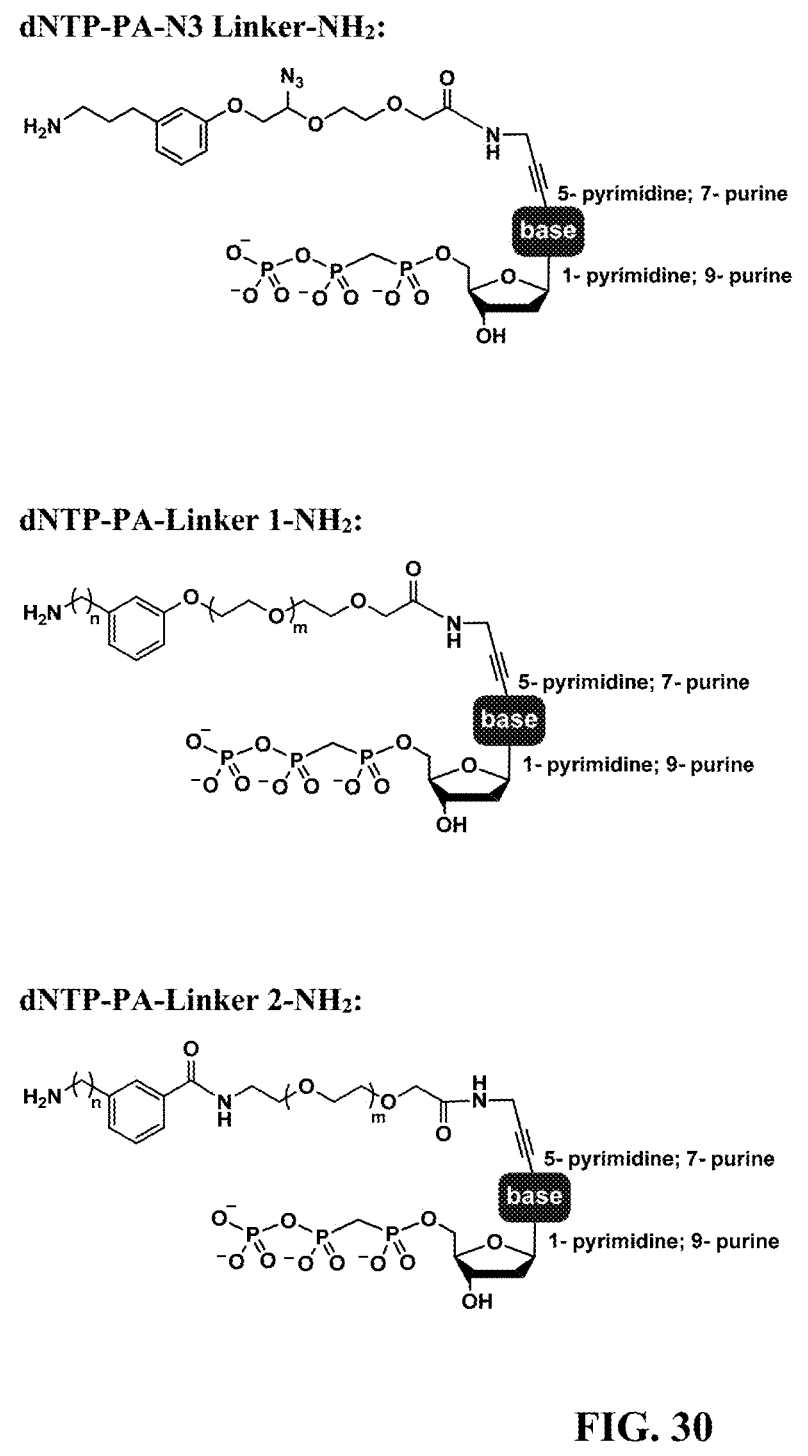

FIG. 30 shows the chemical structures of various exemplary linkers joined/attached to nucleotide units.

Figure 31:
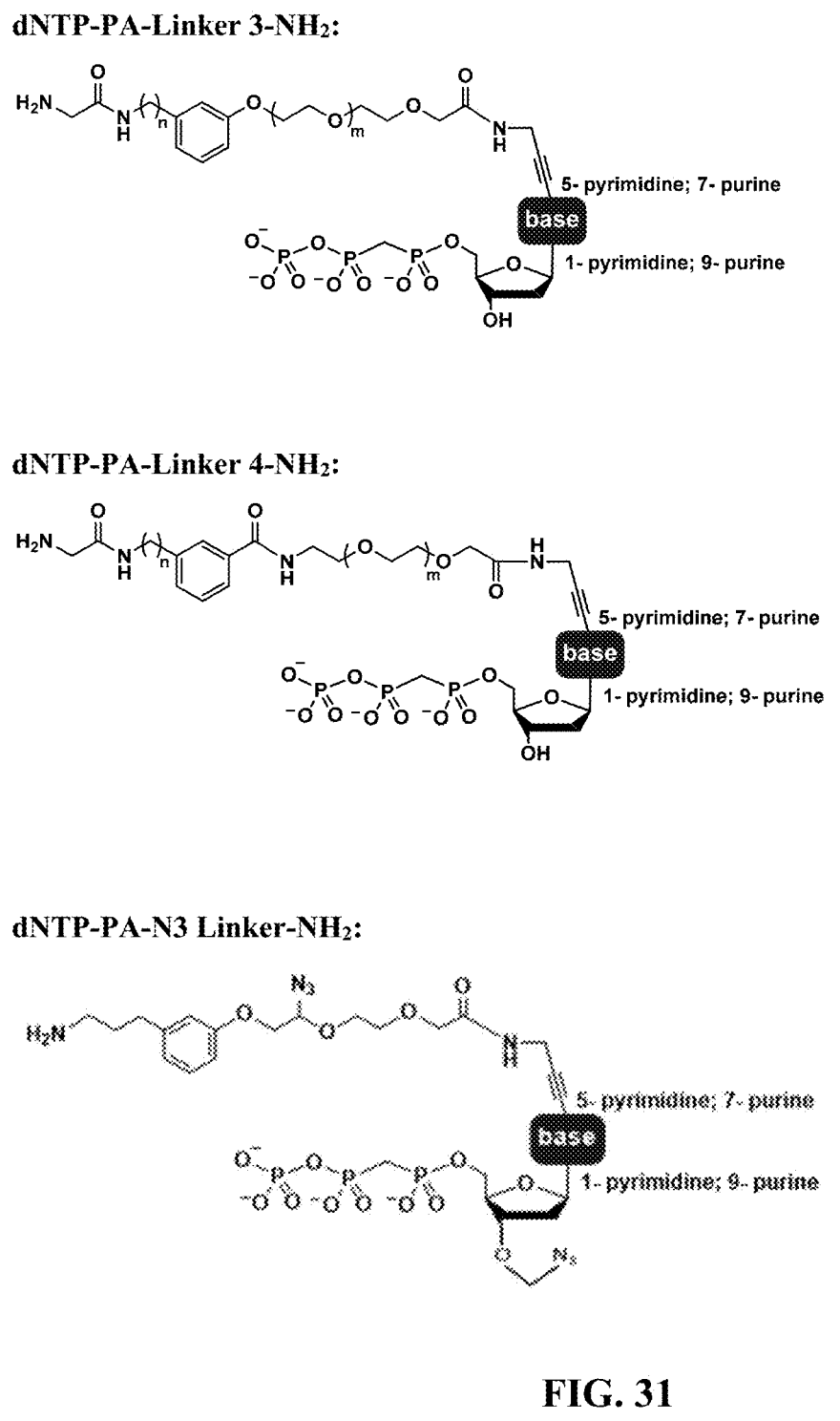

FIG. 31 shows the chemical structures of various exemplary linkers joined/attached to nucleotide units.

Figure 32:
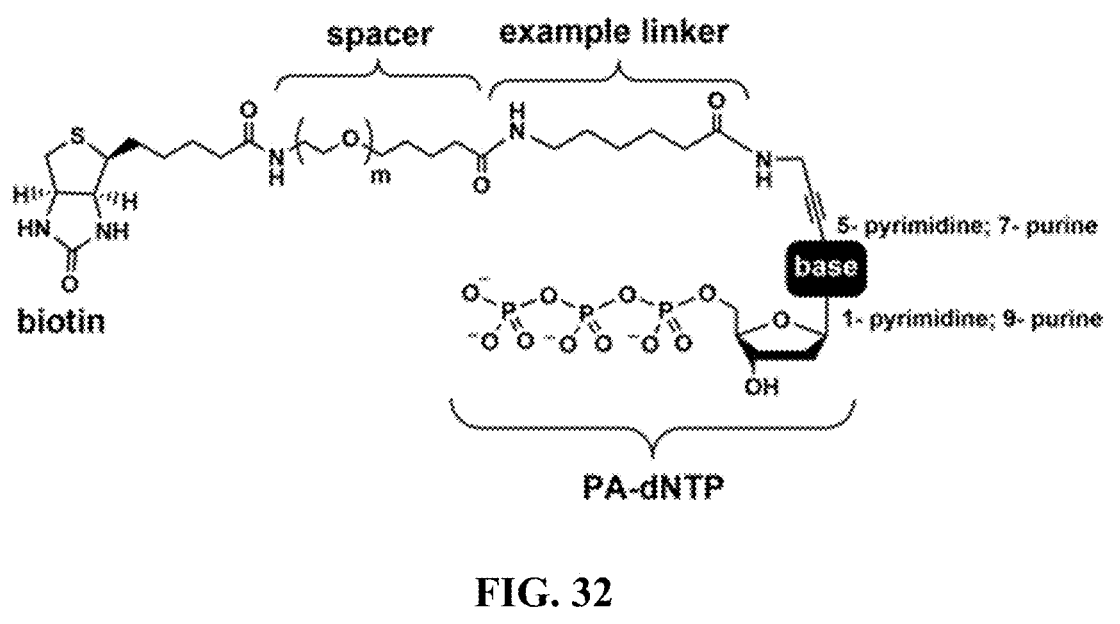

FIG. 32 shows the chemical structure of an exemplary biotinylated nucleotide-arm. In this example, the nucleotide unit is connected to the linker via a propargyl amine attachment at the 5 position of a pyrimidine base or the 7 position of a purine base.

DETAILED DESCRIPTION

Definitions

Figure 1:
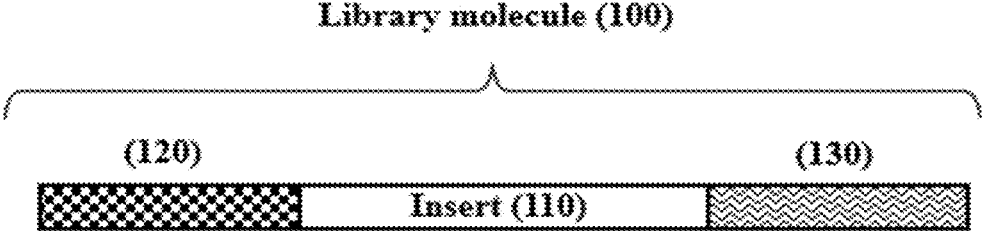
FIG. 1 is a schematic showing an exemplary linear nucleic acid library molecule (100) comprising an insert region (110) (e.g., sequence-of-interest) flanked on one side by a universal adaptor sequence for a forward sequencing primer binding site (120), and the insert region (110) is flanked on the other side by a universal adaptor sequence for a reverse sequencing primer binding site (130).

The headings provided herein are not limitations of the various aspects of the disclosure, which aspects can be understood by reference to the specification as a whole.

Unless defined otherwise, technical and scientific terms used herein have meanings that are commonly understood by those of ordinary skill in the art unless defined otherwise. Generally, terminologies pertaining to techniques of molecular biology, nucleic acid chemistry, protein chemistry, genetics, microbiology, transgenic cell production, and hybridization described herein are those well-known and commonly used in the art. Techniques and procedures described herein are generally performed according to conventional methods well known in the art and as described in various general and more specific references that are cited and discussed throughout the instant specification. For example, see Sambrook et al., Molecular Cloning: A Laboratory Manual (Third ed., Cold Spring Harbor Laboratory Press, Cold Spring Harbor, N.Y. 2000). See also Ausubel et al., Current Protocols in Molecular Biology, Greene Publishing Associates (1992). The nomenclatures utilized in connection with, and the laboratory procedures and techniques described herein are those well-known and commonly used in the art.

Unless otherwise required by context herein, singular terms shall include pluralities and plural terms shall include the singular. Singular forms "a", "an" and "the", and singular use of any word, include plural referents unless expressly and unequivocally limited on one referent.

It is understood the use of the alternative term (e.g., "or") is taken to mean either one or both or any combination thereof of the alternatives.

The term "and/or" used herein is to be taken mean specific disclosure of each of the specified features or components with or without the other. For example, the term "and/or" as used in a phrase such as "A and/or B" herein is intended to include: "A and B"; "A or B"; "A" (A alone); and "B" (B alone). In a similar manner, the term "and/or" as used in a phrase such as "A, B, and/or C" is intended to encompass each of the following aspects: "A, B, and C"; "A, B, or C"; "A or C"; "A or B"; "B or C"; "A and B"; "B and C"; "A and C"; "A" (A alone); "B" (B alone); and "C" (C alone).

As used herein and in the appended claims, terms "comprising", "including", "having" and "containing", and their grammatical variants, as used herein are intended to be non-limiting so that one item or multiple items in a list do not exclude other items that can be substituted or added to the listed items. It is understood that wherever aspects are described herein with the language "comprising," otherwise analogous aspects described in terms of "consisting of" and/or "consisting essentially of" are also provided.

As used herein, the terms "about" and "approximately" refer to a value or composition that is within an acceptable error range for the particular value or composition as determined by one of ordinary skill in the art, which will depend in part on how the value or composition is measured or determined, i.e., the limitations of the measurement system. For example, "about" or "approximately" can mean within one or more than one standard deviation per the practice in the art. Alternatively, "about" or "approximately" can mean a range of up to 10% (i.e., ±10%) or more depending on the limitations of the measurement system. For example, about 5 mg can include any number between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "approximately" should be assumed to be within an acceptable error range for that particular value or composition. Also, where ranges and/or subranges of values are provided, the ranges and/or subranges can include the endpoints of the ranges and/or subranges.

The terms "peptide", "polypeptide" and "protein" and other related terms used herein are used interchangeably and refer to a polymer of amino acids and are not limited to any particular length. Polypeptides may comprise natural and non-natural amino acids. Polypeptides include recombinant or chemically-synthesized forms. Polypeptides also include precursor molecules that have not yet been subjected to post-translation modification such as proteolytic cleavage, cleavage due to ribosomal skipping, hydroxylation, methylation, lipidation, acetylation, SUMOylation, ubiquitination, glycosylation, phosphorylation and/or disulfide bond formation. These terms encompass native and artificial proteins, protein fragments and polypeptide analogs (such as muteins, variants, chimeric proteins and fusion proteins) of a protein sequence as well as post-translationally, or otherwise covalently or non-covalently, modified proteins.

The term "cellular biological sample" refers to a single cell, a plurality of cells, a tissue, an organ, an organism, or section of any of these cellular biological samples. The cellular biological sample can be extracted (e.g., biopsied) from an organism, or obtained from a cell culture grown in liquid or in a culture dish. The cellular biological sample comprises a sample that is fresh, frozen, fresh frozen, or archived (e.g., formalin-fixed paraffin-embedded; FFPE). The cellular biological sample can be embedded in a wax, resin, epoxy or agar. The cellular biological sample can be fixed, for example in any one or any combination of two or more of acetone, ethanol, methanol, formaldehyde, paraformaldehyde-Triton or glutaraldehyde. The cellular biological sample can be sectioned or non-sectioned. The cellular biological sample can be stained, de-stained or non-stained.

The nucleic acids of interest can be extracted from cells or cellular biological samples using any of a number of techniques known to those of skill in the art. For example, a typical DNA extraction procedure comprises (i) collection of the cell sample or tissue sample from which DNA is to be extracted, (ii) disruption of cell membranes (i.e., cell lysis) to release DNA and other cytoplasmic components, (iii) treatment of the lysed sample with a concentrated salt solution to precipitate proteins, lipids, and RNA, followed by centrifugation to separate out the precipitated proteins, lipids, and RNA, and (iv) purification of DNA from the supernatant to remove detergents, proteins, salts, or other reagents used during the cell membrane lysis. A variety of suitable commercial nucleic acid extraction and purification kits are consistent with the disclosure herein. Examples include, but are not limited to, the QIAamp kits (for isolation of genomic DNA from human samples) and DNAeasy kits (for isolation of genomic DNA from animal or plant samples) from Qiagen (Germantown, MD), or the Maxwell® and ReliaPrep™ series of kits from Promega (Madison, WI).

The term "polymerase" and its variants, as used herein, comprises an enzyme comprising a domain that binds a nucleotide (or nucleoside) where the polymerase can form a complex having a template nucleic acid and a complementary nucleotide. The polymerase can have one or more activities including, but not limited to, base analog detection activities, DNA polymerization activity, reverse transcriptase activity, DNA binding, strand displacement activity, and nucleotide binding and recognition. A polymerase can be any enzyme that can catalyze polymerization of nucleotides (including analogs thereof) into a nucleic acid strand. Typically, but not necessarily, such nucleotide polymerization can occur in a template-dependent fashion. Typically, a polymerase comprises one or more active sites at which nucleotide binding and/or catalysis of nucleotide polymerization can occur. In some embodiments, a polymerase includes other enzymatic activities, such as for example, 3' to 5' exonuclease activity or 5' to 3' exonuclease activity. In some embodiments, a polymerase has strand displacing activity. A polymerase can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives, or fragments thereof that retain the ability to catalyze nucleotide polymerization (e.g., catalytically active fragment). The polymerase includes catalytically inactive polymerases, catalytically active polymerases, reverse transcriptases, and other enzymes comprising a nucleotide binding domain. In some embodiments, a polymerase can be isolated from a cell, or generated using recombinant DNA technology or chemical synthesis methods. In some embodiments, a polymerase can be expressed in prokaryote, eukaryote, viral, or phage organisms. In some embodiments, a polymerase can be post-translationally modified proteins or fragments thereof. A polymerase can be derived from a prokaryote, eukaryote, virus or phage. A polymerase comprises DNA-directed DNA polymerase and RNA-directed DNA polymerase.

The term "strand displacing" refers to the ability of a polymerase to locally separate strands of double-stranded nucleic acids and synthesize a new strand in a template-based manner. Strand displacing polymerases displace a complementary strand from a template strand and catalyze new strand synthesis. Strand displacing polymerases include mesophilic and thermophilic polymerases. Strand displacing polymerases include wild type enzymes, and variants including exonuclease minus mutants, mutant versions, chimeric enzymes and truncated enzymes. Examples of strand displacing polymerases include, without limitation, phi29 DNA polymerase, large fragment of Bst DNA polymerase, large fragment of Bsu DNA polymerase (exo-), Bca DNA polymerase (exo-), Klenow fragment of *E. coli* DNA polymerase, T5 polymerase, M-MuLV reverse transcriptase, HIV viral reverse transcriptase, Deep Vent DNA polymerase and KOD DNA polymerase. The phi29 DNA polymerase can be wild type phi29 DNA polymerase (e.g., MagniPhi™ from Expedeon™), or variant EquiPhi29™ DNA polymerase (e.g., from Thermo Fisher Scientific™), or chimeric QualiPhi™ DNA polymerase (e.g., from 4basebio™).

The terms "nucleic acid", "polynucleotide" and "oligonucleotide" and other related terms used herein are used interchangeably and refer to polymers of nucleotides and are not limited to any particular length. Nucleic acids include recombinant and chemically-synthesized forms. Nucleic acids can be isolated. Nucleic acids include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and chimeric forms containing DNA and RNA. Nucleic acids can be single-stranded or double-stranded. Nucleic acids comprise polymers of nucleotides, where the nucleotides may include natural or non-natural bases, and/or sugars. Nucleic acids comprise naturally-occurring internucleosidic linkages, for example and without limitation, phosphdiester linkages. Nucleic acids can comprise non-natural internucleoside linkages, including phosphorothioate, phosphorothiolate, and/or peptide nucleic acid (PNA) linkages. In some embodiments, nucleic acids comprise one type of polynucleotide or a mixture of two or more different types of polynucleotides.

The term "operably linked" and "operably joined" or related terms as used herein refers to juxtaposition of components. The juxtapositioned components can be linked together covalently. For example, two nucleic acid components can be enzymatically ligated together where the linkage that joins together the two components comprises phosphodiester linkage. A first and second nucleic acid component can be linked together, where the first nucleic acid component can confer a function on a second nucleic acid component. For example, linkage between a primer binding sequence and a sequence of interest forms a nucleic acid library molecule having a portion that can bind to a primer. In another example, a transgene (e.g., a nucleic acid encoding a polypeptide or a nucleic acid sequence of interest) can be ligated to a vector where the linkage permits expression or functioning of the transgene sequence contained in the vector. In some embodiments, a transgene is operably linked to a host cell regulatory sequence (e.g., a promoter sequence) that affects expression of the transgene. In some embodiments, the vector comprises at least one host cell regulatory sequence, including a promoter sequence, enhancer, transcription and/or translation initiation sequence, transcription and/or translation termination sequence, polypeptide secretion signal sequences, and the like. In some embodiments, the host cell regulatory sequence controls expression of the level, timing and/or location of the transgene.

The terms "linked", "joined", "attached", "appended" and variants thereof comprise any type of fusion, bond, adherence or association between any combination of compounds or molecules that is of sufficient stability to withstand use in the particular procedure. The procedure can include but is not limited to: nucleotide binding; nucleotide incorporation; de-blocking (e.g., removal of chain-terminating moiety); washing; removing; flowing; detecting; imaging and/or identifying. Such linkage can comprise, for example, covalent, ionic, hydrogen, dipole-dipole, hydrophilic, hydrophobic, or affinity bonding, bonds or associations involving van der Waals forces, mechanical bonding, and the like. In some embodiments, such linkage occurs intramolecularly, for example linking together the ends of a single-stranded or double-stranded linear nucleic acid molecule to form a circular molecule. In some embodiments, such linkage can occur between a combination of different molecules, or between a molecule and a non-molecule, including but not limited to: linkage between a nucleic acid molecule and a solid surface; linkage between a protein and a detectable reporter moiety; linkage between a nucleotide and detectable reporter moiety; and the like. Some examples of linkages can be found, for example, in Hermanson, G., "Bioconjugate Techniques", Second Edition (2008); Aslam, M., Dent, A., "Bioconjugation: Protein Coupling Techniques for the Biomedical Sciences", London: Macmillan (1998); Aslam, M., Dent, A., "Bioconjugation: Protein Coupling Techniques for the Biomedical Sciences", London: Macmillan (1998).

The term "primer" and related terms as used herein refers to an oligonucleotide that is capable of hybridizing with a DNA and/or RNA polynucleotide template to form a duplex molecule. Primers can be single-stranded along their entire length or have single-stranded and double-stranded portions. Primers can comprise natural nucleotides and/or nucleotide analogs. Primers can be recombinant nucleic acid molecules. Primers may have any length, but typically range from 4-50 nucleotides. A typical primer comprises a 5' end and 3' end. The 3' end of the primer can include a 3' OH moiety which serves as a nucleotide polymerization initiation site in a polymerase-catalyzed primer extension reaction. Alternatively, the 3' end of the primer can lack a 3' OH moiety, or can include a terminal 3' blocking group that inhibits nucleotide polymerization in a polymerase-catalyzed reaction. Any one nucleotide, or more than one nucleotide, along the length of the primer can be labeled with a detectable reporter moiety. A primer can be in solution (e.g., a soluble primer) or can be immobilized to a support (e.g., a capture primer).

The term "template nucleic acid", "template polynucleotide", "target nucleic acid" "target polynucleotide", "template strand" and other variations refer to a nucleic acid strand that serves as the basis nucleic acid molecule for any of the amplification and/or sequencing methods describe herein. The template nucleic acid can be single-stranded or double-stranded, or the template nucleic acid can have single-stranded or double-stranded portions. The template nucleic acid can be obtained from a naturally-occurring source, recombinant form, or chemically synthesized to include any type of nucleic acid analog. The template nucleic acid can be linear, concatemeric, circular, or other forms.

When used in reference to nucleic acid molecules, the terms "hybridize" or "hybridizing" or "hybridization" or other related terms refers to hydrogen bonding between two different nucleic acids to form a duplex nucleic acid. Hybridization also includes hydrogen bonding between two different regions of a single nucleic acid molecule to form a self-hybridizing molecule having a duplex region. Hybridization can comprise Watson-Crick or Hoogstein binding to form a duplex double-stranded nucleic acid, or a double-stranded region within a nucleic acid molecule. The double-stranded nucleic acid, or the two different regions of a single nucleic acid, may be wholly complementary, or partially complementary. Complementary nucleic acid strands need not hybridize with each other across their entire length. The complementary base pairing can be the standard A-T or C-G base pairing, or can be other forms of base-pairing interactions. Duplex nucleic acids can include mismatched base-paired nucleotides.

When used in reference to nucleic acids, the terms "extend", "extending", "extension" and other variants, refers to incorporation of one or more nucleotides into a nucleic acid molecule. Nucleotide incorporation comprises polymerization of one or more nucleotides into the terminal 3' OH end of a nucleic acid strand, resulting in extension of the nucleic acid strand. Nucleotide incorporation can be conducted with natural nucleotides and/or nucleotide analogs. Typically, but not necessarily, nucleotide incorporation occurs in a template-dependent fashion. Any suitable method of extending a nucleic acid molecule may be used, including primer extension catalyzed by a DNA polymerase or RNA polymerase.

The term "nucleotides" and related terms refers to a molecule comprising an aromatic base, a five-carbon sugar (e.g., ribose or deoxyribose), and at least one phosphate group. Canonical or non-canonical nucleotides are consistent with use of the term. In some embodiments, the nucleotide comprises a monophosphate, diphosphate, or triphosphate, or corresponding phosphate analog. The term "nucleoside" refers to a molecule comprising an aromatic base and a sugar. Nucleotides and nucleosides can be non-labeled or labeled with a detectable reporter moiety.

Nucleotides (and nucleosides) typically comprise a hetero cyclic base including substituted or unsubstituted nitrogen-containing parent heteroaromatic ring which are commonly found in nucleic acids, including naturally-occurring, substituted, modified, or engineered variants, or analogs of the same. The base of a nucleotide (or nucleoside) is capable of forming Watson-Crick and/or Hoogstein hydrogen bonds with an appropriate complementary base. Exemplary bases include, but are not limited to, purines and pyrimidines such as: 2-aminopurine, 2,6-diaminopurine, adenine (A), etheno-adenine, $N^6$-$\Delta^2$-isopentenyladenine (6iA), $N^6$-$\Delta^2$-isopente-nyl-2-methylthioadenine (2ms6iA), $N^6$-methyladenine, guanine (G), isoguanine, $N^2$-dimethylguanine (dmG), 7-methylguanine (7mG), 2-thiopyrimidine, 6-thioguanine (6sG), hypoxanthine and $O^6$-methylguanine; 7-deaza-purines such as 7-deazaadenine (7-deaza-A) and 7-deazagua-nine (7-deaza-G); pyrimidines such as cytosine (C), 5-pro-pynylcytosine, isocytosine, thymine (T), 4-thiothymine (4sT), 5,6-dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; inosines; hydroxymethyl-cytosines; 5-methycytosines; base (Y); as well as methyl-ated, glycosylated, and acylated base moieties; and the like. Additional exemplary bases can be found in Fasman, 1989, in "Practical Handbook of Biochemistry and Molecular Biology", pp. 385-394, CRC Press, Boca Raton, Fla.

Nucleotides (and nucleosides) typically comprise a sugar moiety, such as carbocyclic moiety (Ferraro and Gotor 2000 Chem. Rev. 100: 4319-48), acyclic moieties (Martinez, et al., 1999 Nucleic Acids Research 27: 1271-1274; Martinez, et al., 1997 Bioorganic & Medicinal Chemistry Letters vol. 7: 3013-3016), and other sugar moieties (Joeng, et al., 1993 J. Med. Chem. 36: 2627-2638; Kim, et al., 1993 J. Med. Chem. 36: 30-7; Eschenmosser 1999 Science 284:2118-2124; and U.S. Pat. No. 5,558,991). The sugar moiety comprises: ribosyl; 2'-deoxyribosyl; 3'-deoxyribosyl; 2', 3'-dideoxyribosyl; 2', 3'-didehydrodideoxyribosyl; 2'-alkoxyribosyl; 2'-azidoribosyl; 2'-aminoribosyl; 2'-fluo-roribosyl; 2'-mercaptoriboxyl; 2'-alkylthioribosyl; 3'-alkoxyribosyl; 3'-azidoribosyl; 3'-aminoribosyl; 3'-fluo-roribosyl; 3'-mercaptoriboxyl; 3'-alkylthioribosyl carbocy-clic; acyclic or other modified sugars.

In some embodiments, nucleotides comprise a chain of one, two or three phosphorus atoms where the chain is typically attached to the 5' carbon of the sugar moiety via an ester or phosphoramide linkage. In some embodiments, the nucleotide is an analog having a phosphorus chain in which the phosphorus atoms are linked together with intervening O, S, NH, methylene or ethylene. In some embodiments, the phosphorus atoms in the chain include substituted side groups including O, S or $BH_3$. In some embodiments, the chain includes phosphate groups substituted with analogs including phosphoramidate, phosphorothioate, phosphordi-thioate, and O-methylphosphoroamidite groups.

As used herein, a "nucleotide unit" or "nucleotide moi-ety" refers to nucleotides (e.g., dATP, dTTP, dGTP, dCTP, or dUTP), or analogs thereof, comprising comprises a base, sugar and at least one phosphate group. Nucleotide units can be attached to the multivalent molecules used in the sequencing reactions described herein. In general, all nucleotide units attached to the same multivalent molecule will have the same identity (e.g., all A, all T, all C, or all G), although the skilled artisan will appreciate that there may be situations in which a multivalent molecule comprising nucleotide units of differing identity will be advantageous.

The term "rolling circle amplification" generally refers to an amplification method that employs a circularized nucleic acid template molecule containing a target sequence of interest, an amplification primer binding sequence, and optionally one or more adaptor sequences such as a sequenc-ing primer binding sequence and/or a sample index sequence. The rolling circle amplification reaction can be conducted under isothermal amplification conditions, and includes the circularized nucleic acid template molecule, an amplification primer, a strand-displacing polymerase and a plurality of nucleotides, to generate a concatemer containing tandem repeat sequences of the circular template molecule and any adaptor sequences present in the original circular-ized nucleic acid template molecule. The concatemer can self-collapse to form a nucleic acid nanoball. The shape and size of the nanoball can be further compacted by including a pair of inverted repeat sequences in the circular template molecule, or by conducting the rolling circle amplification reaction with one or more compaction oligonucleotides. One of the advantages of using rolling circle amplification to generate clonal amplicons for a sequencing workflow, is that the repeat copies of the target sequence in the nanoball can be simultaneously sequenced to increase signal intensity. In some embodiments, the rolling circle amplification reaction can be conducted in the presence of a plurality of compaction oligonucleotides having at least four consecutive guanines (e.g., 4, 5, 6, 7, 8, 9, 10, 11, 12, or more than 12 guanines). The rolling circle amplification reaction may generate concatemers comprising repeat copies of the universal binding sequence for the compaction oligonucleotide. At least one compaction oligonucleotide can form a guanine tetrad and hybridize to the universal binding sequences for the compaction oligonucleotide, and the resulting concatemer can fold to form an intramolecular G-quadruplex structure. The concatemers can self-collapse to form compact nanoballs. Without wishing to be bound by theory, it is hypothesized that formation of the guanine tetrads and G-quadruplexes in the nanoballs may increase the stability of the nanoballs to retain their compact size and shape. which can withstand repeated flows of reagents for conducting any of the sequencing workflows described herein.

When used in reference to nucleic acids, the terms "amplify", "amplifying", "amplification", and other related terms include producing multiple copies of an original polynucleotide template molecule, where the copies comprise a sequence that is complementary to the template sequence, and/or the copies comprise a sequence that is the same as the template sequence. In some embodiments, the copies comprise a sequence that is substantially identical to a template sequence, and/or is substantially identical to a sequence that is complementary to the template sequence.

The term "reporter moiety", "reporter moieties" or related terms refers to a compound that generates, or causes to generate, a detectable signal. A reporter moiety is sometimes called a "label". Any suitable reporter moiety may be used, including luminescent, photoluminescent, electroluminescent, bioluminescent, chemiluminescent, fluorescent, phosphorescent, chromophore, radioisotope, electrochemical, mass spectrometry, Raman, hapten, affinity tag, atom, or an enzyme. A reporter moiety generates a detectable signal resulting from a chemical or physical change (e.g., heat, light, electrical, pH, salt concentration, enzymatic activity, or proximity events). A proximity event includes two reporter moieties approaching each other, or associating with each other, or binding each other. It is well known to one skilled in the art to select reporter moieties so that each absorbs excitation radiation and/or emits fluorescence at a wavelength distinguishable from the other reporter moieties to permit monitoring the presence of different reporter moieties in the same reaction or in different reactions. Two or more different reporter moieties can be selected having spectrally distinct emission profiles, or having minimal overlapping spectral emission profiles. Reporter moieties can be linked (e.g., operably linked) to nucleotides, nucleosides, nucleic acids, enzymes (e.g., polymerases or reverse transcriptases), or support (e.g., surfaces).

A reporter moiety (or label) comprises a fluorescent label or a fluorophore. Exemplary fluorescent moieties which may serve as fluorescent labels or fluorophores include, but are not limited to fluorescein and fluorescein derivatives such as carboxyfluorescein, tetrachlorofluorescein, hexachlorofluorescein, carboxynapthofluorescein, fluorescein isothiocyanate, NHS-fluorescein, iodoacetamidofluorescein, fluorescein maleimide, SAMSA-fluorescein, fluorescein thiosemicarbazide, carbohydrazinomethylthioacetyl-amino fluorescein, rhodamine and rhodamine derivatives such as TRITC, TMR, lissamine rhodamine, Texas Red, rhodamine B, rhodamine 6G, rhodamine 10, NHS-rhodamine, TMR-iodoacetamide, lissamine rhodamine B sulfonyl chloride, lissamine rhodamine B sulfonyl hydrazine, Texas Red sulfonyl chloride, Texas Red hydrazide, coumarin and coumarin derivatives such as AMCA, AMCA-NHS, AMCA-sulfo-NHS, AMCA-HPDP, DCIA, AMCE-hydrazide, BODIPY and derivatives such as BODIPY FL C3-SE, BODIPY 530/550 C3, BODIPY 530/550 C3-SE, BODIPY 530/550 C3 hydrazide, BODIPY 493/503 C3 hydrazide, BODIPY FL C3 hydrazide, BODIPY FL IA, BODIPY 530/551 IA, Br-BODIPY 493/503, Cascade Blue and derivatives such as Cascade Blue acetyl azide, Cascade Blue cadaverine, Cascade Blue ethylenediamine, Cascade Blue hydrazide, Lucifer Yellow and derivatives such as Lucifer Yellow iodoacetamide, Lucifer Yellow CH, cyanine and derivatives such as indolium based cyanine dyes, benzo-indolium based cyanine dyes, pyridium based cyanine dyes, thiozolium based cyanine dyes, quinolinium based cyanine dyes, imidazolium based cyanine dyes, Cy 3, Cy5, lanthanide chelates and derivatives such as BCPDA, TBP, TMT, BHHCT, BCOT, Europium chelates, Terbium chelates, Alexa Fluor dyes, DyLight dyes, Atto dyes, LightCycler Red dyes, CAL Flour dyes, JOE and derivatives thereof, Oregon Green dyes, WellRED dyes, IRD dyes, phycoerythrin and phycobilin dyes, Malachite green, stilbene, DEG dyes, NR dyes, near-infrared dyes and others known in the art such as those described in Haugland, Molecular Probes Handbook, (Eugene, Oreg.) 6th Edition; Lakowicz, Principles of Fluorescence Spectroscopy, 2nd Ed., Plenum Press New York (1999), or Hermanson, Bioconjugate Techniques, 2nd Edition, or derivatives thereof, or any combination thereof. Cyanine dyes may exist in either sulfonated or non-sulfonated forms, and consist of two indolenin, benzo-indolium, pyridium, thiozolium, and/or quinolinium groups separated by a polymethine bridge between two nitrogen atoms. Commercially available cyanine fluorophores include, for example, Cy3, (which may comprise 1-[6-(2,5-dioxopyrrolidin-1-yloxy)-6-oxohexyl]-2-(3-{1-[6-(2,5-di-oxopyrrolidin-1-yloxy)-6-oxohexyl]-3,3-dimethyl-1,3-di-hydro-2H-indol-2-ylidene}prop-1-en-1-yl)-3,3-dimethyl-3H-indolium or 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-5-sulfo-1,3-dihydro-2H-indol-2-ylidene}prop-1-en-1-yl)-3,3-dimethyl-3H-indolium-5-sulfonate), Cy5 (which may comprise 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-indolin-2-ylidene)penta-1,3-dien-1-yl)-3,3-dimethyl-3H-indol-1-ium or 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-sulfoindolin-2-ylidene)penta-1,3-dien-1-yl)-3,3-dimethyl-3H-indol-1-ium-5-sulfonate), and Cy7 (which may comprise 1-(5-carboxypentyl)-2-[(1E,3E,5E,7Z)-7-(1-ethyl-1,3-dihydro-2H-indol-2-ylidene)hepta-1,3,5-trien-1-yl]-3H-indolium or 1-(5-carboxypentyl)-2-[(1E,3E,5E,7Z)-7-(1-ethyl-5-sulfo-1,3-dihydro-2H-indol-2-ylidene)hepta-1,3,5-trien-1-yl]-3H-indolium-5-sulfonate), where "Cy" stands for 'cyanine', and the first digit identifies the number of carbon atoms between two indolenine groups. Cy2 which is an oxazole derivative rather than indolenin, and the benzo-derivatized Cy3.5, Cy5.5 and Cy7.5 are exceptions to this rule.

In some embodiments, the reporter moiety can be a FRET pair, e.g., such that multiple classifications can be performed under a single excitation and imaging step. As used herein, FRET may comprise excitation exchange (Forster) transfers, or electron-exchange (Dexter) transfers.

The term "support" as used herein refers to a substrate that is designed for deposition of biological molecules or biological samples for assays and/or analyses. Examples of biological molecules to be deposited onto a support include nucleic acids (e.g., DNA, RNA), polypeptides, saccharides, lipids, a single cell, or multiple cells. Examples of biological samples include, but are not limited to saliva, phlegm, mucus, blood, plasma, serum, urine, stool, sweat, tears and fluids from tissues or organs.

In some embodiments, the support is solid, semi-solid, or a combination of both. In some embodiments, the support is porous, semi-porous, non-porous, or any combination of porosity. In some embodiments, the support can be substantially planar, concave, convex, or any combination thereof. In some embodiments, the support can be cylindrical, for example, comprising a capillary or interior surface of a capillary.

In some embodiments, the surface of the support can be substantially smooth. In some embodiments, the support can be regularly or irregularly textured, including, for example, bumps, etched, pores, three-dimensional scaffolds, or any combination thereof.

In some embodiments, the support comprises a bead having any shape, including spherical, hemi-spherical, cylindrical, barrel-shaped, toroidal, disc-shaped, rod-like, conical, triangular, cubical, polygonal, tubular or wire-like.

The support can be fabricated from any material, including but not limited to glass, fused-silica, silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET)), or any combination thereof. Various compositions of both glass and plastic substrates are contemplated.

In some aspects, the present disclosure provides a plurality (e.g., two or more) of nucleic acid template molecules immobilized to a support. In some embodiments, the immobilized plurality of nucleic acid template molecules has the same sequence. In some embodiments, the immobilized plurality of nucleic acid template molecules has different sequences. In some embodiments, individual nucleic acid template molecules in the plurality of nucleic acid template molecules are immobilized to a different site on the support. In some embodiments, two or more individual nucleic acid template molecules in the plurality of nucleic acid templates are immobilized to a site on the support.

The term "array" refers to a support comprising a plurality of sites located at pre-determined locations on the support to form an array of sites. The sites can be discrete and separated by interstitial regions. In some embodiments, the pre-determined sites on the support can be arranged in one dimension in a row or a column, or arranged in two dimensions in rows and columns. In some embodiments, the plurality of pre-determined sites is arranged on the support in an organized fashion. In some embodiments, the plurality of pre-determined sites is arranged in any organized pattern, including rectilinear, hexagonal patterns, grid patterns, patterns having reflective symmetry, patterns having rotational symmetry, or the like. The pitch between different pairs of sites can be that same or can vary. In some embodiments, the support comprises at least $10^2$ sites, at least $10^3$ sites, at least $10^4$ sites, at least $10^5$ sites, at least $10^6$ sites, at least $10^7$ sites, at least $10^8$ sites, at least $10^9$ sites, at least $10^{10}$ sites, at least $10^{11}$ sites, at least $10^{12}$ sites, at least $10^{13}$ sites, at least $10^{14}$ sites, at least $10^{15}$ sites, or more, where the sites are located at pre-determined locations on the support. In some embodiments, a plurality of pre-determined sites on the support (e.g., $10^2$-$10^{15}$ sites or more, e.g., $10^2$ sites, $10^3$ sites, $10^4$ sites, $10^5$ sites, $10^6$ sites, $10^7$ sites, $10^8$ sites, $10^9$ sites, $10^{10}$ sites, $10^{11}$ sites, $10^{12}$ sites, $10^3$ sites, $10^{14}$ sites, $10^{15}$ sites, or more) are immobilized with nucleic acid template molecules to form a nucleic acid template array. In some embodiments, the nucleic acid template molecules that are immobilized at a plurality of pre-determined sites by hybridization to immobilized surface capture primers, or the nucleic acid template molecules are covalently attached to the surface capture primers. In some embodiments, the nucleic acid template molecules that are immobilized at a plurality of pre-determined sites, for example, immobilized at $10^2$-$10^{15}$ sites or more (e.g., $10^2$-$10^{15}$ sites or more, e.g., $10^2$ sites, $10^3$ sites, $10^4$ sites, $10^5$ sites, $10^6$ sites, $10^7$ sites, $10^8$ sites, $10^9$ sites, $10^{10}$ sites, $10^{11}$ sites, $10^{12}$ sites, $10^{13}$ sites, $10^{14}$ sites, $10^{15}$ sites, or more). In some embodiments, the immobilized nucleic acid template molecules are clonally-amplified to generate immobilized nucleic acid clusters at the plurality of pre-determined sites. In some embodiments, individual immobilized nucleic acid clusters comprise linear clusters, or comprise single-stranded or double-stranded concatemers.

In some embodiments, a support comprising a plurality of sites located at random locations on the support is referred to herein as a support having randomly located sites thereon. In such embodiments, the location of the randomly located sites on the support are not pre-determined. Consequently, the plurality of randomly-located sites is arranged on the support in a disordered and/or unpredictable fashion. In some embodiments, the support comprises at least $10^2$ sites, at least $10^3$ sites, at least $10^4$ sites, at least $10^5$ sites, at least $10^6$ sites, at least $10^7$ sites, at least $10^8$ sites, at least $10^9$ sites, at least $10^{10}$ sites, at least $10^{11}$ sites, at least $10^{12}$ sites, at least $10^{13}$ sites, at least $10^{14}$ sites, at least $10^{15}$ sites, or more, where the sites are randomly located on the support. In some embodiments, a plurality of randomly located sites on the support (e.g., $10^2$-$10^{15}$ sites or more, e.g., $10^2$-$10^{15}$ sites or more, e.g., $10^2$ sites, $10^3$ sites, $10^4$ sites, $10^5$ sites, $10^6$ sites, $10^7$ sites, $10^8$ sites, $10^9$ sites, $10^{10}$ sites, $10^{11}$ sites, $10^{12}$ sites, $10^{13}$ sites, $10^{14}$ sites, $10^{15}$ sites, or more) are immobilized with nucleic acid template molecules. In some embodiments, the nucleic acid template molecules are immobilized at a plurality of randomly located sites by hybridization to immobilized surface capture primers, or the nucleic acid template molecules are covalently attached to the surface capture primers. In some embodiments, the nucleic acid templates that are immobilized at a plurality of randomly located sites, for example immobilized at $10^2$-$10^{15}$ sites or more, e.g., $10^2$-$10^{15}$ sites or more, e.g., $10^2$ sites, $10^3$ sites, $10^4$ sites, $10^5$ sites, $10^6$ sites, $10^7$ sites, $10^8$ sites, $10^9$ sites, $10^{10}$ sites, $10^{11}$ sites, $10^{12}$ sites, $10^{13}$ sites, $10^{14}$ sites, $10^{15}$ sites, or more. In some embodiments, the immobilized nucleic acid templates are clonally-amplified to generate immobilized nucleic acid clusters at the plurality of randomly located sites. In some embodiments, individual immobilized nucleic acid clusters comprise linear clusters, or comprise single-stranded or double-stranded concatemers.

In some embodiments, the plurality of immobilized surface capture primers on the support (e.g., located at pre-determined or random locations on the support) are in fluid communication with each other to permit flowing a solution of reagents (e.g., nucleic acid template molecules, soluble primers, enzymes, nucleotides, divalent cations, buffers, and the like) onto the support so that the plurality of immobilized surface capture primers on the support can be essentially simultaneously reacted with the reagents in a massively parallel manner. In some embodiments, the fluid communication of the plurality of immobilized surface capture primers can be used to conduct nucleic acid amplification reactions (e.g., RCA, MDA, PCR, and bridge amplification) essentially simultaneously on the plurality of immobilized surface capture primers.

In some embodiments, the plurality of immobilized nucleic acid clusters on the support are in fluid communication with each other to permit flowing a solution of reagents (e.g., enzymes, nucleotides, divalent cations, and the like) onto the support so that the plurality of immobilized nucleic acid clusters on the support can be essentially simultaneously reacted with the reagents in a massively parallel manner. In some embodiments, the fluid communication of the plurality of immobilized nucleic acid clusters can be used to conduct nucleotide binding assays and/or conduct nucleotide polymerization reactions (e.g., primer extension or sequencing) essentially simultaneously on the plurality of immobilized nucleic acid clusters, and optionally to conduct detection and imaging for massively parallel sequencing.

In some embodiments, the term "immobilized" and related terms refer to nucleic acid molecules that are attached to a support through covalent bond or non-covalent interaction, or attached to a coating on the support, or buried within a matrix formed by a coating on the support, where the nucleic acid molecules include surface capture primers, nucleic acid template molecules and extension products of capture primers. Extension products of capture primers can include nucleic acid concatemers (e.g., nucleic acid clusters). The nucleic acid molecules can be immobilized at pre-determined random locations on the support. The nucleic acid molecules can be immobilized at pre-determined or random locations on or within a coating passivated on the support.

In some embodiments, the term "immobilized" and related terms refer to enzymes (e.g., polymerases) that are attached to a support through covalent bond or non-covalent interaction, or attached to a coating on the support, or buried within a matrix formed by a coating on the support. The enzymes can be immobilized at pre-determined or random locations on the support. The enzymes can be immobilized at pre-determined or random locations on or within a coating passivated on the support.

In some embodiments, one or more nucleic acid template molecules are immobilized on the support, for example immobilized at the sites on the support. In some embodiments, the one or more nucleic acid template molecules are clonally-amplified. In some embodiments, the one or more nucleic acid template molecules are clonally-amplified off the support (e.g., in-solution) and then deposited onto the support and immobilized on the support. In some embodiments, the clonal amplification reaction of the one or more nucleic acid template molecules is conducted on the support resulting in immobilization on the support. In some embodiments, the one or more nucleic acid template molecules are clonally-amplified (e.g., in solution or on the support) using a nucleic acid amplification reaction, including any one or any combination of: polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification (RCA), circle-to-circle amplification, helicase-dependent amplification, recombinase-dependent amplification, and/or single-stranded binding (SSB) protein-dependent amplification.

The term "surface primer" and related terms refers to single-stranded oligonucleotides that are immobilized to a support and comprise a sequence that can hybridize to at least a portion of a nucleic acid template molecule. Surface capture primers can be used to immobilize template molecules to a support via hybridization. Surface capture primers can be immobilized to a support in a manner that resists primer removal during flowing, washing, aspirating, and changes in temperature, pH, salts, chemical and/or enzymatic conditions. Typically, but not necessarily, the 5' end of a surface capture primer can be immobilized to a support or to a coating on the support (or embedded in a coating on the support). Alternatively, an interior portion or the 3' end of a surface capture primer can be immobilized to a support.

The sequence of surface capture primers can be wholly or partially complementary along their length to at least a portion of the nucleic acid template molecule. A support can include a plurality of immobilized surface capture primers having the same sequence, or having two or more different sequences. Surface capture primers can be any length, for example 4-50 nucleotides, or 50-100 nucleotides, or 100-150 nucleotides, or longer lengths.

A surface capture primer can have a terminal 3' nucleotide having a sugar 3' OH moiety which is extendible for nucleotide polymerization (e.g., polymerase catalyzed polymerization). A surface capture primer can have a terminal 3' nucleotide having the 3' sugar position linked to a chain-terminating moiety that inhibits nucleotide polymerization. The 3' chain-terminating moiety can be removed (e.g., de-blocked) to convert the 3' end to an extendible 3' OH end using a de-blocking agent. Examples of chain terminating moieties include alkyl group, alkenyl group, alkynyl group, allyl group, aryl group, benzyl group, azide group, amine group, amide group, keto group, isocyanate group, phosphate group, thio group, disulfide group, carbonate group, urea group, acetal group, or silyl group. Azide type chain terminating moieties including azide, azido and azidomethyl groups. Examples of de-blocking agents include a phosphine compound, such as Tris(2-carboxyethyl)phosphine (TCEP) and bis-sulfo triphenyl phosphine (BS-TPP), for chain-terminating groups azide, azido and azidomethyl groups. Examples of de-blocking agents include tetrakis(triphenylphosphine)palladium(0) (Pd(PPh$_3$)$_4$) with piperidine, or with 2,3-Dichloro-5,6-dicyano-1,4-benzo-quinone (DDQ), for chain-terminating groups alkyl, alkenyl, alkynyl and allyl. Examples of a de-blocking agent includes Pd/C for chain-terminating groups aryl and benzyl. Examples of de-blocking agents include phosphine, beta-mercaptoethanol or dithiothritol (DTT), for chain-terminating groups amine, amide, keto, isocyanate, phosphate, thio and disulfide. Examples of de-blocking agents include potassium carbonate (K$_2$CO$_3$) in MeOH, triethylamine in pyridine, and Zn in acetic acid (AcOH), for carbonate chain-terminating groups. Examples of de-blocking agents include tetrabutylammonium fluoride, pyridine-HF, with ammonium fluoride, and triethylamine trihydrofluoride, for chain-terminating groups urea and silyl.

The term "sequencing" and related terms refers to a method for obtaining nucleotide sequence information from a nucleic acid molecule, typically by determining the identity of at least some nucleotides (including their nucleobase components) within the nucleic acid molecule. In some embodiments, the sequence information of a given region of a nucleic acid molecule includes identifying each and every nucleotide within a region that is sequenced. In some embodiments, sequencing information determines only some of the nucleotides a region, while the identity of some nucleotides remains undetermined or incorrectly determined. Any suitable method of sequencing may be used. In an exemplary embodiment, sequencing can include label-free or ion based sequencing methods. In some embodiments, sequencing can include labeled or dye-containing nucleotide or fluorescent based nucleotide sequencing methods. In some embodiments, sequencing can include polony-based sequencing or bridge sequencing methods. In some embodiments, the sequencing employs polymerases and multivalent molecules for generating at least one avidity complex, wherein individual multivalent molecules comprise a plurality of nucleotide units tethered to a core. In some embodiments, the sequencing employs polymerases and free nucleotides for performing sequencing-by-synthesis. In some embodiments, the sequencing employs a ligase enzyme and a plurality of sequence-specific oligonucleotides for performing sequence-by-ligation.

In some aspects, the present disclosure provides various reagents, and methods that employ the reagents for conducting nucleic acid denaturation (de-hybridization) and sequencing. The various reagents can include at least one pH buffering agent. The full name of exemplary, non-limiting pH buffering agents is listed herein.

The term "Tris" refers to a pH buffering agent Tris (hydroxymethyl)-aminomethane. The term "Tris-HCl" refers to a pH buffering agent Tris(hydroxymethyl)-aminomethane hydrochloride. The term "Tris-acetate" refers to a pH buffering agent comprising an acetate salt of Tris (hydroxymethyl)-aminomethane.

The term "Tricine" refers to a pH buffering agent N-[tris (hydroxymethyl)methyl]glycine.

The term "Bicine" refers to a pH buffering agent N,N-bis(2-hydroxyethyl)glycine. The term "Bis-Tris propane" refers to a pH buffering agent 1,3 Bis[tris(hydroxymethyl) methylamino]propane The term "HEPES" refers to a pH buffering agent 4-(2-hydroxyethyl)-1-piperazineethanesulfonic acid.

The term "MES" refers to a pH buffering agent 2-(N-morpholino)ethanesulfonic acid).

The term "MOPS" refers to a pH buffering agent 3-(N-morpholino)propanesulfonic acid.

The term "MOPSO" refers to a pH buffering agent 3-(N-morpholino)-2-hydroxypropanesulfonic acid.

The term "BES" refers to a pH buffering agent N,N-bis (2-hydroxyethyl)-2-aminoethanesulfonic acid.

The term "TES" refers to a pH buffering agent 2-[(2-Hydroxy-1,1bis(hydroxymethyl)ethyl)amino]ethanesulfonic acid).

The term "CAPS" refers to a pH buffering agent 3-(cyclohexylamino)-1 propanesuhinic acid.

The term "TAPS" refers to a pH buffering agent N-[Tris (hydroxymethyl)methyl]-3-amino propane sulfonic acid.

The term "TAPSO" refers to a pH buffering agent N-[Tris (hydroxymethyl)methyl]-3-amino-2-hyidroxypropansulfonic acid.

The term "ACES" refers to a pH buffering agent N-(2-Acetamido)-2-aminoethanesulfonic acid.

The term "PIPES" refers to a pH buffering agent piperazine-1,4-bis(2-ethanesulfonic acid.

The term "ethanolamine" refers to a pH buffering agent that is also known as 2-aminoethanol.

Introduction: Double-Stranded Splint Adaptors

In some aspects, the present disclosure provides compositions comprising nucleic acid double-stranded splint adaptors, including kits, and methods that employ the double-stranded splint adaptors.

The double-stranded splint adaptors (200) can be used in a one-pot, multi-enzyme reaction to introduce one or more new adaptor sequences into a library molecule. In some embodiments, the double-stranded splint adaptor (200) comprises a first splint strand (long splint strand (300)) and a second splint strand (short splint strand (400)). In certain embodiments, the first and second splint strands are hybridized together to form a double-stranded splint adaptor (200) having a double-stranded region and two flanking single-stranded regions (e.g., see FIGS. 2 and 3). In some embodiments, the first splint strand (long splint strand (300)) and a second splint strand (short splint strand (400)) are hybridized to each other along their entire lengths. In some embodiments, the first splint strand (long splint strand (300)) and a second splint strand (short splint strand (400)) include a portion that is not hybridized together. The second splint strand (400) can carry the new adaptor sequence(s) to be introduced, such as for example a new universal binding sequence and/or a new index sequence. The first splint strand can comprise a first region (320), an internal region (310), and a second region (330). The internal region of the first splint strand (310) can be hybridized to the second splint strand (400). In some embodiments, the two flanking single-stranded regions of the double-stranded splinted adaptor (e.g., (320) and (330)) are designed to hybridize to universal adaptor sequences at the ends of a single-stranded linear library molecule (100) having a sequence of interest (110). For example, the first region of the first splint strand (320) may be hybridized to one end of the library molecule (120), and the second region of the first splint strand (330) may be hybridized to the other end of the library molecule (130), thereby circularizing the library molecule to generate a library-splint complex (500) which includes two nicks (e.g., see FIG. 3).

In some embodiments, the linear nucleic acid library molecule (100) comprising an insert region (110) (e.g., sequence-of-interest) flanked on one side by a universal adaptor sequence for a forward sequencing primer binding site (120), and the insert region (110) is flanked on the other side by a universal adaptor sequence for a reverse sequencing primer binding site (130). In some embodiments, the double-stranded splint adaptor (200) comprises a first splint strand (long strand (300)) hybridized to a second splint strand (short strand (400)). The first splint strand can comprise a first region (320) that hybridizes with the universal adaptor sequence for a forward sequencing primer binding site (120) on one end of the linear single stranded library molecule (100), and the first splint strand can comprise a second region (330) that hybridizes with the universal adaptor sequence for a reverse sequencing primer binding site (130) on the other end of the linear single stranded library molecule. The internal region (310) of the first splint strand can hybridize to the second splint strand (400). The nicks can be enzymatically ligated to generate a covalently closed circular molecule (600) in which the second splint strand (400) is covalently joined at both ends to the library molecule, thereby introducing the new adaptor sequences into the library molecule (e.g., see FIG. 4). The ligation reaction may join the sequences from the second splint strand (400) to the ends of the library molecule (100).

Figure 5:
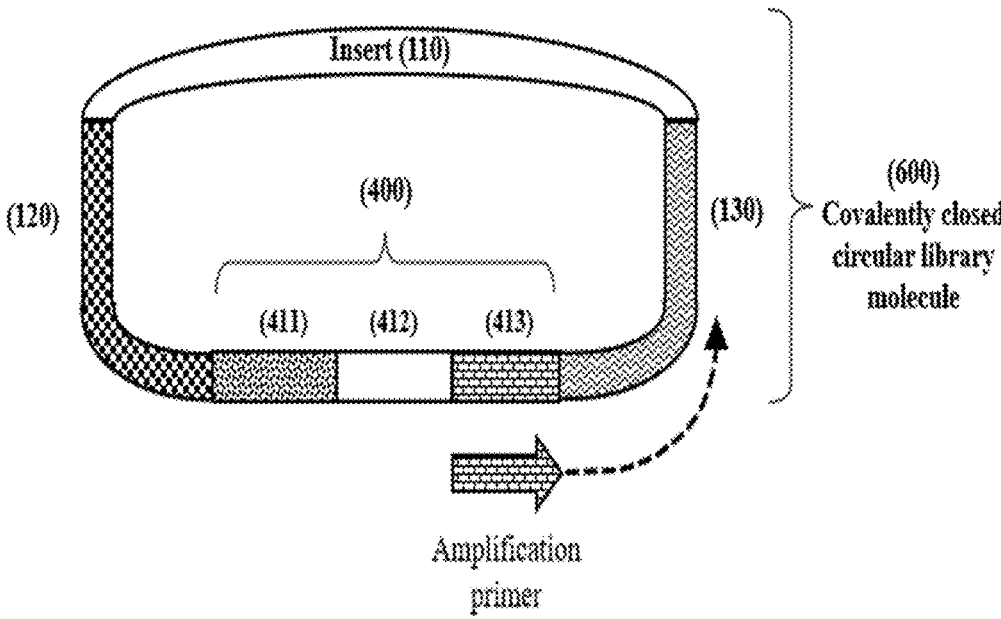
FIG. 5 is a schematic showing an exemplary covalently closed circular library molecule (600) hybridized to an amplification primer. The dotted line represents the nascent extension product.

In some embodiments, any of the sub-regions of the second splint strand (400) can be designed to hybridize to an amplification primer. In some embodiments, the amplification primer has an extendible 3' end which can be used to initiate a primer extension reaction, for example, as shown in FIG. 5. In some embodiments, the amplification primer can be a soluble primer or immobilized to a support (e.g., a surface capture primer). In some embodiments, the amplification primer can be used to conduct a rolling circle amplification reaction to generate a nucleic acid concatemer molecule that is complementary to the covalently closed circular library molecule (600).

Thus, the double-stranded splint adaptors and the methods described herein, can be used to convert any linear library molecule into a covalently closed circular molecule. The second splint strand (400) can include at least one new universal adaptor sequence (e.g., a new surface primer sequence), thereby enabling binding of the covalently closed circular molecule (600) to a support having a plurality of surface capture primers immobilized thereon. The new universal adaptor sequence(s) in the second splint strand (400) permit use of the covalently closed circular molecule (600) in an amplification and sequencing workflow.

The methods described herein also offer the advantage of employing a ligation reaction rather than a gap fill-in reaction to introduce the new adaptor sequences. The ligation reaction gives a high efficiency circularization, with as little as 0.25 pmol library molecules.

The methods described herein can be performed manually or readily adapted for automation, because the annealing and multi-enzyme reactions can be conducted in a single reaction vessel (one-pot) by combining some enzymatic reactions (e.g., phosphorylation and ligation) and by adding subsequent enzymes (e.g., exonucleases) without intervening alcohol precipitations or organic extractions.

Double-Stranded Splint Adaptors

In some aspect, the present disclosure provides nucleic acid double-stranded splint adaptors (200), comprising: (i) a first splint strand (long splint strand (300)) which is hybridized to (ii) a second splint strand (short splint strand (400)) (e.g., see FIGS. 2 and 3). The first splint strand can comprise a first region (320), an internal region (310), and a second region (330). The internal region of the first splint strand (310) can be hybridized to the second splint strand (400) to form a double-stranded splint adaptor (200) having a double-stranded region and two flanking single-stranded regions. The two flanking single-stranded regions of the double-stranded splint adaptor (200) can be designed to hybridize to the end sequences of a linear nucleic acid library molecule (100). The end sequences of the linear nucleic acid library molecule can comprise first (120) and second (130) sequence universal adaptor sequences, respectively. In some embodiments, the first and second universal adaptor sequences of the linear library molecule comprise binding sequences for forward (120) and reverse (130) sequencing primer binding sites, respectively.

Figure 2:
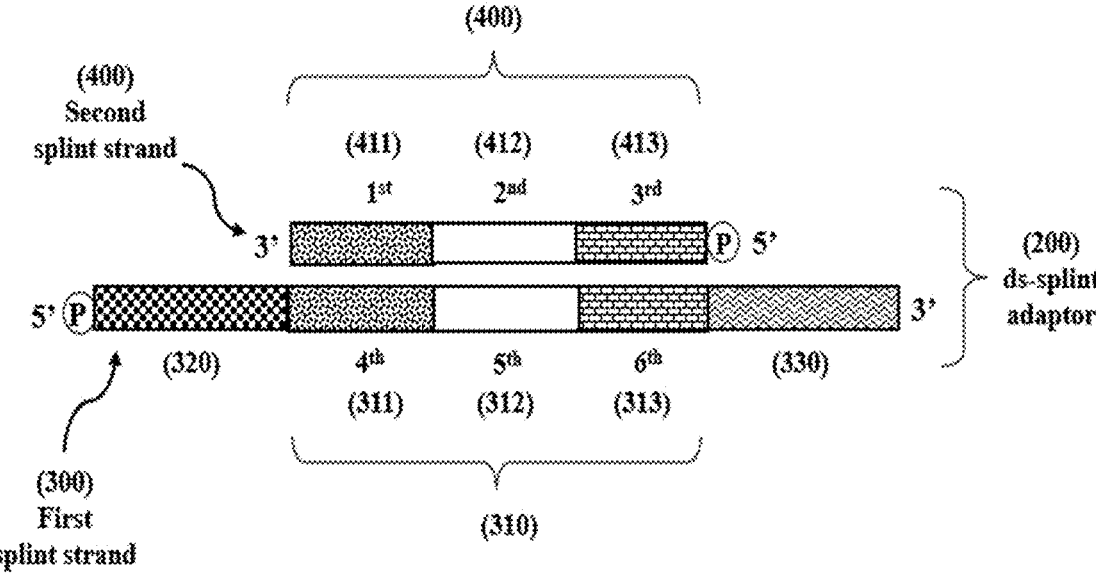
FIG. 2 is a schematic of an exemplary double-stranded splint adaptor (200) which comprises a first splint strand (long strand (300)) hybridized to a second splint strand (short strand (400)).

As exemplified in FIG. 2, in some embodiments, the first splint strand comprises a first region (320) that hybridizes with a sequence on one end of a linear single stranded library molecule, and a second region (330) that hybridizes with a sequence on the other end of the linear single stranded library molecule. The internal region (310) of the first splint strand can hybridize to the second splint strand (400). The internal region (310) of the first splint strand (300) can comprise at least three sub-regions including sub-regions (311), (312) and (313). The second splint strand (400) can comprise at least three sub-regions including sub-regions (411), (412) and (413). For example, sub-region (311) hybridizes to sub-region (411). In another example, subregion (312) hybridizes to sub-region (412). In another example, sub-region (313) hybridizes to sub-region (413). The sub-regions of the second splint strand (400) can comprise any one or more of the following, in any combination, in any order: a universal primer binding sequence for a surface capture primer, a universal primer binding sequence for a surface pinning primer, a sample index sequence, a short random sequence and/or a unique molecular index (UMI) sequence.

In some embodiments, the first region of the first splint strand (320) comprises a first universal adaptor sequence which can hybridize to a first universal binding sequence at one end of a linear nucleic acid library molecule (e.g., see FIG. 2). The second region of the first splint strand (330) can comprise a second universal adaptor sequence which can hybridize to a second universal binding sequence at the other end of the linear nucleic acid library molecule (e.g., see FIG. 2). In some embodiments, the first region of the first splint strand (320) includes a first universal adaptor sequence which comprises a universal binding sequence for a forward or reverse sequencing primer. In some embodiments, the second region of the first splint strand (330) includes a second universal adaptor sequence which comprises a universal binding sequence for a forward or reverse sequencing primer. In some embodiments, the 5' end of the first splint strand (300) is phosphorylated or non-phosphorylated. In some embodiments, the 3' end of the first splint strand (300) comprises a terminal 3' OH group or a terminal 3' blocking group.

Figure 3:
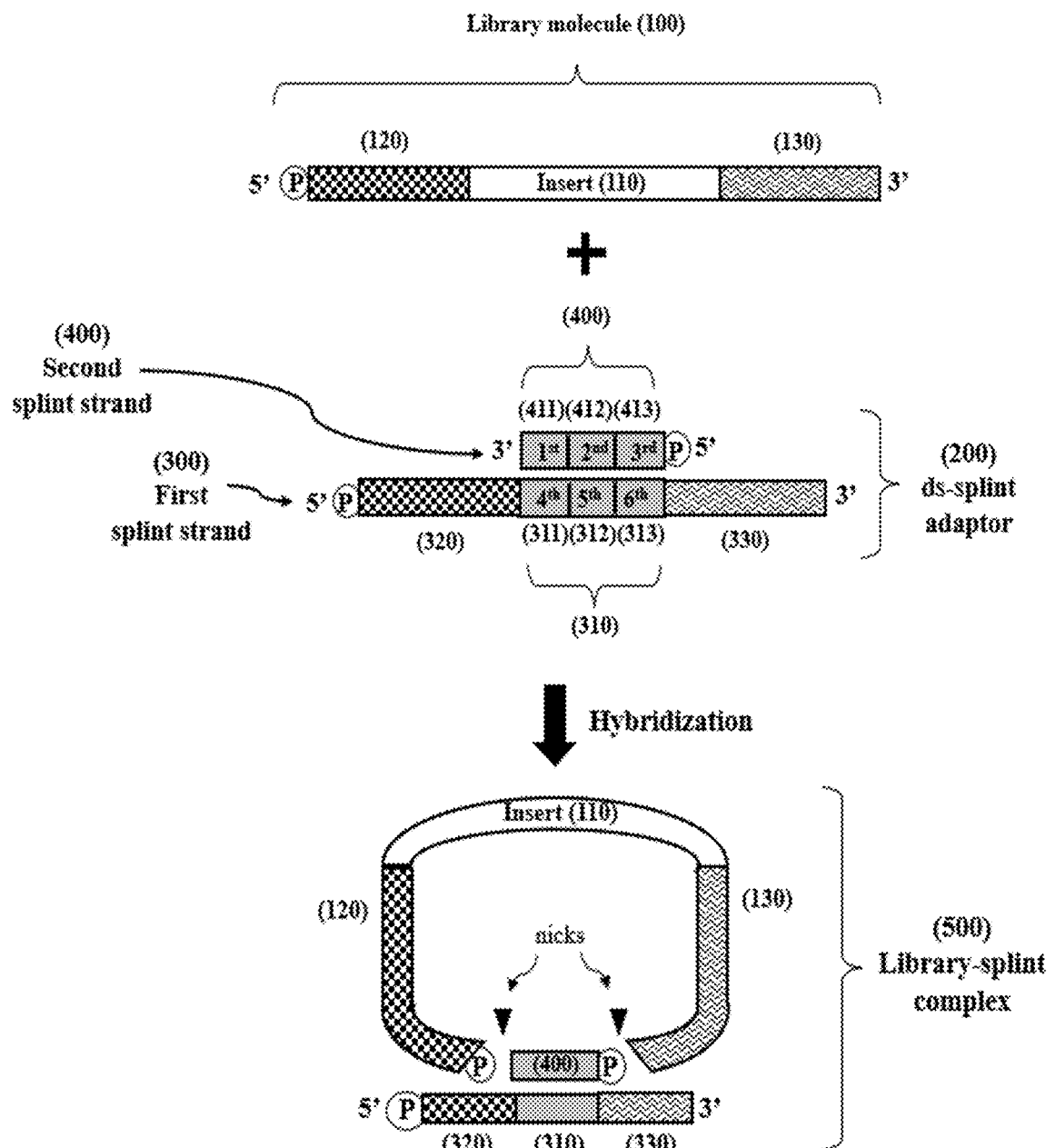
FIG. 3 is a schematic showing an exemplary library circularization workflow, which comprises hybridizing a linear single stranded library molecule (100) with a double-stranded splint adaptor (200), thereby circularizing the library molecule to form a library-splint complex (500) with two nicks.

In some embodiments, the second splint strand (400) comprises at least three sub-regions, including first, second and third sub-regions (e.g., see FIGS. 2 and 3). The first sub-region (411) can comprise a universal binding sequence for an immobilized surface pinning primer, an immobilized surface capture primer, at least one sample index sequence, a short random sequence (NNN) and/or or a unique molecule index (UMI). The second sub-region (412) can comprise a universal binding sequence for an immobilized surface pinning primer, an immobilized surface capture primer, at least one sample index sequence, a short random sequence (NNN) and/or or a unique molecule index (UMI). The third sub-region (413) can comprise a universal binding sequence for an immobilized surface pinning primer, an immobilized surface capture primer, at least one sample index sequence, a short random sequence (e.g., NNN) and/or or a unique molecule index (UMI). In some embodiments, the sample index comprises 5-20 bases (e.g., about 5, 6, 7, 8, 9, 10, 11, 12, 13, 14, 15, 16, 17, 18, 19, or 20 bases) which can be used to distinguish polynucleotides (e.g., insert sequences) from different sample sources in a multiplex assay. In some embodiments, the unique molecular index (UMI) comprises 3-20 bases (e.g., about 3, 4, 5, 6, 7, 8, 9, 10, 11, 12, 13, 14, 15, 16, 17, 18, 19, or 20 bases) which can be used to uniquely identify a nucleic acid molecule to which the adaptor is appended (e.g., molecular tagging). In some embodiments, the unique molecular index (UMI) comprises a random sequence. In some embodiments, the second splint strand (400) is designed to exhibit reduced or no hybridization to the insert sequence (110) of the library molecule (100).

An exemplary arrangement of the sequences in the sub-regions of the second splint strand (400), in a 3' to 5' orientation comprises: [(411) comprises a universal sequence for binding a surface pinning primer]—[(412) comprises a sample index sequence and an optional short random sequence NNN]—[(413) comprises a universal sequence for binding a surface capture primer].

An exemplary arrangement of the sequences in the sub-regions of the second splint strand (400), in a 3' to 5' orientation comprises: [(411) comprises a universal sequence for binding a surface pinning primer]—[(412) comprises a universal sequence for binding a surface capture primer]—[(413) comprises a sample index sequence and an optional short random sequence NNN].

An exemplary arrangement of the sequences in the sub-regions of the second splint strand (400), in a 3' to 5' orientation comprises: [(411) comprises a sample index sequence and an optional short random sequence NNN]—[(412) comprises a universal sequence for binding a surface pinning primer]—[(413) comprises a universal sequence for binding a surface capture primer].

In some embodiments, the second splint strand (400) comprises an additional sub-region carrying a second sample index sequence and an optional short random sequence NNN. For example, the additional sub-region can be located between sub-regions (411) and (412), or between sub-regions (412) and (413).

In some embodiments, the second splint strand (400) can be 20-100 (e.g., about 20, 25, 30, 35, 40, 45, 50, 60, 70, 80, 90, or 100) nucleotides in length. In some embodiments, the second splint strand (400) can be 30-80 nucleotides in length80 (e.g., about 30, 35, 40, 45, 50, 60, 70, or 80) nucleotides in length. 40-60 60 (e.g., about 40, 45, 50, or 60) nucleotides in length. In some embodiments, the 5' end of the second splint strand (400) is phosphorylated; alternatively, the 5' end of the second splint strand (400) is non-phosphorylated. In some embodiments, the 3' end of the second splint strand (400) comprises a terminal 3' OH group; alternatively, the 3' end of the second splint strand (400) comprises a terminal 3' blocking group. In some embodiments, the second splint strands (400) comprise one or more phosphorothioate linkage at the 5' and/or 3' ends to confer exonuclease resistance. In some embodiments, the second splint strands (400) comprise one or more phosphorothioate linkage(s) at an internal position, e.g., to confer endonuclease resistance. In some embodiments, the second splint strands (400) comprise one or more 2'-O-methylcytosine bases at the 5' and/or 3' end, or at an internal position.

In some embodiments, the first splint strand (300) includes an internal region (310) which comprises at least three sub-regions, including a fourth sub-region (311), a fifth sub-region (312), and a sixth sub-region (313). The fourth sub-region (311) can hybridize to the first sub-region (411) of the second splint strand (400). The fourth sub-region (311) can be fully or partially complementary to the first sub-region (411) of the second splint strand (400). The fifth sub-region (312) can hybridize to the second sub-region (412) of the second splint strand (400). The fifth sub-region (312) can be fully or partially complementary to the second sub-region (412) of the second splint strand (400). The sixth sub-region (313) can hybridize to the third sub-region (413) of the second splint strand (400). The sixth sub-region (313) can be fully or partially complementary to the third sub-region (413) of the second splint strand (400). The fourth, fifth and sixth sub-regions do not hybridize (or at least exhibit very little hybridization) to the sequence of interest, the surface capture primers, or surface pinning primers.

In some embodiments, one of the sub-regions of the first splint strand (300) comprises an index or random sequence, for example, a sample index, a short random sequence (e.g., NNN), and/or a unique molecular index (UMI). For example, sub-region (311), (312) or (313) comprises a sample index, a short random sequence (e.g., NNN) and/or a unique molecular index (UMI). In some embodiments, the sample index comprises 5-20 bases (e.g., about 5, 6, 7, 8, 9, 10, 11, 12, 13, 14, 15, 16, 17, 18, 19, or 20 bases) which can be used to distinguish polynucleotides (e.g., insert sequences) from different sample sources in a multiplex assay. In some embodiments, the unique molecular index (UMI) comprises 3-20 bases (e.g., about 3, 4, 5, 6, 7, 8, 9, 10, 11, 12, 13, 14, 15, 16, 17, 18, 19, or 20 bases) which can be used to uniquely identify a nucleic acid molecule to which the adaptor is appended (e.g., molecular tagging). In some embodiments, the unique molecular index (UMI) comprises a random sequence.

Figure 6:
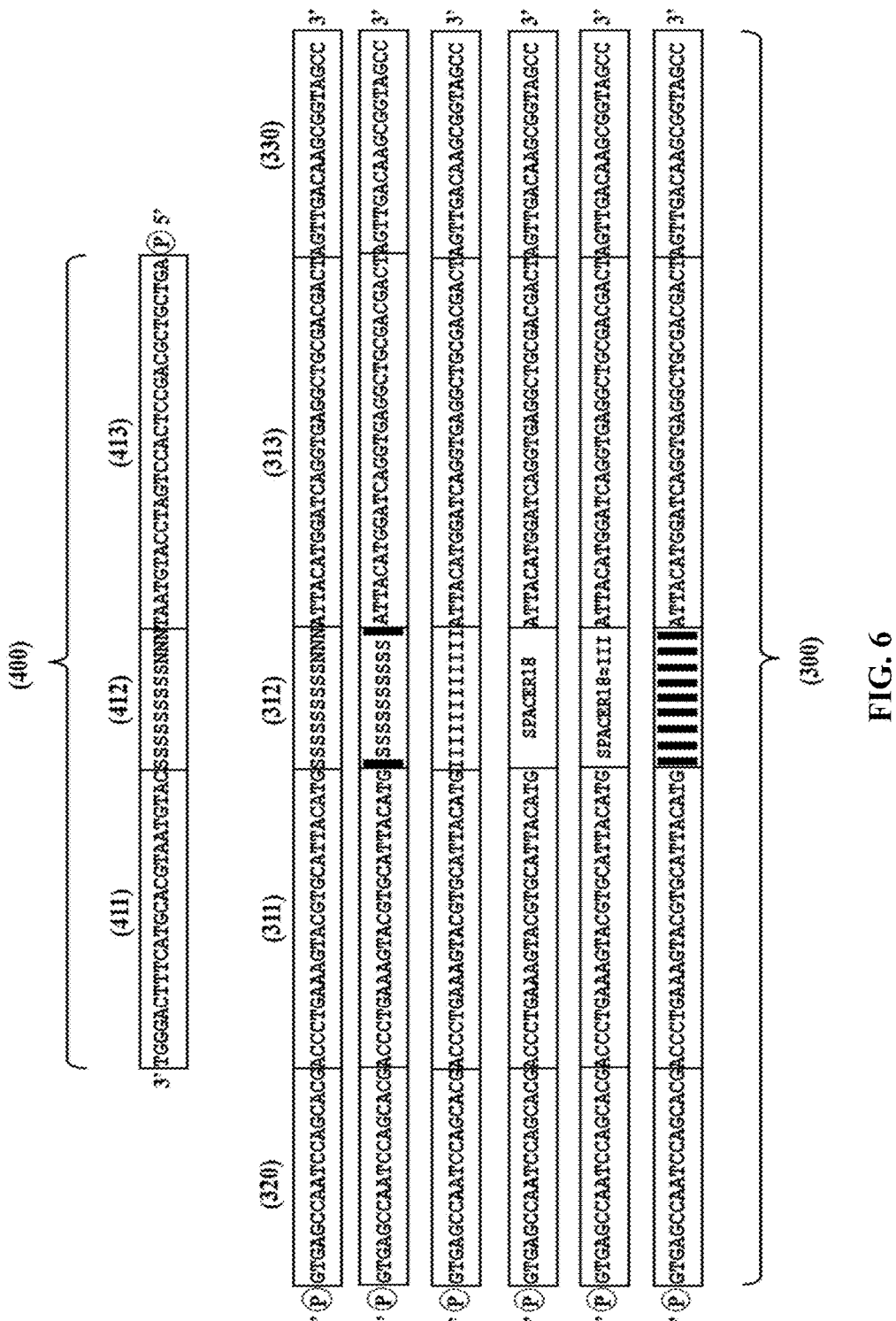
FIG. 6 is a schematic showing several embodiments of nucleic acid sequences of a first splint strand (300; long splint strand) comprising: an external first region (320); an external second region (330); and three internal sub-regions including a sub-region (311), a sub-region (312), and a sub-region (313). The schematic also shows an exemplary nucleic acid sequence of a second splint strand (400; short splint strand) comprising: three sub-regions including: sub-region (411); sub-region (412); and sub-region (413). The exemplary second splint strand (400) comprises SEQ ID NO: 65. From top to bottom, the exemplary first splint strands comprise: SEQ ID NO:66; SEQ ID NO:67; SEQ ID NO:68; SEQ ID NO:69; SEQ ID NO:70, and SEQ ID NO:71.

As shown in FIG. 6, in some embodiments, sub-region (312) comprises any one or any combination of two or more of: a sample index sequence (denoted with "S"); a random sequence (denotes with "N"); at least one nucleotide that can be converted into an abasic base (denoted with a solid black rectangle) (e.g., uridine, 8-oxo-7,8-dihydroguanine (e.g., 8oxoG) or deoxyinosine); deoxyinosine (denoted with "I"); and/or a spacer (e.g., an 18-carbon spacer). FIG. 6 depicts an alternate exemplary nucleic acid sequence of a second splint strand (400; short splint strand) comprising: three sub-regions including: sub-region (411); sub-region (412); and sub-region (413).

In some embodiments, the first splint strand sub-region which comprises the index or random sequence comprises any one or any combination of two or more of: a sample index sequence (denoted with "S"); a random sequence (denotes with "N"); at least one nucleotide that can be converted into an abasic base (denoted with a solid black rectangle) (e.g., uridine, 8-oxo-7,8-dihydroguanine (e.g., 8oxoG) or deoxyinosine); deoxyinosine (denoted with "I"); and/or a spacer. In some embodiments, the spacer comprises an 18-carbon spacer (e.g., comprising a hexa-ethyleneglycol spacer), multiple C3 spacer phosphoramidites, or a spacer 9 comprising a trimethylene glycol spacer. In some embodiments, the spacer comprises a polyethylene glycol spacer, e.g., a PEG2, PEG3, or PEG4 spacer. For a non-limiting example, see FIG. 6.

In some embodiments, a double-stranded splint adaptor (200) comprises a first splint strand (300) which is partially hybridized to a second splint strand (400), where the first splint strand (300) comprises a universal long splint strand. In some embodiments, the universal long splint strand comprises at least one sub-region that that is only partially hybridized to the second splint strand (400). For example, and without limitation, a universal long splint strand (300) comprises a sub-region carrying at least one nucleotide that can be converted into an abasic base (denoted with a solid black rectangle) (e.g., uridine, 8-oxo-7,8-dihydroguanine (e.g., 8oxoG) or deoxyinosine); deoxyinosine (denoted with "I"); and/or a spacer. In some embodiments, the spacer comprises an 18-carbon spacer (e.g., comprising a hexa-ethyleneglycol spacer), multiple C3 spacer phosphoramidites, or a spacer 9 comprising a trimethylene glycol spacer. In some embodiments, the spacer comprises a polyethylene glycol spacer, e.g., a PEG2, PEG3, or PEG4 spacer. Exemplary universal long splint strands (300) are shown in FIG. 6.

Figure 7:
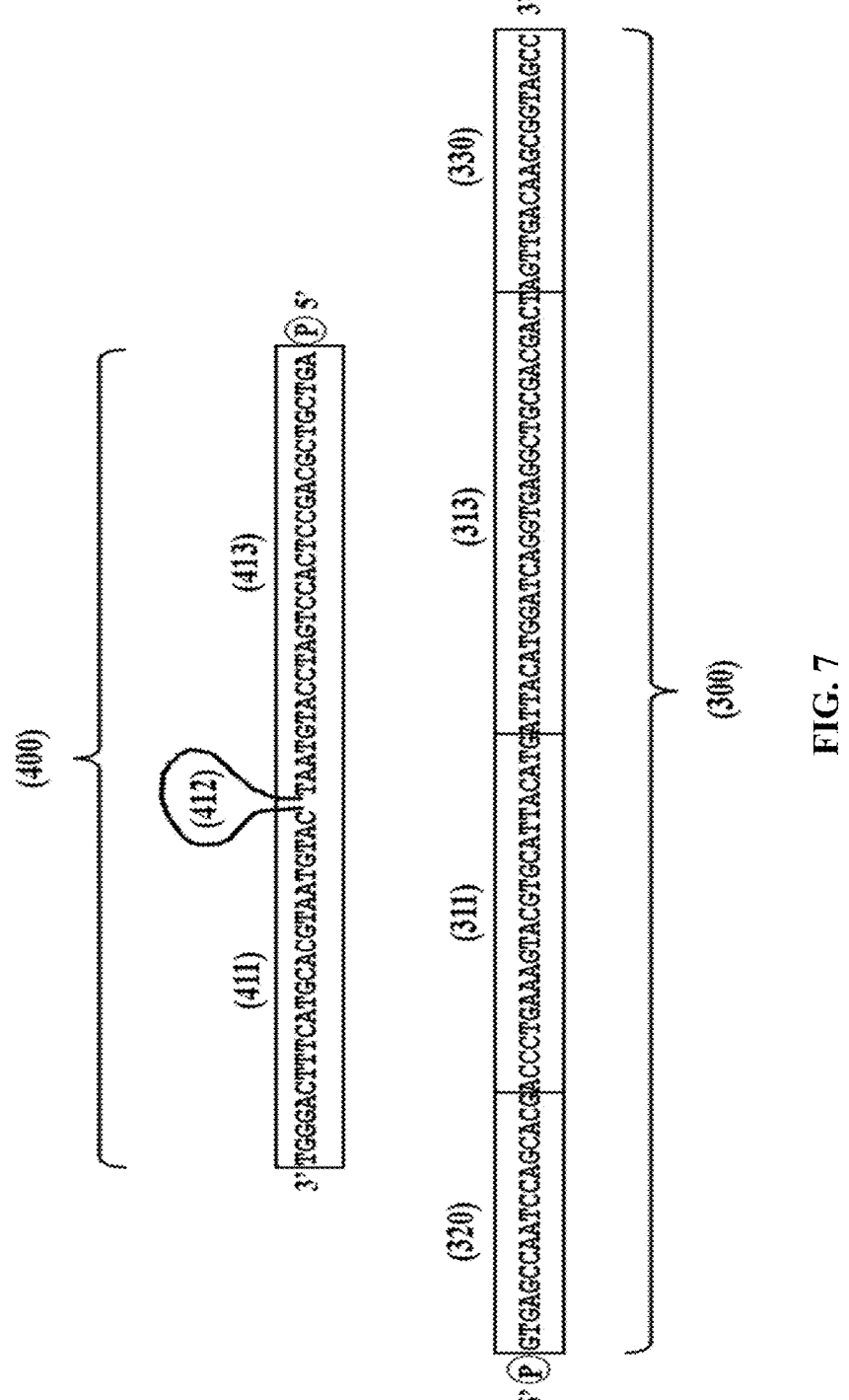
FIG. 7 is a schematic showing exemplary nucleic acid sequences of a first splint strand (300; long splint strand) comprising: an external first region (320); an external second region (330); and two internal sub-regions including a sub-region (311) and a sub-region (313). The schematic also shows an exemplary nucleic acid sequence of a second splint strand (400; short splint strand) comprising: three sub-regions including: sub-region (411); sub-region (412); and sub-region (413). The loop at the sub-region (412) represents a loop formation due to a lack of sub-region (312) of the first splint strand (300). The exemplary second splint strand (300) comprises, from 5' to 3': SEQ ID NO: 72, the loop formation, and SEQ ID NO: 73. The exemplary first splint strand (300) comprises: SEQ ID NO:74.
Figure 8A:
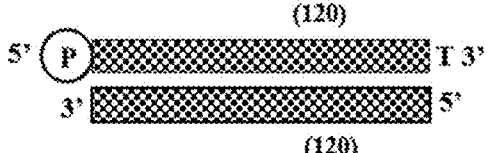
FIGS. 8A-8D are a set of schematics showing various embodiments of double-stranded nucleic acid adaptors each carrying a universal adaptor sequence for a forward sequencing primer binding site (120).
Figure 8C:
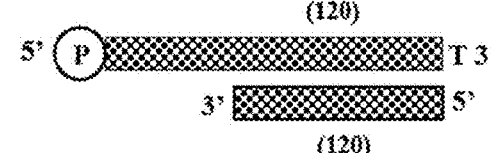
Figure 8B:
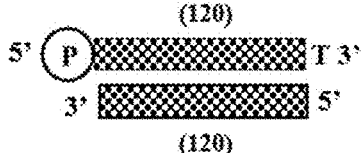
Figure 8D:
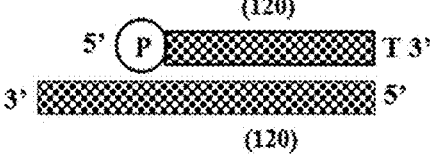
Figure 9A:
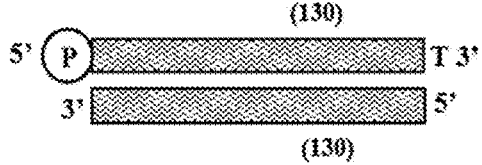
FIGS. 9A-9D are a set of schematics showing various embodiments of double-stranded nucleic acid adaptors each carrying a universal adaptor sequence for a reverse sequencing primer binding site (130).
Figure 9C:
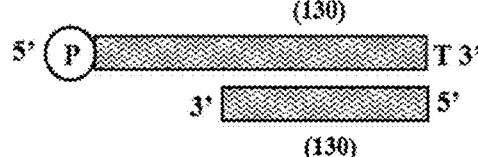
Figure 9B:
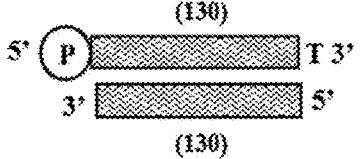
Figure 9D:
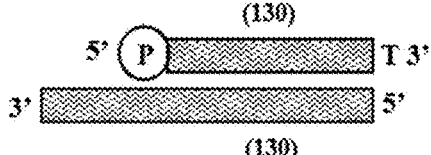
Figure 10A:
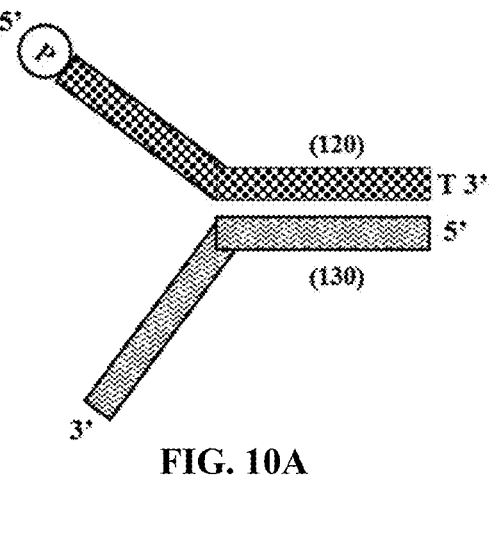
FIGS. 10A-10D are a set of schematics showing various embodiments of Y-shaped adaptors, each comprising two oligonucleotides hybridized together and having a double-stranded annealed region and a mismatched portion.
Figure 10C:
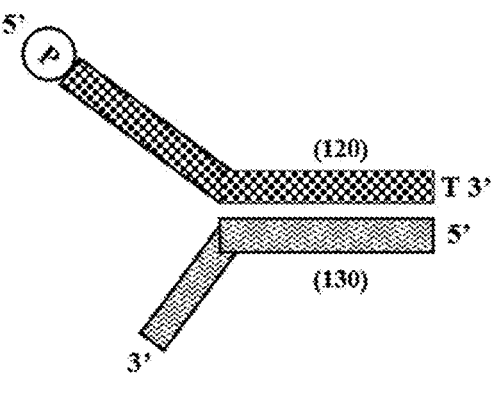
Figure 10B:
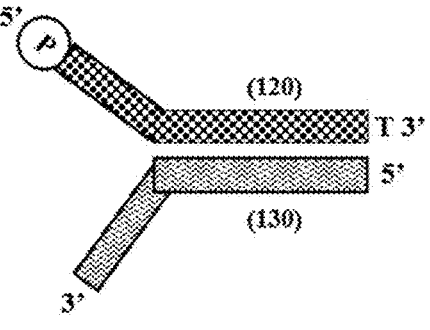
Figure 10D:
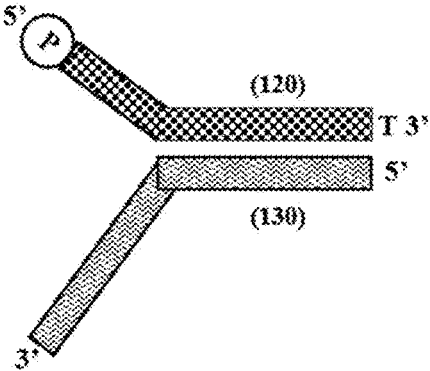

In some embodiments, as depicted in FIG. 7, the first splint strand lacks a sub-region (312). FIG. 7 also shows an exemplary nucleic acid sequence of a second splint strand (400; short splint strand) comprising: three sub-regions including: sub-region (411); sub-region (412); and sub-region (413). In certain embodiments, when the first splint strand (300) hybridizes with the second splint strand (400), the sub-region (412) of the second splint strand (400) loops out because the first splint strand (300) lacks sub-region (312).

In some embodiments, the first splint strand (300) lacks sub-region (311), (312) or (313), so that a duplex formed by hybridization between the first splint strand (300) and the second splint strand (400) has a portion of the second splint strand that loops out. For example, and without limitation, the first splint strand (300) lacks sub-region (312), and in a duplex formed by hybridization between the first splint strand (300) and the second splint strand (400) the sub-region (412) of the second splint strand (400) loops out (e.g., see FIG. 7). In some embodiments, a first splint strand (300) that lacks a sub-region is an example of a universal long splint strand (300).

In some embodiments, the first splint strand (300) can be 50-150 nucleotides in length, or 60-100 nucleotides in length, or 70-90 nucleotides in length. In some embodiments, the first splint strands (300) comprise one or more phosphorothioate linkage at the 5' and/or 3' ends to confer exonuclease resistance. In some embodiments, the first splint strands (300) comprise one or more phosphorothioate linkage at an internal position to confer endonuclease resistance. In some embodiments, the first splint strands (300) comprise one or more 2'-O-methylcytosine bases at the 5' and/or 3' end. In some embodiments, the first splint strands (300) comprise one or more 2'-O-methylcytosine bases at an internal position.

Tables 1-6 below list various embodiments of universal adaptor sequences in the library molecule (100), sequences in the first splint strand (300), sequences in the second splint strand (400), sequences of immobilized surface primers, and sequences of sequencing primers.

In some embodiments, any of the universal adaptor sequences in the library molecule (100) which are listed in Table 1 can be truncated at the 5' end and/or the 3' end, where the truncation can be 1-12 nucleotides. In some embodiments, the truncation can be 1, 2, 3, 4, 5, 6, 7, 8, 9, 10, 11 or 12 nucleotides in length. In certain embodiments, the 5' end is truncated. In certain embodiments, the 3' end is truncated.

In some embodiments, a sequencing primer comprises a sequence that is complementary to any of the sequences listed in Table 1 below.

In some embodiments, a sequencing primer comprises a sequence that is complementary to any of the sequences listed in Table 1 below, wherein the sequencing primer is truncated at the 5' end and/or the 3' end, and wherein the truncation can be 1-12 nucleotides. In some embodiments, the truncation can be 1, 2, 3, 4, 5, 6, 7, 8, 9, 10, 11 or 12 nucleotides in length. In certain embodiments, the 5' end is truncated. In certain embodiments, the 3' end is truncated.

In some embodiments, any of the sequences in the first splint strand (300) and/or the second splint strand (400) comprises sequences that are complementary to any of the sequences listed in Tables 1-6 below.

In some embodiments, any of the sequences in the first splint strand (300) and/or the second splint strand (400) which are listed in Tables 2-3 can be truncated at the 5' end and/or the 3' end, where the truncation can be 1-12 nucleotides. In some embodiments, the truncation can be 1, 2, 3, 4, 5, 6, 7, 8, 9, 10, 11 or 12 nucleotides in length. In certain embodiments, the 5' end is truncated. In certain embodiments, the 3' end is truncated.

TABLE 1

| Universal sequences in a library molecule (100) |
| --- |

SEQ
ID
NO: Sequences in a library molecule (100):

1  Forward sequencing primer binding site (120):
      5'- CGTGCTGGATTGGCTCACCAGACACCTTCCGACAT -3'

2  Forward sequencing primer binding site (120):
      5'- ACACTCTTTCCCTACACGACGCTCTTCCGATCT -3'

3  Forward sequencing primer binding site (120):
      5'- TCGTCGGCAGCGTCAGATGTGTATAAGAGACAG -3'

4  Reverse sequencing primer binding site (130):
      5'- ATGTCGGAAGGTGTGCAGGCTACCGCTTGTCAACT -3'

5  Reverse sequencing primer binding site (130):
      5'- AGATCGGAAGAGCACACGTCTGAACTCCAGTCAC -3'

6  Reverse sequencing primer binding site (130):
      5'- CTGTCTCTTATACACATCTCCGAGCCCACGAGAC -3'

43  Reverse sequencing primer binding site (130):
      5'- ATGTCGGAAGGTGTGCAGGCTACCGCTTGT -3'

44  Reverse sequencing primer binding site (130):
      5'- ATGTCGGAAGGTGTGCAGGCTACCG -3'

TABLE 2

| Sequences in a first splint strand (300): long splint strand |
| --- |

SEQ ID
NO: Sequences in a first splint strand (300): long splint strand:

7  A first region (320) of the long splint strand (300):
      5'- ATGTCGGAAGGTGTCTGGTGAGCCAATCCAGCACG -3'

8  A first region (320) of the long splint strand (300):
      5'- GTGAGCCAATCCAGCACG -3'

9  A first region (320) of the long splint strand (300):
      5' - AGATCGGAAGAGCGTCGTGTAGGGAAAGAGTGT -3'

10  A first region (320) of the long splint strand (300):
      5'- CTGTCTCTTATACACATCTGACGCTGCCGACGA - 3'

11  A second region (330) of the long splint strand (300):
      5'- ATGTCGGAAGGTGTGCAGGCTACCGCTTGTCAACT -3'

12  A second region (330) of the long splint strand (300):
      5'- AGTTGACAAGCGGTAGCC -3'

TABLE 2-continued

| Sequences in a first splint strand (300): long splint strand |
| --- |

| SEQ ID NO: | Sequences in a first splint strand (300): long splint strand: |
| --- | --- |
| 13 | A second region (330) of the long splint strand (300): 5'- GTGACTGGAGTTCAGACGTGTGCTCTTCCGATCT -3' |
| 14 | A second region (330) of the long splint strand (300): 5'- GTCTCGTGGGCTCGGAGATGTGTATAAGAGACAG -3' |
| 15 | In sub-region (311): (311) is a sequence that is fully or partially complementary to the sequence in (411) in the short splint strand (400). |
| 16 | In sub-region (312): (312) is a sequence that is fully or partially complementary to the sequence in (412) in the short splint strand (400). |
| 17 | In sub-region (313): (313) is a sequence that is fully or partially complementary to the sequence in (413) in the short splint strand (400). |
| N/A | In some embodiments, the first splint strand (300) lacks sub-region (312). |

TABLE 3

| Sequences in a second splint strand (400): short splint strand |
| --- |

| SEQ ID NO: | Sequences in a second splint strand (400): short splint strand: |
| --- | --- |
| 18 | A surface capture primer binding site of the short splint strand (400) In sub-region: (411), (412) or (413): 3'-CTAGTCCACTCCGACGCTGCTGA -5' |
| 19 | A surface capture primer binding site of the short splint strand (400) In sub-region: (411), (412) or (413): 3'- TAATGTACCTAGTCCACTCCGA -5' |
| 20 | A surface capture primer binding site of the short splint strand (400) In sub-region: (411), (412) or (413): 3'- TAATGTACCTAGTCCACTCCGACGCTGCTGA -5' |
| 21 | A surface capture primer binding site of the short splint strand (400) In sub-region: (411), (412) or (413): 3'- CTCCGACGCTGCTGA -5' |
| 45 | A surface capture primer binding site of the short splint strand (400) In sub-region: (411), (412) or (413): 3'- TAATGTACCTAGTCCACTCCGACGC -5' |
| 46 | A surface capture primer binding site of the short splint strand (400) In sub-region: (411), (412) or (413): 3'- CGTACTAATGTACCTAGTCCACTCCGA -5' |
| 47 | A surface capture primer binding site of the short splint strand (400) In sub-region: (411), (412) or (413): 3'- TGGGACTTTCATGCACGTAATGTAC -5' |
| 22 | A surface capture primer binding site of the short splint strand (400) In sub-region: (411), (412) or (413): 3'- GTTCGTCTTCTGCCGTATGCTCTA -5' |
| 23 | A surface pinning primer binding site of the short splint strand (400) In sub-region: (411), (412) or (413): 3'- TGGGACTTTCATGCACGTAATGTAC -5' |
| 48 | A surface pinning primer binding site of the short splint strand (400) In sub-region: (411), (412) or (413): 3'- TAATGTAC -5' |
| 24 | A surface pinning primer binding site of the short splint strand (400) In sub-region: (411), (412) or (413): 3'- TGGGACTTTCATGCACG -5' |

TABLE 3-continued

Sequences in a second splint strand (400): short splint strand

| SEQ ID NO: | Sequences in a second splint strand (400): short splint strand: |
|---|---|
| 49 | A surface pinning primer binding site of the short splint strand (400)<br>In sub-region: (411), (412) or (413):<br>3'- TGGGACTTTCATGCACGATTGC -5' |
| 25 | A surface pinning primer binding site of the short splint strand (400)<br>In sub-region: (411), (412) or (413):<br>3'- TGGGACTTTCATGCACGTAATGTACCTAGTCCA -5' |
| 26 | A surface pinning primer binding site of the short splint strand (400)<br>In sub-region: (411), (412) or (413):<br>3'- CTAGAGCCACCAGCGGCATAGTAA -5' |
| 27 | Exemplary sample index of the short splint strand (400)<br>In sub-region: (411), (412) or (413):<br>5'- GTAGGAGCCNNN -3' |
| 28 | Exemplary sample index of the short splint strand (400)<br>In sub-region: (411), (412) or (413):<br>5'- CCGCTGCTANNN -3' |
| 29 | Exemplary sample index of the short splint strand (400)<br>In sub-region: (411), (412) or (413):<br>5'- AACAACAAGNNN -3' |
| 30 | Exemplary sample index of the short splint strand (400)<br>In sub-region: (411), (412) or (413):<br>5'- GGTGGTCTANNN -3' |
| 31 | Exemplary sample index of the short splint strand (400)<br>In sub-region: (411), (412) or (413):<br>5'- TTGGCCAACNNN -3' |
| 32 | Exemplary sample index of the short splint strand (400)<br>In sub-region: (411), (412) or (413):<br>5'- CAGGAGTGCNNN -3' |
| 33 | Exemplary sample index of the short splint strand (400)<br>In sub-region: (411), (412) or (413):<br>5'- ATCACACTANNN -3' |

TABLE 4

Immobilized surface primers

| SEQ: | Immobilized surface primers: |
|---|---|
| 34 | Surface capture primer:<br>5'-GATCAGGTGAGGCTGCGACGACT -3' |
| 35 | Surface capture primer:<br>5'- ATTACATGGATCAGGTGAGGCT -3' |
| 36 | Surface capture primer:<br>5'- GAGGCTGCGACGACT -3' |
| 50 | Surface capture primer:<br>5'- ATTACATGGATCAGGTGAGGCTGCG -3' |
| 37 | Surface capture primer:<br>5'- CAAGCAGAAGACGGCATACGA-3' |
| 38 | Surface capture primer:<br>5'-CAAGCAGAAGACGGCATACGAGAT-3' |
| 39 | Surface pinning primer:<br>5'- CATGTAATGCACGTACTTTCAGGGT -3' |
| 40 | Surface pinning primer:<br>5'- ACCTGATCCATGTAATGCACGTACTTTCAGGGT -3' |

TABLE 4-continued

Immobilized surface primers

| SEQ: | Immobilized surface primers: |
|---|---|
| 41 | Surface pinning primer:<br>5'- AATGATACGGCGACCACCGA-3' |
| 42 | Surface pinning primer:<br>5'- AATGATACGGCGACCACCGAGATC-3' |

TABLE 5

| SEQ ID NO: | Table 5: Sequencing primers for sequencing insert (110) |
|---|---|
| 51 | FWD sequencing primer:<br>5'- CGTGCTGGATTGGCTCACCAGACACCTTCCGACAT -3' |
| 52 | REV sequencing primer:<br>5'- AGTTGACAAGCGGTAGCCTGCACACCTTCCGACAT -3' |
| 53 | REV sequencing primer:<br>5'- ACAAGCGGTAGCCTGCACACCTTCCGACAT -3' |

TABLE 6

| SEQ ID NO: | Table 6: Sequencing primers for sequencing index in sub-region (411), (412) or (413) |
|---|---|
| 54 | FWD sequencing primer:<br>5'- AGCCTCACCTGATCCATGTAAT -3' |
| 55 | FWD sequencing primer:<br>5'- AGCCTCACCTGATCCATGTAATCATGC -3' |
| 56 | FWD sequencing primer:<br>5'- AGTCGTCGCAGCCTCACCTGATC -3' |
| 57 | FWD sequencing primer:<br>5'- AGTCGTCGCAGCCTCACCTGATCCATGTAAT -3' |
| 58 | FWD sequencing primer:<br>5'- AGTCGTCGCAGCCTCACCTGATCCATGTAATCGTGA -3' |
| 59 | FWD sequencing primer:<br>5'- AGTCGTCGCAGCCTCACCTGATCCATGTAATCATGC -3' |
| 60 | FWD sequencing primer:<br>5' - ATGTCGGAAGGTGTGCAGGCTACCGCTTGTCAACT -3' |
| 61 | REV sequencing primer:<br>5'- ACCCTGAAAGTACGTGCATTACATG -3' |
| 62 | REV sequencing primer:<br>5'- ACCCTGAAAGTACGTGC -3' |
| 63 | REV sequencing primer:<br>5'- ACCCTGAAAGTACGTGCTAACG -3' |
| 64 | REV sequencing primer:<br>5'- ACCCTGAAAGTACGTGCATTACATGGATCAGGT -3' |

Library-Splint Complexes

In some aspects, the present disclosure provides a library-splint complex (500) comprising: (i) a single-stranded nucleic acid library molecule (100) comprising an insert region (110) (e.g., sequence-of-interest) flanked on one side by a universal adaptor sequence for a forward sequencing primer binding site (120), and the insert region (110) is flanked on the other side by a universal adaptor sequence for a reverse sequencing primer binding site (130); and (ii) a double-stranded splint adaptor (200) which includes a first splint strand (long splint strand (300)) hybridized to a second splint strand (short splint strand (400)), wherein the first splint strand comprises a first region (320), an internal region (310), and a second region (330). In certain embodiments, the internal region of the first splint strand (310) is hybridized to the second splint strand (400) to form the double-stranded splint adaptor (200) having a double-stranded region and two flanking single-stranded regions.

In some embodiments, the single-stranded nucleic acid library molecule (100) lacks a universal adaptor sequence for a surface capture primer binding site. In some embodiments, the single-stranded nucleic acid library molecule (100) lacks a universal adaptor sequence for a surface pinning primer binding site. In some embodiments, the single-stranded nucleic acid library molecule (100) lacks a universal adaptor sequence for a sample index sequence. In some embodiments, single-stranded nucleic acid library molecule (100) lacks a unique molecular index (UMI) sequence.

Figure 4:
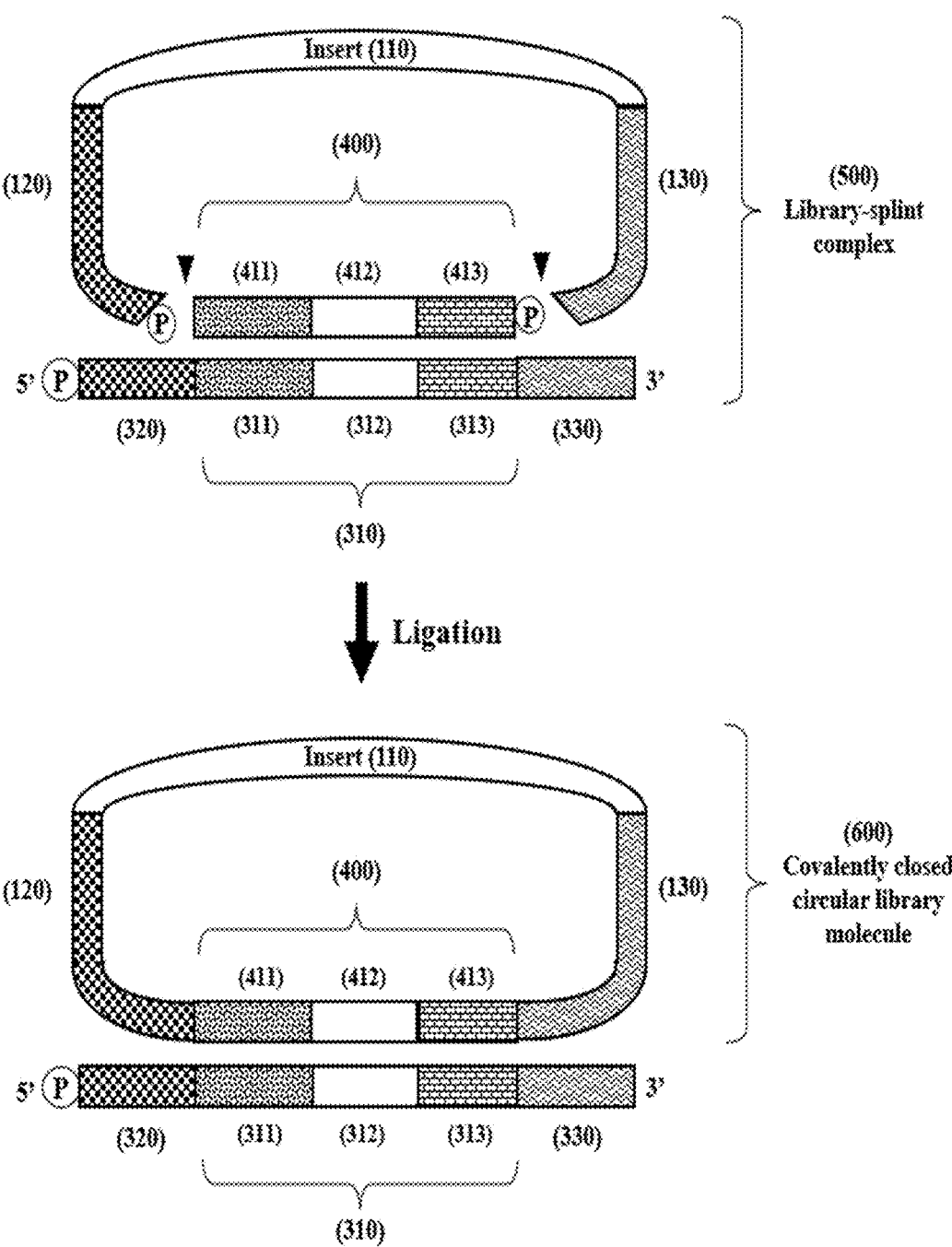
FIG. 4 is a schematic showing an exemplary ligation reaction, which comprises conducting an enzymatic ligation reaction on the nicks in the library-splint complex (500), thereby closing the nicks to form a covalently closed circular library molecule (600) which is hybridized to a first splint strand (300).

In the library-splint complex (500), the first region of the first splint strand (320) can be hybridized to the universal adaptor sequence for a forward sequencing primer binding site (120) of the library molecule, and a second region of the first splint strand (330) can be hybridized to the universal adaptor sequence for a reverse sequencing primer binding site (130) of the library molecule, thereby circularizing the library molecule to generate a library-splint complex (500) (e.g., see FIGS. 3 and 4).

In the library-splint complex (500), the second splint strand (400) can bring the library molecule (100) into proximity with at least a universal adaptor sequence for a surface pinning primer binding site, a universal adaptor sequence for a surface capture primer binding site, and a sample index sequence. In some embodiments, the second splint strand (400) brings the library molecule (100) into proximity with other sequences including a short random sequence (e.g., NNN) and/or a unique molecule index (UMI) sequence.

The library-splint complex (500) can comprise a first nick between the 5' end of the library molecule and the 3' end of the second splint strand. In certain embodiments, the library-splint complex (500) also comprises a second nick between the 5' end of the second splint strand and the 3' end of the library molecule (e.g., see FIGS. 3 and 4). In some embodiments, the first and second nicks are enzymatically ligatable. A ligation reaction would join the sequences from the second splint strand (400) to the ends of the library molecule (100).

In the library-splint complex (500), the first region of the first splint strand (320) can hybridize to a sense or anti-sense strand of a double-stranded nucleic acid library molecule. In the library-splint complex (500), the second region of the first splint strand (330) can hybridize to a sense or anti-sense strand of a double-stranded nucleic acid library molecule. The double-stranded nucleic acid library molecule can be denatured to generate the single-stranded sense and anti-sense library strands.

In the library-splint complex (500), the first region of the first splint strand (320) does not hybridize to the sequence of interest (110), and the second region of the first splint strand (330) does not hybridize to the sequence of interest (110).

In the library-splint complex (500), the second splint strand (400) does not hybridize to the sequence of interest (110), and the internal region of the first splint strand (310) does not hybridize to the sequence of interest (110).

In some embodiments, in the library-splint complex (500), the internal region (310) of the first splint strand (300) hybridizes to the second splint strand (400). The internal region (310) of the first splint strand (300) can comprise at least three sub-regions including sub-regions (311), (312) and (313). The second splint strand (400) can comprise at least three sub-regions including sub-regions (411), (412) and (413). For example, sub-region (311) hybridizes to sub-region (411). In another example, sub-region (312) hybridizes to sub-region (412). In another example, sub-region (313) hybridizes to sub-region (413).

In some embodiments, any of the library-splint complexes (500) described herein comprise a plurality of library-splint complexes (500), wherein the sequence of interest (110) of individual library-splint complexes in the plurality comprise the same sequence of interest or different sequences of interest.

In some embodiments, in the library-splint complex (500), the 5' end of the single-stranded library molecule (100) is phosphorylated. In some embodiments,, in the library-splint complex (500), the 5' end of the single-stranded library molecule (100) lacks a phosphate group. In some embodiments, the 3' end of the single-stranded library molecule includes a terminal 3' OH group or a terminal 3' blocking group.

In some embodiments, in the library-splint complex (500), the first splint strand (300) can be 50-150 (e.g., about 50, 60, 70, 80, 90, 100, 110, 120, 130, 140, or 150) nucleotides in length. In some embodiments, in the library-splint complex (500), the first splint strand (300) can be 60-100 (e.g., about 60, 70, 80, 90, or 100) nucleotides in length,. In some embodiments, in the library-splint complex (500), the first splint strand (300) can be 70-90 (e.g., about 70, 75, 80, 85, or 90) nucleotides in length. In some embodiments, the first splint strands (300) comprise one or more phosphorothioate linkage at the 5' and/or 3' ends to confer exonuclease resistance. In some embodiments, the first splint strands (300) comprise one or more phosphoro-thioate linkage at an internal position to confer endonuclease resistance. In some embodiments, the first splint strands (300) comprise one or more 2'-O-methylcytosine bases at the 5' and/or 3' end. In some embodiments, the first splint strands (300) comprise one or more 2'-O-methylcytosine bases at an internal position. In some embodiments, the 5' end of the first splint strand (300) is phosphorylated. In some embodiments, the 5' end of the first splint strand (300) lacks a phosphate group. In some embodiments, the 3' end of the first splint strand (300) includes a terminal 3' OH group or a terminal 3' blocking group.

In some embodiments, in the library-splint complex (500), the first splint strand (300) includes an internal region (310) which comprises at least three sub-regions, including a fourth sub-region (311), a fifth sub-region (312), and a sixth sub-region (313). The fourth sub-region (311) can hybridize to the first sub-region (411) of the second splint strand (400). The fourth sub-region (311) can be fully or partially complementary to the first sub-region (411) of the second splint strand (400). The fifth sub-region (312) can hybridize to the second sub-region (412) of the second splint strand (400). The fifth sub-region (312) can be fully or partially complementary to the second sub-region (412) of the second splint strand (400). The sixth sub-region (313) can hybridize to the third sub-region (413) of the second splint strand (400). The sixth sub-region (313) can be fully or partially complementary to the third sub-region (413) of the second splint strand (400). The fourth, fifth and sixth sub-regions do not hybridize (e.g., least exhibit very little hybridization) to the sequence of interest, the surface capture primers, or surface pinning primers.

In some embodiments, one of the sub-regions of the first splint strand (300) comprises an index or random sequence, for example, a sample index, a short random sequence (e.g., NNN), and/or a unique molecular index (UMI). For example, and without limitation, sub-region (311), (312) or (313) comprises a sample index, a short random sequence (e.g., NNN) and/or a unique molecular index (UMI). In some embodiments, the sample index comprises 5-20 bases (e.g., about 5, 6, 7, 8, 9, 10, 11, 12, 13, 14, 15, 16, 17, 18, 19, or 20 bases) which can be used to distinguish polynucle-otides (e.g., insert sequences) from different sample sources in a multiplex assay. In some embodiments, the unique molecular index (UMI) comprises 3-20 bases (e.g., about 3, 4, 5, 6, 7, 8, 9, 10, 11, 12, 13, 14, 15, 16, 17, 18, 19, or 20 bases) which can be used to uniquely identify a nucleic acid molecule to which the adaptor is appended (e.g., molecular tagging). In some embodiments, the unique molecular index (UMI) comprises a random sequence.

In some embodiments, the first splint strand sub-region which comprises the index or random sequence comprises any one or any combination of two or more of: a sample index sequence (denoted with "S"); a random sequence (denotes with "N"); at least one nucleotide that can be converted into an abasic base (denoted with a solid black rectangle) (e.g., uridine, 8-oxo-7,8-dihydroguanine (e.g., 8oxoG) or deoxyinosine); deoxyinosine (denoted with "I"); and/or a spacer. In some embodiments, the spacer comprises an 18-carbon spacer (e.g., comprising a hexa-ethyleneglycol spacer), multiple C3 spacer phosphoramidites, or a spacer 9 comprising a trimethylene glycol spacer. In some embodiments, the spacer comprises a polyethylene glycol spacer, e.g., a PEG2, PEG3, or PEG4 spacer.

In some embodiments, a double-stranded splint adaptor (200) comprises a first splint strand (300) which is partially hybridized to a second splint strand (400), where the first splint strand (300) comprises a universal long splint strand. In some embodiments, the universal long splint strand comprises at least one sub-region that that is only partially hybridized to the second splint strand (400). For example, a universal long splint strand (300) can comprise a sub-region carrying at least one nucleotide that can be converted into an abasic base (denoted with a solid black rectangle) (e.g., uridine, 8-oxo-7,8-dihydroguanine (e.g., 8oxoG) or deoxyinosine); deoxyinosine (denoted with "I"); and/or a spacer. In some embodiments, the spacer comprises an 18-carbon spacer (e.g., comprising a hexa-ethyleneglycol spacer), multiple C3 spacer phosphoramidites, or a spacer 9 comprising a trimethylene glycol spacer. In some embodiments, the spacer comprises a polyethylene glycol spacer, e.g., a PEG2, PEG3 or PEG4 spacer. Exemplary universal long splint strands (300) are shown in FIG. 6.

In some embodiments, in the library-splint complex (500), the first splint strand (300) lacks sub-region (311), (312) or (313), so that a duplex formed by hybridization between the first splint strand (300) and the second splint strand (400) has a portion of the second splint strand that loops out. For example, the first splint strand (300) lacks sub-region (312), and in a duplex formed by hybridization between the first splint strand (300) and the second splint strand (400) the sub-region (412) of the second splint strand (400) loops out (e.g., see FIG. 7). In some embodiments, a first splint strand (300) that lacks a sub-region is an example of a universal long splint strand (300).

In some embodiments, in the library-splint complex (500), the second splint strand (400) comprises at least three sub-regions, including first, second and third sub-regions (e.g., see FIGS. 3 and 4). The first sub-region (411) can comprise a universal binding sequence for an immobilized surface pinning primer, an immobilized surface capture primer, at least one sample index sequence, a short random sequence (NNN) and/or or a unique molecule index (UMI). The second sub-region (412) can comprise a universal binding sequence for an immobilized surface pinning primer, an immobilized surface capture primer, at least one sample index sequence, a short random sequence (NNN) and/or or a unique molecule index (UMI). The third sub-region (413) can comprise a universal binding sequence for an immobilized surface pinning primer, an immobilized surface capture primer, at least one sample index sequence, a short random sequence (e.g., NNN) and/or or a unique molecule index (UMI). In some embodiments, the sample index comprises 5-20 bases (e.g., about 5, 6, 7, 8, 9, 10, 11, 12, 13, 14, 15, 16, 17, 18, 19, or 20 bases) which can be used to distinguish polynucleotides (e.g., insert sequences) from different sample sources in a multiplex assay. In some embodiments, the unique molecular index (UMI) comprises 3-20 bases (e.g., about 3, 4, 5, 6, 7, 8, 9, 10, 11, 12, 13, 14, 15, 16, 17, 18, 19, or 20 bases) which can be used to uniquely identify a nucleic acid molecule to which the adaptor is appended (e.g., molecular tagging). In some embodiments, the unique molecular index (UMI) comprises a random sequence. The second splint strand (400) is designed to exhibit reduced or no hybridization to the insert sequence (110) of the library molecule (100).

In some embodiments, in the library-splint complex (500), the arrangement of the sequences in the sub-regions of the second splint strand (400), in a 3' to 5' orientation comprises: [(411) comprises a universal sequence for binding a surface pinning primer]—[(412) comprises a sample index sequence and an optional short random sequence NNN]—[(413) comprises a universal sequence for binding a surface capture primer].

In some embodiments, in the library-splint complex (500), the arrangement of the sequences in the sub-regions of the second splint strand (400), in a 3' to 5' orientation comprises: [(411) comprises a universal sequence for binding a surface pinning primer]—[(412) comprises a universal sequence for binding a surface capture primer]—[(413) comprises a sample index sequence and an optional short random sequence NNN].

In some embodiments, in the library-splint complex (500), the arrangement of the sequences in the sub-regions of the second splint strand (400), in a 3' to 5' orientation comprises: [(411) comprises a sample index sequence and an optional short random sequence NNN]—[(412) comprises a universal sequence for binding a surface pinning primer]—[(413) comprises a universal sequence for binding a surface capture primer].

In some embodiments, in the library-splint complex (500), the second splint strand (400) comprises an additional sub-region carrying a second sample index sequence and an optional short random sequence NNN. For example, and without limitation, the additional sub-region can be located between sub-regions (411) and (412), or between sub-regions (412) and (413).

In some embodiments, in the library-splint complex (500), the second splint strand (400) can be 20-100 (e.g., about 20, 25, 30, 35, 40, 45, 50, 60, 70, 80, 90, or 100) nucleotides in length. In some embodiments, the second splint strand (400) can be 30-80 nucleotides in length80 (e.g., about 30, 35, 40, 45, 50, 60, 70, or 80) nucleotides in length. 40-60 60 (e.g., about 40, 45, 50, or 60) nucleotides in length. In some embodiments, the 5' end of the second splint strand (400) is phosphorylated; alternatively, the 5' end of the second splint strand (400) is non-phosphorylated. In some embodiments, the 3' end of the second splint strand (400) comprises a terminal 3' OH group; alternatively, the 3' end of the second splint strand (400) comprises a terminal 3' blocking group. In some embodiments, the second splint strands (400) comprise one or more phosphorothioate linkage at the 5' and/or 3' ends to confer exonuclease resistance. In some embodiments, the second splint strands (400) comprise one or more phosphorothioate linkage(s) at an internal position, e.g., to confer endonuclease resistance. In some embodiments, the second splint strands (400) comprise one or more 2'-O-methylcytosine bases at the 5' and/or 3' end. In some embodiments, the second splint strands (400) comprise one or more 2'-O-methylcytosine bases at an internal position.

In the library-splint complex (500), the second splint strand (400) brings the library molecule (100) into proximity with at least a universal adaptor sequence for a surface pinning primer binding site, a universal adaptor sequence for a surface capture primer binding site, and a sample index sequence. In some embodiments, the second splint strand (400) brings the library molecule (100) into proximity with other sequences including a short random sequence (e.g., NNN) and/or a unique molecule index (UMI) sequence.

Tables 1-4 above list various embodiments of sequences the various molecules that form the library-splint complex (500), including the library molecule (100), the first splint strand (300), and the second splint strand (400). In some embodiments, the sequences in the first splint strand (300) and/or the second splint strand (400) can be sequences that are complementary to the sequences listed in Tables 2-3. In some embodiments, any of the sequences in the first splint strand (300) and/or the second splint strand (400) which are listed in Tables 2-3 can be truncated at the 5' end and/or the 3' end, where the truncation can be 1-12 nucleotides. In certain embodiments, the 5' end is truncated. In certain embodiments, the 3' end is truncated. In some embodiments, in the library molecule, the sequence of the forward sequencing primer binding site (120) and/or the sequence of the reverse sequencing primer binding site (130), which are listed in Table 1, can be truncated at the 5' end and/or the 3' end, where the truncation can be 1-12 nucleotides. In certain embodiments, the 5' end is truncated. In certain embodiments, the 3' end is truncated.

In some aspects, the present disclosure provides a reaction mixture comprising a plurality of any of the library-splint complexes (500) described herein. In some embodiments, the reaction mixture comprises a plurality of any of the library-splint complexes (500) described herein, and a T4 polynucleotide kinase. In some embodiments, the reaction mixture comprises a plurality of any of the library-splint complexes (500) described herein, and lacks a T4 polynucleotide kinase. In some embodiments, the reaction mixture comprises a plurality of any of the library-splint complexes (500) described herein, and a ligase enzyme. In some embodiments, the reaction mixture comprises a plurality of any of the library-splint complexes (500) described herein, and a T4 polynucleotide kinase and a ligase enzyme. In some embodiments, the reaction mixture comprises a plurality of any of the library-splint complexes (500) described herein and a ligase enzyme and lacks a T4 polynucleotide kinase. In some embodiments, the ligase enzyme comprises T7 DNA ligase, T3 ligase, T4 ligase, or Taq ligase.

Covalently Closed Circular Molecules

In some aspects, the present disclosure provides a covalently closed circular library molecule (600) comprising: a sequence of interest (110), a forward sequencing primer binding site (120), a reverse sequencing primer binding site (130), and sequences form a second splint strand (400). In some embodiments, the covalently closed circular library molecule (600) comprises a sequence of interest (110) flanked on one side by a forward sequencing primer binding site (120), and flanked on the other side by a reverse sequencing primer binding site (130), where the forward sequencing primer binding site (120) and the reverse sequencing primer binding site (130) are covalently joined to a second splint strand (400). Exemplary covalently closed circular library molecules (600) are shown in FIGS. 4 and 5.

In some embodiments, any of the covalently closed circular library molecules (600) described herein further comprise a plurality of covalently closed circular library molecules (600), wherein the sequence of interest (110) of individual covalently closed circular library molecule (600) in the plurality comprise the same sequence of interest. Alternatively, in some embodiments, the sequence of interest (110) comprises different sequences of interest.

In some embodiments, in the covalently closed circular library molecule (600), the second splint strand (400) comprises at least three sub-regions, including first, second and third sub-regions (e.g., see FIGS. 4 and 5). The first sub-region (411) can comprise a universal binding sequence for an immobilized surface pinning primer, an immobilized surface capture primer, at least one sample index sequence, a short random sequence (NNN) and/or or a unique molecule index (UMI). The second sub-region (412) can comprise a universal binding sequence for an immobilized surface pinning primer, an immobilized surface capture primer, at least one sample index sequence, a short random sequence (NNN) and/or or a unique molecule index (UMI). The third sub-region (413) can comprise a universal binding sequence for an immobilized surface pinning primer, an immobilized surface capture primer, at least one sample index sequence, a short random sequence (e.g., NNN) and/or or a unique molecule index (UMI). In some embodiments, the sample index comprises 5-20 bases which can be used to distinguish polynucleotides (e.g., insert sequences) from different sample sources in a multiplex assay. In some embodiments, the unique molecular index (UMI) comprises 3-20 bases which can be used to uniquely identify a nucleic acid molecule to which the adaptor is appended (e.g., molecular tagging). In some embodiments, the unique molecular index (UMI) comprises a random sequence. The second splint strand (400) is designed to exhibit reduced or no hybridization to the insert sequence (110) of the library molecule (100).

In some embodiments, in the covalently closed circular library molecule (600), the arrangement of the sequences in the sub-regions of the second splint strand (400), in a 3' to 5' orientation comprises: [(411) comprises a universal sequence for binding a surface pinning primer]—[(412) comprises a sample index sequence and an optional short random sequence NNN]—[(413) comprises a universal sequence for binding a surface capture primer].

In some embodiments, in the covalently closed circular library molecule (600), the arrangement of the sequences in the sub-regions of the second splint strand (400), in a 3' to 5' orientation comprises: [(411) comprises a universal sequence for binding a surface pinning primer]—[(412) comprises a universal sequence for binding a surface capture primer]—[(413) comprises a sample index sequence and an optional short random sequence NNN].

In some embodiments, in the covalently closed circular library molecule (600), the arrangement of the sequences in the sub-regions of the second splint strand (400), in a 3' to 5' orientation comprises: [(411) comprises a sample index sequence and an optional short random sequence NNN]—[(412) comprises a universal sequence for binding a surface pinning primer]—[(413) comprises a universal sequence for binding a surface capture primer].

In some embodiments, in the covalently closed circular library molecule (600), the second splint strand (400) comprises an additional sub-region carrying a second sample index sequence and an optional short random sequence NNN. For example, the additional sub-region can be located between sub-regions (411) and (412), or between sub-regions (412) and (413).

In some embodiments, in the covalently closed circular library molecule (600), the second splint strand (400) can be 20-100 nucleotides in length, or 30-80 nucleotides in length, or 40-60 nucleotides in length. In some embodiments, the second splint strands (400) comprise one or more phosphorothioate linkage at the 5' and/or 3' ends to confer exonuclease resistance. In some embodiments, the second splint strands (400) comprise one or more phosphorothioate linkage at an internal position to confer endonuclease resistance. In some embodiments, the second splint strands (400) comprise one or more 2'-O-methylcytosine bases at the 5' and/or 3' end, or at an internal position.

In some embodiments, the covalently closed circular library molecule (600) is hybridized to the first splint strand (300) or the first splint strand (300) is absent. In some embodiments, the first splint strand (300) can be 50-150 (e.g., about 50, 60, 70, 80, 90, 100, 110, 120, 130, 140, or 150) nucleotides in length. In some embodiments, the first splint strand (300) can be 60-100 (e.g., about 60, 70, 80, 90, or 100) nucleotides in length. In some embodiments, the first splint strand (300) can be 70-90 (e.g., about 70, 75, 80, 85, or 90) nucleotides in length. In some embodiments, the first splint strands (300) comprise one or more phosphorothioate linkage at the 5' and/or 3' ends, e.g., to confer exonuclease resistance. In some embodiments, the first splint strands (300) comprise one or more phosphorothioate linkage at an internal position, e.g., to confer endonuclease resistance. In some embodiments, the first splint strands (300) comprise one or more 2'-O-methylcytosine bases at the 5' and/or 3' end. In some embodiments, the first splint strands (300) comprise one or more 2'-O-methylcytosine bases at an internal position. In some embodiments, the 5' end of the first splint strand (300) is phosphorylated; alternatively, the 5' end of the first splint strand (300) lacks a phosphate group. In some embodiments, the 3' end of the first splint strand (300) includes a terminal 3' OH group; alternatively, the 3' end of the first splint strand (300) includes a terminal 3' blocking group.

In some embodiments, in the covalently closed circular library molecule (600), the first splint strand (300) includes an internal region (310) which comprises at least three sub-regions, including a fourth sub-region (311), a fifth sub-region (312), and a sixth sub-region (313). The fourth sub-region (311) can hybridize to the first sub-region (411) of the second splint strand (400). The fourth sub-region (311) can be fully or partially complementary to the first sub-region (411) of the second splint strand (400). The fifth sub-region (312) can hybridize to the second sub-region (412) of the second splint strand (400). The fifth sub-region (312) can be fully or partially complementary to the second sub-region (412) of the second splint strand (400). The sixth sub-region (313) can hybridize to the third sub-region (413) of the second splint strand (400). The sixth sub-region (313) can be fully or partially complementary to the third sub-region (413) of the second splint strand (400). The fourth, fifth and sixth sub-regions do not hybridize (e.g., exhibit very little hybridization) to the sequence of interest, the surface capture primers, or surface pinning primers.

In some embodiments, in the covalently closed circular library molecule (600), one of the sub-regions of the first splint strand (300) comprises an index or random sequence, for example a sample index, a short random sequence (e.g., NNN) and/or a unique molecular index (UMI). For example, sub-region (311), (312) or (313) comprises a sample index, a short random sequence (e.g., NNN) and/or a unique molecular index (UMI). In some embodiments, the sample index comprises 5-20 bases which can be used to distinguish polynucleotides (e.g., insert sequences) from different sample sources in a multiplex assay. In some embodiments, the unique molecular index (UMI) comprises 3-20 bases which can be used to uniquely identify a nucleic acid molecule to which the adaptor is appended (e.g., molecular tagging). In some embodiments, the unique molecular index (UMI) comprises a random sequence.

In some embodiments, in the covalently closed circular library molecule (600), sub-region (312) comprises any one or any combination of two or more of: a sample index sequence (denoted with "S"); a random sequence (denotes with "N"); at least one nucleotide that can be converted into an abasic base (denoted with a solid black rectangle) (e.g., uridine, 8-oxo-7,8-dihydroguanine (e.g., 8oxoG) or deoxyinosine); deoxyinosine (denoted with "I"); and/or a spacer. In some embodiments, the spacer comprises an 18-carbon spacer (e.g., comprising a hexa-ethyleneglycol spacer), multiple C3 spacer phosphoramidites, or a spacer 9 comprising a trimethylene glycol spacer. In some embodiments, the spacer comprises a polyethylene glycol spacer, e.g., a PEG2, PEG3, or PEG4 spacer.

In some embodiments, when the covalently closed circular library molecule (600) is hybridized to a first splint strand (300), the first splint strand is partially hybridized to the sequences from a second splint strand (400), where the first splint strand (300) comprises a universal long splint strand. In some embodiments, the universal long splint strand can comprise at least one sub-region that that is only partially hybridized to the sequences from a second splint strand (400). For example, a universal long splint strand (300) can comprise a sub-region carrying at least one nucleotide that can be converted into an abasic base (denoted with a solid black rectangle) (e.g., uridine, 8-oxo-7,8-dihydroguanine (e.g., 8oxoG) or deoxyinosine); deoxyinosine (denoted with "I"); and/or a spacer. In some embodiments, the spacer comprises an 18-carbon spacer (e.g., comprising a hexa-ethyleneglycol spacer), multiple C3 spacer phosphoramidites, or a spacer 9 comprising a trimethylene glycol spacer. In some embodiments, the spacer comprises a polyethylene glycol spacer, e.g., a PEG2, PEG3 or PEG4 spacer. Exemplary universal long splint strands (300) are shown in FIG. 6.

In some embodiments, in the covalently closed circular library molecule (600), the first splint strand (300) lacks sub-region (311), (312) or (313), so that a duplex formed by hybridization between the first splint strand (300) and the second splint strand (400) has a portion of the second splint strand that loops out. For example, the first splint strand (300) can lack sub-region (312), and in a duplex formed by hybridization between the first splint strand (300) and the second splint strand (400) the sub-region (412) of the second splint strand (400) loops out (e.g., see FIG. 7). In some embodiments, a first splint strand (300) that lacks a sub-region is an example of a universal long splint strand (300).

In some embodiments, an exemplary covalently closed circular molecule (600) comprises: (i) a sequence of interest (110); (ii) a universal adaptor sequence having a binding sequence for a forward sequencing primer (140); (iii) a universal adaptor sequence having a binding sequence for a reverse sequencing primer (150); (iv) a universal adaptor sequence having a binding sequence for a surface pinning primer (sub-region 411); (v) a universal adaptor sequence having a binding sequence for a surface capture primer (sub-region 413); and (vi) a sample index, short random sequence (NNN) and/or unique molecular index (UMI) (sub-region 412), wherein the covalently closed circular molecule (600) is optionally hybridized to the first splint strand (300).

In some embodiments, an exemplary covalently closed circular molecule (600) comprises: (i) a sequence of interest (110); (ii) a universal adaptor sequence having a binding sequence for a forward sequencing primer (140); (iii) a universal adaptor sequence having a binding sequence for a reverse sequencing primer (150); (iv) a universal adaptor sequence having a binding sequence for a surface pinning primer (sub-region 411); (v) a universal adaptor sequence having a binding sequence for a surface capture primer (sub-region 412); and (vi) a sample index, short random sequence (NNN) and/or unique molecular index (UMI) (sub-region 413), wherein the covalently closed circular molecule (600) is optionally hybridized to the first splint strand (300).

In some embodiments, an exemplary covalently closed circular molecule (600) comprises: (i) a sequence of interest (110); (ii) a universal adaptor sequence having a binding sequence for a forward sequencing primer (140); (iii) a universal adaptor sequence having a binding sequence for a reverse sequencing primer (150); (iv) a universal adaptor sequence having a binding sequence for a surface pinning primer (sub-region 412); (v) a universal adaptor sequence having a binding sequence for a surface capture primer (sub-region 413); and (vi) a sample index, short random sequence (NNN) and/or unique molecular index (UMI) (sub-region 411), wherein the covalently closed circular molecule (600) is optionally hybridized to the first splint strand (300).

In some embodiments, any of the covalently closed circular molecules (600) described herein comprise a plurality of covalently closed circular molecules (600), wherein the sequence of interest (110) of individual covalently closed circular molecules (600) in the plurality comprise the same sequence of interest. In some embodiments, the sequence of interest (110) of individual covalently closed circular molecules (600) in the plurality comprise different sequences of interest.

Tables 1-4 above list various embodiments of sequences that form the covalently closed circular library molecule (600), including the library molecule (100), the first splint strand (300), and the second splint strand (400). In some embodiments, the sequences in the first splint strand (300) and/or the second splint strand (400) comprise sequences that are complementary to the sequences listed in Tables 2-3. In some embodiments, any of the sequences in the first splint strand (300) and/or the second splint strand (400) which are listed in Tables 2-3 can be truncated at the 5' end and/or the 3' end, where the truncation can be 1-12 nucleotides. In certain embodiments, the 5' end is truncated. In certain embodiments, the 3' end is truncated. In some embodiments, in the library molecule, the sequence of the forward sequencing primer binding site (120) and/or the sequence of the reverse sequencing primer binding site (130), which are listed in Table 1, can be truncated at the 5' end and/or the 3' end, where the truncation can be 1-12 nucleotides. In certain embodiments, the 5' end is truncated. In certain embodiments, the 3' end is truncated.

The present disclosure provides a reaction mixture comprising a plurality of any of the covalently closed circular molecules (600) described herein and at least one exonuclease enzyme. In some embodiments, the exonuclease enzyme comprises any one or any combination of two or more of exonuclease I, thermolabile exonuclease I, and/or T7 exonuclease.

Multiplex workflows are enabled by preparing sample-indexed covalently closed circular library molecules (600) using double-stranded splint adaptors carrying at least one sample index sequence. The sample index sequence can be employed to prepare separate batches of sample-indexed covalently closed circular library molecules (600) using input nucleic acids isolated from different sources. The sample-indexed covalently closed circular library molecules (600) can be pooled together to generate a multiplex covalently closed circular library molecule (600) mixture, and the pooled covalently closed circular library molecules (600) can be amplified and/or sequenced. The sequences of the insert region along with the sample index sequence can be used to identify the source of the input nucleic acids. In some embodiments, any number of batches of sample-indexed covalently closed circular library molecules (600) can be pooled together, for example 2-10, or 10-50, or 50-100, or 100-200, or more than 200 batches of sample-indexed covalently closed circular library molecules (600) can be pooled. Exemplary nucleic acid sources include naturally-occurring, recombinant, or chemically-synthesized sources. Exemplary nucleic acid sources include single cells, a plurality of cells, tissue, biological fluid, environmental sample, or whole organism. Exemplary nucleic acid sources include fresh, frozen, fresh-frozen, or archived sources (e.g., formalin-fixed paraffin-embedded; FFPE). The skilled artisan will recognize that the nucleic acids can be isolated from many other sources. The nucleic acid library molecules can be prepared in single-stranded or double-stranded form.

Kits Comprising Double-Stranded Splint Adaptors

The present disclosure provides a kit for the use of introducing one or more new adaptor sequences into linear nucleic acid library molecules. In some embodiments, the kit can be used to circularize single-stranded nucleic acid library molecules having a sequence of interest (110) flanked on one side by a universal adaptor sequence for a forward sequencing primer binding site (120) and flanked on the other side by a universal adaptor sequence for a reverse sequencing primer binding site (130). In some embodiments, the circularized library molecules can be converted to covalently closed circular molecules which can be subjected to a rolling circle amplification (RCA) reaction to generate nucleic acid concatemers. The concatemers can be immobilized to a support for massively parallel sequencing.

The present disclosure provides kits comprising nucleic acid double-stranded splint adaptors (200), comprising: (i) a first splint strand (long splint strand (300)), and (ii) a second splint strand (short splint strand (400)). The first splint strand comprises a first region (320), an internal region (310), and a second region (330). The internal region of the first splint strand (310) can hybridize to the second splint strand (400) to form a double-stranded splint adaptor (200) having a double-stranded region and two flanking single-stranded regions. The two flanking single-stranded regions of the double-stranded splint adaptor (200) are designed to hybridize to the end sequences of a linear nucleic acid library molecule (100). The end sequences of the linear nucleic acid library molecule comprise first (120) and second (130) sequence universal adaptor sequences, respectively. In some embodiments, the first and second universal adaptor sequences of the linear library molecule comprise binding sequences for forward (120) and reverse (130) sequencing primer binding sites, respectively.

At least a portion of the internal region of the first splint strand (310) can hybridize to the second splint strand (400) to form a double-stranded splint adaptor (200) having a double-stranded region and two flanking single-stranded regions. The second splint strand (400) includes at least one new adaptor sequence. The formation of library-splint complexes (500) brings the library molecule (100) into proximity with the at least one new universal adaptor sequence, including for example a universal sequence for a surface pinning primer binding site, a universal sequence for a surface capture primer binding site, a sample index sequence, a short random sequence (e.g., NNN) and/or a unique molecule index (UMI) sequence. Exemplary double-stranded splint adaptors are shown in FIGS. 2 and 3. The kit can include a container which contains the first splint strands (300) and the second splint strands (400) in hybridized or non-hybridized form. The kit can include a first container which contains the first splint strands (300) and a second container which contains the second splint strands (400).

In some embodiments, in the kit, the first region of the first splint strand (320) comprises a first universal adaptor sequence which can hybridize to a first universal binding sequence at one end of a linear nucleic acid library molecule (e.g., see FIGS. 2 and 3). The second region of the first splint strand (330) comprises a second universal adaptor sequence which can hybridize to a second universal binding sequence at the other end of the linear nucleic acid library molecule (e.g., see FIGS. 2 and 3). In some embodiments, the first region of the first splint strand (320) includes a first universal adaptor sequence which comprises a universal binding sequence for a forward or reverse sequencing primer. In some embodiments, the second region of the first splint strand (330) includes a second universal adaptor sequence which comprises a universal binding sequence for a forward or reverse sequencing primer. In some embodiments, the 5' end of the first splint strand (300) is phosphorylated; alternatively, the 5' end of the first splint strand (300) is non-phosphorylated. In some embodiments, the 3' end of the first splint strand (300) comprises a terminal 3' OH group; alternatively, the 5' end of the first splint strand (300) is a terminal 3' blocking group.

In some embodiments, in the kit, the second splint strand (400) comprises at least three sub-regions, including first, second and third sub-regions (e.g., see FIGS. 2 and 3). The first sub-region (411) can comprise a universal binding sequence for an immobilized surface pinning primer, an immobilized surface capture primer, at least one sample index sequence, a short random sequence (NNN) and/or or a unique molecule index (UMI). The second sub-region (412) can comprise a universal binding sequence for an immobilized surface pinning primer, an immobilized surface capture primer, at least one sample index sequence, a short random sequence (NNN) and/or or a unique molecule index (UMI). The third sub-region (413) can comprise a universal binding sequence for an immobilized surface pinning primer, an immobilized surface capture primer, at least one sample index sequence, a short random sequence (e.g., NNN) and/or or a unique molecule index (UMI). In some embodiments, the sample index comprises 5-20 bases (e.g., about 5, 6, 7, 8, 9, 10, 11, 12, 13, 14, 15, 16, 17, 18, 19, or 20 bases) which can be used to distinguish polynucleotides (e.g., insert sequences) from different sample sources in a multiplex assay. In some embodiments, the unique molecular index (UMI) comprises 3-20 bases (e.g., about 3, 4, 5, 6, 7, 8, 9, 10, 11, 12, 13, 14, 15, 16, 17, 18, 19, or 20 bases) which can be used to uniquely identify a nucleic acid molecule to which the adaptor is appended (e.g., molecular tagging). In some embodiments, the unique molecular index (UMI) comprises a random sequence. The second splint strand (400) is designed to exhibit reduced or no hybridization to the insert sequence (110) of the library molecule (100).

An exemplary arrangement of the sequences in the sub-regions of the second splint strand (400), in a 3' to 5' orientation comprises: [(411) comprises a universal sequence for binding a surface pinning primer]—[(412) comprises a sample index sequence and an optional short random sequence NNN]—[(413) comprises a universal sequence for binding a surface capture primer].

An exemplary arrangement of the sequences in the sub-regions of the second splint strand (400), in a 3' to 5' orientation comprises: [(411) comprises a universal sequence for binding a surface pinning primer]—[(412)

comprises a universal sequence for binding a surface capture primer]—[(413) comprises a sample index sequence and an optional short random sequence NNN].

An exemplary arrangement of the sequences in the sub-regions of the second splint strand (400), in a 3' to 5' orientation comprises: [(411) comprises a sample index sequence and an optional short random sequence NNN]—[(412) comprises a universal sequence for binding a surface pinning primer]—[(413) comprises a universal sequence for binding a surface capture primer].

In some embodiments, in the kit, the second splint strand (400) can be 20-100 (e.g., about 20, 25, 30, 35, 40, 45, 50, 60, 70, 80, 90, or 100) nucleotides in length. In some embodiments, the second splint strand (400) can be 30-80 nucleotides in length80 (e.g., about 30, 35, 40, 45, 50, 60, 70, or 80) nucleotides in length. 40-60 60 (e.g., about 40, 45, 50, or 60) nucleotides in length. In some embodiments, the 5' end of the second splint strand (400) is phosphorylated; alternatively, the 5' end of the second splint strand (400) is non-phosphorylated. In some embodiments, the 3' end of the second splint strand (400) comprises a terminal 3' OH group; alternatively, the 3' end of the second splint strand (400) comprises a terminal 3' blocking group. In some embodiments, the second splint strands (400) comprise one or more phosphorothioate linkage at the 5' and/or 3' ends to confer exonuclease resistance. In some embodiments, the second splint strands (400) comprise one or more phosphorothioate linkage(s) at an internal position, e.g., to confer endonuclease resistance. In some embodiments, the second splint strands (400) comprise one or more 2'-O-methylcytosine bases at the 5' and/or 3' end, or at an internal position.

In some embodiments, in the kit, the first splint strand (300) includes an internal region (310) which comprises at least three sub-regions, including a fourth sub-region (311), a fifth sub-region (312), and a sixth sub-region (313). The fourth sub-region (311) can hybridize to the first sub-region (411) of the second splint strand (400). The fourth sub-region (311) can be fully or partially complementary to the first sub-region (411) of the second splint strand (400). The fifth sub-region (312) can hybridize to the second sub-region (412) of the second splint strand (400). The fifth sub-region (312) can be fully or partially complementary to the second sub-region (412) of the second splint strand (400). The sixth sub-region (313) can hybridize to the third sub-region (413) of the second splint strand (400). The sixth sub-region (313) can be fully or partially complementary to the third sub-region (413) of the second splint strand (400). The fourth, fifth and sixth sub-regions do not hybridize (or at least exhibit very little hybridization) to the sequence of interest, the surface capture primers or surface pinning primers.

In some embodiments, in the kit, one of the sub-regions of the first splint strand (300) comprises an index or random sequence, for example, a sample index, a short random sequence (e.g., NNN), and/or a unique molecular index (UMI). For example, sub-region (311), (312) or (313) comprises a sample index, a short random sequence (e.g., NNN) and/or a unique molecular index (UMI). In some embodiments, the sample index comprises 5-20 bases (e.g., about 5, 6, 7, 8, 9, 10, 11, 12, 13, 14, 15, 16, 17, 18, 19, or 20 bases) which can be used to distinguish polynucleotides (e.g., insert sequences) from different sample sources in a multiplex assay. In some embodiments, the unique molecular index (UMI) comprises 3-20 bases (e.g., about 3, 4, 5, 6, 7, 8, 9, 10, 11, 12, 13, 14, 15, 16, 17, 18, 19, or 20 bases) which can be used to uniquely identify a nucleic acid molecule to which the adaptor is appended (e.g., molecular tagging). In some embodiments, the unique molecular index (UMI) comprises a random sequence.

In some embodiments, in the kit, the first splint strand sub-region which comprises the index or random sequence comprises any one or any combination of two or more of: a sample index sequence (denoted with "S"); a random sequence (denotes with "N"); at least one nucleotide that can be converted into an abasic base (denoted with a solid black rectangle) (e.g., uridine, 8-oxo-7,8-dihydroguanine (e.g., 8oxoG) or deoxyinosine); deoxyinosine (denoted with "I"); and/or a spacer. In some embodiments, the spacer comprises an 18-carbon spacer (e.g., comprising a hexa-ethyleneglycol spacer), multiple C3 spacer phosphoramidites, or a spacer 9 comprising a trimethylene glycol spacer. In some embodiments, the spacer comprises a polyethylene glycol spacer, e.g., a PEG2, PEG3 or PEG4 spacer.

In some embodiments, in the kit, a double-stranded splint adaptor (200) comprises a first splint strand (300) which is partially hybridized to a second splint strand (400), where the first splint strand (300) comprises a universal long splint strand. In some embodiments, the universal long splint strand comprises at least one sub-region that that is only partially hybridized to the second splint strand (400). For example, and without limitation, a universal long splint strand (300) comprises a sub-region carrying at least one nucleotide that can be converted into an abasic base (denoted with a solid black rectangle) (e.g., uridine, 8-oxo-7, 8-dihydroguanine (e.g., 8oxoG) or deoxyinosine); deoxyinosine (denoted with "I"); and/or a spacer. In some embodiments, the spacer comprises an 18-carbon spacer (e.g., comprising a hexa-ethyleneglycol spacer), multiple C3 spacer phosphoramidites, or a spacer 9 comprising a trimethylene glycol spacer. In some embodiments, the spacer comprises a polyethylene glycol spacer, e.g., a PEG2, PEG3 or PEG4 spacer. Exemplary universal long splint strands (300) are shown in FIG. 6.

In some embodiments, in the kit, the first splint strand (300) lacks sub-region (311), (312) or (313), so that a duplex formed by hybridization between the first splint strand (300) and the second splint strand (400) has a portion of the second splint strand that loops out. For example, and without limitation, the first splint strand (300) lacks sub-region (312), and in a duplex formed by hybridization between the first splint strand (300) and the second splint strand (400) the sub-region (412) of the second splint strand (400) loops out (e.g., see FIG. 7). In some embodiments, a first splint strand (300) that lacks a sub-region is an example of a universal long splint strand (300).

In some embodiments, in the kit, the first splint strand (300) can be 50-150 nucleotides in length, or 60-100 nucleotides in length, or 70-90 nucleotides in length. In some embodiments, the first splint strands (300) comprise one or more phosphorothioate linkage at the 5' and/or 3' ends to confer exonuclease resistance. In some embodiments, the first splint strands (300) comprise one or more phosphorothioate linkage at an internal position to confer endonuclease resistance. In some embodiments, the first splint strands (300) comprise one or more 2'-O-methylcytosine bases at the 5' and/or 3' end, or at an internal position.

Tables 1-4 above list various embodiments of universal adaptors sequences in the library molecule (100), the first splint strand (300), the second splint strand (400), and the immobilized surface primers, that may be included in the kit. In some embodiments, in any of the kits described herein, the sequences in the first splint strand (300) and/or the second splint strand (400) comprise sequences that are complementary to the sequences listed in Tables 2-3. In some embodiments, in any of the kits described herein, any of the sequences in the first splint strand (300) and/or the second splint strand (400) which are listed in Tables 2-3 can be truncated at the 5' end and/or the 3' end, where the truncation can be 1-12 nucleotides. In certain embodiments, the 5' end is truncated. In certain embodiments, the 3' end is truncated.

In some embodiments, the kit comprises nucleic acid double-stranded splint adaptors (200) and further comprises a T4 polynucleotide kinase. In some embodiments, the kit further comprises a ligase enzyme, optionally wherein the ligase enzyme comprises T7 DNA ligase, T3 ligase, T4 ligase, or Taq ligase. In some embodiments, the kit further comprises at least one endonuclease, which comprises any one or any combination of two or more of exonuclease I, thermolabile exonuclease I, and/or T7 exonuclease.

In some embodiments, the kit comprises at least one buffer for hybridizing the plurality of the double-stranded splint adaptors (200) and the plurality of nucleic acid library molecules (100). In some embodiments, the kit comprises one buffer for conducting multiple enzymatic reactions in a single reaction vessel, including any combination of (i) phosphorylating the 5' ends of the first and/or second splint strands (e.g., (300) and/or (400)), (ii) ligating the nicks in the library-splint complex (500), and/or (iii) exonuclease digestion of the first splint strand (300) from the covalently closed circular molecule (600). Alternatively, the kit comprises two or more separate buffers, e.g., where the first buffer can be used to conduct the phosphorylation reaction, the second buffer can be used to conduct the ligation reaction, and a third buffer can be used to conduct the exonuclease digestion reaction.

In some embodiments, the kit comprises one or more containers that contain any of the double-stranded splint adaptors (200) described herein, or any of the first and second splint strands (300) and (400), described herein. The kit can further comprise one or more containers that contain a T4 polynucleotide kinase, at least one ligase and/or at least one exonuclease. The kit can comprise any of these components in any combination and can be contained in a single container, or can be contained in separate container, or any combination thereof.

The kit can include instructions for use of the kit, e.g., for conducting reactions to introduce one or more new adaptor sequences into linear nucleic acid library molecules.

Methods for Forming a Plurality of Library-Splint Complexes

In some aspects, the present disclosure provides methods for forming a plurality of library-splint complexes (500) comprising: (a) providing a plurality of double-stranded splint adaptors (200) wherein individual double-stranded splint adaptors (200) in the plurality comprise a first splint strand (300) hybridized to a second splint strand (400), wherein the double-stranded splint adaptor includes a double-stranded region and two flanking single-stranded regions, wherein the first splint strand comprises a first region (320), an internal region (310), and a second region (330), and wherein the internal region of the first splint strand (310) is hybridized to the second splint strand (400). Exemplary double-stranded splint adaptors (200) are shown in FIGS. 2 and 3. In some embodiments, a portion of the internal region (310) of the first splint strand (300) is not hybridized to a portion of the second splint strand (400).

In some embodiments, the methods for forming a plurality of library-splint complexes (500) further comprise step (b): hybridizing the plurality of double-stranded splint adaptors with a plurality of single-stranded nucleic acid library molecule (100) wherein individual library molecules include a sequence of interest (110) flanked on one side by a universal adaptor sequence for a forward sequencing primer binding site (120) and flanked on the other side by a universal adaptor sequence for a reverse sequencing primer binding site (130) (e.g., FIG. 3). The hybridizing can be conducted under a condition suitable for hybridizing the first region of the first splint strand (320) to the portion (120) of the library molecule, and the condition is suitable for hybridizing the second region of the first splint strand (330) to the portion (130) of the library molecule, thereby circularizing the plurality of library molecules to form a plurality of library-splint complexes (500).

In some embodiments, in the methods for forming a plurality of library-splint complexes (500), the first region of the first splint strand (320) comprises a sequence that can hybridize to the universal adaptor sequence for a forward sequencing primer binding site (120) at one end of a linear nucleic acid library molecule.

In some embodiments, in the methods for forming a plurality of library-splint complexes (500), the second region of the first splint strand (330) comprises a sequence that can hybridize to the universal adaptor sequence for a reverse sequencing primer binding site (130) at the other end of the linear nucleic acid library molecule.

In some embodiments, the 5' end of the second splint strand (400) is phosphorylated or lacks a phosphate group. In some embodiments, the 3' end of the second splint strand (400) includes a terminal 3' OH group or a terminal 3' blocking group.

In some embodiments, in the methods for forming a plurality of library-splint complexes (500), the first region of the first splint strand (320) is hybridized to the universal adaptor sequence for a forward sequencing primer binding site (120) of the library molecule, and a second region of the first splint strand (330) is hybridized to the universal adaptor sequence for a reverse sequencing primer binding site (130) of the library molecule, thereby circularizing the library molecule to generate a library-splint complex (500). The library-splint complex (500) can comprise a first nick between the 5' end of the library molecule and the 3' end of the second splint strand (e.g., FIGS. 3 and 4). The library-splint complex (500) can also comprise a second nick between the 5' end of the second splint strand and the 3' end of the library molecule (e.g., FIGS. 3 and 4). In some embodiments, the first and second nicks are enzymatically ligatable. A ligation reaction would join the sequences from the second splint strand (400) to the ends of the library molecule (100).

In some embodiment, in the methods for forming a plurality of library-splint complexes (500), the first region of the first splint strand (320) can hybridize to a sense or anti-sense strand of a double-stranded nucleic acid library molecule. In the library-splint complex (500), the second region of the first splint strand (330) can hybridize to a sense or anti-sense strand of a double-stranded nucleic acid library molecule. The double-stranded nucleic acid library molecule can be denatured to generate the single-stranded sense and anti-sense library strands.

In some embodiments, in the methods for forming a plurality of library-splint complexes (500), the second splint strand (400) does not hybridize to the sequence of interest (110), and the internal region of the first splint strand (310) does not hybridize to the sequence of interest (110).

In some embodiments, in the methods for forming a plurality of library-splint complexes (500), the first region of the first splint strand (320) does not hybridize to the sequence of interest (110), and the second region of the first splint strand (330) does not hybridize to the sequence of interest (110).

In some embodiments, in the methods for forming a plurality of library-splint complexes (500), the 5' end of the single-stranded library molecule (100) is phosphorylated; alternatively, the 5' end of the single-stranded library molecule (100) lacks a phosphate group. In some embodiments, the 3' end of the single-stranded library molecule includes a terminal 3' OH group; alternatively, the 3' end of the single-stranded library molecule includes a terminal 3' blocking group.

In some embodiments, the single-stranded nucleic acid library molecule (100) lacks a universal adaptor sequence for a surface capture primer binding site. In some embodiments, the single-stranded nucleic acid library molecule (100) lacks a universal adaptor sequence for a surface pinning primer binding site. In some embodiments, the single-stranded nucleic acid library molecule (100) lacks a universal adaptor sequence for a sample index sequence. In some embodiments, single-stranded nucleic acid library molecule (100) lacks a unique molecular index (UMI) sequence.

In some embodiments, in the methods for forming a plurality of library-splint complexes (500), the second splint strand (400) comprises at least three sub-regions, including first, second and third sub-regions (e.g., see FIGS. 2 and 3). The first sub-region (411) comprises a universal binding sequence for an immobilized surface pinning primer, an immobilized surface capture primer, at least one sample index sequence and/or or a unique molecule index (UMI). The second sub-region (412) can comprise a universal binding sequence for an immobilized surface pinning primer, an immobilized surface capture primer, at least one sample index sequence and/or or a unique molecule index (UMI). The third sub-region (413) can comprise a universal binding sequence for an immobilized surface pinning primer, an immobilized surface capture primer, at least one sample index sequence, a short random sequence (e.g., NNN) and/or or a unique molecule index (UMI). In some embodiments, the sample index comprises 5-20 bases (e.g., about 5, 6, 7, 8, 9, 10, 11, 12, 13, 14, 15, 16, 17, 18, 19, or 20 bases) which can be used to distinguish polynucleotides (e.g., insert sequences) from different sample sources in a multiplex assay. In some embodiments, the unique molecular index (UMI) comprises 3-20 bases (e.g., about 3, 4, 5, 6, 7, 8, 9, 10, 11, 12, 13, 14, 15, 16, 17, 18, 19, or 20 bases) which can be used to uniquely identify a nucleic acid molecule to which the adaptor is appended (e.g., molecular tagging). In some embodiments, the unique molecular index (UMI) comprises a random sequence. The second splint strand (400) is designed to exhibit reduced or no hybridization to the insert sequence (110) of the library molecule (100).

In some embodiments, in the methods for forming a plurality of library-splint complexes (500), the arrangement of the sequences in the sub-regions of the second splint strand (400), in a 3' to 5' orientation comprises: [(411) comprises a universal sequence for binding a surface pinning primer]—[(412) comprises a sample index sequence and an optional short random sequence NNN]—[(413) comprises a universal sequence for binding a surface capture primer].

In some embodiments, in the methods for forming a plurality of library-splint complexes (500), the arrangement of the sequences in the sub-regions of the second splint strand (400), in a 3' to 5' orientation comprises: [(411)

comprises a universal sequence for binding a surface pinning primer]—[(412) comprises a universal sequence for binding a surface capture primer]—[(413) comprises a sample index sequence and an optional short random sequence NNN].

In some embodiments, in the methods for forming a plurality of library-splint complexes (500), the arrangement of the sequences in the sub-regions of the second splint strand (400), in a 3' to 5' orientation comprises: [(411) comprises a sample index sequence and an optional short random sequence NNN]—[(412) comprises a universal sequence for binding a surface pinning primer]—[(413) comprises a universal sequence for binding a surface capture primer].

In some embodiments, in the methods for forming a plurality of library-splint complexes (500), the second splint strand (400) comprises an additional sub-region carrying a second sample index sequence and an optional short random sequence NNN. For example, the additional sub-region can be located between sub-regions (411) and (412), or between sub-regions (412) and (413).

In some embodiments, in the methods for forming a plurality of library-splint complexes (500), the second splint strand (400) can be 20-100 (e.g., about 20, 25, 30, 35, 40, 45, 50, 60, 70, 80, 90, or 100) nucleotides in length. In some embodiments, the second splint strand (400) can be 30-80 nucleotides in length80 (e.g., about 30, 35, 40, 45, 50, 60, 70, or 80) nucleotides in length. 40-60 60 (e.g., about 40, 45, 50, or 60) nucleotides in length. In some embodiments, the 5' end of the second splint strand (400) is phosphorylated; alternatively, the 5' end of the second splint strand (400) is non-phosphorylated. In some embodiments, the 3' end of the second splint strand (400) comprises a terminal 3' OH group; alternatively, the 3' end of the second splint strand (400) comprises a terminal 3' blocking group. In some embodiments, the second splint strands (400) comprise one or more phosphorothioate linkage at the 5' and/or 3' ends to confer exonuclease resistance. In some embodiments, the second splint strands (400) comprise one or more phosphorothioate linkage(s) at an internal position, e.g., to confer endonuclease resistance. In some embodiments, the second splint strands (400) comprise one or more 2'-O-methylcytosine bases at the 5' and/or 3' end, or at an internal position.

In some embodiments, in the methods for forming a plurality of library-splint complexes (500), the first splint strand (300) can be 50-150 nucleotides in length, or 60-100 nucleotides in length, or 70-90 nucleotides in length. In some embodiments, the first splint strands (300) comprise one or more phosphorothioate linkage at the 5' and/or 3' ends to confer exonuclease resistance. In some embodiments, the first splint strands (300) comprise one or more phosphorothioate linkage at an internal position to confer endonuclease resistance. In some embodiments, the first splint strands (300) comprise one or more 2'-O-methylcytosine bases at the 5' and/or 3' end, or at an internal position. In some embodiments, the 5' end of the first splint strand (300) is phosphorylated or lacks a phosphate group. In some embodiments, the 3' end of the first splint strand (300) includes a terminal 3' OH group or a terminal 3' blocking group.

In some embodiments, in the methods for forming a plurality of library-splint complexes (500), the first splint strand (300) includes an internal region (310) which comprises at least three sub-regions, including a fourth sub-region (311), a fifth sub-region (312), and a sixth sub-region (313). The fourth sub-region (311) can hybridize to the first sub-region (411) of the second splint strand (400). The fourth sub-region (311) can be fully or partially complementary to the first sub-region (411) of the second splint strand (400). The fifth sub-region (312) can hybridize to the second sub-region (412) of the second splint strand (400). The fifth sub-region (312) can be fully or partially complementary to the second sub-region (412) of the second splint strand (400). The sixth sub-region (313) can hybridize to the third sub-region (413) of the second splint strand (400). The sixth sub-region (313) can be fully or partially complementary to the third sub-region (413) of the second splint strand (400). The fourth, fifth and sixth sub-regions do not hybridize (or at least exhibit very little hybridization) to the sequence of interest, the surface capture primers, or surface pinning primers.

In some embodiments, in the methods for forming a plurality of library-splint complexes (500), the first splint strand (300) comprises a sub-region (312) comprising a sample index, a short random sequence (e.g., NNN) and/or a unique molecular index (UMI). In some embodiments, the sample index comprises 5-20 bases (e.g., about 5, 6, 7, 8, 9, 10, 11, 12, 13, 14, 15, 16, 17, 18, 19, or 20 bases) which can be used to distinguish polynucleotides (e.g., insert sequences) from different sample sources in a multiplex assay. In some embodiments, the unique molecular index (UMI) comprises 3-20 bases (e.g., about 3, 4, 5, 6, 7, 8, 9, 10, 11, 12, 13, 14, 15, 16, 17, 18, 19, or 20 bases) which can be used to uniquely identify a nucleic acid molecule to which the adaptor is appended (e.g., molecular tagging). In some embodiments, the unique molecular index (UMI) comprises a random sequence.

In some embodiments, in the methods for forming a plurality of library-splint complexes (500), sub-region (312) comprises any one or any combination of two or more of: a sample index sequence (denoted with "S"); a random sequence (denotes with "N"); at least one nucleotide that can be converted into an abasic base (denoted with a solid black rectangle) (e.g., uridine, 8-oxo-7,8-dihydroguanine (e.g., 8oxoG) or deoxyinosine); deoxyinosine (denoted with "I"); and/or a spacer. In some embodiments, the spacer comprises an 18-carbon spacer (e.g., comprising a hexa-ethyleneglycol spacer), multiple C3 spacer phosphoramidites, or a spacer 9 comprising a trimethylene glycol spacer. In some embodiments, the spacer comprises a polyethylene glycol spacer, e.g., a PEG2, PEG3 or PEG4 spacer.

In some embodiments, in the methods for forming a plurality of library-splint complexes (500), the first splint strand (300) lacks sub-region (311), (312) or (313), so that a duplex formed by hybridization between the first splint strand (300) and the second splint strand (400) has a portion of the second splint strand that loops out. For example, the first splint strand (300) lacks sub-region (312), and in a duplex formed by hybridization between the first splint strand (300) and the second splint strand (400) the sub-region (412) of the second splint strand (400) loops out (e.g., see FIG. 7).

Tables 1-4 above list various embodiments of sequences the various molecules that form the library-splint complex (500), including the library molecule (100), the first splint strand (300), and the second splint strand (400). In some embodiments, in any of the methods for forming a plurality of library-splint complexes (500) described herein, the sequences in the first splint strand (300) and/or the second splint strand (400) comprise sequences that are complementary to the sequences listed in Tables 2-3. In some embodiments, in any of the methods for forming a plurality of library-splint complexes (500) described herein, the sequences in the first splint strand (300) and/or the second splint strand (400) which are listed in Tables 2-3 can be truncated at the 5' end and/or the 3' end, where the truncation can be 1-12 nucleotides. In some embodiments, the truncation can be 1, 2, 3, 4, 5, 6, 7, 8, 9, 10, 11 or 12 nucleotides in length. In certain embodiments, the 5' end is truncated. In certain embodiments, the 3' end is truncated. In some embodiments, in the library molecule, the sequence of the forward sequencing primer binding site (120) and/or the sequence of the reverse sequencing primer binding site (130), which are listed in Table 1, can be truncated at the 5' end and/or the 3' end, where the truncation can be 1-12 nucleotides. In some embodiments, the truncation can be 1, 2, 3, 4, 5, 6, 7, 8, 9, 10, 11 or 12 nucleotides in length. In certain embodiments, the 5' end is truncated. In certain embodiments, the 3' end is truncated.

In some embodiments, any of the methods for forming a plurality of library-splint complexes (500) described herein can further comprise at least one enzymatic reaction, including a phosphorylation reaction, ligation reaction and/or exonuclease reaction. The enzymatic reactions can be conducted sequentially or essentially simultaneously. The enzymatic reactions can be conducted in a single reaction vessel. Alternatively, a first enzymatic reaction can be conducted in a first reaction vessel, then transferred to a second reaction vessel where the second enzymatic reaction is conducted, then transferred to a third reaction vessel where the third enzymatic reaction is conducted.

In some embodiments, any of the methods for forming a plurality of library-splint complexes (500) described herein further comprise conducting separate and sequential phosphorylation and ligation reactions which are conducted in separate reaction vessels. In some embodiments, the methods for forming a plurality of library-splint complexes (500) further comprise step (c1): contacting in a first reaction vessel the plurality of the double-stranded splint adaptors (200) and the plurality of the single-stranded nucleic acid library molecules (100) with a T4 polynucleotide kinase enzyme under a condition suitable to phosphorylate the 5' ends of the plurality of double-stranded splint adaptors (200) and/or the plurality of single-stranded nucleic acid library molecules (100); and transferring the phosphorylation reaction to a second reaction vessel. In some embodiments, the methods for forming a plurality of library-splint complexes (500) further comprise step (d1): contacting in the second reaction vessel the plurality of phosphorylated double-stranded splint adaptors (200) and the plurality of phosphorylated single-stranded nucleic acid library molecules (100) with a ligase, under a condition suitable to enzymatically ligate the first and second nicks, thereby generating a plurality of covalently closed circular library molecules (600) each hybridized to the first splint strand (300). In some embodiments, the ligase enzyme comprises T7 DNA ligase, T3 ligase, T4 ligase, or Taq ligase. An exemplary method for generating a covalently closed circular library molecule (600) is shown in FIG. 4. The enzymatic ligation reaction can join the sequences from the second splint strand (400) to the ends of the library molecule (100). The double-stranded adaptor (200) can join new universal adaptor sequences and sample index sequences to both ends of the library molecule (100) without the need for conducting a primer extension or a PCR reaction. Thus, a PCR-free workflow that employs the double-stranded adaptor (200) can be used to generate covalently circularized library molecules (600) having adaptor sequences needed for downstream workflows such as amplification and sequencing.

As exemplified in FIG. 4, in some embodiments, in the covalently closed circular library molecule (600), the sub-regions of the second splint strand (400) are covalently joined to the universal forward sequencing primer binding site (120) and the universal reverse sequencing primer binding site (130). In some embodiments, the first splint strand (300) has an extendible 3' end which can be used to initiate a primer extension reaction. In some embodiments, the first splint strand (300) can be used as an amplification primer to conduct a rolling circle amplification reaction to generate a nucleic acid concatemer molecule that is complementary to the covalently closed circular library molecule (600).

In some embodiments, any of the methods for forming a plurality of library-splint complexes (500) described herein further comprise conducting sequential phosphorylation and ligation reactions which are conducted sequentially in the same reaction vessel. In some embodiments, the methods for forming a plurality of library-splint complexes (500) further comprise step (c2): contacting in a first reaction vessel the plurality of the double-stranded splint adaptors (200) and the plurality of the single-stranded nucleic acid library molecules (100) with a T4 polynucleotide kinase enzyme under a condition suitable to phosphorylate the 5' ends of the plurality of double-stranded splint adaptors (200) and the plurality of single-stranded nucleic acid library molecules (100). In some embodiments, the methods for forming a plurality of library-splint complexes (500) further comprise step (d2): contacting in the same first reaction vessel the phosphorylated double-stranded splint adaptors (200) and the phosphorylated single-stranded nucleic acid library molecules (100) with a ligase under a condition suitable to enzymatically ligate the first and second nicks, thereby generating a plurality of covalently closed circular library molecules (600) each hybridized to the first splint strand (300). In some embodiments, the ligase enzyme comprises a T7 DNA ligase, T3 ligase, T4 ligase, or Taq ligase. An exemplary method for generating a covalently closed circular library molecule (600) is shown in FIG. 4.

In some embodiments, any of the methods for forming a plurality of library-splint complexes (500) described herein further comprise conducting essentially simultaneous phosphorylation and ligation reactions which are conducted together in the same reaction vessel. In some embodiments, the methods for forming a plurality of library-splint complexes (500) further comprise step (c3): contacting in a first reaction vessel the plurality of the double-stranded splint adaptors (200) and the plurality of the single-stranded nucleic acid library molecules (100) with a (i) T4 polynucleotide kinase enzyme and (ii) a ligase enzyme, under a condition suitable to phosphorylate the 5' ends of the plurality of double-stranded splint adaptors (200) and the plurality of single-stranded nucleic acid library molecules (100), and the conditions are suitable to enzymatically ligate the first and second nicks, thereby generating a plurality of covalently closed circular library molecules (600) each hybridized to the first splint strand (300). In some embodiments, the ligase enzyme comprises T7 DNA ligase, T3 ligase, T4 ligase, or Taq ligase. An exemplary method for generating a covalently closed circular library molecule (600) is shown in FIG. 4.

In some embodiments, any of the methods for forming a plurality of library-splint complexes (500) described herein further comprise the optional step of enzymatically removing the plurality of first splint strands (300) from the plurality of covalently closed circular library molecules (600), which comprises: contacting the plurality of covalently closed circular library molecules (600) with at least one exonuclease enzyme to remove the plurality of first splint strands (300) and retaining the plurality of covalently closed circular library molecules (600). In some embodiments, the exonuclease reaction can be conducted in the same reaction buffer used to conduct the phosphorylation and/or ligation reactions, or in a different reaction buffer. In some embodiments, the exonuclease reaction can be conducted in a third reaction vessel after conducting the phosphorylation reaction in the first reaction vessel (c1), and conducting the ligation reaction in the second reaction vessel (d1). In some embodiments, the exonuclease reaction can be conducted in the first reaction vessel after conducting the phosphorylation reaction in the first reaction vessel (c2), and conducting the sequential ligation reaction in the first reaction vessel (d2). In some embodiments, the exonuclease reaction can be conducted in the first reaction vessel after conducting the essentially simultaneous phosphorylation and ligation reactions in the first reaction vessel (c3). In some embodiments, the at least one exonuclease enzyme comprises any combination of two or more of exonuclease I, thermolabile exonuclease I and/or T7 exonuclease.

Multiplex workflows are enabled by preparing sample-indexed covalently closed circular library molecules (600) using double-stranded splint adaptors carrying at least one sample index sequence. The sample index sequence can be employed to prepare separate batches of sample-indexed covalently closed circular library molecules (600) using input nucleic acids isolated from different sources. The sample-indexed covalently closed circular library molecules (600) can be pooled together to generate a multiplex covalently closed circular library molecule (600) mixture, and the pooled covalently closed circular library molecules (600) can be amplified and/or sequenced. The sequences of the insert region along with the sample index sequence can be used to identify the source of the input nucleic acids. In some embodiments, any number of batches of sample-indexed covalently closed circular library molecules (600) can be pooled together, for example 2-10, or 10-50, or 50-100, or 100-200, or more than 200 batches of sample-indexed covalently closed circular library molecules (600) can be pooled. Exemplary nucleic acid sources include naturally-occurring, recombinant, or chemically-synthesized sources. Exemplary nucleic acid sources include single cells, a plurality of cells, tissue, biological fluid, environmental sample or whole organism. Exemplary nucleic acid sources include fresh, frozen, fresh-frozen or archived sources (e.g., formalin-fixed paraffin-embedded; FFPE). The skilled artisan will recognize that the nucleic acids can be isolated from many other sources. The nucleic acid library molecules can be prepared in single-stranded or double-stranded form.

Methods for Rolling Circle Amplification

The present disclosure provides methods for conducting rolling circle amplification reaction on the covalently closed circular library molecules (600). The rolling circle amplification reaction can be conducted after the phosphorylation and ligation reactions, or after the ligation reaction. In some embodiments, the rolling circle amplification reaction can be conducted on covalently closed circular library molecules (600) that are no longer hybridized to the first splint strands (300) following the exonuclease reaction. In some embodiments, the rolling circle amplification reaction can be conducted on covalently closed circular library molecules (600) that are hybridized to the first splint strands (300). In some embodiments, the covalently closed circular library molecules (600) can be distributed onto a support and then be subjected to rolling circle amplification reaction. In some embodiments, the covalently closed circular library molecules (600) can be subjected to rolling circle amplification reaction in-solution and then distributed onto a support. In some embodiments, the rolling circle amplification reactions can employ the retained first splint strand (300) as an amplification primer (e.g., FIG. 4), or the first splint strand (300) can be removed (e.g., via exonuclease digestion) and replaced with a soluble amplification primer (e.g., FIG. 5).

On-Support Rolling Circle Amplification

In some embodiments, the methods for conducting rolling circle amplification reaction on a plurality of covalently closed circular library molecules (600) which lack hybridized first splint strands (300), and wherein individual covalently closed circular library molecules (600) in the plurality comprise a universal binding sequence for a surface capture primer, comprise step (a): distributing the plurality of covalently closed circular library molecules (600) onto a support having a plurality of the surface capture primers immobilized on the support, under a condition suitable for hybridizing individual covalently closed circular library molecules (600) to individual immobilized surface capture primers thereby immobilizing the plurality of covalently closed circular library molecules (600) to the support.

In some embodiments, the plurality of the surface capture primers comprise any one of the sequences listed in Table 4 or a complementary sequence thereof.

Individual surface capture primers can hybridize to a covalently closed circular library molecule (600) having a universal binding sequence for the surface capture primer.

In some embodiments, the methods for conducting rolling circle amplification reaction further comprises step (b): contacting the plurality of immobilized covalently closed circular library molecules (600) with a plurality of strand-displacing polymerases and a plurality of nucleotides, under a condition suitable to conduct a rolling circle amplification reaction on the support using the plurality of surface capture primers as immobilized amplification primers and the plurality of covalently closed circular library molecules (600) as template molecules, thereby generating a plurality of nucleic acid concatemer molecules immobilized to the surface capture primers. In some embodiments, the plurality of nucleotides comprises any combination of two or more of dATP, dGTP, dCTP, dTTP and/or dUTP. In some embodiments, individual immobilized concatemers are covalently joined to individual surface capture primers. In some embodiments, individual covalently closed circular library molecules (600) in the plurality comprise universal binding sequences for a surface capture primer and a surface pinning primer so that the rolling circle amplification reaction generates concatemer molecules having multiple tandem copies of sequences carried by the covalently closed circular library molecules (600) including universal binding sequences for a surface capture primer and a surface pinning primer. In some embodiments, the support further comprises a plurality of surface pinning primers. In some embodiments, the immobilized surface pinning primers serve to pin down at least one portion of the concatemer molecules to the support. In some embodiments, the immobilized surface pinning primers have a non-extendible 3' end and cannot be used for amplification. In some embodiments, the plurality of the surface pinning primers comprise any one of the sequences listed in Table 4 or a complementary sequence thereof. In some embodiments, the immobilized concatemers can be subjected to sequencing reactions.

Individual surface pinning primers can hybridize to a portion of the concatemer molecules having a universal binding sequence for the surface pinning primer. In some embodiments the immobilized surface pinning primers serve to pin down at least one portion of the concatemer molecules to the support. In some embodiments, the immobilized surface pinning primers have a non-extendible 3' end and cannot be used for amplification. In some embodiments, the immobilized concatemers can be subjected to sequencing reactions.

Figure 21:
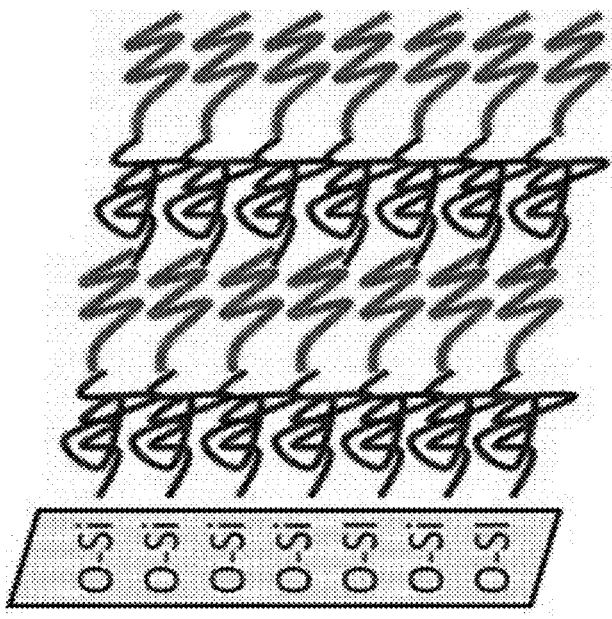
FIG. 21 is a schematic of an exemplary low binding support comprising a glass substrate and alternating layers of hydrophilic coatings which are covalently or non-covalently adhered to the glass, and which further comprises chemically-reactive functional groups that serve as attachment sites for oligonucleotide primers (e.g., capture oligonucleotides and circularization oligonucleotides).
Figure 22:
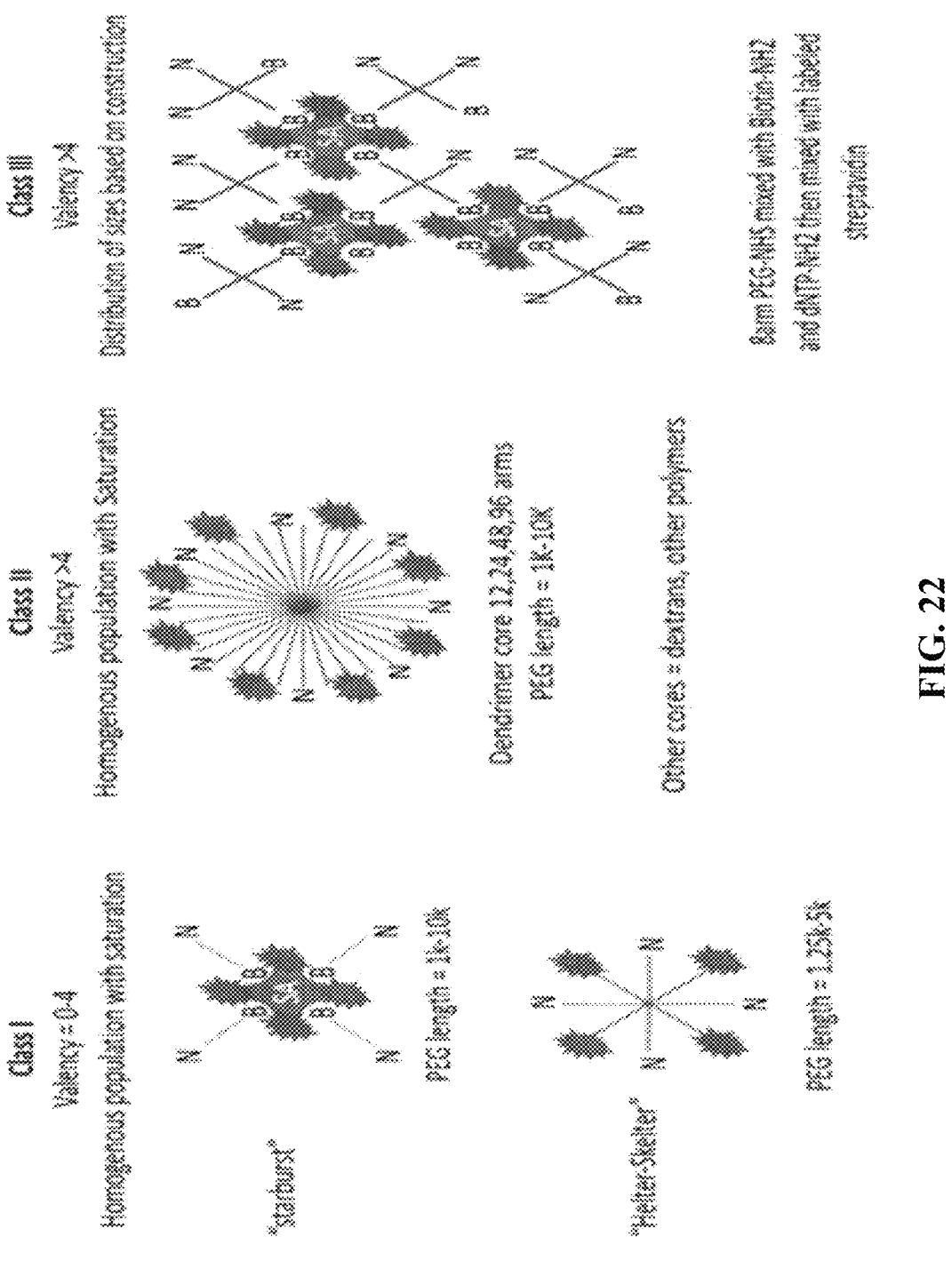
FIG. 22 is a schematic of various exemplary configurations of multivalent molecules. Left: schematics of multivalent molecules having a starburst or helter-skelter configuration. Center: a schematic of a multivalent molecule having a dendrimer configuration. Right: a schematic of multiple multivalent molecules formed by reacting streptavidin with 4-arm or 8-arm PEG-NHS with biotin and dNTPs. Nucleotide units are designated 'N', biotin is designated 'B', and streptavidin is designated 'SA'.
Figure 23:
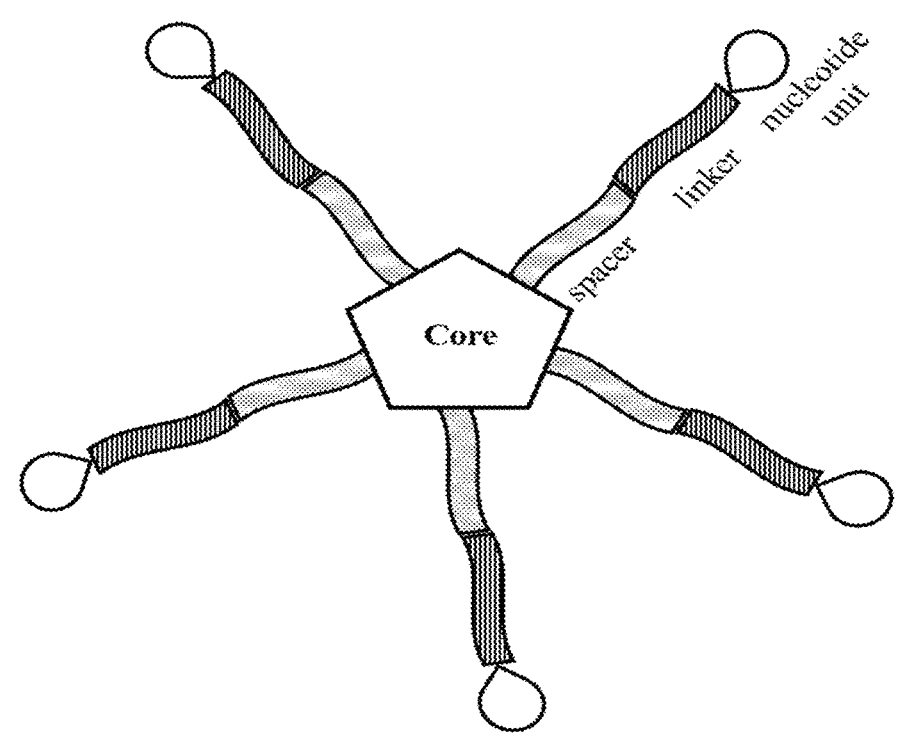
FIG. 23 is a schematic of an exemplary multivalent molecule comprising a generic core attached to a plurality of nucleotide-arms.
Figure 24:
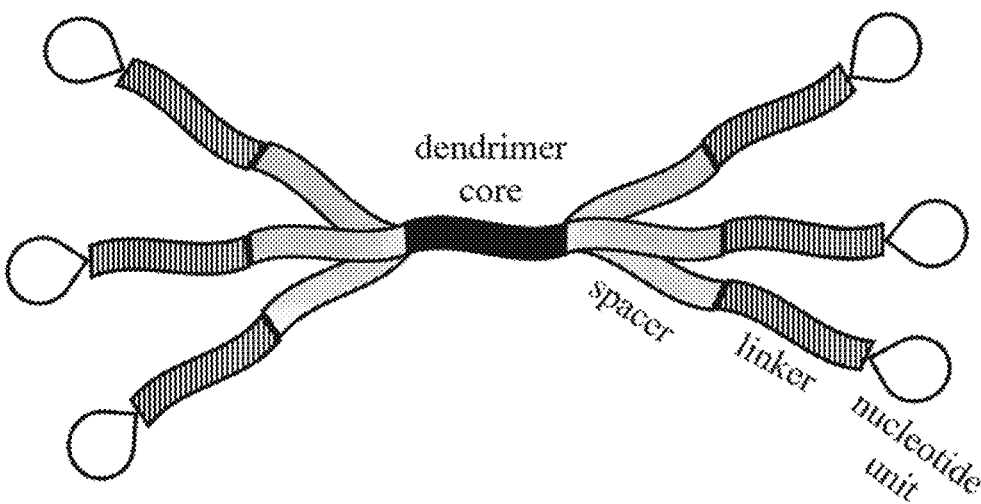
FIG. 24 is a schematic of an exemplary multivalent molecule comprising a dendrimer core attached to a plurality of nucleotide-arms.

In some embodiments, in the methods for conducting rolling circle amplification reaction, the plurality of covalently closed circular library molecules (600) can be distributed onto a support that is coated with one or more compounds to produce a passivated layer on the support (e.g., FIG. 21). In some embodiments, the passivated layer forms a porous or semi-porous layer. In some embodiments, one or more types of surface primers, concatemer template molecules and/or polymerases, can be attached to the passivated layer for immobilization to the support. In some embodiments, the support comprises a low non-specific binding surface that enable improved nucleic acid hybridization and amplification performance on the support. In general, the support may comprise one or more layers of a covalently or non-covalently attached low-binding, chemical modification layers, e.g., silane layers, polymer films, and one or more covalently or non-covalently attached oligonucleotides that can be used for immobilizing a plurality of nucleic acid concatemer molecules to the support. In some embodiments, the support can comprise a functionalized polymer coating layer covalently bound at least to a portion of the support via a chemical group on the support, a primer grafted to the functionalized polymer coating, and a water-soluble protective coating on the primer and the functionalized polymer coating. In some embodiments, the functionalized polymer coating comprises a poly(N-(5-azidoacetamidylpentyl)acrylamide-co-acrylamide (PAZAM). In some embodiments, the support comprises a surface coating having at least one hydrophilic polymer coating layer and at least one layer of a plurality of oligonucleotides. The hydrophilic polymer coating layer can comprise polyethylene glycol (PEG). The hydrophilic polymer coating layer can comprise branched PEG having at least 4 branches. In some embodiments, the low non-specific binding coating has a degree of hydrophilicity which can be measured as a water contact angle, where the water contact angle is no more than 45 degrees. In some embodiments, the density of the covalently closed circular library molecules (600) immobilized to the support or immobilized to the coating on the support is about $10^2$-$10^6$ per mm$^2$ (e.g., about $10^2$, $10^3$, $10^4$, $10^5$, or $10^6$). In some embodiments, the density of the covalently closed circular library molecules (600) immobilized to the support or immobilized to the coating on the support is about $10^6$-$10^9$ per mm$^2$ (e.g., about $10^6$, $10^7$, $\mathbf{10^8}$, or $10^9$). In some embodiments, the density of the covalently closed circular library molecules (600) immobilized to the support or immobilized to the coating on the support is about $10^9$-$10^{12}$ (e.g., about $10^9$, $10^{10}$, $10^{11}$, or $10^{12}$) per mm$^2$. In some embodiments, the plurality of covalently closed circular library molecules (600) is immobilized to the support or immobilized to the coating on the support at pre-determined sites on the support (or the coating on the support). In some embodiments, the plurality of covalently closed circular library molecules (600) is immobilized to the support or immobilized to the coating on the support at random sites on the support (or the coating on the support).

In-Solution Rolling Circle Amplification Using Soluble Amplification Primers

In some embodiments, the methods for conducting rolling circle amplification reaction on a plurality of covalently closed circular library molecules (600) which lack hybridized first splint strands (300), wherein individual covalently closed circular library molecules (600) in the plurality comprise a universal binding sequence for a forward amplification primer and a universal binding sequence for a surface capture primer, the method comprises: (a) hybridizing in solution a plurality of covalently closed circular library molecules and a plurality of soluble forward amplification primers; and (b) conducting a first rolling circle amplification reaction by contacting the plurality of covalently closed circular library molecules (600) with a plurality of strand-displacing polymerases and a plurality of nucleotides, under a condition suitable to conduct a rolling circle amplification reaction in solution using the plurality of forward amplification primers and the plurality of covalently closed circular library molecules (600) as template molecules, thereby generating a plurality of nucleic acid concatemer molecules having a portion which are still hybridized to their covalently closed circular library molecules (600). In some embodiments, the methods for conducting rolling circle amplification reaction further comprises step (c): distributing the plurality of concatemer molecules onto a support having a plurality of the surface capture primers immobilized thereon, under a condition suitable for hybridizing at least a portion of the concatemers to the plurality of the immobilized surface capture primers thereby immobilizing the plurality of concatemer molecules. The plurality of immobilized concatemer molecules is still hybridized to their covalently closed circular library molecules (600). In some embodiments, the methods for conducting rolling circle amplification reaction further comprises step (d): contacting the immobilized plurality of concatemer molecules with a plurality of strand-displacing polymerases and a plurality of nucleotides, under a condition suitable to conduct a second rolling circle amplification reaction on the support using the plurality of covalently closed circular library molecules (600) as template molecules, thereby extending the plurality of immobilized nucleic acid concatemer molecules. In some embodiments, the first and/or the second rolling circle amplification reactions can be conducted with a plurality of nucleotides which comprise any combination of two or more of dATP, dGTP, dCTP, dTTP and/or dUTP. In some embodiments, individual immobilized concatemers are hybridized to individual surface capture primers. In some embodiments, individual covalently closed circular library molecules (600) in the plurality comprise universal binding sequences for a surface capture primer and a surface pinning primer so that the in-solution rolling circle amplification reaction generates concatemer molecules having multiple tandem copies of sequences carried by the covalently closed circular library molecules (600) including universal binding sequences for a surface capture primer and a surface pinning primer. In some embodiments, the support further comprises a plurality of surface pinning primers. In some embodiments, the immobilized surface pinning primers serve to pin down at least one portion of the concatemer molecules to the support. In some embodiments, the immobilized surface pinning primers have a non-extendible 3' end and cannot be used for amplification. In some embodiments, the immobilized concatemers can be subjected to sequencing reactions. In some embodiments, the soluble forward amplification primers have the same sequence as the surface capture primers.

In some embodiments, the plurality of the surface capture primers comprises any one of the sequences listed in Table 4 or a complementary sequence thereof. In some embodiments, the plurality of the surface pinning primers comprises any one of the sequences listed in Table 4 or a complementary sequence thereof.

In some embodiments, in the methods for conducting rolling circle amplification reaction, the plurality of the surface capture primers immobilized on the support comprise the sequence 5'-GATCAGGT-GAGGCTGCGACGACT-3' (SEQ ID NO:34) (or a complementary sequence thereof).

In some embodiments, in the methods for conducting rolling circle amplification reaction, the plurality of the surface capture primers immobilized on the support comprise the sequence 5'-ATTACATGGATCAGGTGAGGCT-3' (SEQ ID NO:35) (or a complementary sequence thereof).

In some embodiments the immobilized surface pinning primers serve to pin down at least one portion of the concatemer molecules to the support. In some embodiments, the immobilized surface pinning primers have a non-extendible 3' end and cannot be used for amplification. In some embodiments, the immobilized concatemers can be subjected to sequencing reactions.

In some embodiments, the plurality of concatemer molecules of step (c) can be distributed onto a support that is coated with one or more compounds to produce a passivated layer on the support, e.g., glass, (see, e.g., FIG. 21). In an alternative embodiment, the support can be made of any material such as glass, plastic or a polymer material. In some embodiments, the passivated layer forms a porous or semi-porous layer. In some embodiments, the one or more types of surface primers, concatemer template molecules and/or polymerases, can be attached to the passivated layer for immobilization to the support. In some embodiments, the support comprises a low non-specific binding surface that enable improved nucleic acid hybridization and amplification performance on the support. In general, the support may comprise one or more layers of a covalently or non-covalently attached low-binding, chemical modification layers, e.g., silane layers, polymer films, and one or more covalently or non-covalently attached oligonucleotides that can be used for immobilizing a plurality of nucleic acid concatemer molecules to the support. In some embodiments, the support can comprise a functionalized polymer coating layer covalently bound at least to a portion of the support via a chemical group on the support, a primer grafted to the functionalized polymer coating, and a water-soluble protective coating on the primer and the functionalized polymer coating. In some embodiments, the functionalized polymer coating comprises a poly(N-(5-azidoacetamidylpentyl)acrylamide-co-acrylamide (PAZAM). In some embodiments, the support comprises a surface coating having at least one hydrophilic polymer coating layer and at least one layer of a plurality of oligonucleotides. The hydrophilic polymer coating layer can comprise polyethylene glycol (PEG). The hydrophilic polymer coating layer can comprise branched PEG having at least 4 branches at least 4 branches (e.g., 4, 5, 6, 7, 8, 9, 10, or more branches). In some embodiments, the low non-specific binding coating has a degree of hydrophilicity which can be measured as a water contact angle, where the water contact angle is no more than 45 degrees (e.g., no more than 5 degrees, no more than 10 degrees, no more than 15 degrees, no more than 20 degrees, no more than 25 degrees, no more than 30 degrees, no more than 35 degrees, no more than 40 degrees, or no more than 45 degrees). In some embodiments, the density of the concatemer molecules immobilized to the support or immobilized to the coating on the support is about $10^2$-$10^6$ per mm$^2$(e.g., about $10^2$, $10^3$, $10^4$, $10^5$, or $10^6$). In some embodiments, the density of the concatemer molecules immobilized to the support or immobilized to the coating on the support is about $10^6$-$10^9$ per mm$^2$ (e.g., about $10^6$, $10^7$, $10^8$, or $10^9$). In some embodiments, the density of the concatemer molecules immobilized to the support or immobilized to the coating on the support is about $10^9$-$10^{12}$ (e.g., about $10^9$, $10^{10}$, $10^{11}$, or $10^{12}$) per $mm^2$. In some embodiments, the plurality of the concatemer molecules is immobilized to the support or immobilized to the coating on the support at pre-determined sites on the support (or the coating on the support). In some embodiments, the plurality of the concatemer molecules is immobilized to the coating on the support at random sites on the support (or the coating on the support).

In-Solution Rolling Circle Amplification Using First Splint Strands

In some embodiments, the methods for conducting rolling circle amplification reaction on a plurality of covalently closed circular library molecules which are hybridized to first splint strands (300), wherein individual covalently closed circular library molecules (600) in the plurality comprise a universal binding sequence for a surface capture primer, the method comprises (a): contacting in solution the plurality of covalently closed circular library molecules (600) which are hybridized to first splint strands (300) with a plurality of strand-displacing polymerases and a plurality of nucleotides under a condition suitable for conducting a first rolling circle amplification reaction using the first splint strand (300) as an amplification primer thereby generating a plurality of concatemer molecules which are still hybridized to their covalently closed circular library molecules (600) (e.g., see FIG. 4).

In some embodiments, the methods for conducting rolling circle amplification reaction further comprises step (b): distributing the plurality of concatemer molecules which are hybridized to their covalently closed circular library molecule (600) onto a support having a plurality of the surface capture primers immobilized thereon, under a condition suitable for hybridizing at least a portion of the concatemers to the plurality of the immobilized surface capture primers thereby immobilizing the plurality of concatemer molecules. The plurality of immobilized concatemer molecules is still hybridized to their covalently closed circular library molecules (600).

In some embodiments, the methods for conducting rolling circle amplification reaction further comprise step (c): contacting the plurality of immobilized concatemer molecules with a plurality of strand-displacing polymerases and a plurality of nucleotides, under a condition suitable to conduct a second rolling circle amplification reaction on the support using the plurality of covalently closed circular library molecules (600) as template molecules, thereby extending the plurality of immobilized nucleic acid concatemer molecules.

In some embodiments, the first and/or the second rolling circle amplification reactions can be conducted with a plurality of nucleotides which comprise any combination of two or more of dATP, dGTP, dCTP, dTTP, and/or dUTP. In some embodiments, individual immobilized concatemers are hybridized to individual surface capture primers. In some embodiments, individual covalently closed circular library molecules (600) in the plurality comprise universal binding sequences for a surface capture primer and a surface pinning primer so that the in-solution rolling circle amplification reaction generates concatemer molecules having multiple tandem copies of sequences carried by the covalently closed circular library molecules (600) including universal binding sequences for a surface capture primer and a surface pinning primer. In some embodiments, the support further comprises a plurality of surface pinning primers. In some embodiments, the immobilized surface pinning primers serve to pin down at least one portion of the concatemer molecules to the support. In some embodiments, the immobilized surface pinning primers have a non-extendible 3' end and cannot be used for amplification. In some embodiments, the immobilized concatemers can be subjected to sequencing reactions.

In some embodiments, the plurality of the surface capture primers comprise any one of the sequences listed in Table 4 or a complementary sequence thereof. In some embodiments, the plurality of the surface pinning primers comprises any one of the sequences listed in Table 4 or a complementary sequence thereof.

In some embodiments the immobilized surface pinning primers serve to pin down at least one portion of the concatemer molecules to the support. In some embodiments, the immobilized surface pinning primers have a non-extendible 3' end and cannot be used amplification. In some embodiments, the immobilized concatemers can be subjected to sequencing reactions.

In some embodiments, the plurality of concatemer molecules of step (b) can be distributed onto a support that is coated with one or more compounds to produce a passivated layer on the support (e.g., FIG. 21). In some embodiments, the passivated layer forms a porous or semi-porous layer. In some embodiments, the surface primer, concatemer template molecule and/or polymerase, can be attached to the passivated layer for immobilization to the support. In some embodiments, the support comprises a low non-specific binding surface that enable improved nucleic acid hybridization and amplification performance on the support. In some embodiments, the support may comprise one or more layers of a covalently or non-covalently attached low-binding, chemical modification layers, e.g., silane layers, polymer films, and one or more covalently or non-covalently attached oligonucleotides that can be used for immobilizing a plurality of nucleic acid concatemer molecules to the support. In some embodiments, the support can comprise a functionalized polymer coating layer covalently bound at least to a portion of the support via a chemical group on the support, a primer grafted to the functionalized polymer coating, and a water-soluble protective coating on the primer and the functionalized polymer coating. In some embodiments, the functionalized polymer coating comprises a poly (N-(5-azidoacetamidylpentyl)acrylamide-co-acrylamide (PAZAM). In some embodiments, the support comprises a surface coating having at least one hydrophilic polymer coating layer and at least one layer of a plurality of oligonucleotides. The hydrophilic polymer coating layer can comprise polyethylene glycol (PEG). The hydrophilic polymer coating layer can comprise branched PEG having at least 4 branches (e.g., 4, 5, 6, 7, 8, 9, 10, or more branches). In some embodiments, the low non-specific binding coating has a degree of hydrophilicity which can be measured as a water contact angle, where the water contact angle is no more than 45 degrees (e.g., no more than 5 degrees, no more than 10 degrees, no more than 15 degrees, no more than 20 degrees, no more than 25 degrees, no more than 30 degrees, no more than 35 degrees, no more than 40 degrees, or no more than 45 degrees). In some embodiments, the density of the concatemer molecules immobilized to the support or immobilized to the coating on the support is about $10^2$-$10^6$ per $mm^2$ (e.g., about $10^2$, $10^3$, $10^4$, $10^5$, or $10^6$). In some embodiments, the density of the concatemer molecules immobilized to the support or immobilized to the coating on the support is about $10^6$-$10^9$ per $mm^2$ (e.g., about $10^6$, $10^7$, $10^8$, or $10^9$). In some embodiments, the density of the concatemer molecules immobilized to the support or immobilized to the coating on the support is about $10^9$-$10^{12}$ (e.g., about $10^9$, $10^{10}$, $10^{11}$, or $10^{12}$) per $mm^2$. In some embodiments, the plurality of the concatemer molecules is immobilized to the support or immobilized to the coating on the support at pre-determined sites on the support (or the coating on the support). In some embodiments, the plurality of the concatemer molecules is immobilized to the coating on the support at random sites on the support (or the coating on the support).

Compaction Oligonucleotides

In some aspects, the present disclosure provides compositions and methods for conducting rolling circle amplification in the presence or in the absence of a plurality of compaction oligonucleotides. Compaction oligonucleotides are single-stranded and can include a 5' region, an optional internal region, and a 3' region. The 5' and 3' regions of the compaction oligonucleotide can hybridize to the concatemer to pull together distal portions of the concatemer causing compaction of the concatemer to form a nanostructure. For example, and without limitation, the 5' region of the compaction oligonucleotide can be designed to hybridize to a first portion (e.g., a first universal adaptor sequence) of the concatemer molecule, and the 3' region of the compaction oligonucleotide can be designed to hybridized to a second portion (e.g., a second universal adaptor sequence) of the concatemer molecule. Inclusion of compaction oligonucleotides during rolling circle amplification can promote formation of nanostructures having tighter size and shape compared to concatemers generated in the absence of the compaction oligonucleotides. The compact and stable characteristics of the nucleic acid nanostructures improves sequencing accuracy, for example, by increasing signal intensity, and they retain their shape and size during multiple sequencing cycles. In some embodiments, the 3' ends of the compaction oligonucleotides are designed block primer extension.

In some embodiments, the compaction oligonucleotides are single stranded oligonucleotides comprising DNA, RNA, or a combination of DNA and RNA. The compaction oligonucleotides can be any length, including 20-150 nucleotides, e.g., 20, 30, 40, 50, 60, 70, 80, 90, 100, 110, 120, 130, 140, or 150 nucleotides, or any range therebetween. In some embodiments, the compaction oligonucleotides can be 30-100 nucleotides in length. In some embodiments, the compaction oligonucleotides can 40-80 nucleotides in length.

In some embodiments, the compaction oligonucleotide comprises a 5' region and a 3' region, and optionally an intervening region between the 5' and 3' regions. The intervening region can be any length, for example, about 2-20 nucleotides in length, e.g., 2, 3, 4, 5, 6, 7, 8, 9, 10, 11, 12, 13, 14, 15, 16, 17, 18, 19, or 20, or any range therebetween. In some embodiments, the intervening region comprises a homopolymer having consecutive identical bases (e.g., AAA, GGG, CCC, TTT, or UUU). In some embodiments, the intervening region comprises a non-homopolymer sequence.

In some embodiments, the 5' region of the compaction oligonucleotides can be wholly complementary or partially complementary along its length to a first portion of a concatemer molecule. For example, and without limitation, the 5' region of the compaction oligonucleotide comprises a sequence that can hybridize to a universal adaptor sequence which is listed in Tables 1-3, including a surface capture primer binding site, a surface pinning primer binding site, a forward sequencing primer binding site, or a reverse sequencing primer binding site.

In some embodiments, the 3' region of the compaction oligonucleotides can be wholly complementary or partially complementary along its length to a second portion of a concatemer molecule. For example, and without limitation, the 3' region of the compaction oligonucleotide comprises a sequence that can hybridize to a universal adaptor sequence which is listed in Tables 1-3, including a surface capture primer binding site, a surface pinning primer binding site, a forward sequencing primer binding site, or a reverse sequencing primer binding site.

The 5' region of the compaction oligonucleotides can hybridize to a first universal sequence portion of a concatemer molecule. The 3' region of the compaction oligonucleotides can hybridize to a second universal sequence portion of a concatemer molecule. The 5' and 3' regions of the compaction oligonucleotide can hybridize to the concatemer to pull together distal portions of the concatemer causing compaction of the concatemer to form a nanostructure.

In some embodiments, the 5' region of the compaction oligonucleotide can have the same sequence as the 3' region. In some embodiments, the 5' region of the compaction oligonucleotide can have a sequence that is different from the 3' region. In some embodiments, the 3' region of the compaction oligonucleotide can have a sequence that is a reverse sequence of the 5' region.

In some embodiments, the compaction oligonucleotides comprise one or more modified bases or linkages at their 5' or 3' ends to confer certain functionalities. In some embodiments, the compaction oligonucleotides comprise at least one phosphorothioate linkage at their 5' and/or 3' ends, e.g., to confer exonuclease resistance. In some embodiments, at least one nucleotide at or near the 3' end comprises a 2' fluoro base which confers exonuclease resistance. In some embodiments, the 3' end of the compaction oligonucleotides comprise at least one 2'-O-methyl RNA base which blocks polymerase-catalyzed extension. In some embodiments, the compaction oligonucleotides comprise a 3' inverted dT at their 3' ends which blocks polymerase-catalyzed extension. In some embodiments, the compaction oligonucleotides comprise 3' phosphorylation which blocks polymerase-catalyzed extension. In some embodiments, the internal region of the compaction oligonucleotides comprises at least one locked nucleic acid (LNA) which increases the thermal stability of duplexes formed by hybridizing a compaction oligonucleotide to a concatemer molecule.

The compaction oligonucleotides can include at least one region having consecutive guanines. For example, the compaction oligonucleotides can include at least one region having 2, 3, 4, 5, 6 or more consecutive guanines. In some embodiments, the compaction oligonucleotides comprise four consecutive guanines which can form a guanine tetrad structure. The guanine tetrad structure can be stabilized, e.g., via Hoogsteen hydrogen bonding. The guanine tetrad structure can be stabilized by a central cation, e.g., potassium, sodium, lithium, rubidium, or cesium.

The rolling circle amplification reaction can be conducted in the presence of a plurality of compaction oligonucleotides having at least four consecutive guanines. The resulting concatemers comprise repeat copies of the universal binding sequence for the compaction oligonucleotide. At least one compaction oligonucleotide can form a guanine tetrad and hybridize to the universal binding sequences for the compaction oligonucleotide, and the resulting concatemer can fold to form an intramolecular G-quadruplex structure. The concatemers can self-collapse to form compact nanostructures. Formation of the guanine tetrads and G-quadruplexes in the nanostructures may increase the stability of the nanostructures to retain their compact size and shape which can withstand changes in pH, temperature and/or repeated flows of reagents.

Methods for Sequencing

The present disclosure provides methods for sequencing any of the immobilized concatemer molecules described herein. Any of the methods for conducting rolling circle amplification reaction described herein can be used to generate a plurality of concatemer molecules immobilized to a support, and the immobilized concatemers can be subjected to sequencing reactions. In some embodiments, the sequencing reactions employ detectably labeled nucleotide analogs. In some embodiments, the sequencing reactions employ a two-stage sequencing reaction comprising binding detectably labeled multivalent molecules, and incorporating nucleotide analogs. The terms concatemer molecule and template molecule are used interchangeably herein.

In some embodiments, any of the rolling circle amplification reaction described herein (e.g., RCA conducted on-support or in-solution) can be used to generate immobilized concatemers each containing tandem repeat units of the sequence-of-interest and any adaptor sequences present in the covalently closed circular library molecules (600).

In some embodiments, an exemplary tandem repeat unit comprises: (i) a universal adaptor sequence having a binding sequence for a surface capture primer (sub-region 413); (ii) a universal adaptor sequence having a binding sequence for a reverse sequencing primer (130); (iii) a sequence of interest (110); (iv) a universal adaptor sequence having a binding sequence for a forward sequencing primer (120); (v) a universal adaptor sequence having a binding sequence for a surface pinning primer (sub-region 411); and (vi) a sample index, short random sequence (NNN) and/or unique molecular index (UMI) (sub-region 412).

In some embodiments, an exemplary tandem repeat unit comprises: (i) a universal adaptor sequence having a binding sequence for a surface capture primer (sub-region 412); (ii) a sample index, short random sequence (NNN) and/or unique molecular index (UMI) (sub-region 413); (iii) a universal adaptor sequence having a binding sequence for a reverse sequencing primer (130); (iv) a sequence of interest (110); (v) a universal adaptor sequence having a binding sequence for a forward sequencing primer (120); and (vi) a universal adaptor sequence having a binding sequence for a surface pinning primer (sub-region 411).

In some embodiments, an exemplary tandem repeat unit comprises: (i) a universal adaptor sequence having a binding sequence for a surface capture primer (sub-region 413); (ii) a universal adaptor sequence having a binding sequence for a reverse sequencing primer (150); (iii) a sequence of interest (110); (iv) a universal adaptor sequence having a binding sequence for a forward sequencing primer (140); (v) a sample index, short random sequence (NNN) and/or unique molecular index (UMI) (sub-region 412); and (vi) a universal adaptor sequence having a binding sequence for a surface pinning primer (sub-region 411).

The immobilized concatemer can self-collapse into a compact nucleic acid nanoball. Inclusion of one or more compaction oligonucleotides during the RCA reaction can further compact the size and/or shape of the nanoball. An increase in the number of tandem repeat units in a given concatemer increases the number of sites along the concatemer for hybridizing to multiple sequencing primers (e.g., sequencing primers having a universal sequence) which serve as multiple initiation sites for polymerase-catalyzed sequencing reactions. When the sequencing reaction employs detectably labeled nucleotides and/or detectably labeled multivalent molecules (e.g., having nucleotide units), the signals emitted by the nucleotides or nucleotide units that participate in the parallel sequencing reactions along the concatemer can yield an increased signal intensity for each concatemer. Multiple portions of a given concatemer can be simultaneously sequenced. Furthermore, a plurality of binding complexes can form along a particular concatemer molecule, each binding complex comprising a sequencing polymerase bound to a multivalent molecule, wherein the plurality of binding complexes remains stable without dissociation resulting in increased persistence time which increases signal intensity and reduces imaging time.

Sequencing Methods Using Engineered Polymerases

In some aspects, the present disclosure provides concatemer template molecules that can be sequenced using any nucleic acid sequencing method that employs labeled or non-labeled chain terminating nucleotides, where the chain terminating nucleotides include a 3'-O-azido group (or 3'-O-methylazido group) or any other type of bulky blocking group at the sugar 3' position. In some embodiments, the concatemer template molecules can be sequenced using a sequencing-by-avidity method (SBA) using labeled multivalent molecules and non-labeled chain terminating nucleotides. In some embodiments, the concatemer template molecules can be sequenced using a sequencing-by-synthesis (SBS) method which employs labeled chain-terminating nucleotides. In some embodiments, the concatemer template molecules can be sequenced using a sequencing-by-binding method (SBB) which employ non-labeled chain-terminating nucleotides. In some embodiments, the concatemer template molecules can be sequenced using phosphate-chain labeled nucleotides.

Methods for Sequencing using Nucleotide Analogs

In some aspects, the present disclosure provides methods for sequencing, comprising step (a): contacting a sequencing polymerase to (i) a nucleic acid concatemer molecule and (ii) a nucleic acid primer, wherein the contacting is conducted under a condition suitable to bind the sequencing polymerase to the nucleic acid concatemer molecule which is hybridized to the nucleic acid primer, wherein the nucleic acid concatemer molecule hybridized to the nucleic acid primer forms the nucleic acid duplex. In some embodiments, the sequencing polymerase comprises a recombinant mutant sequencing polymerase. In some embodiments, the primer comprises a 3' extendible end.

In some embodiments, the methods for sequencing further comprise step (b): contacting the sequencing polymerase with a plurality of nucleotides under a condition suitable for binding at least one nucleotide to the sequencing polymerase which is bound to the nucleic acid duplex and suitable for polymerase-catalyzed nucleotide incorporation. In some embodiments, the sequencing polymerase is contacted with the plurality of nucleotides in the presence of at least one catalytic cation comprising magnesium and/or manganese. In some embodiments, the plurality of nucleotides comprises at least one nucleotide analog having a chain terminating moiety at the sugar 2' or 3' position. In some embodiments, the plurality of nucleotides comprises at least one nucleotide that lacks a chain terminating moiety.

In some embodiments, the methods for sequencing further comprise step (c): incorporating at least one nucleotide into the 3' end of the extendible primer under a condition suitable for incorporating the at least one nucleotide. In some embodiments, the suitable conditions for nucleotide binding the polymerase and for incorporation the nucleotide can be the same or different. In some embodiments, conditions suitable for incorporating the nucleotide comprise inclusion of at least one catalytic cation comprising magnesium and/or manganese. In some embodiments, the at least one nucleotide binds the sequencing polymerase and incorporates into the 3' end of the extendible primer. In some embodiments, the incorporating the nucleotide into the 3' end of the primer in step (c) comprises a primer extension reaction.

In some embodiments, the methods for sequencing further comprise step (d): repeating the incorporating at least one nucleotide into the 3' end of the extendible primer of step (c) at least once. In some embodiments, the plurality of nucleotides comprises a plurality of nucleotides labeled with detectable reporter moiety. The detectable reporter moiety comprises a fluorophore. In some embodiments, the fluorophore is attached to the nucleotide base. In some embodiments, the fluorophore is attached to the nucleotide base with a linker which is cleavable/removable from the base. In some embodiments, at least one of the nucleotides in the plurality is not labeled with a detectable reporter moiety. In some embodiments, a particular detectable reporter moiety (e.g., fluorophore) that is attached to the nucleotide can correspond to the nucleotide base (e.g., dATP, dGTP, dCTP, dTTP or dUTP) to permit detection and identification of the nucleotide base. In some embodiments, the method further comprises detecting the at least one incorporated nucleotide at step (c) and/or (d). In some embodiments, the method further comprises identifying the at least one incorporated nucleotide at step (c) and/or (d). In some embodiments, the sequence of the nucleic acid concatemer molecule can be determined by detecting and identifying the nucleotide that binds the sequencing polymerase, thereby determining the sequence of the concatemer molecule. In some embodiments, the sequence of the nucleic acid concatemer molecule can be determined by detecting and identifying the nucleotide that incorporates into the 3' end of the primer, thereby determining the sequence of the concatemer molecule.

In some embodiments, in the methods for sequencing, the plurality of sequencing polymerases that are bound to the nucleic acid duplexes comprise a plurality of complexed polymerases, having at least a first and second complexed polymerase, wherein (a) the first complexed polymerases comprises a first sequencing polymerase bound to a first nucleic acid duplex comprising a first nucleic acid template sequence which is hybridized to a first nucleic acid primer, (b) the second complexed polymerases comprises a second sequencing polymerase bound to a second nucleic acid duplex comprising a second nucleic acid template sequence which is hybridized to a second nucleic acid primer, (c) the first and second nucleic acid template sequences comprise the same or different sequences, (d) the first and second nucleic acid concatemers are clonally-amplified, (e) the first and second primers comprise extendible 3' ends or non-extendible 3' ends, and (f) the plurality of complexed polymerases are immobilized to a support. In some embodiments, the density of the plurality of complexed polymerases is about $10^2$-$10^{15}$ (e.g., $10^2$-$10^{15}$ or more, e.g., $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$) complexed polymerases per $mm^2$ that are immobilized to the support.

Two-Stage Methods for Nucleic Acid Sequencing

In some aspects, the present disclosure provides a two-stage method for sequencing nucleic acid molecules. In some embodiments, the first stage generally comprises binding multivalent molecules to complexed polymerases to form multivalent-complexed polymerases, and detecting the multivalent-complexed polymerases.

In some embodiments, the first stage comprises step (a): contacting a plurality of a first sequencing polymerase to (i)

a plurality of nucleic acid concatemer molecules and (ii) a plurality of nucleic acid primers, wherein the contacting is conducted under a condition suitable to bind the plurality of first sequencing polymerases to the plurality of nucleic acid concatemer molecules and the plurality of nucleic acid primers thereby forming a plurality of first complexed polymerases each comprising a first sequencing polymerase bound to a nucleic acid duplex wherein the nucleic acid duplex comprises a nucleic acid concatemer molecule hybridized to a nucleic acid primer. In some embodiments, the first polymerase comprises a recombinant mutant sequencing polymerase.

In some embodiments, in the methods for sequencing concatemer molecules, the primer comprises a 3' extendible end or a 3' non-extendible end. In some embodiments, the plurality of nucleic acid concatemer molecules comprise amplified template molecules (e.g., clonally amplified template molecules). In some embodiments, the plurality of nucleic acid concatemer molecules comprise one copy of a target sequence of interest. In some embodiments, the plurality of nucleic acid molecules comprise two or more tandem copies of a target sequence of interest (e.g., concatemers). In some embodiments, the nucleic acid concatemer molecules in the plurality of nucleic acid concatemer molecules comprise the same target sequence of interest or different target sequences of interest. In some embodiments, the plurality of nucleic acid concatemer molecules and/or the plurality of nucleic acid primers are in solution or are immobilized to a support. In some embodiments, when the plurality of nucleic acid concatemer molecules and/or the plurality of nucleic acid primers are immobilized to a support, the binding with the first sequencing polymerase generates a plurality of immobilized first complexed polymerases. In some embodiments, the plurality of nucleic acid concatemer molecules and/or nucleic acid primers are immobilized to $10^2$-$10^{15}$ different sites on a support. In some embodiments, the binding of the plurality of concatemer molecules and nucleic acid primers with the plurality of first sequencing polymerases generates a plurality of first complexed polymerases immobilized to $10^2$-$10^{15}$ different sites on the support (e.g., $10^2$-$10^{15}$ sites or more, e.g., $10^2$ sites, $10^3$ sites, $10^4$ sites, $10^5$ sites, $10^6$ sites, $10^7$ sites, $10^8$ sites, $10^9$ sites, $10^{10}$ sites, $10^{11}$ sites, $10^{12}$ sites, $10^{13}$ sites, $10^{14}$ sites, $10^{15}$ sites). In some embodiments, the plurality of immobilized first complexed polymerases on the support are immobilized to pre-determined or to random sites on the support. In some embodiments, the plurality of immobilized first complexed polymerases are in fluid communication with each other to permit flowing a solution of reagents (e.g., enzymes including sequencing polymerases, multivalent molecules, nucleotides, and/or divalent cations) onto the support so that the plurality of immobilized complexed polymerases on the support are reacted with the solution of reagents in a massively parallel manner.

In some embodiments, the methods for sequencing further comprise step (b): contacting the plurality of first complexed polymerases with a plurality of multivalent molecules to form a plurality of multivalent-complexed polymerases (e.g., binding complexes). In some embodiments, individual multivalent molecules in the plurality of multivalent molecules comprise a core attached to multiple nucleotide arms and each nucleotide arm is attached to a nucleotide (e.g., nucleotide unit) (e.g., FIGS. 22-25). In some embodiments, the contacting of step (b) is conducted under a condition suitable for binding complementary nucleotide units of the multivalent molecules to at least two of the plurality of first complexed polymerases thereby forming a plurality of multivalent-complexed polymerases. In some embodiments, the condition is suitable for inhibiting polymerase-catalyzed incorporation of the complementary nucleotide units into the primers of the plurality of multivalent-complexed polymerases. In some embodiments, the plurality of multivalent molecules comprises at least one multivalent molecule having multiple nucleotide arms (e.g., FIGS. 22-25) each attached with a nucleotide analog (e.g., nucleotide analog unit), where the nucleotide analog includes a chain terminating moiety at the sugar 2' and/or 3' position. In some embodiments, the plurality of multivalent molecules comprises at least one multivalent molecule comprising multiple nucleotide arms each attached with a nucleotide unit that lacks a chain terminating moiety. In some embodiments, at least one of the multivalent molecules in the plurality of multivalent molecules is labeled with a detectable reporter moiety. Any portion of the multivalent molecule can be labeled including the core, nucleotide arm or nucleo-base. In some embodiments, the detectable reporter moiety comprises a fluorophore. In some embodiments, the contacting of step (b) is conducted in the presence of at least one non-catalytic cation comprising strontium, barium and/or calcium.

In some embodiments, the methods for sequencing further comprise step (c): detecting the plurality of multivalent-complexed polymerases. In some embodiments, the detecting includes detecting the multivalent molecules that are bound to the complexed polymerases, where the complementary nucleotide units of the multivalent molecules are bound to the primers but incorporation of the complementary nucleotide units is inhibited. In some embodiments, the multivalent molecules are labeled with a detectable reporter moiety to permit detection. In some embodiments, the labeled multivalent molecules comprise a fluorophore attached to the core, linker and/or nucleotide unit of the multivalent molecules.

In some embodiments, the methods for sequencing further comprise step (d): identifying the base of the complementary nucleotide units that are bound to the plurality of first complexed polymerases, thereby determining the sequence of the concatemer molecule. In some embodiments, the multivalent molecules are labeled with a detectable reporter moiety that corresponds to the particular nucleotide units attached to the nucleotide arms to permit identification of the complementary nucleotide units (e.g., nucleotide base adenine, guanine, cytosine, thymine or uracil) that are bound to the plurality of first complexed polymerases.

In some embodiments, the second stage of the two-stage sequencing method generally comprises nucleotide incorporation. In some embodiments, the methods for sequencing further comprise step (e): dissociating the plurality of multivalent-complexed polymerases and removing the plurality of first sequencing polymerases and their bound multivalent molecules, and retaining the plurality of nucleic acid duplexes.

In some embodiments, the methods for sequencing further comprises step (f): contacting the plurality of the retained nucleic acid duplexes of step (e) with a plurality of second sequencing polymerases, wherein the contacting is conducted under a condition suitable for binding the plurality of second sequencing polymerases to the plurality of the retained nucleic acid duplexes, thereby forming a plurality of second complexed polymerases each comprising a second sequencing polymerase bound to a nucleic acid duplex. In some embodiments, the second sequencing polymerase comprises a recombinant mutant sequencing polymerase.

In some embodiments, the plurality of first sequencing polymerases of step (a) have an amino acid sequence that is 100% identical to the amino acid sequence as the plurality of the second sequencing polymerases of step (f). In some embodiments, the plurality of first sequencing polymerases of step (a) have an amino acid sequence that differs from the amino acid sequence of the plurality of the second sequencing polymerases of step (f).

In some embodiments, the methods for sequencing further comprise step (g): contacting the plurality of second complexed polymerases with a plurality of nucleotides, wherein the contacting is conducted under a condition suitable for binding complementary nucleotides from the plurality of nucleotides to at least two of the second complexed polymerases thereby forming a plurality of nucleotide-complexed polymerases. In some embodiments, the contacting of step (g) is conducted under a condition that is suitable for promoting polymerase-catalyzed incorporation of the bound complementary nucleotides into the primers of the nucleotide-complexed polymerases thereby forming a plurality of nucleotide-complexed polymerases. In some embodiments, the incorporating the nucleotide into the 3' end of the primer in step (g) comprises a primer extension reaction. In some embodiments, the contacting of step (g) is conducted in the presence of at least one catalytic cation comprising magnesium and/or manganese. In some embodiments, the contacting of step (g) is conducted in the presence of magnesium and/or manganese. In some embodiments, the plurality of nucleotides comprises native nucleotides (e.g., non-analog nucleotides) or nucleotide analogs. In some embodiments, the plurality of nucleotides comprises a 2' and/or 3' chain terminating moiety which is removable or is not removable. In some embodiments, the plurality of nucleotides comprises a plurality of nucleotides labeled with detectable reporter moiety. The detectable reporter moiety may comprise a fluorophore. In some embodiments, the fluorophore is attached to the nucleotide base. In some embodiments, the fluorophore is attached to the nucleotide base with a linker which is cleavable/removable from the base or is not removable from the base. In some embodiments, a particular detectable reporter moiety (e.g., fluorophore) that is attached to the nucleotide can correspond to the nucleotide base (e.g., dATP, dGTP, dCTP, dTTP or dUTP) to permit detection and identification of the nucleotide base. In some embodiments, at least one of the nucleotides in the plurality is not labeled with a detectable reporter moiety. In some embodiments, the plurality of nucleotides is not labeled with a detectable reporter moiety.

In some embodiments, the methods for sequencing further comprise step (h): when the nucleotides are labeled with a detectable reporter moiety, step (h) comprises detecting the complementary nucleotides which are incorporated into the primers of the nucleotide-complexed polymerases. In some embodiments, the plurality of nucleotides is labeled with a detectable reporter moiety to permit detection. In some embodiments, in the methods for sequencing concatemer molecules, when the nucleotides are non-labeled then the detecting step is omitted.

In some embodiments, the methods for sequencing further comprise step (i): when the nucleotides are labeled with a detectable reporter moiety, step (i) comprises identifying the bases of the complementary nucleotides which are incorporated into the primers of the nucleotide-complexed polymerases. In some embodiments, the identification of incorporated complementary nucleotides in step (i) can be used to confirm the identity of the complementary nucleotides of the multivalent molecules that are bound to the plurality of first complexed polymerases in step (d). In some embodiments, the identifying of step (i) can be used to determine the sequence of the nucleic acid concatemer molecules. In some embodiments, in the methods for sequencing concatemer molecules, when the nucleotides are non-labeled then the identifying step is omitted.

In some embodiments, the methods for sequencing further comprise step (j): removing the chain terminating moiety from the incorporated nucleotide when step (g) is conducted by contacting the plurality of second complexed poly- merases with a plurality of nucleotides that comprise at least one nucleotide having a 2' and/or 3' chain terminating moiety.

In some embodiments, the methods for sequencing further comprise step (k): repeating steps (a)-(j) at least once. In some embodiments, the sequence of the nucleic acid con- catemer molecules can be determined by detecting and identifying the multivalent molecules that bind the sequenc- ing polymerases but do not incorporate into the 3' end of the primer at steps (c) and (d). In some embodiments, the sequence of the nucleic acid concatemer molecule can be determined (or confirmed) by detecting and identifying the nucleotide that incorporates into the 3' end of the primer at steps (h) and (i).

In some embodiments, in any of the methods for sequenc- ing nucleic acid molecules, the binding of the plurality of first complexed polymerases with the plurality of multiva- lent molecules forms at least one avidity complex, the method comprising the steps: (a) binding a first nucleic acid primer, a first sequencing polymerase, and a first multivalent molecule to a first portion of a concatemer template mol- ecule thereby forming a first binding complex, wherein a first nucleotide unit of the first multivalent molecule binds to the first sequencing polymerase; and (b) binding a second nucleic acid primer, a second sequencing polymerase, and the first multivalent molecule to a second portion of the same concatemer template molecule thereby forming a second binding complex, wherein a second nucleotide unit of the first multivalent molecule binds to the second sequencing polymerase, wherein the first and second binding complexes which include the same multivalent molecule forms an avidity complex. In some embodiments, the first sequencing polymerase comprises any wild type or mutant polymerase described herein. In some embodiments, the second sequencing polymerase comprises any wild type or mutant polymerase described herein. The concatemer template mol- ecule comprises tandem repeat sequences of a sequence of interest and at least one universal sequencing primer binding site. The first and second nucleic acid primers can bind to a sequencing primer binding site along the concatemer tem- plate molecule. Exemplary multivalent molecules are shown in FIGS. 22-25.

In some embodiments, in any of the methods for sequenc- ing nucleic acid molecules, wherein the method includes binding the plurality of first complexed polymerases with the plurality of multivalent molecules to form at least one avidity complex, the method comprising the steps: (a) con- tacting the plurality of sequencing polymerases and the plurality of nucleic acid primers with different portions of a concatemer nucleic acid concatemer molecule to form at least first and second complexed polymerases on the same concatemer template molecule; (b) contacting a plurality of multivalent molecules to the at least first and second com- plexed polymerases on the same concatemer template mol- ecule, under conditions suitable to bind a single multivalent molecule from the plurality to the first and second com- plexed polymerases, wherein at least a first nucleotide unit of the single multivalent molecule is bound to the first complexed polymerase which includes a first primer hybrid- ized to a first portion of the concatemer template molecule thereby forming a first binding complex (e.g., first ternary complex), and wherein at least a second nucleotide unit of the single multivalent molecule is bound to the second complexed polymerase which includes a second primer hybridized to a second portion of the concatemer template molecule thereby forming a second binding complex (e.g., second ternary complex), wherein the contacting is con- ducted under a condition suitable to inhibit polymerase- catalyzed incorporation of the bound first and second nucleotide units in the first and second binding complexes, and wherein the first and second binding complexes which are bound to the same multivalent molecule forms an avidity complex; and (c) detecting the first and second binding complexes on the same concatemer template molecule, and (d) identifying the first nucleotide unit in the first binding complex thereby determining the sequence of the first por- tion of the concatemer template molecule, and identifying the second nucleotide unit in the second binding complex thereby determining the sequence of the second portion of the concatemer template molecule. In some embodiments, the plurality of sequencing polymerases comprise any wild type or mutant sequencing polymerase described herein. The concatemer template molecule comprises tandem repeat sequences of a sequence of interest and at least one universal sequencing primer binding site. The plurality of nucleic acid primers can bind to a sequencing primer binding site along the concatemer template molecule. Exemplary multivalent molecules are shown in FIGS. 22-25.

Sequencing-by-Binding

In some aspects, the present disclosure provides methods for sequencing any of the immobilized concatemer mol- ecules described herein, wherein the sequencing methods comprise a sequencing-by-binding (SBB) procedure which employs non-labeled chain-terminating nucleotides. In some embodiments, the sequencing-by-binding (SBB) method comprises the steps of (a) sequentially contacting a primed template nucleic acid with at least two separate mixtures under ternary complex stabilizing conditions, wherein the at least two separate mixtures each include a polymerase and a nucleotide, whereby the sequentially contacting results in the primed template nucleic acid being contacted, under the ternary complex stabilizing conditions, with nucleotide cog- nates for first, second and third base type base types in the template; (b) examining the at least two separate mixtures to determine whether a ternary complex formed; and (c) iden- tifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b); (d) adding a next correct nucleotide to the primer of the primed template nucleic acid after step (b), thereby producing an extended primer; and (e) repeating steps (a) through (d) at least once on the primed template nucleic acid that comprises the extended primer. Exemplary sequencing-by-binding methods are described in U.S. Pat. Nos. 10,246,744 and 10,731,141 (where the contents of both patents are hereby incorporated by reference in their entire- ties).

Methods for Sequencing using Phosphate-Chain Labeled Nucleotides

The present disclosure provides methods for sequencing using immobilized sequencing polymerases which bind non-immobilized template molecules, wherein the sequencing reactions are conducted with phosphate-chain labeled nucleotides. In some embodiments, the covalently closed circular library molecule (600) can serve as a non-immobilized template molecule. In some embodiments, the sequencing methods comprise step (a): providing a support having a plurality of sequencing polymerases immobilized thereon. In some embodiments, the sequencing polymerase comprises a processive DNA polymerase. In some embodiments, the sequencing polymerase comprises a wild type or mutant DNA polymerase, including, for example and without limitation, a Phi29 DNA polymerase. In some embodiments, the support comprise a plurality of separate compartments and a sequencing polymerase is immobilized to the bottom of a compartment. In some embodiments, the separate compartments comprise a silica bottom through which light can penetrate. In some embodiments, the separate compartments comprise a silica bottom configured with a nanophotonic confinement structure comprising a hole in a metal cladding film (e.g., aluminum cladding film). In some embodiments, the hole in the metal cladding has a small aperture, for example, approximately 70 nm. In some embodiments, the height of the nanophotonic confinement structure is approximately 100 nm. In some embodiments, the nanophotonic confinement structure comprises a zero-mode waveguide (ZMW). In some embodiments, the nanophotonic confinement structure contains a liquid.

In some embodiments, the sequencing method further comprises step (b): contacting the plurality of immobilized sequencing polymerases with a plurality of single stranded circular nucleic acid template molecules (e.g., covalently closed circular library molecules (600)) and a plurality of oligonucleotide sequencing primers, under a condition suitable for individual immobilized sequencing polymerases to bind a single stranded circular template molecule, and suitable for individual sequencing primers to hybridize to individual single stranded circular template molecules, thereby generating a plurality of polymerase/template/primer complexes. In some embodiments, the individual sequencing primers hybridize to a universal sequencing primer binding site on the single stranded circular template molecule.

In some embodiments, the sequencing method further comprises step (c): contacting the plurality of polymerase/template/primer complexes with a plurality of phosphate chain labeled nucleotides each comprising an aromatic base, a five carbon sugar (e.g., ribose or deoxyribose), and phosphate chain comprising 3-20 phosphate groups (e.g., about 3, 4, 5, 6, 7, 8, 9, 10, 11, 12, 13, 14, 15, 16, 17, 18, 19, or 20 phosphate groups), where the terminal phosphate group is linked to a detectable reporter moiety (e.g., a fluorophore). The first, second and third phosphate groups can be referred to as alpha, beta, and gamma phosphate groups. In some embodiments, a particular detectable reporter moiety which is attached to the terminal phosphate group corresponds to the nucleotide base (e.g., dATP, dGTP, dCTP, dTTP or dUTP) to permit detection and identification of the nucleobase. In some embodiments, the plurality of polymerase/template/primer complexes are contacted with the plurality of phosphate chain labeled nucleotides under a condition suitable for polymerase-catalyzed nucleotide incorporation. In some embodiments, the sequencing polymerases are capable of binding a complementary phosphate chain labeled nucleotide and incorporating the complementary nucleotide opposite a nucleotide in a template molecule. In some embodiments, the polymerase-catalyzed nucleotide incorporation reaction cleaves between the alpha and beta phosphate groups thereby releasing a multi-phosphate chain linked to a fluorophore.

In some embodiments, the sequencing method further comprises step (d): detecting the fluorescent signal emitted by the phosphate chain labeled nucleotide that is bound by the sequencing polymerase, and incorporated into the terminal end of the sequencing primer. In some embodiments, step (d) further comprises identifying the phosphate chain labeled nucleotide that is bound by the sequencing polymerase, and incorporated into the terminal end of the sequencing primer.

In some embodiments, the sequencing method further comprises step (d): repeating steps (c)-(d) at least once. In some embodiments, sequencing methods that employ phosphate chain labeled nucleotides can be conducted according to the methods described in U.S. Pat. Nos. 7,170,050; 7,302,146; and/or 7,405,281.

A Conventional Pooling Workflow for Multiplexing

In one embodiment, a method for preparing a multiplex mixture of sequences-of-interest isolated from a plurality of sample sources, comprises: (a) providing two or more populations of single-stranded nucleic acid library molecules (100), each population of library molecules (100) contained in a separate compartment, wherein the nucleic acid library molecules in a given population comprise (i) a sequence of interest (110); (ii) a universal adaptor sequence having a binding sequence for a forward sequencing primer (120); and (iii) a universal adaptor sequence having a binding sequence for a reverse sequencing primer (130) (e.g., FIG. 1).

In some embodiments, the method for preparing a multiplex mixture of sequences-of-interest isolated from a plurality of sample sources further comprises step (b): providing a plurality of double-stranded splint adaptors (200) wherein individual double-stranded splint adaptors (200) comprise a first splint strand (300) hybridized to a second splint strand (400) (e.g., FIG. 2). In some embodiments, the second splint strand (400) comprises at least one sample index sequence and optionally a short random sequence NNN.

In some embodiments, the method for preparing a multiplex mixture of sequences-of-interest isolated from a plurality of sample sources further comprises step (c): contacting in the separate compartments the population of single-stranded nucleic acid library molecules (100) with an allotment of the plurality of double-stranded splint adaptors (200), wherein the contacting is conducted under a condition suitable to hybridize portions of the first splint strand (300) to portions of the library molecules (100) thereby circularizing the library molecules to generate a population of library-splint complexes (500), such that the region (320) of an individual first splint strand is hybridized to the universal adaptor sequence for a forward sequencing primer binding site (120) of an individual library molecule (100), and the region (330) of the individual first splint strand is hybridized to the universal adaptor sequence for a reverse sequencing primer binding site (130) of the individual library molecule (100), wherein each of the library-splint complexes (500) comprise a first nick between the 5' end of the library molecule and the 3' end of the second splint strand (300), wherein each of the library-splint complexes (500) comprises a second nick between the 5' end of the second splint strand (300) and the 3' end of the library molecule (100), and wherein the first and second nicks are enzymatically ligatable (e.g., see FIGS. 3 and 4).

In some embodiments, the method for preparing a multiplex mixture of sequences-of-interest isolated from a plurality of sample sources further comprises step (d): contacting in the separate compartments the populations of library-splint complexes (500) with a ligase, under a condition suitable to enzymatically ligate the first and second nicks, thereby generating a population of covalently closed circular library molecules (600) each hybridized to the first splint strand (300) (e.g., see FIG. 4).

In some embodiments, the method for preparing a multiplex mixture of sequences-of-interest isolated from a plurality of sample sources further comprises step (e): pooling together the population of covalently closed circular library molecules (600) from the separate compartments to generate a multiplex mixture of covalently closed circular library molecules (600) which comprise the multiplex mixture of sequences-of-interest isolated from a plurality of sample sources.

In some embodiments, the sequences of interest can be isolated from two or more different sample sources (e.g., 2-10, 10-50, 50-100, 100-250, any range therebetween, or more than 250 different sample sources). Exemplary nucleic acid sources include naturally-occurring, recombinant, or chemically-synthesized sources. Exemplary nucleic acid sources include single cells, a plurality of cells, tissue, biological fluid, environmental sample or whole organism. Exemplary nucleic acid sources include fresh, frozen, fresh-frozen or archived sources (e.g., formalin-fixed paraffin-embedded; FFPE). The skilled artisan will recognize that the nucleic acids can be isolated from many other sources. The sequences of interest in a given population have the same or different sequences.

In some embodiments, the number of populations of single-stranded nucleic acid library molecules (100) of step (a) can be 2-10, 10-50, 50-100, 100-250, any range therebetween, or more than 250 different population of single-stranded nucleic acid library molecules (100). In some embodiments, any number of different populations of covalently closed circular library molecules (600) can be pooled together in step (e), for example 2-10, 10-50, 50-100, 100-200, any range therebetween, or more than 200 different populations of covalently closed circular library molecules (600) can be pooled together.

The skilled artisan will recognize that any number of separate compartments can be used in step (a) (e.g., 2-10, 10-50, 50-100, 100-250, any range therebetween, or more separate compartments) (e.g., multi-well plate such as for example a 96-well plate).

In some embodiments, the 3' end of the first splint strand (300) that are hybridized to the covalently closed circular library molecules (600) of step (d) or (e) comprise an extendible 3'OH ends which can serve as an initiation point for a primer extension reaction (e.g., rolling circle amplification reaction).

In some embodiments, at step (d) or (e) the population of covalently closed circular library molecules (600) that are hybridized to the first splint strand (300) can optionally be reacted with at least one exonuclease enzyme to remove the plurality of first splint strands (300) and retaining the plurality of covalently closed circular library molecules (600). In some embodiments, the at least one exonuclease enzyme comprises exonuclease I, thermolabile exonuclease I and/or T7 exonuclease.

In some embodiments, the single-stranded nucleic acid library molecules (100) of step (a) further comprise any one or any combination of two or more of: a universal binding sequence for a forward amplification primer; a universal binding sequence for a reverse amplification primer; and/or a universal binding sequence for a compaction oligonucleotide.

Sample Indexes for Improved Base Calling

Generally, it is desirable to prepare nucleic acid libraries that will be distributed onto a support (e.g., coated flowcell), where the library molecules are converted into template molecules that are immobilized at a high density to the support for massively parallel sequencing. For template molecules that are immobilized at high densities at random locations on the support, the challenge of resolving high density fluorescent images for accurate base calling during sequencing runs becomes challenging.

The nucleotide diversity of a population of immobilized template molecules refers to the relative proportion of nucleotides A, G, C and T that are present in each sequencing cycle. In some embodiments, an optimal high diversity template molecule includes a sequence-of-interest (insert) regions having approximately equal proportions of all four nucleotides represented in each cycle of a sequencing run. In some embodiments, low diversity template molecules include sequence-of-interest (insert) regions having a high proportion of certain nucleotides and low proportion of other nucleotides. To overcome the problem of low diversity template molecules, a small amount of a high diversity molecules prepared from PhiX bacteriophage may be mixed with the template molecules-of-interest (e.g., PhiX spike-in library) and sequenced together, e.g., on the same flowcell. While the PhiX spike-in library provides nucleotide diversity, it also occupies space on the flowcell, thereby replacing the template molecules carrying the sequence-of-interest and reduces the amount of sequencing data obtainable from the template molecule (e.g., reduces sequencing throughput).

Another method to overcome the problem of low diversity template molecules is to prepare template molecules having at least one sample index sequence that is designed to be color-balanced. However, it may be desirable to design a large number of sample index sets, for example a set of single index sample sequences or paired index sample sequences for 16-plex, 24-plex, 96-plex or larger plexy levels. It can be challenging to design sample index sequences, as a single or paired sample indexes, for large sample index sets, where all of the sample index sequences are color-balanced (e.g., see FIGS. 19 and 20).

As described herein, an alternative method to overcome the challenges of sequencing low diversity template molecules (e.g., at high density on the support) is to prepare template molecules having at least one sample index sequence comprising a short random sequence (e.g., NNN) linked directly to a sample index sequence, where the short random sequence (NNN) provides nucleotide diversity and color balance. In some embodiments, a sample index sequence includes a short random sequence (NNN) linked directly to a sample index sequence. In some embodiments, the short random sequence (NNN) is upstream or downstream of the sample index sequence. Some exemplary sample index sequences include but are not limited to: NNNGTAGGAGCC; NNNCCGCTGCTA; NNNAACAACAAG; NNNGGTGGTCTA; NNNTTGGC-CAAC; NNNCAGGAGTGC; and NNNATCACACTA (e.g., see Table 3).

The skilled artisan will recognize that the universal sample index can be any length and have any sequence that can be used to distinguish sequences of interest obtained from different sample sources in a multiplex assay. In a population of a given sample index, for example and without limitation, NNNGTAGGAGCC, the population contains a mixture of individual sample index molecules each carrying the same universal sample index sequence (e.g., GTAG-GAGCC) and a different short random sequence (e.g., NNN), where up to 64 different short random sequences may be present in the population of the given sample index.

Figure 19:
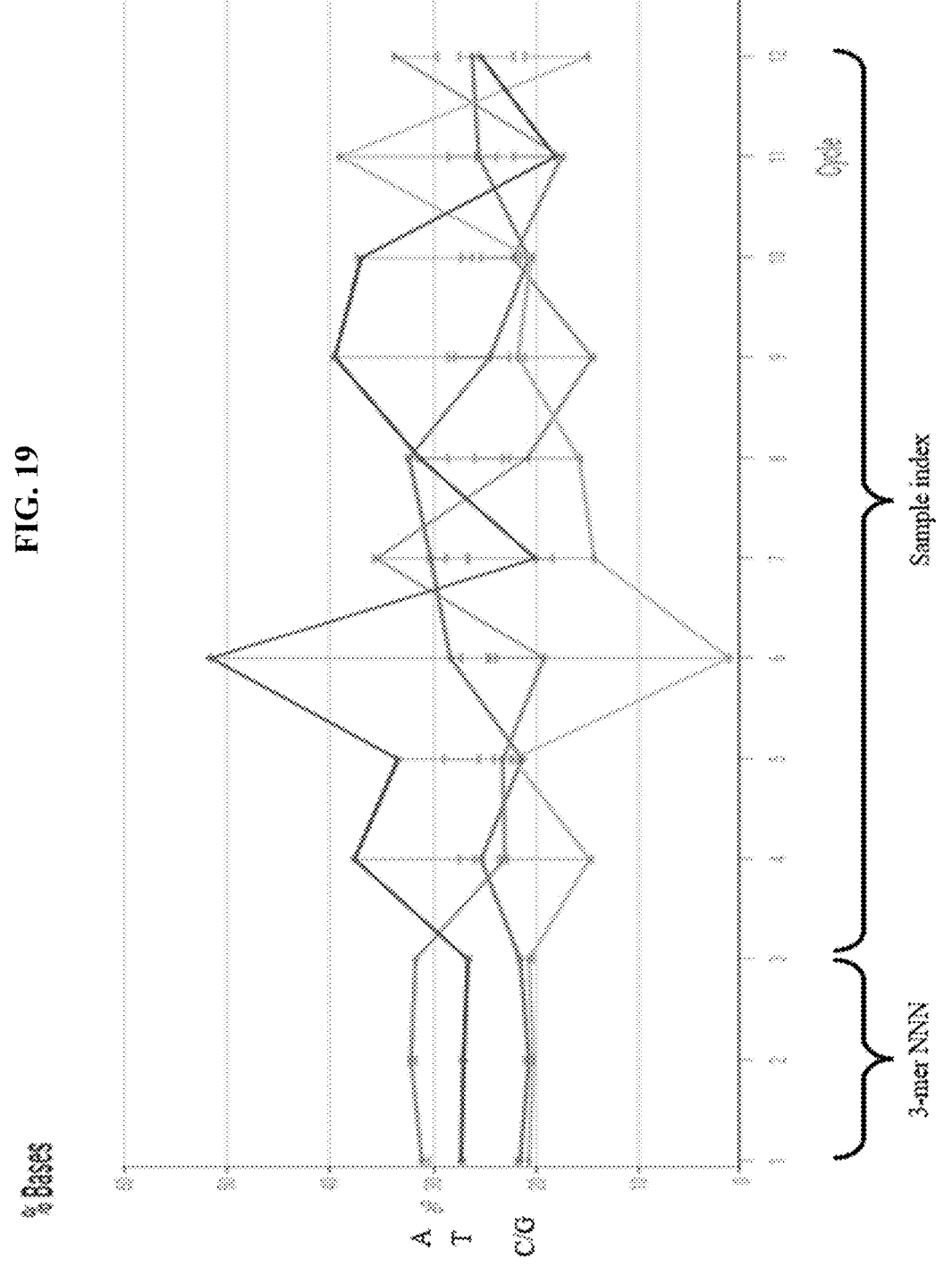
FIG. 19 is a graph showing the nucleotide base diversity of a sample index sequence which includes a short 3-mer random sequence (NNN). The graph shows a nucleotide diversity of the 3-mer random sequence (NNN) of approximately 30% for A and T base calls, and approximately 20% for C and G base calls.
Figure 20:
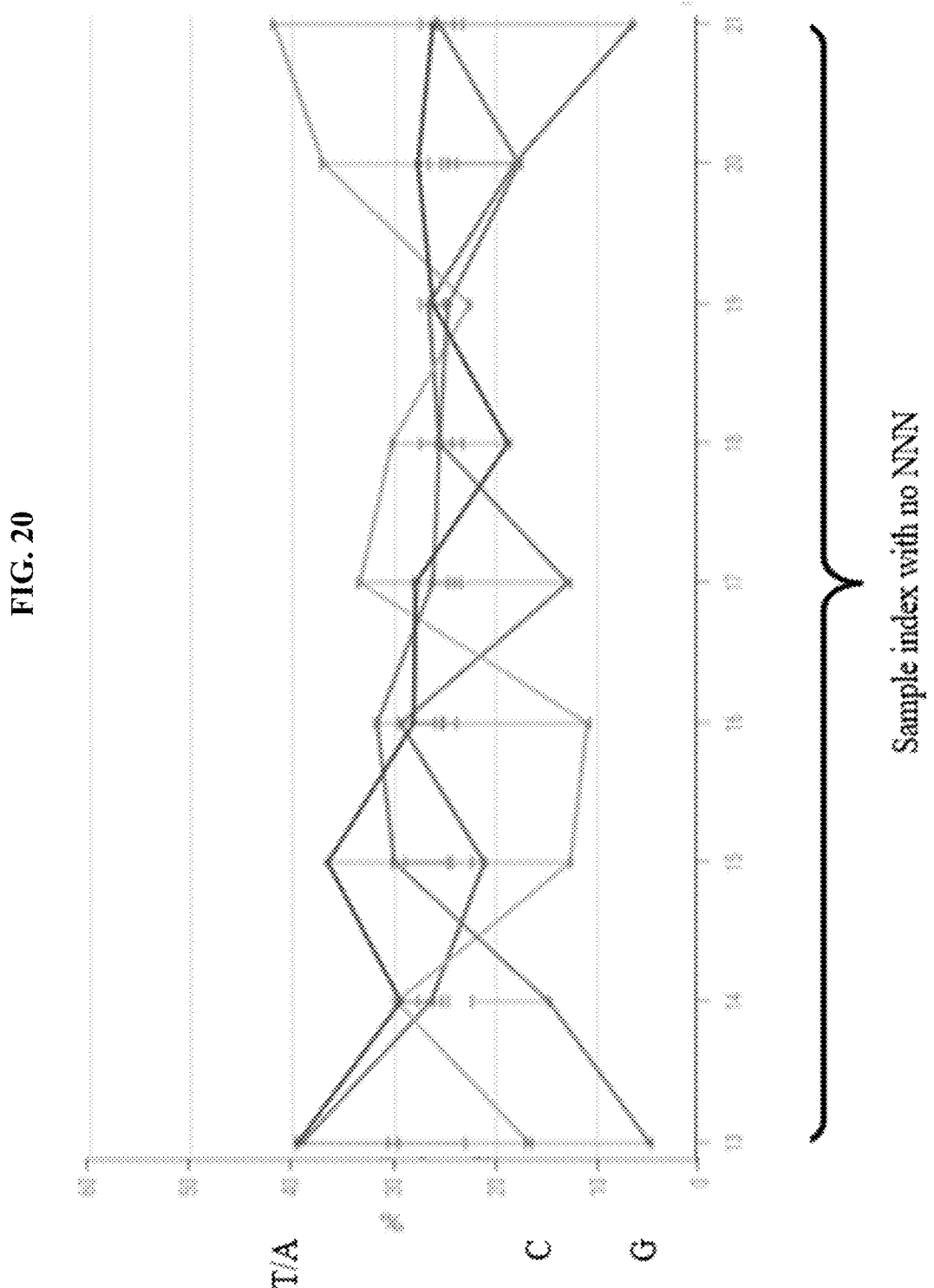
FIG. 20 is a graph showing the nucleotide base diversity of a sample index sequence which lacks a short 3-mer random sequence (NNN). The graph shows a nucleotide diversity of approximately 40% for A and T base calls, approximately 15% for C base calls, and approximately 5% for G base calls.

In a population of sample-indexed template molecules, the short random sequence (NNN) of the sample index can provide high nucleotide diversity which includes approximately equal proportions of all four nucleotides (e.g., A, G, C, T and/or U) that will be represented in each cycle of a sequencing run (see FIGS. 19 and 20). The high nucleotide diversity of the short random sequence also can provide color balance during each cycle of the sequencing run. An advantage of designing sample indexes to include a short random sequence (e.g., NNN) is that, in a low-plexy population of template molecules (e.g., 2-plex or 4-plex), the universal sample index sequences that identify the two or four different samples need not exhibit nucleotide diversity (e.g., see FIGS. 19 and 20). Additionally, the nucleotide diversity of the short random sequence (e.g., NNN) can obviate the need to include a PhiX spike-in library, or permits use of a reduced amount of PhiX spike-in library to be distributed onto the flowcell and sequenced.

The template molecules can include a first sample index sequence which includes a short random sequence (NNN), and a second sample index sequence which lack a short random sequence. In some embodiments, the sequencing data from only the sample index sequence with the short random sequence (NNN) is used for polony mapping and template registration because the short random sequence (e.g., NNN) provides sufficient nucleotide diversity and color balance. Both types of sample indexes can be used to distinguish sequences of interest obtained from different sample sources in a multiplex assay.

The order of sequencing the sequence-of-interest region and the sample index region(s) can also be used to improve the challenges of sequencing low diversity template molecules. For example, and without limitation, the sample index region can be sequenced first before sequencing the sequence-of-interest region, and the sample index sequence can be associated with the sequence-of-interest region. For example, and without limitation, the sample index region can be sequenced first including sequencing the short random sequence (e.g., NNN) and optionally sequencing at least a portion of the universal sample index), and then sequencing the sequence-of-interest region. In a population of sample indexed template molecules, the short random sequence (e.g., NNN) can provide nucleotide diversity which may not be provided by the sequence-of-interest regions of the template molecules. The sequence of the sample index can provide improved nucleotide diversity and color balance for polony mapping and template registration.

Additionally, when sequencing the sample index region first, the length of the sequenced sample index region may be relatively short (e.g., less than 30 nucleotides in length) so that de-hybridization of the product of the sequenced sample index region is more complete. Gentler de-hybridization conditions can be used to remove most or all of the product of the sequenced sample index region which reduces the level of residual signals from any sequencing products remaining hybridized to the template molecules. By contrast, the sequence-of-interest region is typically much longer than the sample index region (e.g., more than 100 nucleotides in length). In some embodiments, when the sequence-of-interest region is sequenced before the sample index region, the product of the sequenced sequence-ofinterest region must be subjected to harsher de-hybridization conditions to remove any products remaining hybridized to the template molecules which may damage the template molecules.

In some aspects, the present disclosure provides template molecules each comprising at least one sample index sequence that can be used to distinguish sequences of interest obtained from different sample sources in a multiplex assay, where the at least one sample index sequence comprises a short random sequence (e.g., NNN) linked to a universal sample index sequence. The at least one sample index sequence can include sequence diversity for improved base calling. The at least one sample index sequence can be used to improve base calling accuracy.

In some embodiments, the short random sequence (e.g., NNN) is positioned upstream of the universal sample index sequence so that during a sequencing run the random sequence portion is sequenced before the universal sample index sequence. In some embodiments, the short random sequence is positioned downstream of the universal sample index sequence so that during a sequencing run the random portion is sequenced after the universal sample index sequence.

In some embodiments, in the random sequence each base "N" at a given position is independently selected from A, G, C, T or U. In some embodiments, the random sequence lacks consecutive repeat sequences having 2 or 3 of the same nucleo-base, for example, and without limitation, AA, TT, CC, GG, UU, AAA, TTT, CCC, GGG or UUU. In some embodiments, in a population of template molecules the universal sample index sequences include a short random sequence having a high diversity sequence which includes approximately equal proportions of all four nucleotides (e.g., A, G, C, T and/or U) that will be represented in each cycle of a sequencing run.

In some embodiments, the short random sequence (e.g., NNN) comprises 3-20 nucleotides, 3-10 nucleotides, 3-8 nucleotides, 3-6 nucleotides, 3-5 nucleotides, or 3-4 nucleotides, or any range therebetween.

In some embodiments, the short random sequence (e.g., NNN) includes, but is not limited to, AGC, AGT, GAC, GAT, CAT, CAG, TAG, TAC. The skilled artisan will recognize that many more random sequences can be prepared (e.g., 64 possible combinations) where each base "N" at a given position in the random sequence is independently selected from A, G, C, T or U.

In some embodiments, the universal sample index sequence comprises 5-20 nucleotides, 7-18 nucleotides, or 9-16 nucleotides, or any range therebetween.

In some embodiments, individual sample index sequences in a population of sample indexes comprise a universal sample index sequence and a short random sequence (e.g., NNN). In some embodiments, the short random sequences in the population of sample index sequences have an overall base composition of about 25% or about 20-30% of all four nucleotide bases (e.g., A, G, C and T/U) to provide nucleotide diversity at each sequencing cycle during sequencing the short random sequence (e.g., NNN).

In some embodiments, in the population of sample index sequences the proportion of adenine (A) at any given position in the short random sequence is about 20-30%, about 15-35%, about 10-40%, or any range therebetween. In some embodiments, in the population of sample index sequences the proportion of guanine (G) at any given position in the short random sequence is about 20-30%, about 15-35%, about 10-40%, or any range therebetween. In some embodiments, in the population of sample index sequences the proportion of cytosine (C) at any given position in the short random sequence is about 20-30%, about 15-35%, about 10-40%, or any range therebetween In some embodiments, in the population of sample index sequences the proportion of thymine (T) or uracil (U) at any given position in the short random sequence is about 20-30%, about 15-35%, about 10-40%, or any range therebetween.

In some embodiments, in the population of sample index sequences the proportion of adenine (A) and thymine (T), or the proportion of adenine (A) and uracil (U), at any given position in the short random sequence is about 10-65%. In some embodiments, in the population of sample index sequences the proportion of guanine (G) and cytosine (C) at any given position in the short random sequence is about 10-65%.

In some embodiments, in the population of sample index sequences the sequence diversity of the short random sequences ensures that no sequencing cycle is presented with fewer than four different nucleotide bases during sequencing at least the short random sequence (e.g., NNN).

In some embodiments, the random sequence (e.g., NNN) provides a balanced ratio of nucleo-bases adenine, cytosine, guanine, thymine and/or uracil (see FIG. 19). In some embodiments, in a population of sample-indexed template molecules, the random sequence (e.g., NNN) together with at least a portion of the universal sample index sequence provide a balanced ratio of nucleo-bases adenine, cytosine, guanine, thymine and/or uracil represented in each cycle of a sequencing run.

In some embodiments, a sequencing reaction includes use of polymerases and nucleotides (e.g., nucleotide analogs) that are labeled with a different fluorophore that corresponds to the nucleo-base. In some embodiments, sequencing the random sequence (e.g., NNN) using labeled nucleotides provides a balanced ratio of fluorescent colors that correspond to the nucleo-bases adenine, cytosine, guanine, thymine and/or uracil in each cycle of a sequencing run. In some embodiments, sequencing the random sequence (e.g., NNN) and at least a portion of the universal sample index sequence using labeled nucleotides provides a balanced ratio of fluorescent colors that correspond to nucleo-bases adenine, cytosine, guanine, thymine and/or uracil (e.g., see FIG. 19). The labeled nucleotides emit fluorescent signals during the sequencing reactions. In some embodiments, the sequencing reaction is conducted on a sequencing apparatus having a detector that captures fluorescent images from sequencing reactions on the immobilized template molecules. The sequencing apparatus can be configured to relay the fluorescent imaging data captured by the detector to a computer system that is programmed to determine the location (e.g., mapping) of the immobilized template molecules on the flowcell. The computer system can generate a map of the locations of the immobilized template molecules based on the fluorescent imaging data of only the random sequence (e.g., NNN), or based on the random sequence (e.g., NNN) and at least a portion the universal sample index sequence. Thus, the few numbers of sequencing cycles used to sequence the random sequence (e.g., NNN) and optionally a portion of the universal sample index sequence can be used to generate a map of the location of the immobilized template molecules. The computer system can be configured to extract the fluorescent color and intensity of only the random sequence (e.g., NNN), or the random sequence (e.g., NNN) and at least a portion of the universal sample index sequence. The computer system can be configured to use the location of a given immobilized template molecule and the fluorescent color and intensity associated with the given template molecule (which were established while sequencing the random sequence) for base calling while sequencing the insert region (110). The computer system can be configured to detect phasing and pre-phasing while sequencing the random sequence (e.g., NNN) and the universal sample index sequence, and the insert region (110). In some embodiments, the balanced ratio of fluorescent colors provided by the random sequence (e.g., NNN) at each sequencing cycle can improve the quality of the data which is processed from the fluorescent images captured by the detector, and can in turn improve the capability by the computer system to determine the location of the immobilized template molecules on the flowcell, and the color and intensity, all of which can improve base calling accuracy and quality scores of the sequenced insert region (110).

In some embodiments, a sequencing reaction includes use of polymerases and multivalent molecules that are labeled with a different fluorophore that corresponds to the nucleo-base (e.g., adenine, guanine, cytosine, thymine, or uracil) of the nucleotide units that are attached to the nucleotide arms in a given multivalent molecule. In some embodiments, the core of individual multivalent molecules is attached to a fluorophore which corresponds to the nucleotide units (e.g., adenine, guanine, cytosine, thymine, or uracil) that are attached to the nucleotide arms in a given multivalent molecule (e.g., see FIGS. 22-25). In some embodiments, at least one of the nucleotide arms of the multivalent molecule comprises a linker and/or nucleotide base that is attached to a fluorophore, and wherein the fluorophore which is attached to a given linker or nucleotide base corresponds to the nucleotide base (e.g., adenine, guanine, cytosine, thymine, or uracil) of the nucleotide arm. In some embodiments, sequencing the random sequence (e.g., NNN) using labeled multivalent molecules provides a balanced ratio of fluorescent colors that correspond to the nucleo-bases adenine, cytosine, guanine, thymine and/or uracil in each cycle of a sequencing run. In some embodiments, sequencing the random sequence (e.g., NNN) and at least a portion of the universal sample index sequence using labeled multivalent molecules provides a balanced ratio of fluorescent colors that correspond to nucleo-bases adenine, cytosine, guanine, thymine and/or uracil (e.g., see FIG. 19). The labeled multivalent molecules emit fluorescent signals during the sequencing reactions. In some embodiments, the sequencing reaction is conducted on a sequencing apparatus having a detector that captures fluorescent images from sequencing reactions on the immobilized template molecules. The sequencing apparatus can be configured to relay the fluorescent imaging data captured by the detector to a computer system that is programmed to determine the location (e.g., mapping) of the immobilized template molecules (polonies) on the flowcell. The computer system can generate a map of the locations of the immobilized template molecules based on the fluorescent imaging data of only the random sequence (e.g., NNN), or based on the random sequence (e.g., NNN) and at least a portion of the universal sample index sequence. Thus, the few numbers of sequencing cycles used to sequence the random sequence (e.g., NNN) and optionally a portion of the universal sample index sequence can be used to generate a map of the location of the immobilized template molecules. The computer system can be configured to extract the fluorescent color and intensity of only the random sequence (e.g., NNN) or the random sequence (e.g., NNN) and the universal sample index sequence. The computer system can be configured to use the location of a given immobilized template molecule and the fluorescent color and intensity associated with the given template molecule (which were established while sequencing the random sequence) for base calling while sequencing the insert region (110). The computer system can be configured to detect phasing and pre-phasing while sequencing the random sequence (e.g., NNN) and the universal sample index sequence, and the insert region (110). In some embodiments, the balanced ratio of fluorescent colors provided by the random sequence (e.g., NNN) at each sequencing cycle can improve the quality of the data which is processed from the fluorescent images captured by the detector, and can in turn improve the capability by the computer system to determine the location of the immobilized template molecules on the flowcell, and the color and intensity, all of which can improve base calling accuracy and quality scores of the sequenced insert region (110).

A First Embodiment: Order of Sequencing Sample Index Sequences

In some embodiments, a covalently closed circular library molecule (600) comprises: (i) a first sub-region (411) comprising a universal binding sequence for an immobilized surface pinning primer; (ii) a second sub-region (412) comprising a short random sequence (NNN) and a sample index sequence; (iii) a third sub-region (413) comprising a universal binding sequence for an immobilized surface capture primer; (iv) a universal binding sequence for a reverse sequencing primer (130); (v) an insert sequence (110); and (vi) a universal binding sequence for a forward sequencing primer (120) (e.g., see FIG. 4). In some embodiments, a plurality of covalently closed circular library molecules (600) are subjected to rolling circle amplification by hybridizing the plurality of covalently closed circular library molecules (600) to a plurality of surface capture primers immobilized to a support where the surface capture primers initiate amplification thereby generating a plurality of immobilized concatemers each having tandem repeat sequences of its cognate covalently closed circular library molecule (600). In some embodiments, the rolling circle amplification is conducted in the presence of a plurality of compaction oligonucleotides which can hybridize to the concatemers at their universal binding sequence for a surface pinning primer, universal binding sequence for a surface capture primer, universal binding sequence for a reverse sequencing primer and/or universal binding sequence for a forward sequencing primer. In some embodiments, the plurality of immobilized capture primers lacks uracil bases. In some embodiments, the rolling circle amplification reaction includes a plurality of nucleotides including dATP, dGTP, dCTP, dTTP and dUTP, to generate a plurality of immobilized concatemers wherein individual concatemer molecules comprise randomly-distributed uracil bases. In some embodiments, at least a portion of the immobilized concatemer is sequenced.

In some embodiments, the order of sequencing comprises: (1) sequencing the short random sequence (NNN) and a sample index sequence (412) of the concatemers; and (2) sequencing the insert region (110) of the concatemers. In some embodiments, the order of sequencing further comprises: (3) conducting a pairwise turn reaction so that the immobilized concatemer molecule is replaced with an immobilized second strand that is complementary to the concatemer molecule; and (4) sequencing the insert region (110) on the second strand. In some embodiments, sequencing the short random sequence (NNN) and the sample index sequence (412) may provide sufficient nucleotide diversity and color balance for polony mapping and concatemer registration.

In some embodiments, methods for sequencing the concatemer molecules immobilized to the support comprises step (a): hybridizing the concatemer molecules with a first plurality of soluble sequencing primers that hybridize to at least a portion of the third sub-region (413) and sequencing the short random sequence (e.g., NNN) and the universal sample index sequence of third sub-region (413) thereby generating a plurality of sample index extension products that are hybridized to the immobilized concatemer molecules, wherein the plurality of sample index extension products are complementary to the short random sequence (e.g., NNN) and the universal sample index sequence.

In some embodiments, the methods for sequencing further comprise step (b): removing the first plurality of sample index extension products and retaining the immobilized concatemer molecules.

In some embodiments, the methods for sequencing further comprise step (c): hybridizing the retained immobilized concatemer molecules with a second plurality of soluble sequencing primers that hybridize to the universal binding sequence for the forward sequencing primer (120) and sequencing the insert region (110) thereby generating a plurality of insert sequence extension products that are hybridized to the immobilized concatemer molecules.

In some embodiments, the methods for sequencing further comprise step (d): replacing the plurality of insert sequence extension products that are hybridized to the immobilized concatemer molecules by conducting a primer extension reaction using strand-displacing polymerases and a plurality of nucleotides to generate second strand extension products that are hybridized to the immobilized concatemer molecules including the immobilized capture primer.

In some embodiments, the methods for sequencing further comprise step (e): removing the immobilized concatemer molecules by generating abasic sites in the immobilized concatemer molecules at the uracil sites and generating gaps at the abasic sites thereby generating gap-containing concatemer molecules while retaining the second strand extension products that were generated in step (d) where individual second strand extension products are retained by hybridization to an immobilized capture primer. In some embodiments, pairwise turn is achieved by conducting steps (d) and (e).

In some embodiments, the methods for sequencing further comprise step (f): hybridizing the retained second strand extension products with a third plurality of soluble sequencing primers that hybridize to universal binding sequence for a reverse sequencing primer (130) and sequencing at least of portion of the insert region (110).

In some embodiments, the methods for sequencing further comprise: assigning the sequence of (i) the insert region (110) to (ii) the sample index sequence, thereby identifying the insert region as being obtained from a first source. In some embodiments, the assigning can be conducted after step (c) and/or (f).

In some embodiments, the removing of the plurality of sequencing extension products of step (b) can be conducted using a denaturation reagent comprising SSC (e.g., saline-sodium citrate) buffer with or without formamide, at a temperature that promotes nucleic acid denaturation, such as for example, 50-90° C. In some embodiments, the removing of the plurality of sequencing extension products of step (b) can be conducted using a de-hybridization reagent at a temperature that promotes nucleic acid denaturation, such as for example, 50-90° C. In some embodiments, the de-hybridization reagent comprises a pH buffering agent, a reducing agent, a monovalent salt, and a crowding agent. In some embodiments, the de-hybridization reagent further comprises a chaotropic agent.

In some embodiments, the sequencing of steps (a), (c) and (f) include conducting any of the sequencing methods described herein that employ sequencing polymerases and detectably labeled nucleotide analogs. In some embodiments, the sequencing of steps (a), (c) and (f) include conducting any of the two-stage sequencing methods described herein that employ sequencing polymerases, detectably labeled multivalent molecules, and labeled nucleotide analogs or non-labeled nucleotide analogs. In some embodiments, the sequencing of steps (a), (c) and (f) include conducting any of the sequencing-by-binding methods or any of the sequencing methods that employ phosphate-chain labeled nucleotides described herein.

In some embodiments, the density of the plurality of concatemer molecules immobilized to the support is about $10^2$-$10^{15}$ per mm$^2$ (e.g., $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$). In some embodiments, the plurality of concatemer molecules is immobilized at random locations on the support. In some embodiments, the plurality of concatemer molecules is immobilized on the support in a predetermined pattern.

A Second Embodiment: Order of Sequencing Sample Index Sequences

In some embodiments, a covalently closed circular library molecule (600) comprises: (i) a first sub-region (411) comprising a universal binding sequence for an immobilized surface pinning primer; (ii) a second sub-region (412) comprising a short random sequence (NNN) and a sample index sequence; (iii) a third sub-region (413) comprising a universal binding sequence for an immobilized surface capture primer; (iv) a universal binding sequence for a reverse sequencing primer (130); (v) an insert sequence (110); and (vi) a universal binding sequence for a forward sequencing primer (120) (e.g., see FIG. 4). In some embodiments, a plurality of covalently closed circular library molecules (600) are subjected to rolling circle amplification by hybridizing the plurality of covalently closed circular library molecules (600) to a plurality of surface capture primers immobilized to a support where the surface capture primers initiate amplification thereby generating a plurality of immobilized concatemers each having tandem repeat sequences of its cognate covalently closed circular library molecule (600). In some embodiments, the rolling circle amplification is conducted in the presence of a plurality of compaction oligonucleotides which can hybridize to the concatemers at their universal binding sequence for a surface pinning primer, universal binding sequence for a surface capture primer, universal binding sequence for a reverse sequencing primer and/or universal binding sequence for a forward sequencing primer. In some embodiments, the plurality of immobilized capture primers lack uracil bases. In some embodiments, the rolling circle amplification reaction includes a plurality of nucleotides including dATP, dGTP, dCTP, dTTP and dUTP, to generate a plurality of immobilized concatemers wherein individual concatemer molecules comprise randomly-distributed uracil bases. In some embodiments, at least a portion of the immobilized concatemer is sequenced.

In some embodiments, the order of sequencing comprises: (1) sequencing the insert region (110) of the concatemers;

and (2) sequencing the short random sequence (NNN) and a sample index sequence (412) of the concatemers. In some embodiments, the order of sequencing further comprises: (3) conducting a pairwise turn reaction so that the immobilized concatemer molecule is replaced with an immobilized second strand that is complementary to the concatemer molecule; and (4) sequencing the insert region (110) on the second strand. In some embodiments, sequencing the short random sequence (NNN) and the sample index sequence (412) may provide sufficient nucleotide diversity and color balance for polony mapping and concatemer registration.

In some embodiments, methods for sequencing the concatemer molecules immobilized to the support comprises step (a): hybridizing the immobilized concatemer molecules with a first plurality of soluble sequencing primers that hybridize to the universal binding sequence for the forward sequencing primer (120) and sequencing the insert region (110) thereby generating a plurality of insert sequence extension products that are hybridized to the immobilized concatemer molecules.

In some embodiments, the methods for sequencing further comprise step (b): removing the plurality of insert sequence extension products and retaining the immobilized concatemer molecules.

In some embodiments, the methods for sequencing further comprise step (c): hybridizing the retained concatemer molecules with a second plurality of soluble sequencing primers that hybridize to at least a portion of the third sub-region (413) and sequencing the short random sequence (e.g., NNN) and the universal sample index sequence of third sub-region (412) thereby generating a plurality of sample index extension products that are hybridized to the immobilized concatemer molecules, wherein the plurality of sample index extension products are complementary to the short random sequence (e.g., NNN) and the universal sample index sequence.

In some embodiments, the methods for sequencing further comprise step (d): replacing the plurality of plurality of sample index extension products that are hybridized to the immobilized concatemer molecules by conducting a primer extension reaction using strand-displacing polymerases and a plurality of nucleotides to generate second strand extension products that are hybridized to the immobilized concatemer molecules including the immobilized capture primer.

In some embodiments, the methods for sequencing further comprise step (e): removing the immobilized concatemer molecules by generating abasic sites in the immobilized concatemer molecules at the uracil sites and generating gaps at the abasic sites thereby generating gap-containing concatemer molecules while retaining the second strand extension products that were generated in step (d) where individual second strand extension products are retained by hybridization to an immobilized capture primer. In some embodiments, pairwise turn is achieved by conducting steps (d) and (e).

In some embodiments, the methods for sequencing further comprise step (f): hybridizing the retained second strand extension products with a third plurality of soluble sequencing primers that hybridize to universal binding sequence for a reverse sequencing primer (130) and sequencing at least of portion of the insert region (110).

In some embodiments, the methods for sequencing further comprise: assigning the sequence of (i) the insert region (110) to (ii) the sample index sequence, thereby identifying the insert region as being obtained from a first source. In some embodiments, the assigning can be conducted after step (c) and/or (f).

In some embodiments, the removing of the plurality of sequencing extension products of step (b) can be conducted using a denaturation reagent comprising SSC (e.g., saline-sodium citrate) buffer with or without formamide, at a temperature that promotes nucleic acid denaturation, such as, for example, 50-90° C. In some embodiments, the removing of the plurality of sequencing extension products of step (b) can be conducted using a de-hybridization reagent at a temperature that promotes nucleic acid denaturation, such as, for example, 50-90° C. In some embodiments, the de-hybridization reagent comprises a pH buffering agent, a reducing agent, a monovalent salt and a crowding agent. In some embodiments, the de-hybridization reagent further comprises a chaotropic agent.

In some embodiments, the sequencing of steps (a), (c) and (f) include conducting any of the sequencing methods described herein that employ sequencing polymerases and detectably labeled nucleotide analogs. In some embodiments, the sequencing of steps (a), (c) and (f) include conducting any of the two-stage sequencing methods described herein that employ sequencing polymerases, detectably labeled multivalent molecules, and labeled nucleotide analogs or non-labeled nucleotide analogs. In some embodiments, the sequencing of steps (a), (c) and (f) include conducting any of the sequencing-by-binding methods or any of the sequencing methods that employ phosphate-chain labeled nucleotides described herein.

In some embodiments, the density of the plurality of concatemer molecules immobilized to the support is about $10^2$-$10^{15}$ per mm$^2$ (e.g., $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$). In some embodiments, the plurality of concatemer molecules is immobilized at random locations on the support. In some embodiments, the plurality of concatemer molecules is immobilized on the support in a predetermined pattern.

A Third Embodiment: Order of Sequencing

In some embodiments, a covalently closed circular library molecule (600) comprises: (i) a first sub-region (411) comprising a universal binding sequence for an immobilized surface pinning primer; (ii) a second sub-region (412) comprising a short random sequence (NNN) and a sample index sequence; (iii) a third sub-region (413) comprising a universal binding sequence for an immobilized surface capture primer; (iv) a universal binding sequence for a reverse sequencing primer (130); (v) an insert sequence (110); and (vi) a universal binding sequence for a forward sequencing primer (120) (e.g., see FIG. 4). In some embodiments, a plurality of covalently closed circular library molecules (600) are subjected to rolling circle amplification by hybridizing the plurality of covalently closed circular library molecules (600) to a plurality of surface capture primers immobilized to a support where the surface capture primers initiate amplification thereby generating a plurality of immobilized concatemers each having tandem repeat sequences of its cognate covalently closed circular library molecule (600). In some embodiments, the rolling circle amplification is conducted in the presence of a plurality of compaction oligonucleotides which can hybridize to the concatemers at their universal binding sequence for a surface pinning primer, universal binding sequence for a surface capture primer, universal binding sequence for a reverse sequencing primer and/or universal binding sequence for a forward sequencing primer. In some embodiments, the plurality of immobilized capture primers lacks uracil bases. In some embodiments, the rolling circle amplification reaction includes a plurality of nucleotides including dATP, dGTP, dCTP, dTTP and dUTP, to generate a plurality of immobilized concatemers wherein individual concatemer molecules comprise randomly-distributed uracil bases. In some embodiments, at least a portion of the immobilized concatemer is sequenced.

In some embodiments, the order of sequencing comprises: (1) sequencing the first 3-5 bases of the insert region (110) of the concatemers; (2) sequencing the short random sequence (NNN) and the sample index sequence (412) of the concatemers; and (3) sequencing the remaining portion of the insert region (110) of the concatemers. In some embodiments, the order of sequencing further comprises: (4) conducting a pairwise turn reaction so that the immobilized concatemer molecule is replaced with an immobilized second strand that is complementary to the concatemer molecule; and (5) sequencing the insert region (110) on the second strand. In some embodiments, sequencing the first 3-5 bases of the insert regions (110) of the concatemers may provide sufficient nucleotide diversity and color balance for polony mapping and concatemer registration. In some embodiments, sequencing the short random sequence (NNN) and the sample index sequence (412) may provide sufficient nucleotide diversity and color balance for polony mapping and concatemer registration.

In some embodiments, methods for sequencing the concatemer molecules immobilized to the support comprises step (a): hybridizing the concatemer molecules with a first plurality of soluble sequencing primers that hybridize to the universal binding sequence for a forward sequencing primer (120) and sequencing the first 3-5 bases of the insert region (110) thereby generating a plurality of insert extension products that are hybridized to the immobilized concatemer molecules, wherein the plurality of insert extension products are complementary to the sequence of interest (110). The sequence of the first 3-5 bases of the insert region (110) may provide sufficient sequence diversity and color balance for polony mapping and concatemer registration.

In some embodiments, the methods for sequencing further comprise step (b): removing the plurality of insert extension products and retaining the immobilized concatemer molecules.

In some embodiments, the methods for sequencing further comprise step (c): hybridizing the retained concatemer molecules with a second plurality of soluble sequencing primers that hybridize to at least a portion of the third sub-region (413) and sequencing the short random sequence (e.g., NNN) and the universal sample index sequence of third sub-region (412) thereby generating a plurality of sample index extension products that are hybridized to the immobilized concatemer molecules, wherein the plurality of sample index extension products are complementary to the short random sequence (e.g., NNN) and the universal sample index sequence.

In some embodiments, the methods for sequencing further comprise step (d): removing the plurality of sample index extension products and retaining the immobilized concatemer molecules.

In some embodiments, the methods for sequencing further comprise step (e): hybridizing the retained concatemer molecules with a third plurality of soluble sequencing primers that hybridize to the universal binding sequence for a forward sequencing primer (120) and sequencing the remainder of the insert region (110), or sequencing the full length of the insert region (110), thereby generating a plurality of insert extension products that are hybridized to the immobilized concatemer molecules wherein the plurality of the insert extension products are complementary to the sequence of interest (110). In some embodiments, in step (e), the first 3-5 bases of the insert region (110) can be sequenced using labeled nucleotides and/or labeled multivalent molecules. In some embodiments, in step (e), the first 3-5 bases of the insert region (110) can be sequenced using non-labeled nucleotides and/or non-labeled multivalent molecules (e.g., dark sequencing). In some embodiments, in step (e), the remainder of the insert region (110) can be sequenced using labeled nucleotides and/or labeled multivalent molecules. In some embodiments, in step (e), the full length of the insert region (110) can be sequenced using labeled nucleotides and/or labeled multivalent molecules.

In some embodiments, the methods for sequencing further comprise step (f): replacing the plurality of insert sequence extension products that are hybridized to the immobilized concatemer molecules by conducting a primer extension reaction using strand-displacing polymerases and a plurality of nucleotides to generate second strand extension products that are hybridized to the immobilized concatemer molecules including the immobilized capture primer.

In some embodiments, the methods for sequencing further comprise step (g): removing the immobilized concatemer molecules by generating abasic sites in the immobilized concatemer molecules at the uracil sites and generating gaps at the abasic sites thereby generating gap-containing concatemer molecules while retaining the second strand extension products that were generated in step (f) where individual second strand extension products are retained by hybridization to an immobilized capture primer. In some embodiments, pairwise turn is achieved by conducting steps (f) and (g).

In some embodiments, the methods for sequencing further comprise step (h): hybridizing the retained second strand extension products with a third plurality of soluble sequencing primers that hybridize to universal binding sequence for a reverse sequencing primer (130) and sequencing at least of portion of the insert region (110).

In some embodiments, the methods for sequencing further comprise: assigning the sequence of (i) the insert region (110) to (ii) the sample index sequence, thereby identifying the insert region as being obtained from a first source. In some embodiments, the assigning can be conducted after step (c), (e) and/or (h).

In some embodiments, the removing of the plurality of sequencing extension products of steps (b) and (d) can be conducted using a denaturation reagent comprising SSC (e.g., saline-sodium citrate) buffer with or without formamide, at a temperature that promotes nucleic acid denaturation, such as for example, 50-90° C. In some embodiments, the removing of the plurality of sequencing extension products of steps (b) and (d) can be conducted using a de-hybridization reagent at a temperature that promotes nucleic acid denaturation, such as for example, 50-90° C. In some embodiments, the de-hybridization reagent comprises a pH buffering agent, a reducing agent, a monovalent salt, and a crowding agent. In some embodiments, the de-hybridization reagent further comprises a chaotropic agent.

In some embodiments, the sequencing of steps (a), (c) and (e) include conducting any of the sequencing methods described herein that employ sequencing polymerases and detectably labeled nucleotide analogs. In some embodiments, the sequencing of steps (a), (c) and (e) include conducting any of the two-stage sequencing methods described herein that employ sequencing polymerases, detectably labeled multivalent molecules, and labeled or non-labeled nucleotide analogs. In some embodiments, the sequencing of steps (a), (c) and (e) include conducting any of the sequencing-by-binding methods or any of the sequencing methods that employ phosphate-chain labeled nucleotides described herein.

In some embodiments, the density of the plurality of concatemer molecules immobilized to the support is about $10^2$-$10^{15}$ per mm$^2$ (e.g., $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$). In some embodiments, the plurality of concatemer molecules is immobilized at random locations on the support. In some embodiments, the plurality of concatemer molecules is immobilized on the support in a predetermined pattern.

A Fourth Embodiment: Order of Sequencing

In some embodiments, a covalently closed circular library molecule (600) comprises: (i) a first sub-region (411) comprising a universal binding sequence for an immobilized surface pinning primer; (ii) a second sub-region (412) comprising a short random sequence (NNN) and a sample index sequence; (iii) a third sub-region (413) comprising a universal binding sequence for an immobilized surface capture primer; (iv) a universal binding sequence for a reverse sequencing primer (130); (v) an insert sequence (110); and (vi) a universal binding sequence for a forward sequencing primer (120) (e.g., see FIG. 4). In some embodiments, a plurality of covalently closed circular library molecules (600) are subjected to rolling circle amplification by hybridizing the plurality of covalently closed circular library molecules (600) to a plurality of surface capture primers immobilized to a support where the surface capture primers initiate amplification thereby generating a plurality of immobilized concatemers each having tandem repeat sequences of its cognate covalently closed circular library molecule (600). In some embodiments, the rolling circle amplification is conducted in the presence of a plurality of compaction oligonucleotides which can hybridize to the concatemers at their universal binding sequence for a surface pinning primer, universal binding sequence for a surface capture primer, universal binding sequence for a reverse sequencing primer and/or universal binding sequence for a forward sequencing primer. In some embodiments, the plurality of immobilized capture primers lack uracil bases. In some embodiments, the rolling circle amplification reaction includes a plurality of nucleotides including dATP, dGTP, dCTP, dTTP and dUTP, to generate a plurality of immobilized concatemers wherein individual concatemer molecules comprise randomly-distributed uracil bases. In some embodiments, at least a portion of the immobilized concatemer is sequenced.

In some embodiments, the order of sequencing comprises: (1) sequencing the first 3-5 bases of the insert region (110) of the concatemers; and (2) sequencing the short random sequence (NNN) and the sample index sequence (412) of the concatemers. In some embodiments, the order of sequencing further comprises: (3) conducting a pairwise turn reaction so that the immobilized concatemer molecule is replaced with an immobilized second strand that is complementary to the concatemer molecule; and (4) sequencing the insert region (110) on the second strand. In some embodiments, sequencing the first 3-5 bases of the insert regions (110) of the concatemers may provide sufficient nucleotide diversity and color balance for polony mapping and concatemer registration. In some embodiments, sequencing the short random sequence (NNN) and the sample index sequence (412) may provide sufficient nucleotide diversity and color balance for polony mapping and concatemer registration.

In some embodiments, methods for sequencing the concatemer molecules immobilized to the support comprises step (a): hybridizing the concatemer molecules with a first plurality of soluble sequencing primers that hybridize to the universal binding sequence for a forward sequencing primer (120) and sequencing the first 3-5 bases of the insert region (110) thereby generating a plurality of insert extension products that are hybridized to the immobilized concatemer molecules, wherein the plurality of insert extension products are complementary to the sequence of interest (110). The sequence of the first 3-5 bases of the insert region (110) may provide sufficient sequence diversity and color balance for polony mapping and concatemer registration.

In some embodiments, the methods for sequencing further comprise step (b): removing the plurality of insert extension products and retaining the immobilized concatemer molecules.

In some embodiments, the methods for sequencing further comprise step (c): hybridizing the retained concatemer molecules with a second plurality of soluble sequencing primers that hybridize to at least a portion of the third sub-region (413) and sequencing the short random sequence (e.g., NNN) and the universal sample index sequence of third sub-region (412) thereby generating a plurality of sample index extension products that are hybridized to the immobilized concatemer molecules, wherein the plurality of sample index extension products are complementary to the short random sequence (e.g., NNN) and the universal sample index sequence.

In some embodiments, the methods for sequencing further comprise step (d): replacing the plurality of insert sequence extension products that are hybridized to the immobilized concatemer molecules by conducting a primer extension reaction using strand-displacing polymerases and a plurality of nucleotides to generate second strand extension products that are hybridized to the immobilized concatemer molecules including the immobilized capture primer.

In some embodiments, the methods for sequencing further comprise step (e): removing the immobilized concatemer molecules by generating abasic sites in the immobilized concatemer molecules at the uracil sites and generating gaps at the abasic sites thereby generating gap-containing concatemer molecules while retaining the second strand extension products that were generated in step (d) where individual second strand extension products are retained by hybridization to an immobilized capture primer. In some embodiments, pairwise turn is achieved by conducting steps (d) and (e).

In some embodiments, the methods for sequencing further comprise step (f): hybridizing the retained second strand extension products with a third plurality of soluble sequencing primers that hybridize to universal binding sequence for a reverse sequencing primer (130) and sequencing at least of portion of the insert region (110).

In some embodiments, the methods for sequencing further comprise: assigning the sequence of (i) the insert region (110) to (ii) the sample index sequence, thereby identifying the insert region as being obtained from a first source. In some embodiments, the assigning can be conducted after step (c) and/or (f).

In some embodiments, the removing of the plurality of sequencing extension products of step (b) can be conducted using a denaturation reagent comprising SSC (e.g., saline-sodium citrate) buffer with or without formamide, at a temperature that promotes nucleic acid denaturation, such as for example, 50-90° C. In some embodiments, the removing of the plurality of sequencing extension products of step (b) can be conducted using a de-hybridization reagent at a temperature that promotes nucleic acid denaturation, such as for example, 50-90° C. In some embodiments, the de-hybridization reagent comprises a pH buffering agent, a reducing agent, a monovalent salt, and a crowding agent. In some embodiments, the de-hybridization reagent further comprises a chaotropic agent.

In some embodiments, the sequencing of steps (a), (c) and (f) include conducting any of the sequencing methods described herein that employ sequencing polymerases and detectably labeled nucleotide analogs. In some embodiments, the sequencing of steps (a), (c) and (f) include conducting any of the two-stage sequencing methods described herein that employ sequencing polymerases, detectably labeled multivalent molecules, and labeled nucleotide analogs or non-labeled nucleotide analogs. In some embodiments, the sequencing of steps (a), (c) and (f) include conducting any of the sequencing-by-binding methods or any of the sequencing methods that employ phosphate-chain labeled nucleotides described herein.

In some embodiments, the density of the plurality of concatemer molecules immobilized to the support is about $10^2$-$10^{15}$ per mm$^2$. In some embodiments, the plurality of concatemer molecules is immobilized at random locations on the support. In some embodiments, the plurality of concatemer molecules is immobilized on the support in a predetermined pattern.

A Fifth Embodiment: Order of Sequencing Sample Index Sequences

In some embodiments, a covalently closed circular library molecule (600) comprises: (i) a first sub-region (411) comprising a universal binding sequence for an immobilized surface pinning primer; (ii) a second sub-region (412) comprising a universal binding sequence for an immobilized surface capture primer; (iii) a third sub-region (413) comprising a short random sequence (NNN) and a sample index sequence; (iv) a universal binding sequence for a reverse sequencing primer (130); (v) an insert sequence (110); and (vi) a universal binding sequence for a forward sequencing primer (120) (e.g., see FIG. 4).

In some embodiments, a plurality of covalently closed circular library molecules (600) are subjected to rolling circle amplification by hybridizing the plurality of covalently closed circular library molecules (600) to a plurality of surface capture primers immobilized to a support where the surface capture primers initiate amplification thereby generating a plurality of immobilized concatemers each having tandem repeat sequences of its cognate covalently closed circular library molecule (600). In some embodiments, the rolling circle amplification is conducted in the presence of a plurality of compaction oligonucleotides which can hybridize to the concatemers at their universal binding sequence for a surface pinning primer, universal binding sequence for a surface capture primer, universal binding sequence for a reverse sequencing primer and/or universal binding sequence for a forward sequencing primer. In some embodiments, the plurality of immobilized capture primers lacks uracil bases. In some embodiments, the rolling circle amplification reaction includes a plurality of nucleotides including dATP, dGTP, dCTP, dTTP and dUTP, to generate a plurality of immobilized concatemers wherein individual concatemer molecules comprise randomly-distributed uracil bases. In some embodiments, at least a portion of the immobilized concatemer is sequenced.

In some embodiments, the order of sequencing comprises: (1) sequencing the short random sequence (NNN) and a sample index sequence (413) of the concatemers; and (2) sequencing the insert region (110) of the concatemers. In some embodiments, the order of sequencing further comprises: (3) conducting a pairwise turn reaction so that the immobilized concatemer molecule is replaced with an immobilized second strand that is complementary to the concatemer molecule; and (4) sequencing the insert region (110) on the second strand. In some embodiments, sequencing the short random sequence (NNN) and the sample index sequence (413) may provide sufficient nucleotide diversity and color balance for polony mapping and concatemer registration.

In some embodiments, methods for sequencing the concatemer molecules immobilized to the support comprises step (a): hybridizing the concatemer molecules with a first plurality of soluble sequencing primers that hybridize to at least a portion of the universal binding sequence for a reverse sequencing primer (130) and sequencing the short random sequence (e.g., NNN) and the universal sample index sequence of third sub-region (413) thereby generating a plurality of sample index extension products that are hybridized to the immobilized concatemer molecules, wherein the plurality of sample index extension products are complementary to the short random sequence (e.g., NNN) and the universal sample index sequence.

In some embodiments, the methods for sequencing further comprise step (b): removing the first plurality of sample index extension products and retaining the immobilized concatemer molecules.

In some embodiments, the methods for sequencing further comprise step (c): hybridizing the retained immobilized concatemer molecules with a second plurality of soluble sequencing primers that hybridize to the universal binding sequence for the forward sequencing primer (120) and sequencing the insert region (110) thereby generating a plurality of insert sequence extension products that are hybridized to the immobilized concatemer molecules.

In some embodiments, the methods for sequencing further comprise step (d): replacing the plurality of insert sequence extension products that are hybridized to the immobilized concatemer molecules by conducting a primer extension reaction using strand-displacing polymerases and a plurality of nucleotides to generate second strand extension products that are hybridized to the immobilized concatemer molecules including the immobilized capture primer.

In some embodiments, the methods for sequencing further comprise step (e): removing the immobilized concatemer molecules by generating abasic sites in the immobilized concatemer molecules at the uracil sites and generating gaps at the abasic sites thereby generating gap-containing concatemer molecules while retaining the second strand extension products that were generated in step (d) where individual second strand extension products are retained by hybridization to an immobilized capture primer. In some embodiments, pairwise turn is achieved by conducting steps (d) and (e).

In some embodiments, the methods for sequencing further comprise step (f): hybridizing the retained second strand extension products with a third plurality of soluble sequencing primers that hybridize to universal binding sequence for a reverse sequencing primer (130) and sequencing at least of portion of the insert region (110).

In some embodiments, the methods for sequencing further comprise: assigning the sequence of (i) the insert region (110) to (ii) the sample index sequence, thereby identifying the insert region as being obtained from a first source. In some embodiments, the assigning can be conducted after step (c) and/or (f).

In some embodiments, the removing of the plurality of sequencing extension products of step (b) can be conducted using a denaturation reagent comprising SSC (e.g., saline-sodium citrate) buffer with or without formamide, at a temperature that promotes nucleic acid denaturation, such as for example, 50-90° C. In some embodiments, the removing of the plurality of sequencing extension products of step (b) can be conducted using a de-hybridization reagent at a temperature that promotes nucleic acid denaturation, such as for example, 50-90° C. In some embodiments, the de-hybridization reagent comprises a pH buffering agent, a reducing agent, a monovalent salt, and a crowding agent. In some embodiments, the de-hybridization reagent further comprises a chaotropic agent.

In some embodiments, the sequencing of steps (a), (c) and (f) include conducting any of the sequencing methods described herein that employ sequencing polymerases and detectably labeled nucleotide analogs. In some embodiments, the sequencing of steps (a), (c) and (f) include conducting any of the two-stage sequencing methods described herein that employ sequencing polymerases, detectably labeled multivalent molecules, and labeled nucleotide analogs or non-labeled nucleotide analogs. In some embodiments, the sequencing of steps (a), (c) and (f) include conducting any of the sequencing-by-binding methods or any of the sequencing methods that employ phosphate-chain labeled nucleotides described herein.

In some embodiments, the density of the plurality of concatemer molecules immobilized to the support is about $10^2$-$10^{15}$ per mm$^2$ (e.g., $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$). In some embodiments, the plurality of concatemer molecules is immobilized at random locations on the support. In some embodiments, the plurality of concatemer molecules is immobilized on the support in a predetermined pattern.

De-Hybridization Reagents

In some aspects, the present disclosure provides one or more nucleic acid de-hybridization reagents that can promote nucleic acid denaturation between any two nucleic acid strands. In some embodiments, the de-hybridization reagents can promote nucleic acid denaturation between a nucleic acid template molecule and a nucleic acid extension product. In some embodiments, the de-hybridization reagents can promote nucleic acid denaturation between concatemer molecules and the plurality of sample index extension products while retaining the immobilized concatemer molecules. In some embodiments, the de-hybridization reagents can promote nucleic acid denaturation between concatemer molecules and the plurality of insert extension products while retaining the immobilized concatemer molecules. In some embodiments, the de-hybridization reagents can promote nucleic acid denaturation between second strand molecules and the plurality of insert extension products while retaining the immobilized second strand molecules.

In some aspects, the present disclosure provides one or more nucleic acid de-hybridization reagents (e.g., denaturation reagent), and methods that employ the nucleic acid de-hybridization reagents where the methods comprise any of the order of sequencing workflows. For example, the order of sequencing workflows can include those described above, for example methods comprising removing the plurality of sample index extension products from the immobilized concatemer molecules, removing the plurality of insert extension products from the immobilized concatemer molecules and/or removing the plurality of insert extension products from the immobilized second strand molecules.

In some embodiments, the de-hybridization reagent comprises a pH buffering agent, a reducing agent, a monovalent salt, and a crowding agent. In some embodiments, the de-hybridization reagent further comprises a chaotropic agent. In some embodiments, the de-hybridization reagent is at a pH range of about 5-5.25, or a pH range of about 5.25-5.5, or a pH range of about 5.5-5.75, or a pH range of about 5.75-6, or any range therebetween.

In some embodiments, any of the de-hybridization reagents described herein can include a pH buffering agent which can maintain the pH of the reagent in a range that is suitable for nucleic acid hybridization. The pH buffering agent may comprise any one or any combination of two or more of Tris, Tris-HCl, Tris-acetate, Tricine, Bicine, Bis-Tris propane, HEPES, MES, MOPS, MOPSO, BES, TES, CAPS, TAPS, TAPSO, ACES, PIPES, ethanolamine (a.k.a 2-amino methanol; MEA), a citrate compound, a citrate mixture, NaOH and/or KOH. In some embodiments, the pH buffering agent can be present in any of the de-hybridization reagents described herein at a concentration of about 1-100 mM, or about 10-50 mM, or about 10-25 mM, or any range therebetween. In some embodiments, the pH of the pH buffering agent which is present in any of the reagents described here in can be adjusted to a pH of about 4-9.5, or a pH of about 5-9, or a pH of about 5-8, or a pH of about 5.5-7, or any range therebetween.

In some embodiments, any of the de-hybridization reagents described herein can include at least one reducing agent comprising DTT (dithiothreitol), 2-beta mercaptoethanol, TCEP, (tris(2-carboxyethyl)phosphine), formamide, DMSO (dimethylsulfoxide), sodium dithionite ($Na^2S_2O_4$), glutathione, methionine, betaine, Tris(3-hydroxypropyl) phosphine (THPP) and/or N-acetyl cysteine. The de-hybridization reagents can include the reducing agent at a concentration of about 0.1-0.5 M, or about 0.5-1 M, or about 1-2 M, or any range therebetween. The de-hybridization reagents can include the reducing agent at a concentration of about 0.01-0.1 mM, or about 0.1-1 mM, or about 1-2.5 mM, or about 2.5-5 mM, or about 5-7.5 mM, or about 7.5-9 mM, or about 9-12 mM, or about 12-25 mM, or about 25-50 mM, or any range therebetween. The de-hybridization reagents can include the reducing agent at a concentration of about 1%-5%, or about 5%-10%, or about 10%-20%, or about 20%-30%, or about 30%-40%, or about 40%-50%, or any range therebetween.

In some embodiments, any of the de-hybridization reagents described herein can include at least one monovalent salt comprising NaCl, KCl, $NH_2SO_4$ and/or potassium glutamate. The de-hybridization reagents can include the monovalent salt at a concentration of about 25-500 mM, or about 50-250 mM, or about 100-200 mM, or about 500 mM-750 mM, or about 750 mM-1 M, or about 1 M-1.5 M, or any range therebetween.

In some embodiments, any of the de-hybridization reagents described herein can include a crowding agent that increases molecular crowding. In some embodiments, the crowding agent comprises polyethylene glycol (PEG, e.g., 1-50K molecular weight), dextran, dextran sulfate, hydroxypropyl methyl cellulose (HPMC), hydroxyethyl methyl cellulose (HEMC), hydroxybutyl methyl cellulose, hydroxypropyl cellulose, methycellulose, and hydroxyl methyl cellulose. The crowding agent can be present in the de-hybridization reagent at about 1-10%, or about 10-25%, or about 25-50%, or higher percentages by volume based on the total volume of the hybridization reagent.

In some embodiments, any of the de-hybridization reagents described herein can include a chaotropic agent that can disrupt non-covalent bonds such as hydrogen bonds or van der Waals forces. In some embodiments, the chaotropic agent comprises SDS (sodium dodecyl sulfate), urea, thiourea, guanidinium chloride, guanidine hydrochloride, guanidine thiocyanate, guanidine isothiocyanate, guanidine isothionate, potassium thiocyanate, lithium chloride, sodium iodide or sodium perchlorate. The de-hybridization reagents can include a chaotropic agent at a concentration of about 0.5-1 M, 0.1-1 M, or about 1-2 M, or about 2-3 M, or about 3-4 M, or about 4-5 M, or any range therebetween.

In some embodiments, the de-hybridization reagent further comprises (a) a plurality of immobilized concatemer molecules and (b) a plurality of soluble sequencing primers that hybridize to a sub-region (411), (412) or (413). In some embodiments, individual concatemer molecules comprise tandem repeat polynucleotide units wherein each unit comprises (i) a first sub-region (411); (ii) a second sub-region (412); (iii) a third sub-region (413); (iv) a universal binding sequence for a reverse sequencing primer (130); (v) an insert sequence (110); and (vi) a universal binding sequence for a forward sequencing primer (120).

In some embodiments, the de-hybridization reagent further comprises (a) a plurality of immobilized concatemer molecules and (b) a plurality of sample index extension products each comprising a short random sequence (e.g., NNN) and a universal sample index sequence of a sub-region (411), (412) or (413). In some embodiments, individual concatemer molecules comprise tandem repeat polynucleotide units wherein each unit comprises (i) a first sub-region (411); (ii) a second sub-region (412); (iii) a third sub-region (413); (iv) a universal binding sequence for a reverse sequencing primer (130); (v) an insert sequence (110); and (vi) a universal binding sequence for a forward sequencing primer (120).

In some embodiments, the de-hybridization reagent further comprises (a) a plurality of immobilized concatemer molecules and (b) a plurality of soluble sequencing primers that hybridize to the universal binding sequence for a forward sequencing primer (120). In some embodiments, individual concatemer molecules comprise tandem repeat polynucleotide units wherein each unit comprises (i) a first sub-region (411); (ii) a second sub-region (412); (iii) a third sub-region (413); (iv) a universal binding sequence for a reverse sequencing primer (130); (v) an insert sequence (110); and (vi) a universal binding sequence for a forward sequencing primer (120).

In some embodiments, the de-hybridization reagent further comprises (a) a plurality of immobilized concatemer molecules and (b) a plurality of soluble sequencing primers that hybridize to the universal binding sequence for a reverse sequencing primer (130). In some embodiments, individual concatemer molecules comprise tandem repeat polynucleotide units wherein each unit comprises (i) a first sub-region (411); (ii) a second sub-region (412); (iii) a third sub-region (413); (iv) a universal binding sequence for a reverse sequencing primer (130); (v) an insert sequence (110); and (vi) a universal binding sequence for a forward sequencing primer (120).

In some embodiments, the de-hybridization reagent further comprises a plurality of sequencing polymerases and a plurality of detectably labeled multivalent molecules. In some embodiments, the de-hybridization reagent further comprises a plurality of sequencing polymerases and a plurality of nucleotide analogs. In some embodiments, the plurality of nucleotide analogs is non-labeled. In some embodiments, the plurality of nucleotide analogs is detectably labeled. In some embodiments, the plurality of nucleotide analogs comprises a mixture of non-labeled nucleotide analogs and detectably labeled nucleotide analogs.

In some embodiments, the plurality of immobilized concatemer molecules is immobilized to a support at a density of about $10^2$-$10^{15}$ per mm$^2$ (e.g., $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$). In some embodiments, the plurality of immobilized concatemer molecules is immobilized to a support passivated with a hydrophilic polymer coating having a water contact angle of about 45-50 degrees. In some embodiments, the plurality of concatemer molecules is immobilized at random locations on the support. In some embodiments, the plurality of concatemer molecules is immobilized on the support in a predetermined pattern.

Kits Comprising De-Hybridization Reagents

In some aspects, the present disclosure provides a kit for conducting any of the order of sequencing workflows described above, for example methods comprising removing the plurality of sample index extension products from the immobilized concatemer molecules, removing the plurality of insert extension products from the immobilized concatemer molecules and/or removing the plurality of insert extension products from the immobilized second strand molecules. In some embodiments, the kit comprises a de-hybridization reagent comprising a pH buffering agent, a reducing agent, a monovalent salt and a crowding agent. In some embodiments, the de-hybridization reagent further comprises a chaotropic agent. In some embodiments, the kit further comprises any one or any combination of two or more of: a plurality of forward sequencing primers for sequencing an insert region, a plurality of reverse sequencing primers for sequencing an insert region, a plurality of sequencing primers that hybridize to a sub-region (411), (412) or (413), a plurality of sequencing polymerases, plurality of detectably labeled nucleotide analogs, a plurality of non-labeled nucleotide analogs, a plurality of detectably labeled multivalent molecules and/or a cleaving reagent that can remove a chain terminating moiety (e.g., blocking moiety) from the 2' sugar position or 3' sugar position of a nucleotide analog.

Sequencing 3-mer Random Sequences to Generate a Polony Map

In some aspects, the present disclosure provides methods for sequencing nucleic acids comprising: (a) providing a plurality of nucleic acid template molecules immobilized on a support (e.g., immobilized at random or pre-determined locations), wherein individual immobilized template molecules comprise an insert sequence region and one sample index, wherein each sample index comprises a 3-mer random sequence (e.g., a short random sequence NNN) joined to a universal sample index sequence which identifies the sample source of the insert sequence, wherein different immobilized template molecules have a different 3-mer random sequence and the same universal sample index sequence, and wherein the immobilized template molecules have different insert sequences; (b) conducting three cycles of polymerase-mediated sequencing reactions of the 3-mer random sequence of the plurality of immobilized template molecules using a plurality of detectably labeled nucleotide reagents comprising a mixture of different types of nucleobases A, G, C, and T/U, wherein the nucleotide reagents comprise a different detectable color label that corresponds with each different type of nucleo-base, wherein the three cycles of sequencing include detecting and imaging the optical color signals emitted from the detectably labeled nucleotide reagents that are bound to the immobilized template molecules thereby determining the sequences of the 3-mer random sequences in individual template molecules of the plurality of immobilized template molecules, and wherein a balanced diversity of nucleo-bases of A, G, C, and T/U is detected and imaged in each of the first, second and third sequencing cycles among the plurality of immobilized template molecules; and (c) generating a map of the locations of the plurality of immobilized template molecules using the images obtained in step (b), wherein the sequence of the insert region is not used to generate the map.

In some embodiments, in the methods for sequencing nucleic acids, the balanced diversity of step (b) is about 5-85%, or about 5-60%, or about 10-50%, or about 15-55%, or about 25-75%, or any range therebetween, of each of the nucleo-bases A, G, C, and T/U that are detected and imaged in each of the first, second and third sequencing cycles.

In some embodiments, in the methods for sequencing nucleic acids, the method further comprises: (a) sequencing the universal sample index sequence of the plurality of immobilized template molecules; (b) sequencing the insert sequence region of the plurality of immobilized template molecules; and (c) assigning the insert sequence of a given template molecule obtained in step (b) with the universal sample index sequence from the same given template molecule obtained in step (a), thereby identifying the sample source of the given insert sequence.

In some embodiments, in the methods for sequencing nucleic acids, the plurality of nucleic acid template molecules further comprises a second sample index which comprises a second universal sample index sequence which identifies the sample source of the insert sequence and the second sample index lacks a short random sequence.

In some embodiments, in the methods for sequencing nucleic acids, the method further comprises: (a) sequencing the 3-mer random sequence of the plurality of immobilized template molecules to obtain a balanced diversity of nucleo-bases of A, G, C and T/U that are detected and imaged in each of the first, second and third sequencing cycles to generate a map of the locations of the plurality of immobilized template molecules; (b) sequencing the first universal sample index sequence of the plurality of immobilized template molecules; (c) sequencing the second universal sample index sequence of the plurality of immobilized template molecules; (d) sequencing the insert sequence region of the plurality of immobilized template molecules; and (e) assigning the insert sequence of a given template molecule obtained in step (c) with the first and second universal sample index sequences from the same given template molecule obtained in steps (a) and (b), thereby identifying the sample source of the given insert sequence.

The present disclosure provides methods for sequencing nucleic acids comprising: (a) providing a plurality of nucleic acid template molecules immobilized on a support (e.g., immobilized at random or pre-determined locations), wherein individual immobilized template molecules comprise an insert sequence region and one sample index, wherein each sample index comprises a 3-mer random sequence (e.g., a short random sequence NNN) joined to a universal sample index sequence which identifies the sample source of the insert sequence, wherein the universal sample index sequence comprises 3-20 nucleotides, wherein different immobilized template molecules have a different 3-mer random sequence and the same universal sample index sequence, and wherein the immobilized template molecules have different insert sequences; (b) conducting four cycles of polymerase-mediated sequencing reactions of the 3-mer random sequence and the first base position of the universal sample index sequence of the plurality of immobilized template molecules using a plurality of detectably labeled nucleotide reagents comprising a mixture of different types of nucleo-bases A, G, C, and T/U, wherein the nucleotide reagents comprise a different detectable color label that corresponds with each different type of nucleo-base, wherein the four cycles of sequencing include detecting and imaging the optical color signals emitted from the detectably labeled nucleotide reagents that are bound to the immobilized template molecules thereby determining the sequences of the 3-mer random sequences and the first base position of the universal sample index sequences in individual template molecules of the plurality of immobilized template molecules, and wherein a balanced diversity of nucleo-bases of A, G, C, and T/U is detected and imaged in each of the first, second, third and fourth sequencing cycles among the plurality of immobilized template molecules; and (c) generating a map of the locations of the plurality of immobilized template molecules using the images of the four cycles of polymerase-mediated sequencing reactions obtained in step (b), wherein the sequence of the insert region is not used to generate the map.

In some embodiments, in the methods for sequencing nucleic acids, the balanced diversity of step (b) is about 5-85%, or about 5-60%, or about 10-50%, or about 15-55%, or about 25-75%, or any range therebetween, of each of the nucleo-bases A, G, C and T/U that are detected and imaged in each of the first, second, third and fourth sequencing cycles.

In some embodiments, in the methods for sequencing nucleic acids, the method further comprises: (a) sequencing the remaining base positions of the universal sample index sequence of the plurality of immobilized template molecules; (b) sequencing the insert sequence region of the plurality of immobilized template molecules; and (c) assigning the insert sequence of a given template molecule obtained in step (b) with the universal sample index sequence from the same given template molecule obtained in step (a), thereby identifying the sample source of the given insert sequence.

In some embodiments, in the methods for sequencing nucleic acids, the plurality of nucleic acid template molecules further comprises: a second sample index which comprises a second universal sample index sequence which identifies the sample source of the insert sequence and the second sample index lacks a random sequence.

In some embodiments, in the methods for sequencing nucleic acids, the method further comprises: (a) sequencing the 3-mer random sequence and the first base position of the universal sample index sequence of the plurality of immobilized template molecules to obtain a balanced diversity of nucleo-bases of A, G, C and T/U that are detected and imaged in each of the first, second, third and fourth sequencing cycles to generate a map of the locations of the plurality of immobilized template molecules; (b) sequencing the remaining base positions of the first universal sample index sequence of the plurality of immobilized template molecules; (c) sequencing the second universal sample index sequence of the plurality of immobilized template molecules; (d) sequencing the insert sequence region of the plurality of immobilized template molecules; and (e) assigning the insert sequence of a given template molecule obtained in step (c) with the first and second universal sample index sequences from the same given template molecule obtained in steps (a) and (b), thereby identifying the sample source of the given insert sequence.

In some embodiments, in any of the methods for sequencing nucleic acids, the support comprises a glass or plastic substrate. In some embodiments, the support is configured on a flowcell channel, a flow cell, or a capillary lumen. In some embodiments, the support is passivated with at least one hydrophilic polymer coating having a water contact angle of not more than 45 degrees. In some embodiments, the at least one hydrophilic polymer coating comprises a molecule selected from the group consisting of polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, and dextran. In some embodiments, the at least one hydrophilic polymer coating comprises branched hydrophilic polymer molecules having at least four branches. In some embodiments, the at least one hydrophilic polymer coating comprises polymer molecules having a molecular weight of at least 1000 Daltons.

In some embodiments, in any of the methods for sequencing nucleic acids, the immobilized template molecules comprise a plurality of immobilized concatemer molecules having tandem repeat sequences of the insert sequence and the one sample index. In some embodiments, the immobilized template molecules comprise a plurality of different clustered template molecules having one copy of the insert sequence and one copy of the one sample index, wherein the clustered template molecules are generated via bridge amplification. In some embodiments, the density of the immobilized nucleic acid template molecules positioned at random or pre-determined locations on the support is $10^4$-$10^8$ per $mm^2$, or any range therebetween. In some embodiments, the sample source of the insert sequences is genomic DNA, double-stranded cDNA, or cell free circulating DNA.

In some embodiments, in any of the methods for sequencing nucleic acids, the detectably labeled nucleotide reagents comprise nucleotides each comprising an aromatic nucleo-base, a five carbon sugar moiety, 1-10 phosphate groups, and a fluorophore. In some embodiments, the detectably labeled nucleotide reagents comprise nucleotides each comprising an aromatic nucleo-base, a five carbon sugar moiety having a chain terminating group at the 3' carbon sugar position, 1-10 phosphate groups, and a fluorophore. In some embodiments, the detectably labeled nucleotide reagents comprise multivalent molecules each comprising (1) a core, (2) a plurality of nucleotide arms, and (3) at least one fluorophore, wherein individual nucleotide arms comprise (i) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit.

In some embodiments, in any of the methods for sequencing nucleic acids, the detectably labeled nucleotide reagents that are bound to the immobilized template molecules in step (b) comprise individual immobilized template molecules hybridized to a sequencing primer to form a duplex, and the duplex is bound to a polymerase to form a complexed polymerase, and the complexed polymerase is bound to a detectably labeled nucleotide reagent. In some embodiments, the complexed polymerase is bound to a detectably labeled nucleotide reagent under a condition suitable for binding the detectably labeled nucleotide reagent to the complexed polymerase and incorporating the detectably labeled nucleotide into the hybridized sequencing primer, wherein the detectably labeled nucleotide reagent comprises an aromatic nucleo-base, a five carbon sugar moiety, 1-10 phosphate groups, and a fluorophore. In some embodiments, the complexed polymerase is bound to a detectably labeled nucleotide reagent under a condition suitable for binding the detectably labeled nucleotide reagent to the complexed polymerase and incorporating the detectably labeled nucleotide into the hybridized sequencing primer, wherein the detectably labeled nucleotide reagent comprises an aromatic nucleo-base, a five carbon sugar moiety having a chain terminating group at the 3' carbon sugar position, 1-10 phosphate groups, and a fluorophore. In some embodiments, the complexed polymerase is bound to a detectably labeled nucleotide reagent under a condition suitable for binding the detectably labeled nucleotide reagent to the complexed polymerase and the condition is suitable for inhibiting nucleotide incorporation, wherein the detectably labeled nucleotide reagent comprises a multivalent molecule which includes (1) a core, (2) a plurality of nucleotide arms, and (3) at least one fluorophore, wherein individual nucleotide arms comprise (i) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit.

In some embodiments, in any of the methods for sequencing nucleic acids, the immobilized template molecule comprises an immobilized concatemer molecule which is hybridized to a plurality of sequencing primers to form at least a first and second duplex on the same concatemer molecule, wherein the first and duplex is bound to a first polymerase and the second duplex is bound to a second polymerase to form first and second complexed polymerases, and wherein the method comprises: (a) contacting a plurality of multivalent molecules to the first and second complexed polymerases on the same concatemer template molecule, wherein individual multivalent molecules include (1) a core, (2) a plurality of nucleotide arms, and (3) at least one fluorophore, wherein individual nucleotide arms comprise (i) a core attachment moiety, (ii) a spacer comprising a PEG moiety, (iii) a linker, and (iv) a nucleotide unit, wherein the core is attached to the plurality of nucleotide arms, and the spacer is attached to the linker, and the linker is attached to the nucleotide unit, wherein the contacting is conducted under conditions suitable to bind a single multivalent molecule from the plurality to the first and second complexed polymerases, wherein a first nucleotide unit of the single multivalent molecule is bound to the first complexed polymerase which includes the first sequencing primer hybridized to a first portion of the concatemer template molecule thereby forming a first binding complex, and wherein a second nucleotide unit of the single multivalent molecule is bound to the second complexed polymerase which includes the second sequencing primer hybridized to a second portion of the concatemer template molecule thereby forming a second binding complex, wherein the first and second binding complexes which are bound to the same multivalent molecule forms an avidity complex, and wherein the contacting is conducted under a condition suitable to inhibit polymerase-catalyzed incorporation of the bound first and second nucleotide units in the first and second binding complexes; (b) detecting the first and second binding complexes on the same concatemer template molecule; (c) imaging the optical color signals emitted from the detectably labeled multivalent molecule which forms the first and second binding complexes on the same concatemer template molecule; and (d) identifying the first nucleotide unit in the first binding complex thereby determining the sequence of the first portion of the concatemer template molecule, and identifying the second nucleotide unit in the second binding complex thereby determining the sequence of the second portion of the concatemer template molecule. Multiplex Sequencing 3-mer Random Sequences to Generate a Polony Map In some aspects, the present disclosure provides methods for multiplex sequencing nucleic acids comprising: (a) providing a first plurality of library molecules each molecule in the plurality comprising (i) an insert sequence region derived from a first sample source, (ii) a first sample index having a 3-mer random sequence (e.g., a short random sequence NNN) joined to a first universal sample index sequence, and (iii) a second sample index having a second universal sample index sequence which lacks a random sequence, wherein the combination of the first and second universal sample index sequences uniquely identifies a first sample source of the insert sequence, wherein different first library molecules have a different 3-mer random sequence and have a different insert sequence; (b) providing a second plurality of library molecules each molecule in the plurality comprising (i) an insert sequence region derived from a second sample source, (ii) a third sample index having a 3-mer random sequence joined to a third universal sample index sequence, and (iii) a fourth sample index having a fourth universal sample index sequence which lacks a random sequence, wherein the combination of the third and fourth universal sample index sequences uniquely identifies a second sample source of the insert sequence, wherein different second library molecules have a different 3-mer random sequence and have a different insert sequence; (c) pooling the first and second plurality of library molecules; (d) distributing the pooled library molecules onto a support and conducting an amplification reaction to generate a plurality of clonally amplified template molecules immobilized to the support (e.g., immobilized at random or predetermined locations); (e) conducting three cycles of polymerase-mediated sequencing reactions of the 3-mer random sequence of the first and third sample indexes using a plurality of detectably labeled nucleotide reagents comprising a mixture of different types of nucleo-bases A, G, C, and T/U, wherein the nucleotide reagents comprise a different detectable color label that corresponds with each different type of nucleo-base, wherein the three cycles of sequencing include detecting and imaging the optical color signals emitted from the detectably labeled nucleotide reagents that are bound to the immobilized amplified template molecules thereby determining the sequences of the 3-mer random sequences in individual template molecules of the plurality of immobilized template molecules, and wherein a balanced diversity of nucleo-bases of A, G, C and T/U is detected and imaged in each of the first, second and third sequencing cycles among the plurality of immobilized amplified template molecules; and (f) generating a map of the locations of the plurality of immobilized template molecules using the images obtained in step (e), wherein the sequence of the insert regions are not used to generate the map.

In some embodiments, in the methods for multiplex sequencing nucleic acids, the balanced diversity of step (e) is about 5-85%, or about 5-60%, or about 10-50%, or about 15-55%, or about 25-75%, or any range therebetween, of each of the nucleo-bases A, G, C, and T/U that are detected and imaged in each of the first, second, and third sequencing cycles.

In some embodiments, in the methods for multiplex sequencing nucleic acids, the method further comprises: (a) sequencing the first universal sample index sequences of the plurality of immobilized template molecules; (b) sequencing the second universal sample index sequences of the plurality of immobilized template molecules; (c) sequencing the insert sequence regions of the plurality of immobilized template molecules derived from the first library molecules; and (d) assigning the insert sequence of a given template molecule obtained in step (c) with the first and second universal sample index sequences from the same given template molecule thereby identifying the first sample source of the given insert sequence.

In some embodiments, in the methods for multiplex sequencing nucleic acids, the method further comprises: (a) sequencing the third universal sample index sequences of the plurality of immobilized template molecules; (b) sequencing the fourth universal sample index sequences of the plurality of immobilized template molecules; (c) sequencing the insert sequence regions of the plurality of immobilized template molecules derived from the second library molecules; and (d) assigning the insert sequence of a given template molecule obtained in step (c) with the third and fourth universal sample index sequences from the same given template molecule thereby identifying the second sample source of the given insert sequence.

In some aspects, the present disclosure provides methods for multiplex sequencing nucleic acids comprising: (a) providing a first plurality of library molecules each molecule in the plurality comprising (i) an insert sequence region derived from a first sample source, (ii) a first sample index having a 3-mer random sequence (e.g., a short random sequence NNN) joined to a first universal sample index sequence, and (iii) a second sample index having a second universal sample index sequence which lacks a random sequence, wherein the combination of the first and second universal sample index sequences uniquely identifies a first sample source of the insert sequence, wherein the first universal sample index sequence comprises 3-20 nucleotides (e.g., about 3, 4, 5, 6, 7, 8, 9, 10, 11, 12, 13, 14, 15, 16, 17, 18, 19, or 20 nucleotides), wherein different first library molecules have a different 3-mer random sequence and have a different insert sequence; (b) providing a second plurality of library molecules each molecule in the plurality comprising (i) an insert sequence region derived from a second sample source, (ii) a third sample index having a 3-mer random sequence joined to a third universal sample index sequence, and (iii) a fourth sample index having a fourth universal sample index sequence which lacks a random sequence, wherein the combination of the third and fourth universal sample index sequences uniquely identifies a second sample source of the insert sequence, wherein the third universal sample index sequence comprises 3-20 nucleotides (e.g., about 3, 4, 5, 6, 7, 8, 9, 10, 11, 12, 13, 14, 15, 16, 17, 18, 19, or 20 nucleotides), wherein different second library molecules have a different 3-mer random sequence and have a different insert sequence; (c) pooling the first and second plurality of library molecules; (d) distributing the pooled library molecules onto a support and conducting an amplification reaction to generate a plurality of clonally amplified template molecules immobilized to the support (e.g., immobilized at random or pre-determined locations); (e) conducting four cycles of polymerase-mediated sequencing reactions of the 3-mer random sequence of the first and third sample indexes and sequencing the first base position of the first and third universal sample index sequences using a plurality of detectably labeled nucleotide reagents comprising a mixture of different types of nucleo-bases A, G, C and T/U, wherein the nucleotide reagents comprise a different detectable color label that corresponds with each different type of nucleo-base, wherein the three cycles of sequencing include detecting and imaging the optical color signals emitted from the detectably labeled nucleotide reagents that are bound to the immobilized amplified template molecules thereby determining the sequences of the 3-mer random sequences in individual template molecules of the plurality of immobilized template molecules, and wherein a balanced diversity of nucleo-bases of A, G, C and T/U is detected and imaged in each of the first, second, third and fourth sequencing cycles among the plurality of immobilized amplified template molecules; and (f) generating a map of the locations of the plurality of immobilized template molecules using the images obtained in step (e), wherein the sequence of the insert regions are not used to generate the map.

In some embodiments, in the methods for multiplex sequencing nucleic acids, the balanced diversity of step (e) is about 5-85%, or about 5-60%, or about 10-50%, or about 15-55%, or about 25-75%, or any range therebetween, of each of the nucleo-bases A, G, C and T/U that are detected and imaged in each of the first, second, third and fourth sequencing cycles.

In some embodiments, in the methods for multiplex sequencing nucleic acids, the method further comprises: (a) sequencing the remaining base positions of the first universal sample index sequences of the plurality of immobilized template molecules; (b) sequencing the second universal sample index sequences of the plurality of immobilized template molecules; (c) sequencing the insert sequence regions of the plurality of immobilized template molecules derived from the first library molecules; and (d) assigning the insert sequence of a given template molecule obtained in step (c) with the first and second universal sample index sequences from the same given template molecule thereby identifying the first sample source of the given insert sequence.

In some embodiments, in the methods for multiplex sequencing nucleic acids, the method further comprises: (a) sequencing the remaining base positions of the third universal sample index sequences of the plurality of immobilized template molecules; (b) sequencing the fourth universal sample index sequences of the plurality of immobilized template molecules; (c) sequencing the insert sequence regions of the plurality of immobilized template molecules derived from the second library molecules; and (d) assigning the insert sequence of a given template molecule obtained in step (c) with the third and fourth universal sample index sequences from the same given template molecule thereby identifying the second sample source of the given insert sequence.

In some embodiments, in any of the methods for multiplex sequencing nucleic acids, the support comprises a glass or plastic substrate. In some embodiments, the support is configured on a flowcell channel, a flow cell, or a capillary lumen. In some embodiments, the support is passivated with at least one hydrophilic polymer coating having a water contact angle of not more than 45 degrees. In some embodiments, the at least one hydrophilic polymer coating comprises a molecule selected from the group consisting of polyethylene glycol (PEG), poly(vinyl alcohol) (PVA), poly (vinyl pyridine), poly(vinyl pyrrolidone) (PVP), poly (acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo (ethylene glycol) methyl ether methacrylate) (POEGMA), polyglutamic acid (PGA), poly-lysine, poly-glucoside, streptavidin, and dextran. In some embodiments, the at least one hydrophilic polymer coating comprises branched hydrophilic polymer molecules having at least four branches. In some embodiments, the at least one hydrophilic polymer coating comprises polymer molecules having a molecular weight of at least 1000 Daltons.

In some embodiments, in any of the methods for multiplex sequencing nucleic acids, the immobilized template molecules comprise a plurality of immobilized concatemer molecules having tandem repeat sequences of the insert sequence and the one sample index. In some embodiments, the immobilized template molecules comprise a plurality of different clustered template molecules having one copy of the insert sequence and one copy of the one sample index, wherein the clustered template molecules are generated via bridge amplification. In some embodiments, the density of the immobilized nucleic acid template molecules (e.g., immobilized at random or pre-determined locations) on the support is $10^4$-$10^8$ per mm$^2$. In some embodiments, the sample source of the insert sequences is genomic DNA, double-stranded cDNA or cell free circulating DNA.

In some embodiments, in any of the methods for multiplex sequencing nucleic acids, the detectably labeled nucleotide reagents comprise nucleotides each comprising an aromatic nucleo-base, a five carbon sugar moiety, 1-10 phosphate groups, and a fluorophore. In some embodiments, the detectably labeled nucleotide reagents comprise nucleotides each comprising an aromatic nucleo-base, a five carbon sugar moiety having a chain terminating group at the 3' carbon sugar position, 1-10 phosphate groups, and a fluorophore. In some embodiments, the detectably labeled multivalent nucleotide reagents comprise multivalent molecules each comprising (1) a core, (2) a plurality of nucleotide arms, and (3) at least one fluorophore, wherein individual nucleotide arms comprise (i) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit.

In some embodiments, in any of the methods for multiplex sequencing nucleic acids, the detectably labeled nucleotide reagents that are bound to the immobilized template molecules in step (e) comprise individual immobilized template molecules hybridized to a sequencing primer to form a duplex, and the duplex is bound to a polymerase to form a complexed polymerase, and the complexed polymerase is bound to a detectably labeled nucleotide reagent. In some embodiments, the complexed polymerase is bound to a detectably labeled nucleotide reagent under a condition suitable for binding the detectably labeled nucleotide reagent to the complexed polymerase and incorporating the detectably labeled nucleotide into the hybridized sequencing primer, wherein the detectably labeled nucleotide reagent comprises an aromatic nucleo-base, a five carbon sugar moiety, 1-10 phosphate groups, and a fluorophore. In some embodiments, the complexed polymerase is bound to a detectably labeled nucleotide reagent under a condition suitable for binding the detectably labeled nucleotide reagent to the complexed polymerase and incorporating the detectably labeled nucleotide into the hybridized sequencing primer, wherein the detectably labeled nucleotide reagent comprises an aromatic nucleo-base, a five carbon sugar moiety having a chain terminating group at the 3' carbon sugar position, 1-10 phosphate groups, and a fluorophore. In some embodiments, the complexed polymerase is bound to a detectably labeled nucleotide reagent under a condition suitable for binding the detectably labeled nucleotide reagent to the complexed polymerase and the condition is suitable for inhibiting nucleotide incorporation, wherein the detectably labeled nucleotide reagent comprises a multivalent molecule which includes (1) a core, (2) a plurality of nucleotide arms, and (3) at least one fluorophore, wherein individual nucleotide arms comprise (i) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit.

In some embodiments, in any of the methods for multiplex sequencing nucleic acids, the immobilized template molecule comprises an immobilized concatemer molecule which is hybridized to a plurality of sequencing primers to form at least a first and second duplex on the same concatemer molecule, wherein the first and duplex is bound to a first polymerase and the second duplex is bound to a second polymerase to form first and second complexed polymerases, and wherein the method comprises: (a) contacting a plurality of multivalent molecules to the first and second complexed polymerases on the same concatemer template molecule, wherein individual multivalent molecules include (1) a core, (2) a plurality of nucleotide arms, and (3) at least one fluorophore, wherein individual nucleotide arms comprise (i) a core attachment moiety, (ii) a spacer comprising a PEG moiety, (iii) a linker, and (iv) a nucleotide unit, wherein the core is attached to the plurality of nucleotide arms, and the spacer is attached to the linker, and the linker is attached to the nucleotide unit, wherein the contacting is conducted under conditions suitable to bind a single multivalent molecule from the plurality to the first and second complexed polymerases, wherein a first nucleotide unit of the single multivalent molecule is bound to the first complexed polymerase which includes the first sequencing primer hybridized to a first portion of the concatemer template molecule thereby forming a first binding complex, and wherein a second nucleotide unit of the single multivalent molecule is bound to the second complexed polymerase which includes the second sequencing primer hybridized to a second portion of the concatemer template molecule thereby forming a second binding complex, wherein the first and second binding complexes which are bound to the same multivalent molecule forms an avidity complex, and wherein the contacting is conducted under a condition suitable to inhibit polymerase-catalyzed incorporation of the bound first and second nucleotide units in the first and second binding complexes; (b) detecting the first and second binding complexes on the same concatemer template molecule; (c) imaging the optical color signals emitted from the detectably labeled multivalent molecule which forms the first and second binding complexes on the same concatemer template molecule; and (d) identifying the first nucleotide unit in the first binding complex thereby determining the sequence of the first portion of the concatemer template molecule, and identifying the second nucleotide unit in the second binding complex thereby determining the sequence of the second portion of the concatemer template molecule.

Library Molecules

In some embodiments, the present disclosure provides nucleic acid library molecules (100), library-splint complexes (500) and covalently closed circular library molecules (600), and methods for preparing thereof. The nucleic acid library molecules comprise DNA, RNA, cDNA or chimeric DNA/RNA. The nucleic acid library molecule can be single-stranded or double-stranded, or can include single-stranded or double-stranded portions. The nucleic acid library molecule can be linear, concatemeric, covalently closed circular, dumbbell, hairpin, or other forms.

The nucleic acid library molecules described herein typically refer to a population of nucleic acid molecules each comprising a sequence of interest (e.g., insert (100)) covalently joined to at least one universal adaptor sequence (e.g., (120) and (130). In some embodiments, individual library molecules in the population further comprise, or lack, additional universal adaptor sequences, at least one sample index sequence and/or unique molecular index (UMI). Individual library molecules in the population can have a sequence of interest that is the same or different as other library molecules in the population.

In some embodiments, the insert region of a nucleic acid library molecule comprises a sequence of interest extracted from any source including a biological sample (e.g., fresh or live sample) such as a single cell, a plurality of cells, or tissue. The insert region can be isolated from healthy or diseases cells or tissues. The insert region can be obtained from an archived sample such as a fresh frozen paraffin embedded (FFPE) sample, or from needle biopsies, circulating tumor cells, cell free circulating DNA (e.g., from tumor cells or a fetus). In some embodiments, cells or tissues are treated with a lysis buffer to release their DNA and RNA, and the desired nucleic acid is separated from non-desired macromolecules such as proteins.

The insert region of a nucleic acid library molecule can be isolated in any form, including chromosomal, genomic (e.g., whole genomic), organellar (e.g., mitochondrial, chloroplast or ribosomal), recombinant molecules, cloned or amplified. The insert region of a nucleic acid library molecule can be methylated or non-methylated.

The insert region can be isolated from any organism including viruses, fungi, prokaryotes or eukaryotes. The insert region can be isolated from any organism including human, simian, ape, canine, feline, bovine, equine, murine, porcine, caprine, lupine, ranine, piscine, plant, insect, or bacteria. The insert region can be isolated from organisms borne in air, water, soil, or food.

The insert region can be isolated from any biological fluid, including blood, urine, serum, lymph, tumor, saliva, anal secretions, vaginal secretions, amniotic samples, perspiration, semen, environmental samples or culture samples. The insert region can be isolated from any organ, including head, neck, brain, breast, ovary, cervix, colon, rectum, endometrium, gallbladder, intestines, bladder, prostate, testicles, liver, lung, kidney, esophagus, pancreas, thyroid, pituitary, thymus, skin, heart, larynx, or other organs.

The insert region can be prepared using recombinant nucleic acid technology including but not limited to any combination of vector cloning, transgenic host cell preparation, host cell culturing and/or PCR amplification.

The insert region can be appended on one or both ends to at least one universal adaptor sequence to form a recombinant nucleic acid library molecule. The universal adaptor sequences can be prepared using chemical synthesis procedures using native nucleotides with or without nucleotide analogs or modified nucleotide linkages that confer certain properties, including resistance to enzymatic digestion, or increased thermal stability. Examples of nucleotide analogs and modified nucleotide linkages that inhibit nuclease digestion include phosphorothioate, 2'-O-methyl RNA, inverted dT, and 2' 3' dideoxy-dT. Insert regions that include locked nucleic acids (LNA) have increased thermal stability.

The insert region can be in fragmented or un-fragmented form. Fragmented insert regions can be obtained by mechanical force, enzymatic or chemical fragmentation methods. The fragmented insert regions can be generated using procedures that yield a population of fragments having overlapping sequences or non-overlapping sequences.

Mechanical fragmentation typically generates randomly fragmented nucleic acid molecules. Mechanical fragmentation methods include, for example and without limitation, mechanical shearing such as fluid shear, constant shear and pulsatile shear. Mechanical fragmentation methods can also include mechanical stress including sonication, nebulization and acoustic cavitation. In some embodiments, focused acoustic energy can be used to randomly fragment nucleic acid molecules. A commercially-available apparatus (e.g., Covaris™) can be used to fragment nucleic acid molecules using focused acoustic energy.

Enzymatic fragmentation procedures can be conducted under conditions suitable to generate randomly or non-randomly fragmented nucleic acid molecules. For example, and without limitation, restriction endonuclease enzyme digestion can be conducted to completion to generate non-randomly fragmented nucleic acid molecule. Alternatively, partial or incomplete restriction enzyme digestion can be conducted to generate randomly-fragmented nucleic acid molecules. Enzymatic fragmentation using restriction endonuclease enzymes can include any one or any combination of two or more restriction enzymes selected from the group consisting of type I, type II, type IIs, type IIB, type III, or type IV restriction enzymes. Enzymatic fragmentation can include digestion of the nucleic acid with a rare-cutting restriction enzyme, comprising Not I, Asc I, Bae I, AspC I, Pac I, Fse I, Sap I, Sfi I or Psr I. Enzymatic fragmentation can include use of any combination of a nicking restriction endonuclease, endonuclease and/or exonuclease. Enzymatic fragmentation can be achieved by conducting a nick translation reaction.

In some embodiments, enzymatic fragmentation can be achieved by reacting nucleic acids with an enzyme mixture, for example an enzyme that generates single-stranded nicks and another enzyme that catalyzes double-stranded cleavage. An exemplary enzyme mixture is FRAGMENTASE™ (e.g., from New England Biolabs™).

Fragments of the insert region can be generated with PCR using sequence-specific primers that hybridize to target regions in the input DNA samples to generate insert regions having known fragment lengths and sequences.

Targeted fragmentation methods using CRISPR/Cas9 can be used to generate fragmented insert regions from genomic DNA or other sources of input DNA.

Fragments of the insert portion can also be generated using a transposase-based tagmentation method using NEXTERA™ (from Epicentre™).

In some embodiments, input DNA can be fragmented using a Tn5 transposase-based workflow that employs a transposon end sequence comprising a double-stranded DNA having sequences that can bind a transposase enzyme to form a DNA-transposase complex (e.g., a transposome), where the complex can transpose/insert the transposon end sequences into DNA in an in vitro tagmentation reaction. The transposon end sequence comprises a first and second DNA strand. In some embodiments, the first DNA strand comprises a 19 base transfer end sequence 5'AGATGTGTATAAGAGACAG 3' (SEQ ID NO:3). In such embodiments, the second DNA strand comprises a 19 base non-transfer end sequence 5' CTGTCTCTTATACA-CATCT 3' (SEQ ID NO:6), which can be phosphorylated at its 5' end.

Figures 11A, 11B:
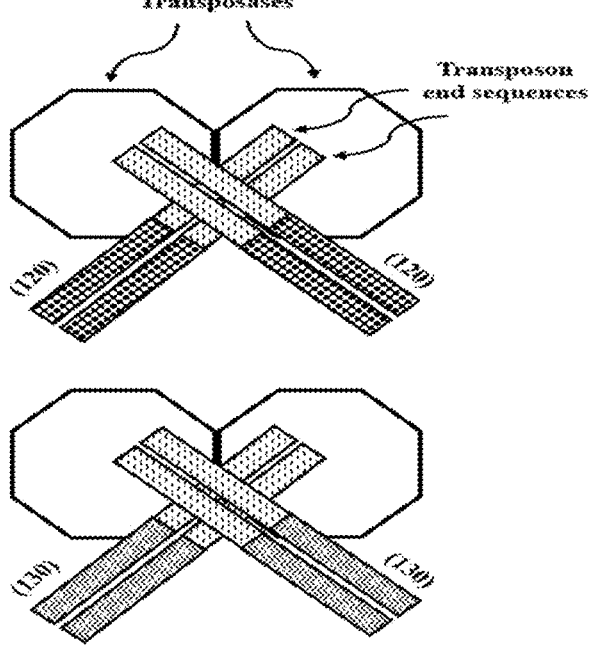
FIGS. 11A-11B are a set of schematics showing embodiments of transpososomes.
Figure 12:
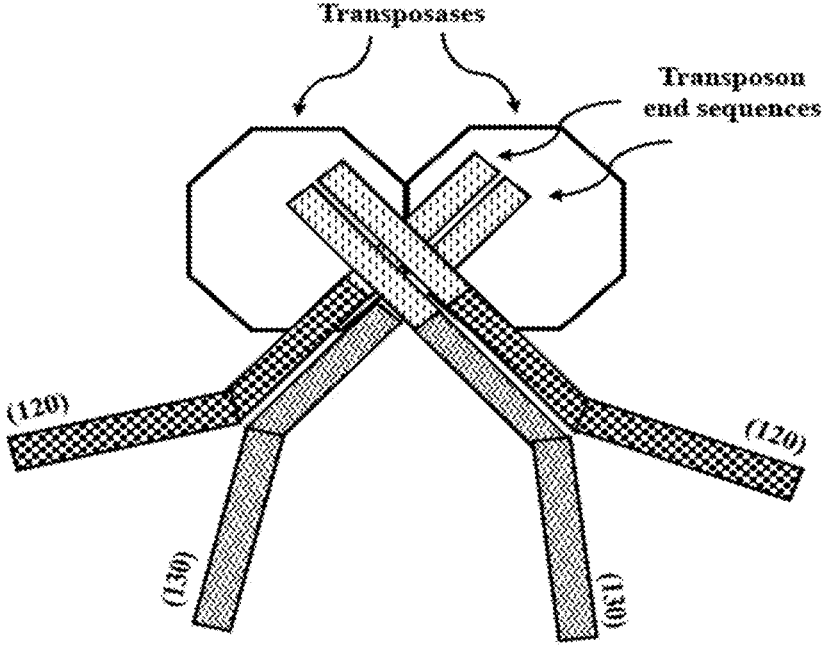
FIG. 12 is a schematic showing an embodiment of a transpososome comprising a transposase bound to a Y-shaped adaptor. Each Y-shaped adaptor comprises two oligonucleotides hybridized together and having a double-stranded annealed region and a mismatched portion.

When it is desirable to fragment input DNA and append adaptors using the Tn5 transposase-based workflow (e.g., tagmentation workflow), the first transposon DNA strand further comprises a first strand of an adaptor sequence. In some embodiments, the second transposon DNA strand further comprises a second strand of an adaptor sequence. In some embodiments, the first and second adaptor sequences are fully complementary along their lengths thereby forming a linear double-stranded transposon-end-adaptor molecule (FIG. 11). In some embodiments, as demonstrated in FIG. 11, the transposon end sequence specifically binds the transposase. In some embodiments, the first and second adaptor sequences are partially complementary along their lengths thereby forming a Y-shaped double-stranded transposon-end-adaptor molecule (FIG. 12). Within a Y-shaped adaptor, the first oligonucleotide can comprise a transposon end sequence and universal adaptor sequence for a forward sequencing primer binding site (120), and the second oligonucleotide can comprise a transposon end sequence and universal adaptor sequence for a reverse sequencing primer binding site (130). The transposon end sequence can specifically bind the transposase. In some embodiments, the Y-shaped double-stranded transposon-end-adaptor molecule can be full length or stubby Y-shaped adaptors.

In some embodiments, a plurality of Tn5 transposases and a plurality of double-stranded transposon-end-adaptor molecules can be mixed together under conditions suitable to bind/load the double-stranded transposon-end-adaptor molecules onto the transposase enzymes to form a plurality of DNA-transposase complexes (e.g., transpososomes) (e.g., FIGS. 11 and 12).

Figure 17:
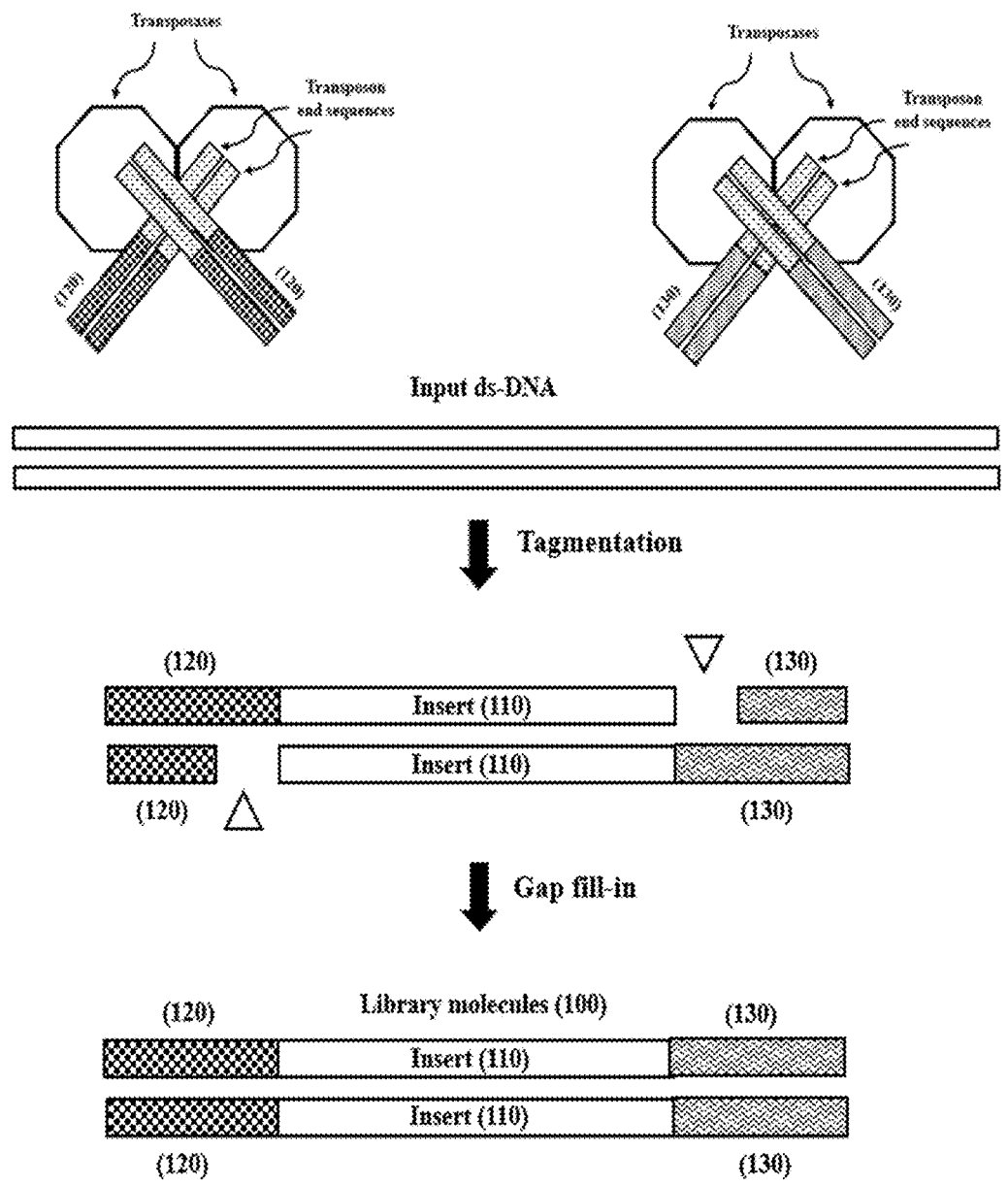
FIG. 17 is a schematic of a an exemplary tagmentation workflow using a plurality of transpososomes. Input double-stranded DNA is contacted with a plurality of transpososomes wherein individual transpososomes comprise a transposase bound to a first double-stranded polynucleotide comprising a transposon end sequence and universal adaptor sequence for a forward sequencing primer binding site (120), and the transposase is bound to a second double-stranded polynucleotide comprising a transposon end sequence and universal adaptor sequence for a reverse sequencing primer binding site (130).
Figure 18:
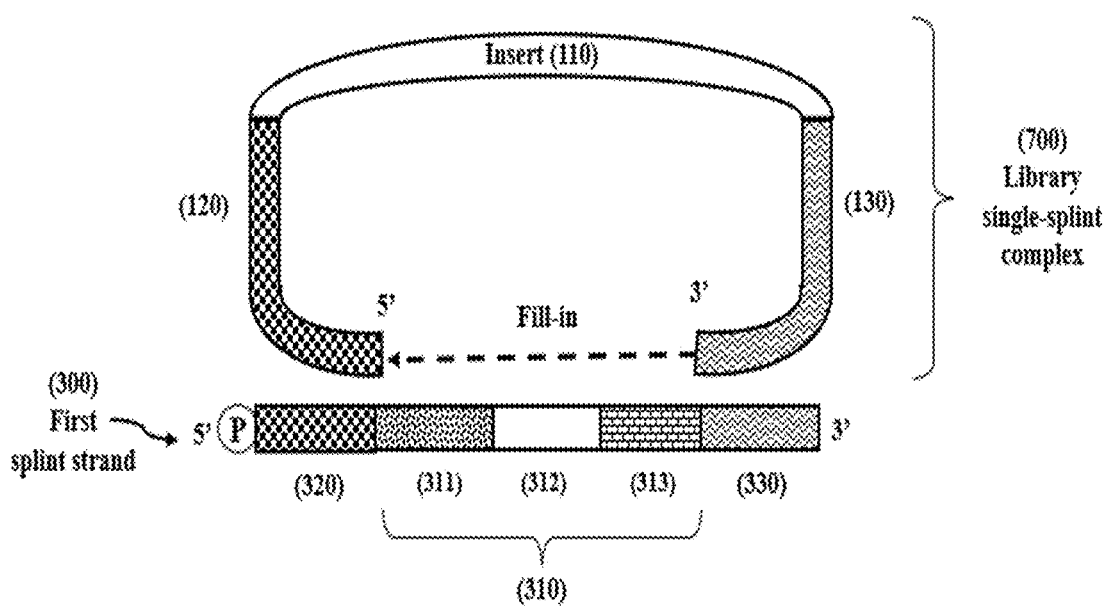
FIG. 18 is a schematic of an exemplary library circularization workflow, which comprises hybridizing a linear single stranded library molecule (100) with a first splint strand (200) thereby circularizing the library molecule to form a library single-splint complex (700) with a gap between the terminal ends of the library molecule. The linear nucleic acid library molecule (100) comprising an insert region (110) (e.g., sequence-of-interest) flanked on one side by a universal adaptor sequence for a forward sequencing primer binding site (120), and the insert region (110) is flanked on the other side by a universal adaptor sequence for a reverse sequencing primer binding site (130). The first splint strand (200) comprises a first region (320) that hybridizes with the universal adaptor sequence for a forward sequencing primer binding site (120) on one end of the linear single stranded library molecule (100), and the first splint strand comprises a second region (330) that hybridizes with the universal adaptor sequence for a reverse sequencing primer binding site (130) on the other end of the linear single stranded library molecule. The gap is closed with a polymerase-catalyzed fill-in reaction and enzymatic ligation reaction to generate a covalently closed circular molecule.

In some embodiments, input DNA (e.g., double-stranded DNA) can be mixed with a plurality of transpososomes under a condition suitable for transposing/inserting the transposon end sequences into random sites in the input DNA which fragments the input DNA and covalently attaches the transferred end sequence to the 5' end of one strand of the input DNA, and the non-transferred end sequence is hybridized to the transferred end sequence with a gap (e.g., 9 base gap) at the 3' end of the complementary input DNA strand. The gap can be subjected to a polymerase-catalyzed fill-in reaction and enzymatic ligation to generate tagmented double-stranded DNA with no gaps and carrying adaptors at both ends (FIG. 17). The transposon end sequence can specifically bind the transposase. The contacting of the input DNA and plurality of transpososomes may be suitable for insertion of the transposon end sequences and their universal adaptor sequences into random sites of the input DNA which generates a double-stranded fragment of the input DNA having a universal adaptor sequence for a forward sequencing primer binding site (120) covalently joined to one end of a first fragment strand and a universal adaptor sequence for a reverse sequencing primer binding site (130) annealed to the joined universal adaptor sequence for a forward sequencing primer binding site (120), and a gap (open triangle) between the universal adaptor sequence for a forward sequencing primer binding site (120) and the second fragment strand. Insertion of the transposon end sequences can also generate a double-stranded fragment of the input DNA having a universal adaptor sequence for a reverse sequencing primer binding site (130) covalently joined to one end of a second fragment strand and a universal adaptor sequence for a reverse sequencing primer binding site (130) annealed to the joined universal adaptor sequence for a reverse sequencing primer binding site (130), and a gap (open triangle) between the universal adaptor sequence for a reverse sequencing primer binding site (130) and the first fragment strand. The gaps can be closed by conducting a polymerase-catalyzed fill-in reaction and enzymatic ligation to generate a double-stranded DNA library molecules comprising a first and second DNA strand, each comprising an insert region (110) (e.g., sequence-of-interest) flanked on one side by a universal adaptor sequence for a forward sequencing primer binding site (120), and the insert region (110) is flanked on the other side by a universal adaptor sequence for a reverse sequencing primer binding site (130).

The transposase-based tagmentation workflow can be conducted using any of the methods described in U.S. Pat. Nos. 10,184,122, 10,287,574, 11,028,438, and published U.S. application No. 2019/0194737, the contents of all of these documents are incorporated by reference in their entireties.

In some embodiments, the insert region can be single-stranded or double-stranded. In some embodiments, any of the fragmentation methods described above can be used to generate DNA fragments having one or both ends that are blunt-ended, or have a 5' overhang end, or have a 3' overhang end, or any combination thereof.

In some embodiments, the fragmented nucleic acids can be subjected to enzymatic reactions for end-repair and/or A-tailing. One or both ends of the fragmented nucleic acids can be subjected to an enzymatic tailing reaction to generate a non-template A tail by employing a terminal transferase reaction. The fragmented nucleic acids can be contacted with a plurality of enzymes under a condition suitable to generate nucleic acid fragments having blunt-ended 5' phosphorylated ends. In some embodiments, the plurality of enzymes generates blunt-ended fragment having a non-template A-tail at their 3' ends. The plurality of enzymes comprises two or more enzymes that can catalyze nucleic acid end-repair, phosphorylation and/or A-tailing. The end-repair enzymes can include a DNA polymerase (e.g., T4 DNA polymerase) and Klenow fragment. The 5' end phosphorylation enzyme can comprise T4 polynucleotide kinase. The A-tailing enzyme can include a Taq polymerase (e.g., non-proof-reading polymerase) and dATP. In some embodiments, the fragmenting, end-repair, phosphorylation and A-tailing can be conducted in a one-pot reaction using a mixture of enzymes. The ends of the fragmented nucleic acids can be compatible for joining to at least one adaptor.

The insert region can be any length, for example the insert region can be about 50-250, or about 250-500, or about 500-750, or about 750-1000 bases, or any range therebetween, or base pairs in length.

The fragments containing the insert region can be subjected to a size selection process, or the fragments are not size selected. For example, the fragments can be size selected by gel electrophoresis and gel slice extraction. The fragments can be size selected using a solid phase adherence/immobilization method which typically employs micro paramagnetic beads coated with a chemical functional group that interacts with nucleic acids under certain ionic strength conditions with or without polyethylene glycol or polyalkylene glycol. Commercially-available solid phase adherence beads include SPRI™ (Solid Phase Reversible Immobilization) beads from Beckman Coulter™ (AMPUR XP™ paramagnetic beads, catalog No. B23318), MAGNA PURE™ magnetic glass particles (Roche Diagnostics™, catalog No. 03003990001), MAGNASIL™ paramagnetic beads from Promega™ (catalog No. MD1360), MAGTRA- TION™ paramagnetic beads and system from Precision System Science (catalog Nos. A1120 and A1060), MAG-BIND™ from Omega Bio-Tek™ (catalog No. M1378-01), MAGPREP™ silica from Millipore™ (catalog No. 101193), SNARE DNA purification systems from Bangs Laboratories (catalog Nos. BP691, BP692 and BP693), and CHEMA-GEN M-PVA™ beads from Perkin Elmer™ (catalog No. CMG-200).

Appending Adaptors to Fragmented Nucleic Acids

In some aspects, the present disclosure provides reagents, kits and methods used to append one or more adaptor sequences to fragmented nucleic acids. In some embodiments, individual fragmented nucleic acids will be covalently joined to at least one universal adaptor sequence for library preparation. In general, a nucleic acid fragment is covalently joined at both ends to one or more universal adaptors to generate a linear library molecule having the arrangement left adaptor-insert-right adaptor. In some embodiments, at least one fragment in the population of fragmented nucleic acids comprises a sequence-of-interest. Individual library molecules in the population of library molecules can have an insert region that is the same or different as other library molecules in the population. In some embodiments, about 1-10 ng, or about 10-50 ng, or about 50-100 ng, or any range therebetween, of input fragmented nucleic acids can be appended to one or more universal adaptors to generate a linear library.

In some embodiments, an adaptor comprises an oligo-nucleotide that can be operably linked (appended) to a target polynucleotide, where the adaptor confers a function to the co-joined adaptor-target molecule. Adaptors can comprise DNA, RNA, chimeric DNA/RNA, or analogs thereof. Adaptors can include at least one ribonucleoside residue. Adaptors can be single-stranded, double-stranded, or have single-stranded and/or double-stranded portions. Adaptors can be configured to be linear (e.g., FIGS. 8 and 9), stem-looped, hairpin, or Y-shaped forms (e.g., FIG. 10). In some embodiments, any of the Y-shaped adaptors (e.g., as shown in FIG. 10) also include a sample index sequence and an optional short random sequence (e.g., NNN) on one or both mismatched portion(s). Adaptors can be any length, including 4-100 nucleotides or longer. Adaptors can have blunt ends, overhang ends, or a combination of both. Overhang ends include 5' overhang and 3' overhang ends. The 5' end of a single-stranded adaptor, or one strand of a double-stranded adaptor, can have a 5' phosphate group or lack a 5' phosphate group. Adaptors can include a 5' tail that does not hybridize to a target polynucleotide (e.g., tailed adaptor), or adaptors can be non-tailed. At least a portion of the adaptors can comprise a known and pre-determined sequence. An adaptor can include a sequence that is the same or is complementary to at least a portion of an amplification primer binding site, a forward sequencing primer binding site, a reverse sequencing primer binding site, a surface capture primer binding site and/or a surface pinning primer binding site. Adaptors can include at least one sample index sequence which can be used to distinguish polynucleotides (e.g., insert sequences) from different sample sources in a multiplex assay. Adaptors can include a random sequence or degenerate sequence. Adaptors can include at least one inosine residue. Adaptors can include at least one unique molecular index (e.g., UMI, a molecular tag) that can be used to uniquely identify a nucleic acid molecule to which the adaptor is appended. In some embodiments, the unique identification sequence comprises 2-12 or more nucleotides having a known sequence. For example, and without limitation, the unique identification sequence comprises a known random sequence where a nucleotide at each position is randomly selected from nucleotides having a base A, G, C, T or U. Adaptors can include at least one restriction enzyme recognition sequence, including any one or any combination of two or more selected from the group consisting of type I, type II, type III, type IV, type Hs or type IIB. Adaptors can include at least one phosphorothioate, phosphorothiolate and/or phosphoramidate linkage.

In some embodiments, an adaptor comprises a universal sequence which is a sequence in a nucleic acid molecule that is common among two or more polynucleotide molecules in a population of polynucleotide molecules. For example, and without limitation, an adaptor having a universal sequence can be operably joined to a plurality of polynucleotides so that the population of co-joined molecules carry the same universal adaptor sequence. Examples of universal adaptor sequences include, without limitation, a universal amplification primer binding site, a universal forward sequencing primer binding site, a universal reverse sequencing primer binding site, a universal surface capture primer binding site and a universal surface pinning primer binding site.

In some embodiments, an adaptor comprises at least one sample index sequence. Sample indexes can be employed to prepare separate sample-indexed linear libraries using input nucleic acids isolated from different sources. The sample-indexed libraries can be pooled together to generate a multiplex library mixture, and the pooled libraries can be circularized, amplified and/or sequenced. The sequences of the insert region (110) along with one or more sample index sequences can be used to identify the source of the input nucleic acids. The sample index sequences can be used to distinguish sequences of interest obtained from different sample sources in a multiplex assay. In some embodiments, a sample index comprises 3-10 nucleotides. In some embodiments, the sample index includes a short random sequence (e.g., NNN) which can be located upstream or downstream of the sample index sequence. Exemplary sample indexes are listed in Table 3 above. In some embodiments, any number of sample-indexed libraries can be pooled together, for example 2-10, or 10-50, or 50-100, or 100-200, or any range therebetween, or more than 200 sample-indexed libraries can be pooled together. Exemplary nucleic acid sources include naturally-occurring, recombinant, or chemically-synthesized sources. Exemplary nucleic acid sources include single cells, a plurality of cells, tissue, biological fluid, environmental sample or whole organism. Exemplary nucleic acid sources include fresh, frozen, fresh-frozen or archived sources (e.g., formalin-fixed paraffin-embedded; FFPE). The skilled artisan will recognize that nucleic acids can be isolated from many other sources. The sample-indexed linear library molecules can be prepared in single-stranded or double-stranded form.

In some embodiments, the adaptors can be prepared using chemical synthesis procedures using native nucleotides with or without nucleotide analogs or modified nucleotide linkages that confer certain properties, including resistance to enzymatic digestion, or increased thermal stability. Examples of nucleotide analogs and modified nucleotide linkages that inhibit nuclease digestion include phosphoro-thioate, 2'-O-methyl RNA, inverted dT, and 2' 3' dideoxy-dT. Insert regions that include locked nucleic acids (LNA) have increased thermal stability.

In some embodiments, the adaptor comprises a double-stranded linear adaptor having two oligonucleotides strands which are hybridized together (e.g., FIGS. 8 and 9). In some embodiments, one or both ends of a double-stranded linear adaptor can have a blunt end, 5' overhang end or 3' overhang end. In some embodiments, one or both ends of a double-stranded linear adaptor can have at least a one base overhang (e.g., an A-base overhang) that is complementary to an overhang end on a nucleic acid fragment. In some embodiment, one or both ends of a double-stranded linear adaptor comprises a terminal 5' end that is phosphorylated or non-phosphorylated. In some embodiment, one or both ends of a double-stranded linear adaptor comprises a terminal 3' end that is extendible with a polymerase-catalyzed primer extension reaction, or the terminal 3' end is blocked and non-extendible. In some embodiment, one or both strands of a double-stranded linear adaptor comprises one or more phosphorothioate linkage at the 5' and/or 3' ends to confer exonuclease resistance. In some embodiments, one or both strands of a double-stranded linear adaptor comprises one or more phosphorothioate linkage at an internal position to confer endonuclease resistance. In some embodiments, one or both strands of a double-stranded linear adaptor comprises one or more 2'-O-methylcytosine bases at the 5' and/or 3' end, or at an internal position.

In some embodiments, the double-stranded linear adaptor comprises at least one adaptor sequence. For example, the double-stranded linear adaptor comprises a full-length or partial-length sequence of a universal sequence for a forward sequencing primer binding site (120) (e.g., FIG. 8). In some embodiments, any of the double-stranded nucleic acid adaptors (e.g., as shown in FIG. 8) also include a sample index sequence and an optional short random sequence (e.g., NNN). In some embodiments, the double-stranded linear adaptor comprises a full-length or partial-length sequence of a universal sequence for a reverse sequencing primer binding site (130) (e.g., FIG. 9). In some embodiments, any of the double-stranded nucleic acid adaptors (e.g., as shown in FIG. 9) also include a sample index sequence and an optional short random sequence (e.g., NNN). In some embodiments, the double-stranded linear adaptor further comprises a sample index sequence. In some embodiments, the double-stranded linear adaptor further comprises a unique molecular index (UMI) sequence. In some embodiments, the double-stranded linear adaptor lacks additional sequences to be appended to nucleic acid fragments. In some embodiments, the double-stranded linear adaptor lacks a sequence for a universal amplification primer binding site, a universal surface capture primer binding site and/or a universal surface pinning primer binding site. In some embodiments, the double-stranded linear adaptor lacks a sequence for a sample index. In some embodiments, the double-stranded linear adaptor lacks a sequence for a unique molecular index (UMI) sequence.

In some embodiments, any of the double-stranded linear adaptors described herein comprise a universal forward sequencing primer binding site (120) or a universal reverse sequencing primer binding site (130) which are listed in Table 1 above, or complementary to the sequences listed in Table 1 above. In some embodiments, any of the universal forward sequencing primer binding site (120) or the universal reverse sequencing primer binding site (130) which are listed in Table 1 can be truncated at the 5' end and/or the 3' end, where the truncation can be 1-12 nucleotides. In certain embodiments, the 5' end is truncated. In certain embodiments, the 3' end is truncated.

In some embodiments, the adaptor comprises a Y-shaped adaptor having two oligonucleotides strands which are hybridized together to form a double-stranded annealed region and a mismatched region (e.g., FIG. 10). In some embodiments, the annealed portion of a Y-shaped adaptor can have a blunt end, 5' overhang end or 3' overhang end. In some embodiments, the annealed portion of a Y-shaped adaptor can have at least a one base overhang (e.g., an A-base overhang) that is complementary to an overhang end on a nucleic acid fragment. In some embodiment, the annealed portion of a Y-shaped adaptor comprises a terminal 5' end that is phosphorylated or non-phosphorylated. In some embodiment, the annealed portion of a Y-shaped adaptor comprises a terminal 3' end that is extendible with a polymerase-catalyzed primer extension reaction, or the terminal 3' end is blocked and non-extendible. In some embodiment, the annealed portion and/or the mismatched portion comprises one or more phosphorothioate linkage at the 5' and/or 3' ends to confer exonuclease resistance. In some embodiments, the annealed portion and/or the mismatched portion comprises one or more phosphorothioate linkage at an internal position to confer endonuclease resistance. In some embodiments, the annealed portion and/or the mismatched portion comprises one or more 2'-O-methylcytosine bases at the 5' and/or 3' end, or at an internal position.

In some embodiments, the annealed portion and/or the mismatched portion of a Y-shaped adaptor comprises at least one adaptor sequence. For example, the first oligonucleotide strand of a Y-shaped adaptor comprises a full-length or partial-length sequence of a universal sequence for a forward sequencing primer binding site (120). In some embodiments, the second oligonucleotide strand of a Y-shaped adaptor comprises a full-length or partial-length sequence of a universal sequence for a reverse sequencing primer binding site (130). FIG. 10 shows exemplary Y-shaped adaptors.

In some embodiments, a plurality of Y-shaped adaptors comprises at least a first and second Y-shaped adaptor. In some embodiments, the Y-shaped adaptors in the plurality are the same and have the same first and second oligonucleotide strands. In some embodiments, the Y-shaped adaptors in the plurality are different and have different first and second oligonucleotide strands.

In some embodiments, the Y-shaped adaptors are "stubby" Y-shaped adaptors where the first and/or second oligonucleotide strands of the Y-shaped adaptor lack additional sequences to be appended to nucleic acid fragments, or the stubby Y-shaped adaptors have partial-length universal adaptor sequences. In some embodiments, the first and/or second oligonucleotide strands of a full-length Y-shaped adaptor or a stubby Y-shaped adaptor further comprise a sample index sequence. In some embodiments, the sample index sequence is located on the mis-matched region of the first and/or second oligonucleotide. In some embodiments, the first and/or second oligonucleotide strands of a full-length Y-shaped adaptor or a stubby Y-shaped adaptor further comprise a unique molecular index (UMI) sequence. In some embodiments, the unique molecular index (UMI) sequence is located on the mis-matched region of the first and/or second oligonucleotide. In some embodiments, the first and/or second oligonucleotide strands of a full-length Y-shaped adaptor or a stubby Y-shaped adaptor lack a sequence for a universal amplification primer binding site, a universal surface capture primer binding site and/or a universal surface pinning primer binding site. In some embodiments, the first and/or second oligonucleotide strands of a full-length Y-shaped adaptor or a stubby Y-shaped adaptor lack a sequence for a sample index. In some embodiments, the first and/or second oligonucleotide strands of a full-length Y-shaped adaptor or a stubby Y-shaped adaptor lack a sequence for a unique molecular index (UMI) sequence. The advantage of using shorter stubby Y-shaped adaptors is that the higher ligation efficiency of the stubby Y-shaped adaptors compared to the ligation efficiency of the longer Y-shaped adaptors.

Figure 15:
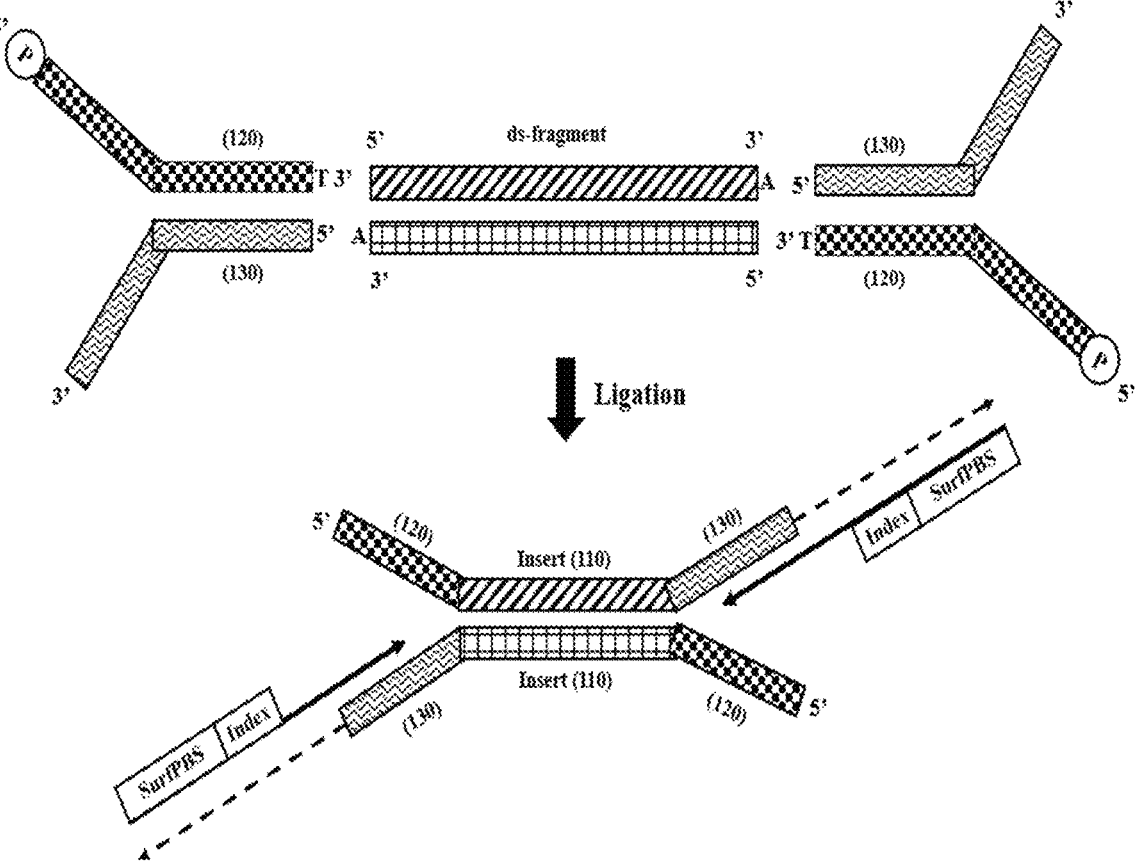
FIG. 15 is a schematic showing an exemplary adaptor ligation workflow to generate a double-stranded linear nucleic acid library molecule. A double-stranded nucleic acid fragment is enzymatically ligated on one side to a first Y-shaped adaptor comprising a first oligonucleotide carrying a full-length sequence of a universal adaptor sequence for a forward sequencing primer binding site (120), and a second oligonucleotide carrying a full-length sequence of a universal adaptor sequence for a reverse sequencing primer binding site (130). The double-stranded nucleic acid fragment is enzymatically ligated on the other side to a second Y-shaped adaptor comprising a first oligonucleotide carrying a full-length sequence of a universal adaptor sequence for a forward sequencing primer binding site (120), and a second oligonucleotide carrying a full-length sequence of a universal adaptor sequence for a reverse sequencing primer binding site (130). The resulting double-stranded linear nucleic acid library molecule is subjected to a primer extension using primers having a region that hybridizes to one of the mis-matched portions (e.g., (130)), and the primers also carry a sample index sequence and a universal surface primer binding site (SurfPBS) at the other end. A primer extension reaction is conducted using the hybridized primer as a template, to generate extended library molecules comprising: a forward sequencing primer binding site (120); insert sequence (110); a reverse sequencing primer binding site (130); a sample index sequence; and a universal surface primer binding site (SurfPBS).

In some embodiments, Y-shaped adaptors can be ligated to the ends of nucleic acid fragments to generate library molecules having adaptor sequences appended to both ends of the sequence of interest. In some embodiments, additional adaptor sequences can be appended by conducting a primer extension reaction using tailed primers (e.g., tailed PCR primers). For example, the primer extension reaction comprises contacting/hybridizing the mis-matches portion of the now-ligated Y-shaped adaptor with a tailed primer which carries an additional adaptor sequence, and conducting at least one primer extension reaction (e.g., FIG. 15). In some embodiments, the first and second Y-shaped adaptors carry the same universal adaptor sequence for a forward sequencing primer binding site (120), and carry the same universal adaptor sequence for a reverses sequencing primer binding site (130). The resulting double-stranded linear nucleic acid library molecule can be subjected to a primer extension using primers having a region that hybridizes to one of the mis-matched portions (e.g., (130)), and the primers may also carry a sample index sequence and a universal surface primer binding site (SurfPBS) at the other end. A primer extension reaction can be conducted using the hybridized primer as a template, to generate extended library molecules comprising: a forward sequencing primer binding site (120); insert sequence (110); a reverse sequencing primer binding site (130); a sample index sequence; and a universal surface primer binding site (SurfPBS). In some embodiments, the extended library molecules can be subjected to another primer extension reaction using second primers having a region that hybridizes to one of the mis-matched portions (e.g., (120)), and the primers may also carry a universal surface primer binding site (SurfPBS) and an optional sample index sequence and at the other end. A primer extension reaction is conducted using the second hybridized primer as a template.

Figure 16:
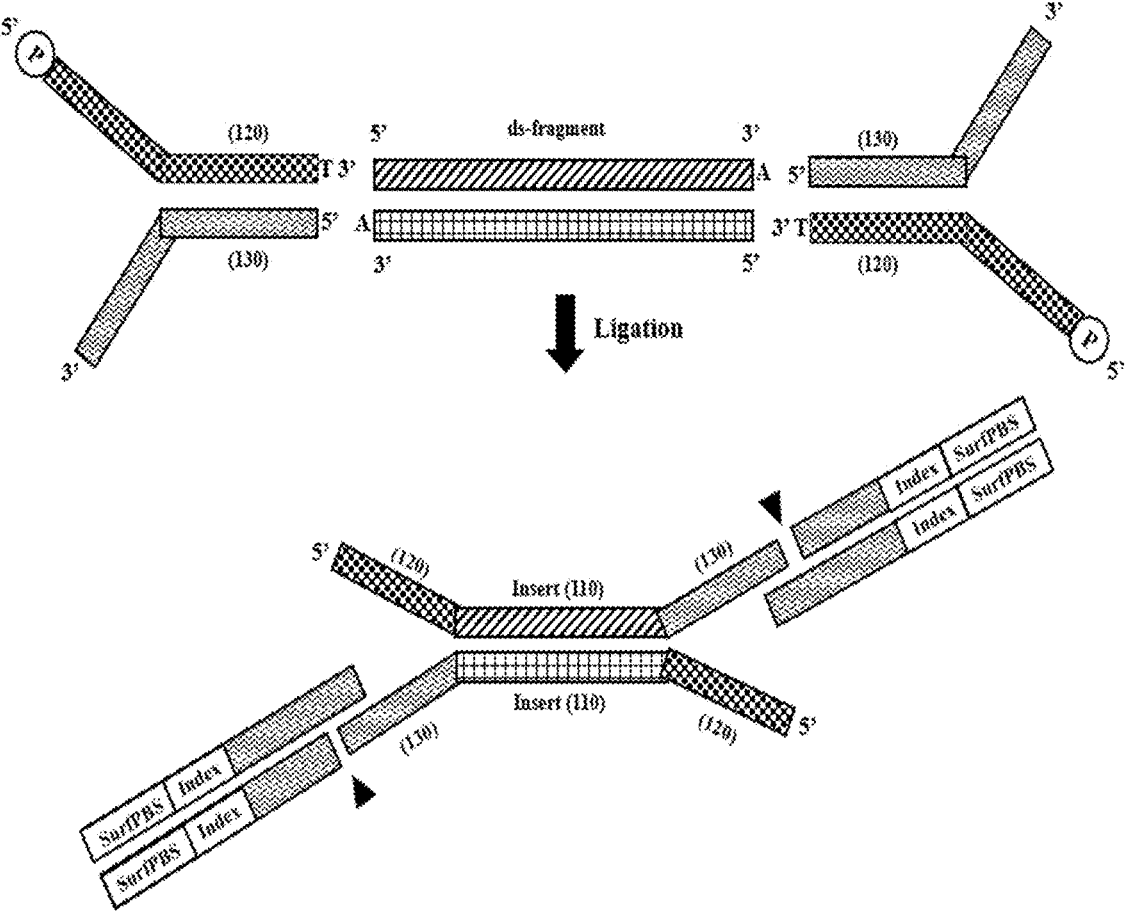
FIG. 16 is a schematic showing an exemplary adaptor ligation workflow to generate a double-stranded linear nucleic acid library molecule. A double-stranded nucleic acid fragment is enzymatically ligated on one side to a first Y-shaped adaptor comprising a first oligonucleotide carrying a full-length sequence of a universal adaptor sequence for a forward sequencing primer binding site (120), and a second oligonucleotide carrying a full-length sequence of a universal adaptor sequence for a reverse sequencing primer binding site (130). The double-stranded nucleic acid fragment is enzymatically ligated on the other side to a second Y-shaped adaptor comprising a first oligonucleotide carrying a full-length sequence of a universal adaptor sequence for a forward sequencing primer binding site (120), and a second oligonucleotide carrying a full-length sequence of a universal adaptor sequence for a reverse sequencing primer binding site (130). The resulting double-stranded linear nucleic acid library molecule is hybridized with a linear double-stranded adaptor having a 3' overhang end and a blunt end. The 3' overhang end comprises a sequence that can hybridize with the mis-matched portion having a reverse sequencing primer binding site (130), which generates a partially double-stranded region with a nick (solid triangle). The nicks can be ligated and the non-ligated strand can be removed.

As shown in FIG. 16, in some embodiments, the first and second Y-shaped adaptors carry the same universal adaptor sequence for a forward sequencing primer binding site (120), and carry the same universal adaptor sequence for a reverse sequencing primer binding site (130). In some embodiments, the Y-shaped adaptors also include a sample index sequence and an optional short random sequence (e.g., NNN) on one or both mis-matched portion(s). The resulting double-stranded linear nucleic acid library molecule can be hybridized with a linear double-stranded adaptor having a 3' overhang end and a blunt end. The 3' overhang end comprises a sequence that can hybridize with the mis-matched portion having a reverse sequencing primer binding site (130), which generates a partially double-stranded region with a nick (solid triangle). The nicks can be ligated, and the non-ligated strand can be removed.

The tailed primers can carry any one or any combination of additional adaptor sequences, including a universal amplification primer binding site, a universal surface capture primer binding site, a universal surface pinning primer binding site, a sample index sequence and/or a unique molecular index (UMI).

In some embodiments, a first tailed PCR primer can be used to conduct a first primer extension reaction and a second tailed PCR primers can be used conduct a second primer extension to generate library molecules comprising an insert region appended on both sides with at least one additional adaptor. In some embodiments, the first and second tailed PCR primers can be used to conduct multiple PCR cycles (e.g., about 5-20 PCR cycles) to generate library molecules comprising an insert region appended on both sides with at least one additional adaptor. In some embodiments, the workflow does not include PCR using first or second tailed PCR primers.

In some embodiments, any of the first or second oligonucleotide strands described herein that are part of a Y-shaped adaptor comprise a universal forward sequencing primer binding site (120) (or a complementary sequence thereof) or a universal reverse sequencing primer binding site (130) (or a complementary sequence thereof) which are listed in Table 1 above. In some embodiments, in the first or second oligonucleotide strands of a Y-shaped adaptor, any of the universal forward sequencing primer binding site (120) or the universal reverse sequencing primer binding site (130) which are listed in Table 1 can be truncated at the 5' end and/or the 3' end, where the truncation can be 1-12 nucleotides. In certain embodiments, the 5' end is truncated. In certain embodiments, the 3' end is truncated.

In some embodiments, the adaptor comprises a hairpin adaptor having one oligonucleotide strand with an intramolecular annealed region that is double-stranded and a single-stranded non-complementary loop portion. In some embodiments, the double-stranded portion of a hairpin adaptor can have a blunt end, 5' overhang end or 3' overhang end. In some embodiments, the double-stranded portion of a hairpin adaptor can have at least a one base overhang (e.g., an A-base overhang) that is complementary to an overhang end on a nucleic acid fragment. In some embodiment, the double-stranded portion of a hairpin adaptor comprises a terminal 5' end that is phosphorylated or non-phosphorylated. In some embodiment, the double-stranded portion of a hairpin adaptor comprises a terminal 3' end that is extendible with a polymerase-catalyzed primer extension reaction, or the terminal 3' end is blocked and non-extendible. In some embodiments, the loop portion comprises at least one cleavable site, including an endonuclease restriction enzyme site, an abasic site and/or a ribonucleotide. In some embodiments, the abasic site comprises one or more uridine, deoxy-8-oxo-guanine triphosphate (d-8-oxoG); 8-oxo-7,8-dihydroguanine (8oxoG) or deoxyinosine. In some embodiment, the double-stranded portion and/or the loop portion comprises one or more phosphorothioate linkage at the 5' and/or 3' ends to confer exonuclease resistance. In some embodiments, the double-stranded portion and/or the loop portion comprises one or more phosphorothioate linkage at an internal position to confer endonuclease resistance. In some embodiments, the double-stranded portion and/or the loop portion comprises one or more 2'-O-methylcytosine bases at the 5' and/or 3' end, or at an internal position.

In some embodiments, the double-stranded portion and/or the loop portion of a hairpin adaptor comprises at least one adaptor sequence. For example, one strand of the double-stranded portion of a hairpin adaptor comprises a full-length or partial-length sequence of a universal sequence for a forward sequencing primer binding site (120). In some embodiments, the other strand of the double-stranded portion of the hairpin adaptor comprises a full-length or partial-length sequence of a universal sequence for a reverse sequencing primer binding site (130). In some embodiments, one region of the loop portion of the hairpin adaptor comprises a full-length or partial-length sequence of a universal sequence for a forward sequencing primer binding site (120). In some embodiments, another region of the loop portion of the hairpin adaptor comprises a full-length or partial-length sequence of a universal sequence for a reverse sequencing primer binding site (130). In some embodiments, the hairpin adaptor further comprises a sample index sequence. In some embodiments, the hairpin adaptor further comprises a unique molecular index (UMI) sequence. In some embodiments, the hairpin adaptor lacks additional sequences to be appended to nucleic acid fragments. In some embodiments, the hairpin adaptor lacks a sequence for a universal amplification primer binding site, a universal surface capture primer binding site and/or a universal surface pinning primer binding site. In some embodiments, the hairpin adaptor lacks a sequence for a sample index. In some embodiments, the hairpin adaptor lacks a sequence for a unique molecular index (UMI) sequence.

In some embodiments, any of the oligonucleotide strands described herein that are part of a hairpin adaptor comprise a universal forward sequencing primer binding site (120) and a universal reverse sequencing primer binding site (130) which are listed in Table 1 above. In some embodiments, any of the oligonucleotide strands described herein that are part of a hairpin adaptor comprise a complement sequence of the universal forward sequencing primer binding site (120) and/or a complement sequence of a universal reverse sequencing primer binding site (130) which are listed in Table 1 above. In some embodiments, in the first or second oligonucleotide strands of a strand that is part of the hairpin, any of the universal forward sequencing primer binding site (120) or the universal reverse sequencing primer binding site (130) which are listed in Table 1 can be truncated at the 5' end and/or the 3' end, where the truncation can be 1-12 nucleotides. In certain embodiments, the 5' end is truncated. In certain embodiments, the 3' end is truncated.

Individual nucleic acid fragments can be appended on one or both ends to at least one universal adaptor sequence to form a recombinant nucleic acid linear library molecule having the general arrangement left adaptor-insert-right adaptor.

In some embodiments, the nucleic acid fragments can be joined at one or both ends to at least one universal adaptor sequence using a ligase enzyme and/or primer extension reaction to generate a linear library molecule. Covalent linkage between nucleic acid fragments and the universal adaptor(s) can be achieved with a DNA ligase or RNA ligase. Exemplary non-limiting DNA ligases that can ligate double-stranded DNA molecules include T4 DNA ligase and T7 DNA ligase. In some embodiments, universal adaptor sequences can be appended to nucleic acid fragments by primer extension or PCR using a tailed primer having 5' region carrying a universal adaptor sequence and a 3' region that is complementary to a portion of the nucleic acid fragments. In some embodiments, universal adaptor sequences can be appended to an insert sequence which is flanked on one side or both sides with first and second universal adaptor sequences by primer extension or PCR using a tailed primer having a 5' region carrying an additional universal adaptor sequence and a 3' region that is complementary to a portion of the first or second universal adaptor sequence.

Figure 13:
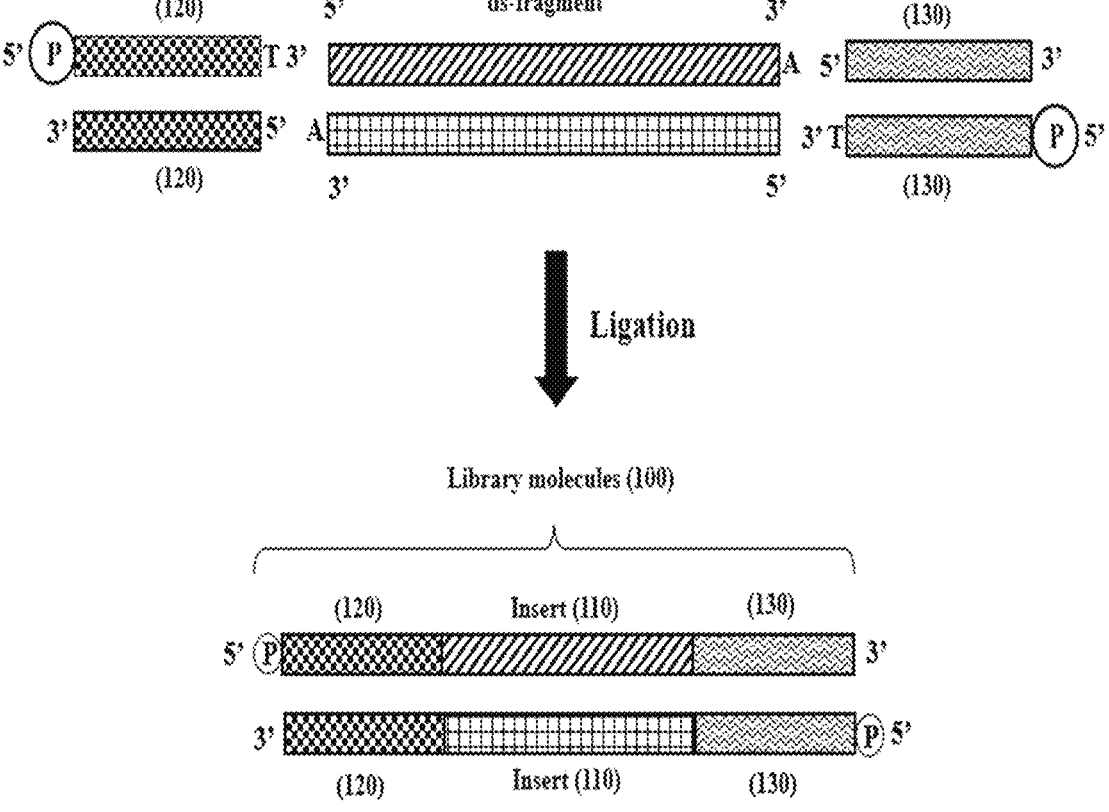
FIG. 13 is a schematic showing an exemplary adaptor ligation workflow to generate a double-stranded linear nucleic acid library molecule. A double-stranded nucleic acid fragment is enzymatically ligated on one side to a double-stranded adaptor carrying a universal adaptor sequence for a forward sequencing primer binding site (120). The double-stranded nucleic acid fragment is enzymatically ligated on the other side to a double-stranded adaptor carrying a universal adaptor sequence for a reverse sequencing primer binding site (130).

In some embodiments, a library molecule (100) can be generated by employing a ligation reaction and then then generating a library-splint complex (500) using a double-stranded splint adaptor (200). In some embodiments, methods for generating a library molecule comprise: (a) providing a double-stranded nucleic acid fragment comprising a sequence-of-interest (e.g., a double-stranded insert region (110)); and (b) joining the first end of the double-stranded insert region (110) to a first double-stranded linear adaptor having a universal sequence for a forward sequencing primer binding site (120), and joining the second end of the double-stranded insert region (110) to a second double-stranded linear adaptor having a universal sequence for a reverse sequencing primer binding site (130), wherein the joining is conducted using a DNA ligase enzyme to generate a double-stranded recombinant library molecule (100) (e.g., FIG. 13). The double-stranded nucleic acid fragment can be enzymatically ligated on the other side to a double-stranded adaptor carrying a universal adaptor sequence for a reverse sequencing primer binding site (130). In some embodiments, one or both of the double-stranded adaptors may also include a sample index sequence and an optional short random sequence (e.g., NNN).

In some embodiments, the methods for generating a library molecule further comprise step (c): denaturing the double-stranded recombinant library molecule (100) to generating two single-stranded library molecules (100). Both of the single-stranded library molecules (100) can be hybridized with any of the double-stranded splint adaptors (200) described herein to generate a plurality of library-splint complexes (500), as described in step (d) below.

In some embodiments, the methods for generating a library molecule further comprise step (d): hybridizing the single-stranded library molecules (100) with a plurality of any of the double-stranded splint adaptors (200) described herein. In some embodiments, individual double-stranded splint adaptors (200) comprise a first splint strand (300) hybridized to a second splint strand (400), wherein the double-stranded splint adaptor includes a double-stranded region and two flanking single-stranded regions, wherein the first splint strand comprises a first region (320), an internal region (310), and a second region (330), and wherein the internal region of the first splint strand (310) is hybridized to the second splint strand (400). In some embodiments, the first region (320) of the first splint strand is designed to hybridize with the universal sequence for a forward sequencing primer binding site (120) of the library molecule (100). In some embodiments, the second region (330) of the first splint strand is designed to hybridize with the universal sequence for a reverse sequencing primer binding site (130) of the library molecule (100). In some embodiments, the hybridizing of step (c) is conducted under a condition suitable for hybridizing the first region of the first splint strand (320) to at least a portion of (120) of the single-stranded library molecules, and the condition is suitable for hybridizing the second region of the first splint strand (330) to at least a portion of (130) of the single-stranded library molecule, thereby circularizing the single-stranded library molecules to form a plurality of library-splint complexes (500) each having two nicks (e.g., FIG. 3).

In some embodiments, the methods for generating a library molecule further comprise step (e): contacting the plurality of library-splint complexes (500) with a ligase to generate a plurality of covalently closed circular library molecules (600) (e.g., FIG. 4).

In some embodiments, a primer extension or PCR reaction is not conducted after step (b) to join to the double-stranded recombinant library molecule (100) any additional adaptor sequences including: a universal amplification primer binding site, a universal surface capture primer binding site, a universal surface pinning primer binding site, a sample index or unique molecular index (UMI) sequence.

In some embodiments, a library molecule (100) can be generated by employing a ligation reaction and then then generating a library-splint complex (500) using a double-stranded splint adaptor (200). In some embodiments, methods for generating a library molecule comprise: (a) providing a double-stranded nucleic acid fragment comprising a sequence-of-interest (e.g., a double-stranded insert region (110)).

Figure 14:
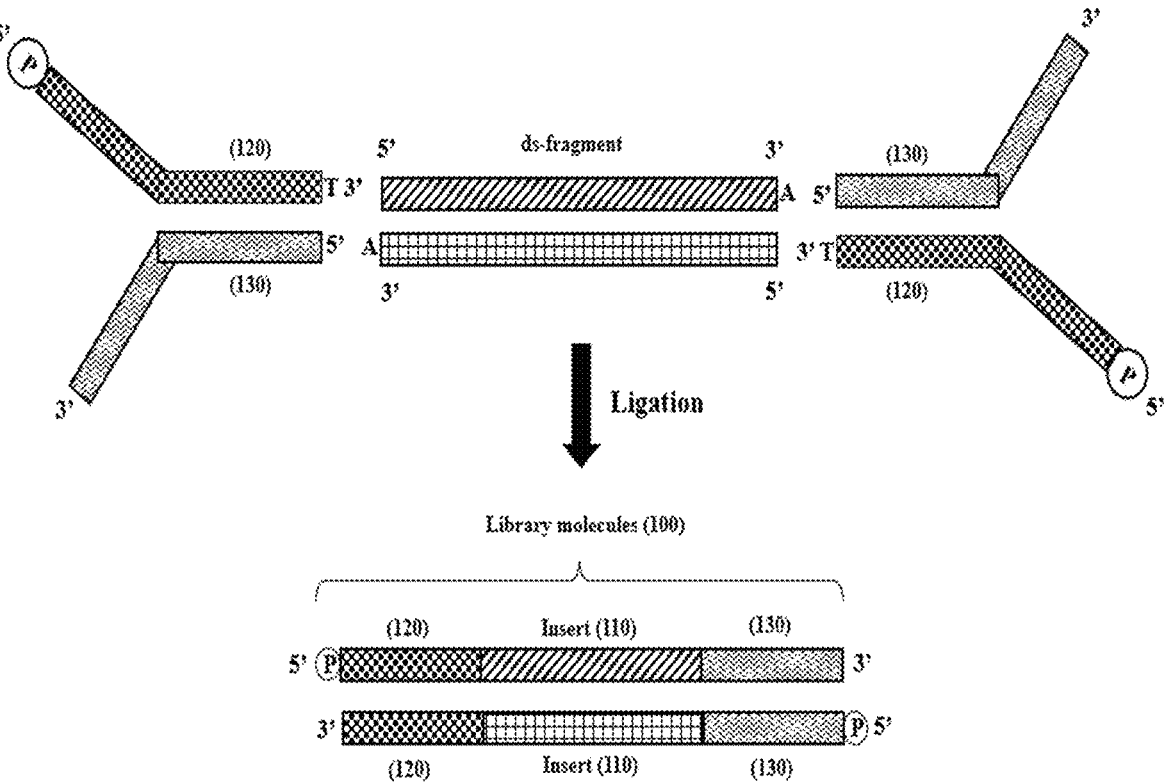
FIG. 14 is a schematic showing an exemplary adaptor ligation workflow to generate a double-stranded linear nucleic acid library molecule. A double-stranded nucleic acid fragment is enzymatically ligated on one side to a first Y-shaped adaptor comprising a first oligonucleotide carrying a full-length sequence of a universal adaptor sequence for a forward sequencing primer binding site (120), and a second oligonucleotide carrying a full-length sequence of a universal adaptor sequence for a reverse sequencing primer binding site (130). The double-stranded nucleic acid fragment is enzymatically ligated on the other side to a second Y-shaped adaptor comprising a first oligonucleotide carrying a full-length sequence of a universal adaptor sequence for a forward sequencing primer binding site (120), and a second oligonucleotide carrying a full-length sequence of a universal adaptor sequence for a reverse sequencing primer binding site (130).

In some embodiments, methods for generating a library molecule further comprise step (b): joining the first end of the double-stranded insert region (110) to a first Y-shaped adaptor, and joining the second end of the double-stranded insert region (110) to a second Y-shaped adaptor, wherein the joining is conducted using a DNA ligase enzyme to generate a double-stranded recombinant library molecule (100). In some embodiments, the first and second Y-shaped adaptor are the same, and each comprise two oligonucleotides strands which are hybridized together to form a double-stranded annealed region and a mismatched region. In some embodiments, the first oligonucleotide strand of the Y-shaped adaptors comprise a full-length or partial-length sequence of a universal sequence for a forward sequencing primer binding site (120) (e.g., FIG. 14). In some embodiments, the second oligonucleotide strand of the Y-shaped adaptors comprises a full-length or partial-length sequence of a universal sequence for a reverse sequencing primer binding site (130) (e.g., FIG. 14). The double-stranded nucleic acid fragment can be enzymatically ligated on the other side to a second Y-shaped adaptor comprising a first oligonucleotide carrying a full-length sequence of a universal adaptor sequence for a forward sequencing primer binding site (120), and a second oligonucleotide carrying a full-length sequence of a universal adaptor sequence for a reverse sequencing primer binding site (130). In some embodiments, the first and second Y-shaped adaptors carry the same universal adaptor sequence for a forward sequencing primer binding site (120), and carry the same universal adaptor sequence for a reverses sequencing primer binding site (130). In some embodiments, the Y-shaped adaptors also include a sample index sequence and an optional short random sequence (e.g., NNN) on one or both mis-matched portion(s). In some embodiments, the first and/or second oligonucleotide strands of the Y-shaped adaptors lack a sequence for a universal amplification primer binding site, a universal surface capture primer binding site and/or a universal surface pinning primer binding site. In some embodiments, the first and/or second oligonucleotide strands of the Y-shaped adaptors lack a sequence for a sample index. In some embodiments, the first and/or second oligonucleotide strands of the Y-shaped adaptors lack a sequence for a unique molecular index (UMI) sequence.

In some embodiments, the methods for generating a library molecule further comprise step (c): denaturing the double-stranded recombinant library molecule (100) to generating two single-stranded library molecules (100). Both of the single-stranded library molecules (100) can be hybridized with any of the double-stranded splint adaptors (200) described herein to generate a plurality of library-splint complexes (500), as described in step (d) below.

In some embodiments, the methods for generating a library molecule further comprise step (d): hybridizing the single-stranded library molecules (100) with a plurality of any of the double-stranded splint adaptors (200) described herein. In some embodiments, individual double-stranded splint adaptors (200) comprise a first splint strand (300) hybridized to a second splint strand (400), wherein the double-stranded splint adaptor includes a double-stranded region and two flanking single-stranded regions, wherein the first splint strand comprises a first region (320), an internal region (310), and a second region (330), and wherein the internal region of the first splint strand (310) is hybridized to the second splint strand (400). In some embodiments, the first region (320) of the first splint strand is designed to hybridize with the universal sequence for a forward sequencing primer binding site (120) of the library molecule (100). In some embodiments, the second region (330) of the first splint strand is designed to hybridize with the universal sequence for a reverse sequencing primer binding site (130) of the library molecule (100). In some embodiments, the hybridizing of step (c) is conducted under a condition suitable for hybridizing the first region of the first splint strand (320) to at least a portion of (120) of the single-stranded library molecules, and the condition is suitable for hybridizing the second region of the first splint strand (330) to at least a portion of (130) of the single-stranded library molecule, thereby circularizing the single-stranded library molecules to form a plurality of library-splint complexes (500) each having two nicks (e.g., FIG. 3).

In some embodiments, the methods for generating a library molecule further comprise step (e): contacting the plurality of library-splint complexes (500) with a ligase to generate a plurality of covalently closed circular library molecules (600) (e.g., FIG. 4).

In some embodiments, a primer extension or PCR reaction is not conducted after step (b) to join to the double-stranded recombinant library molecule (100) any additional adaptor sequences including: a universal amplification primer binding site, a universal surface capture primer binding site, a universal surface pinning primer binding site, a sample index or unique molecular index (UMI) sequence.
Supports with Low Non-Specific Binding Coatings In some aspects, the present disclosure provides compositions and methods for sequencing which employ a support having a plurality of surface primers immobilized thereon. In some embodiments, the support is passivated with a low non-specific binding coating. In some embodiments, the surface coatings described herein exhibit very low non-specific binding to reagents typically used for nucleic acid capture, amplification and sequencing workflows, such as dyes, nucleotides, enzymes, and nucleic acid primers. The surface coatings can exhibit low background fluorescence signals or high contrast-to-noise (CNR) ratios compared to conventional surface coatings.

In some embodiments, the supports comprise a substrate (or support structure), one or more layers of a covalently or non-covalently attached low-binding, chemical modification layers, e.g., silane layers, polymer films, and one or more covalently or non-covalently attached primer sequences that may be used for tethering single-stranded target nucleic acid(s) to the support surface. In some embodiments, the formulation of the surface, e.g., the chemical composition of one or more layers, the coupling chemistry used to cross-link the one or more layers to the support surface and/or to each other, and the total number of layers, may be varied such that non-specific binding of proteins, nucleic acid molecules, and other hybridization and amplification reaction components to the support surface is minimized or reduced relative to a comparable monolayer. Often, the formulation of the surface may be varied such that non-specific hybridization on the support surface is minimized or reduced relative to a comparable monolayer. The formulation of the surface may be varied such that non-specific amplification on the support surface is minimized or reduced relative to a comparable monolayer. The formulation of the surface may be varied such that specific amplification rates and/or yields on the support surface are maximized. Amplification levels suitable for detection are achieved in no more than 2, 3, 4, 5, 6, 7, 8, 9, 10, 15, 20, 25, 30, or more than 30 amplification cycles in some cases disclosed herein.

The substrate or support structure that comprises the one or more chemically-modified layers, e.g., layers of a low non-specific binding polymer, may be independent or integrated into another structure or assembly. For example, in some embodiments, the substrate or support structure may comprise one or more surfaces within an integrated or assembled microfluidic flow cell. The substrate or support structure may comprise one or more surfaces within a microplate format, e.g., the bottom surface of the wells in a microplate. As noted above, in some preferred embodiments, the substrate or support structure comprises the interior surface (such as the lumen surface) of a capillary. In alternate preferred embodiments the substrate or support structure comprises the interior surface (such as the lumen surface) of a capillary etched into a planar chip.

The attachment chemistry used to graft a first chemically-modified layer to a surface will generally be dependent on both the material from which the surface is fabricated and the chemical nature of the layer. In some embodiments, the first layer may be covalently attached to the surface. In some embodiments, the first layer may be non-covalently attached, e.g., adsorbed to the surface through non-covalent interactions such as electrostatic interactions, hydrogen bonding, or van der Waals interactions between the surface and the molecular components of the first layer. In either case, the substrate surface may be treated prior to attachment or deposition of the first layer. Any of a variety of surface preparation techniques known to those of skill in the art may be used to clean or treat the surface. For example, glass or silicon surfaces may be acid-washed using a Piranha solution (a mixture of sulfuric acid ($H_2SO_4$) and hydrogen peroxide ($H_2O_2$)), base treatment in KOH and NaOH, and/or cleaned using an oxygen plasma treatment method.

Silane chemistries constitute one non-limiting approach for covalently modifying the silanol groups on glass or silicon surfaces to attach more reactive functional groups (e.g., amines or carboxyl groups), which may then be used in coupling linker molecules (e.g., linear hydrocarbon molecules of various lengths, such as C6, C12, C18 hydrocarbons, or linear polyethylene glycol (PEG) molecules) or layer molecules (e.g., branched PEG molecules or other polymers) to the surface. Examples of suitable silanes that may be used in creating any of the disclosed low binding surfaces include, but are not limited to, (3-Aminopropyl) trimethoxysilane (APTMS), (3-Aminopropyl) triethoxysilane (APTES), any of a variety of PEG-silanes (e.g., comprising molecular weights of 1K, 2K, 5K, 10K, 20K, etc.), amino-PEG silane (i.e., comprising a free amino functional group), maleimide-PEG silane, biotin-PEG silane, and the like.

Any of a variety of molecules known to those of skill in the art including, but not limited to, amino acids, peptides, nucleotides, oligonucleotides, other monomers or polymers, or combinations thereof may be used in creating the one or more chemically-modified layers on the surface, where the choice of components used may be varied to alter one or more properties of the surface, e.g., the surface density of functional groups and/or tethered oligonucleotide primers, the hydrophilicity/hydrophobicity of the surface, or the three three-dimensional nature (i.e., "thickness") of the surface. Examples of preferred polymers that may be used to create one or more layers of low non-specific binding material in any of the disclosed surfaces include, but are not limited to, polyethylene glycol (PEG) of various molecular weights and branching structures, streptavidin, polyacrylamide, polyester, dextran, poly-lysine, and poly-lysine copolymers, or any combination thereof. Examples of conjugation chemistries that may be used to graft one or more layers of material (e.g. polymer layers) to the surface and/or to cross-link the layers to each other include, but are not limited to, biotin-streptavidin interactions (or variations thereof), his tag—Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, and silane.

The low non-specific binding surface coating may be applied uniformly across the substrate. Alternately, the surface coating may be patterned, such that the chemical modification layers are confined to one or more discrete regions of the substrate. For example, the surface may be patterned using photolithographic techniques to create an ordered array or random pattern of chemically-modified regions on the surface. Alternately or in combination, the substrate surface may be patterned using, e.g., contact printing and/or ink-jet printing techniques. In some embodiments, an ordered array or random patter of chemically-modified regions may comprise at least 1, 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 or more discrete regions.

In order to achieve low nonspecific binding surfaces, hydrophilic polymers may be nonspecifically adsorbed or covalently grafted to the surface. Typically, passivation is performed utilizing poly(ethylene glycol) (PEG, also known as polyethylene oxide (PEO) or polyoxyethylene) or other hydrophilic polymers with different molecular weights and end groups that are linked to a surface using, for example, silane chemistry. The end groups distal from the surface can include, but are not limited to, biotin, methoxy ether, carboxylate, amine, NHS ester, maleimide, and bis-silane. In some embodiments, two or more layers of a hydrophilic polymer, e.g., a linear polymer, branched polymer, or multi-branched polymer, may be deposited on the surface. In some embodiments, two or more layers may be covalently coupled to each other or internally cross-linked to improve the stability of the resulting surface. In some embodiments, oligonucleotide primers with different base sequences and base modifications (or other biomolecules, e.g., enzymes or antibodies) may be tethered to the resulting surface layer at various surface densities. In some embodiments, for example, both surface functional group density and oligonucleotide concentration may be varied to target a certain primer density range. Additionally, primer density can be controlled by diluting oligonucleotide with other molecules that carry the same functional group. For example, and without limitation, amine-labeled oligonucleotide can be diluted with amine-labeled polyethylene glycol in a reaction with an NHS-ester coated surface to reduce the final primer density. Primers with different lengths of linker between the hybridization region and the surface attachment functional group can also be applied to control surface density. Examples of suitable linkers include poly-T and poly-A strands at the 5' end of the primer (e.g., 0 to 20 bases, e.g., 0, 1, 2, 3, 4, 5, 6, 7, 8, 9, 10, 11, 12, 13, 14, 15, 16, 17, 18, 19, or 20), PEG linkers (e.g., 3 to 20 monomer units, e.g., about 3, 4, 5, 6, 7, 8, 9, 10, 11, 12, 13, 14, 15, 16, 17, 18, 19, or 20 monomer units), and carbon-chain (e.g., C6, C12, C18, etc.). To measure the primer density, fluorescently-labeled primers may be tethered to the surface and a fluorescence reading then compared with that for a dye solution of known concentration.

In order to scale primer surface density and add additional dimensionality to hydrophilic or amphoteric surfaces, surfaces comprising multi-layer coatings of PEG and other hydrophilic polymers have been developed. By using hydrophilic and amphoteric surface layering approaches that include, but are not limited to, the polymer/co-polymer materials described below, it is possible to increase primer loading density on the surface significantly. Traditional PEG coating approaches use monolayer primer deposition, which have been generally reported for single molecule applications, but do not yield high copy numbers for nucleic acid amplification applications. As described herein, "layering" can be accomplished using traditional crosslinking approaches with any compatible polymer or monomer subunits such that a surface comprising two or more highly crosslinked layers can be built sequentially. Examples of suitable polymers include, but are not limited to, streptavidin, poly acrylamide, polyester, dextran, poly-lysine, and copolymers of poly-lysine and PEG. In some embodiments, the different layers may be attached to each other through any of a variety of conjugation reactions including, but not limited to, biotin-streptavidin binding, azide-alkyne click reaction, amine-NHS ester reaction, thiol-maleimide reaction, and ionic interactions between positively charged polymer and negatively charged polymer. In some embodiments, high primer density materials may be constructed in solution and subsequently layered onto the surface in multiple steps.

As described above, the low non-specific binding coatings of the present disclosure exhibit reduced non-specific binding of proteins, nucleic acids, and other components of the hybridization and/or amplification formulation used for solid-phase nucleic acid amplification. The degree of non-specific binding exhibited by a given support surface may be assessed either qualitatively or quantitatively. For example, in some embodiments, exposure of the surface to fluorescent dyes (e.g., cyanine dyes such as Cy3, or Cy5, etc., fluoresceins, coumarins, rhodamines, etc. or other dyes disclosed herein), fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a qualitative tool for comparison of non-specific binding on supports comprising different surface formulations. In some embodiments, exposure of the surface to fluorescent dyes, fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a quantitative tool for comparison of non-specific binding on supports comprising different surface formulations—provided that care has been taken to ensure that the fluorescence imaging is performed under a condition where fluorescence signal is linearly related (or related in a predictable manner) to the number of fluorophores on the support surface (e.g., under a condition where signal saturation and/or self-quenching of the fluorophore is not an issue) and suitable calibration standards are used. In some embodiments, other techniques known to those of skill in the art, for example, radioisotope labeling and counting methods may be used for quantitative assessment of the degree to which non-specific binding is exhibited by the different support surface formulations of the present disclosure.

Some surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. Some surfaces disclosed herein exhibit a ratio of specific to nonspecific fluorescence of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

As noted, in some embodiments, the degree of non-specific binding exhibited by the disclosed low-binding supports may be assessed using a standardized protocol for contacting the surface with a labeled protein (e.g., bovine serum albumin (BSA), streptavidin, a DNA polymerase, a reverse transcriptase, a helicase, a single-stranded binding protein (SSB), etc., or any combination thereof), a labeled nucleotide, a labeled oligonucleotide, etc., under a standardized set of incubation and rinse conditions, followed be detection of the amount of label remaining on the surface and comparison of the signal resulting therefrom to an appropriate calibration standard. In some embodiments, the label may comprise a fluorescent label. In some embodiments, the label may comprise a radioisotope. In some embodiments, the label may comprise any other detectable label known to one of skill in the art. In some embodiments, the degree of non-specific binding exhibited by a given support surface formulation may thus be assessed in terms of the number of non-specifically bound protein molecules (or other molecules) per unit area. In some embodiments, the low-binding supports of the present disclosure may exhibit non-specific protein binding (or non-specific binding of other specified molecules, (e.g., cyanine dyes such as Cy3, or Cy5, etc., fluoresceins, coumarins, rhodamines, etc. or other dyes disclosed herein)) of less than 0.001 molecule per $\mu m^2$, less than 0.01 molecule per $\mu m^2$, less than 0.1 molecule per $\mu m^2$, less than 0.25 molecule per $\mu m^2$, less than 0.5 molecule per $\mu m^2$, less than 1molecule per $\mu m^2$, less than 10 molecules per $\mu m^2$, less than 100 molecules per $\mu m^2$, or less than 1,000 molecules per $\mu m^2$. Those of skill in the art will realize that a given support surface of the present disclosure may exhibit non-specific binding falling anywhere within this range, for example, of less than 86 molecules per $\mu m^2$. For example, some modified surfaces disclosed herein exhibit nonspecific protein binding of less than 0.5 molecule/$\mu m^2$ following contact with a 1 $\mu M$ solution of Cy3 labeled streptavidin (GE Amersham) in phosphate buffered saline (PBS) buffer for 15 minutes, followed by 3 rinses with deionized water. Some modified surfaces disclosed herein exhibit nonspecific binding of Cy3 dye molecules of less than 0.25 molecules per $\mu m^2$. In independent nonspecific binding assays, 1 $\mu M$ labeled Cy3 SA (ThermoFisher), 1 $\mu M$ Cy5 SA dye (ThermoFisher), 10 $\mu M$ Aminoallyl-dUTP—ATTO-647N (Jena Biosciences), 10 $\mu M$ Aminoallyl-dUTP—ATTO-Rhol 1 (Jena Biosciences), 10 $\mu M$ Aminoallyl-dUTP— ATTO-Rhol 1 (Jena Biosciences), 10 $\mu M$ 7-Propargylamino-7-deaza-dGTP-Cy5 (Jena Biosciences, and 10 $\mu M$ 7-Propargylamino-7-deaza-dGTP—Cy3 (Jena Biosciences) were incubated on the low binding substrates at 37° C. for 15 minutes in a 384 well plate format. Each well was rinsed 2-3× with 50 $\mu l$ deionized Rnase/Dnase Free water and 2-3× with 25 mM ACES buffer pH 7.4. The 384 well plates were imaged on a GE Typhoon instrument using the Cy3, AF555, or Cy5 filter sets (according to dye test performed) as specified by the manufacturer at a PMT gain setting of 800 and resolution of 50-100 m. For higher resolution imaging, images were collected on an Olympus IX83 microscope (Olympus Corp., Center Valley, PA) with a total internal reflectance fluorescence (TIRF) objective (100λ, 1.5 NA, Olympus), a CCD camera (e.g., an Olympus EM-CCD monochrome camera, Olympus XM-10 monochrome camera, or an Olympus DP80 color and monochrome camera), an illumination source (e.g., an Olympus 100 W Hg lamp, an Olympus 75 W Xe lamp, or an Olympus U-HGLGPS fluorescence light source), and excitation wavelengths of 532 nm or 635 nm. Dichroic mirrors were purchased from Semrock (IDEX Health & Science, LLC, Rochester, New York), e.g., 405, 488, 532, or 633 nm dichroic reflectors/beamsplitters, and band pass filters were chosen as 532 LP or 645 LP concordant with the appropriate excitation wavelength. Some modified surfaces disclosed herein exhibit nonspecific binding of dye molecules of less than 0.25 molecules per $\mu m^2$.

In some embodiments, the surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. In some embodiments, the surfaces disclosed herein exhibit a ratio of specific to nonspecific fluorescence signals for a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

The low-background surfaces consistent with the disclosure herein may exhibit specific dye attachment (e.g., Cy3 attachment) to non-specific dye adsorption (e.g., Cy3 dye adsorption) ratios of at least 4:1, 5:1, 6:1, 7:1, 8:1, 9:1, 10:1, 15:1, 20:1, 30:1, 40:1, 50:1, or more than 50 specific dye molecules attached per molecule nonspecifically adsorbed. Similarly, when subjected to an excitation energy, low-background surfaces consistent with the disclosure herein to which fluorophores, e.g., Cy3, have been attached may exhibit ratios of specific fluorescence signal (e.g., arising from Cy3-labeled oligonucleotides attached to the surface) to non-specific adsorbed dye fluorescence signals of at least 4:1, 5:1, 6:1, 7:1, 8:1, 9:1, 10:1, 15:1, 20:1, 30:1, 40:1, 50:1, or more than 50:1.

In some embodiments, the degree of hydrophilicity (or "wettability" with aqueous solutions) of the disclosed support surfaces may be assessed, for example, through the measurement of water contact angles in which a small droplet of water is placed on the surface and its angle of contact with the surface is measured using, e.g., an optical tensiometer. In some embodiments, a static contact angle may be determined. In some embodiments, an advancing or receding contact angle may be determined. In some embodiments, the water contact angle for the hydrophilic, low-binding support surfaced disclosed herein may range from about 0 degrees to about 30 degrees. In some embodiments, the water contact angle for the hydrophilic, low-binding support surfaced disclosed herein may no more than 50 degrees, 40 degrees, 30 degrees, 25 degrees, 20 degrees, 18 degrees, 16 degrees, 14 degrees, 12 degrees, 10 degrees, 8 degrees, 6 degrees, 4 degrees, 2 degrees, or 1 degree. In many cases the contact angle is no more than 40 degrees. Those of skill in the art will realize that a given hydrophilic, low-binding support surface of the present disclosure may exhibit a water contact angle having a value of anywhere within this range.

In some embodiments, the hydrophilic surfaces disclosed herein facilitate reduced wash times for bioassays, often due to reduced nonspecific binding of biomolecules to the low-binding surfaces. In some embodiments, adequate wash steps may be performed in less than 60, 50, 40, 30, 20, 15, 10, or less than 10 seconds. For example, in some embodiments adequate wash steps may be performed in less than 30 seconds.

The low-binding surfaces of the present disclosure may exhibit significant improvement in stability or durability to prolonged exposure to solvents and elevated temperatures, or to repeated cycles of solvent exposure or changes in temperature. For example, in some embodiments, the stability of the disclosed surfaces may be tested by fluorescently labeling a functional group on the surface, or a tethered biomolecule (e.g., an oligonucleotide primer) on the surface, and monitoring fluorescence signal before, during, and after prolonged exposure to solvents and elevated temperatures, or to repeated cycles of solvent exposure or changes in temperature. In some embodiments, the degree of change in the fluorescence used to assess the quality of the surface may be less than 1%, 2%, 3%, 4%, 5%, 10%, 15%, 20%, or 25% over a time period of 1 minute, 2 minutes, 3 minutes, 4 minutes, 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 hours, 50 hours, or 100 hours of exposure to solvents and/or elevated temperatures (or any combination of these percentages as measured over these time periods). In some embodiments, the degree of change in the fluorescence used to assess the quality of the surface may be less than 1%, 2%, 3%, 4%, 5%, 10%, 15%, 20%, or 25% over 5 cycles, 10 cycles, 20 cycles, 30 cycles, 40 cycles, 50 cycles, 60 cycles, 70 cycles, 80 cycles, 90 cycles, 100 cycles, 200 cycles, 300 cycles, 400 cycles, 500 cycles, 600 cycles, 700 cycles, 800 cycles, 900 cycles, or 1,000 cycles of repeated exposure to solvent changes and/or changes in temperature (or any combination of these percentages as measured over this range of cycles).

In some embodiments, the surfaces disclosed herein may exhibit a high ratio of specific signal to nonspecific signal or other background. For example, when used for nucleic acid amplification, some surfaces may exhibit an amplification signal that is at least 4, 5, 6, 7, 8, 9, 10, 15, 20, 30, 40, 50, 75, 100, or greater than 100 fold greater than a signal of an adjacent unpopulated region of the surface. Similarly, some surfaces exhibit an amplification signal that is at least 4, 5, 6, 7, 8, 9, 10, 15, 20, 30, 40, 50, 75, 100, or greater than 100 fold greater than a signal of an adjacent amplified nucleic acid population region of the surface.

In some embodiments, fluorescence images of the disclosed low background surfaces when used in nucleic acid hybridization or amplification applications to create clusters of hybridized or clonally-amplified nucleic acid molecules (e.g., that have been directly or indirectly labeled with a fluorophore) exhibit contrast-to-noise ratios (CNRs) of at least 10, 20, 30, 40, 50, 60, 70, 80, 90, 100, 110, 120, 130, 140, 150, 160, 170, 180, 190, 20, 210, 220, 230, 240, 250, or greater than 250.

One or more types of primer (e.g., capture oligonucleotides and/or circularization oligonucleotides) may be attached or tethered to the support surface. In some embodiments, the one or more types of adaptors or primers may comprise spacer sequences, adaptor sequences for hybridization to adaptor-ligated target library nucleic acid sequences, forward amplification primers, reverse amplification primers, sequencing primers, and/or molecular barcoding sequences, or any combination thereof. In some embodiments, 1 primer or adaptor sequence may be tethered to at least one layer of the surface. In some embodiments, at least 2, 3, 4, 5, 6, 7, 8, 9, 10, or more than 10 different primer or adaptor sequences may be tethered to at least one layer of the surface.

In some embodiments, the tethered adaptor and/or primer sequences may range in length from about 10 nucleotides to about 100 nucleotides. In some embodiments, the tethered adaptor and/or primer sequences may be at least 10, at least 20, at least 30, at least 40, at least 50, at least 60, at least 70, at least 80, at least 90, or at least 100 nucleotides in length. In some embodiments, the tethered adaptor and/or primer sequences may be at most 100, at most 90, at most 80, at most 70, at most 60, at most 50, at most 40, at most 30, at most 20, or at most 10 nucleotides in length. Any of the lower and upper values described in this paragraph may be combined to form a range included within the present disclosure, for example, in some embodiments the length of the tethered adaptor and/or primer sequences may range from about 20 nucleotides to about 80 nucleotides. Those of skill in the art will recognize that the length of the tethered adaptor and/or primer sequences may have any value within this range, e.g., about 24 nucleotides.

In some embodiments, the resultant surface density of primers on the low binding support surfaces of the present disclosure may range from about 100 primer molecules per $\mu m^2$ to about 100,000 primer molecules per $\mu m^2$. In some embodiments, the resultant surface density of primers on the low binding support surfaces of the present disclosure may range from about 100,000 primer molecules per $\mu m^2$ to about $10^{15}$ primer molecules per $\mu m^2$. In some embodiments, the surface density of primers may be at least 1,000, at least 10,000, at least 100,000, or at least $10^{15}$ primer molecules per $\mu m^2$. In some embodiments, the surface density of primers may be at most 10,000, at most 100,000, at most 1,000,000, or at most $10^{15}$ primer molecules per $\mu m^2$. Any of the lower and upper values described in this paragraph may be combined to form a range included within the present disclosure, for example, in some embodiments the surface density of primers may range from about 10,000 molecules per $\mu m^2$ to about $10^{15}$ molecules per $\mu m^2$. Those of skill in the art will recognize that the surface density of primer molecules may have any value within this range, e.g., about 455,000 molecules per $\mu m^2$. In some embodiments, the surface density of target library nucleic acid sequences initially hybridized to adaptor or primer sequences on the support surface may be less than or equal to that indicated for the surface density of tethered primers. In some embodiments, the surface density of clonally-amplified target library nucleic acid sequences hybridized to adaptor or primer sequences on the support surface may span the same range as that indicated for the surface density of tethered primers.

Local densities as listed above do not preclude variation in density across a surface, such that a surface may comprise a region having an oligo density of, for example, 500,000 per $\mu m^2$, while also comprising at least a second region having a substantially different local density.

The low non-specific binding coating comprise one or more layers of a multi-layered surface coating may comprise a branched polymer or may be linear. Examples of suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly (N-isopropylacrylamide) (branched PNIPAM), branched poly(methyl methacrylate) (branched PMA), branched poly (2-hydroxyethyl methacrylate) (branched PHEMA), branched poly(oligo(ethylene glycol) methyl ether methacrylate) (branched POEGMA), branched polyglutamic acid (branched PGA), branched poly-lysine, branched poly-glucoside, and dextran.

In some embodiments, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branched.

Linear, branched, or multi-branched polymers used to create one or more layers of any of the multi-layered surfaces disclosed herein may have a molecular weight of at least 500, at least 1,000, at least 2,000, at least 3,000, at least 4,000, at least 5,000, at least 10,000, at least 15,000, at least 20,000, at least 25,000, at least 30,000, at least 35,000, at least 40,000, at least 45,000, or at least 50,000 daltons.

In some embodiments, e.g., wherein at least one layer of a multi-layered surface comprises a branched polymer, the number of covalent bonds between a branched polymer molecule of the layer being deposited and molecules of the previous layer may range from about one covalent linkage per molecule to about 32 covalent linkages per molecule. In some embodiments, the number of covalent bonds between a branched polymer molecule of the new layer and molecules of the previous layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32 covalent linkages per molecule.

Any reactive functional groups that remain following the coupling of a material layer to the surface may optionally be blocked by coupling a small, inert molecule using a high yield coupling chemistry. For example, in the case that amine coupling chemistry is used to attach a new material layer to the previous one, any residual amine groups may subsequently be acetylated or deactivated by coupling with a small amino acid such as glycine.

The number of layers of low non-specific binding material, e.g., a hydrophilic polymer material, deposited on the surface, may range from 1 to about 10. In some embodiments, the number of layers is at least 1, at least 2, at least 3, at least 4, at least 5, at least 6, at least 7, at least 8, at least 9, or at least 10. In some embodiments, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some embodiments the number of layers may range from about 2 to about 4. In some embodiments, all of the layers may comprise the same material. In some embodiments, each layer may comprise a different material. In some embodiments, the plurality of layers may comprise a plurality of materials. In some embodiments at least one layer may comprise a branched polymer. In some embodiments, all of the layers may comprise a branched polymer.

One or more layers of low non-specific binding material may in some cases be deposited on and/or conjugated to the substrate surface using a polar protic solvent, a polar or polar aprotic solvent, a nonpolar solvent, or any combination thereof. In some embodiments the solvent used for layer deposition and/or coupling may comprise an alcohol (e.g., methanol, ethanol, propanol, etc.), another organic solvent (e.g., acetonitrile, dimethyl sulfoxide (DMSO), dimethyl formamide (DMF), etc.), water, an aqueous buffer solution (e.g., phosphate buffer, phosphate buffered saline, 3-(N-morpholino)propanesulfonic acid (MOPS), etc.), or any combination thereof. In some embodiments, an organic component of the solvent mixture used may comprise at least 1%, 5%10%, 15%, 20%, 25%, 30%, 35%, 40%, 45%, 50%, 55%, 60%, 70%, 75%, 80%, 85%, 90%, 95%, 98%, or 99% of the total, with the balance made up of water or an aqueous buffer solution. In some embodiments, an aqueous component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of an organic solvent. The pH of the solvent mixture used may be less than 6, about 6, 6.5, 7, 7.5, 8, 8.5, 9, or greater than pH 9.

Fluorescence imaging may be performed using any of a variety of fluorophores, fluorescence imaging techniques, and fluorescence imaging instruments known to those of skill in the art. Examples of suitable fluorescence dyes that may be used (e.g., by conjugation to nucleotides, oligonucleotides, or proteins) include, but are not limited to, fluorescein, rhodamine, coumarin, cyanine, and derivatives thereof, including the cyanine derivatives Cyanine dye-3 (Cy3), Cyanine dye-5 (Cy5), Cyanine dye-7 (Cy7), etc. Examples of fluorescence imaging techniques that may be used include, but are not limited to, fluorescence microscopy imaging, fluorescence confocal imaging, two-photon fluorescence, and the like. Examples of fluorescence imaging instruments that may be used include, but are not limited to, fluorescence microscopes equipped with an image sensor or camera, confocal fluorescence microscopes, two-photon fluorescence microscopes, or custom instruments that comprise a suitable selection of light sources, lenses, mirrors, prisms, dichroic reflectors, apertures, and image sensors or cameras, etc. A non-limiting example of a fluorescence microscope equipped for acquiring images of the disclosed low-binding support surfaces and clonally-amplified colonies (polonies) of template nucleic acid sequences hybridized thereon is the Olympus IX83 inverted fluorescence microscope equipped with) 20×, 0.75 NA, a 532 nm light source, a bandpass and dichroic mirror filter set optimized for 532 nm long-pass excitation and Cy3 fluorescence emission filter, a Semrock 532 nm dichroic reflector, and a camera (Andor sCMOS, Zyla 4.2) where the excitation light intensity is adjusted to avoid signal saturation. Often, the support surface may be immersed in a buffer (e.g., 25 mM ACES, pH 7.4 buffer) while the image is acquired.

In some instances, the performance of nucleic acid hybridization and/or amplification reactions using the disclosed reaction formulations and low non-specific binding supports may be assessed using fluorescence imaging techniques, where the contrast-to-noise ratio (CNR) of the images provides a key metric in assessing amplification specificity and non-specific binding on the support. CNR is commonly defined as: CNR=(Signal–Background)/Noise. The background term is commonly taken to be the signal measured for the interstitial regions surrounding a particular feature (diffraction limited spot, DLS) in a specified region of interest (ROI). While signal-to-noise ratio (SNR) is often considered to be a benchmark of overall signal quality, it can be shown that improved CNR can provide a significant advantage over SNR as a benchmark for signal quality in applications that require rapid image capture (e.g., sequencing applications for which cycle times must be minimized), as shown in the example below. The surfaces of the instant disclosure are also provided in co-pending International Application Serial No. PCT/US2019/061556, which is hereby incorporated by reference in its entirety.

In most ensemble-based sequencing approaches, the background term is typically measured as the signal associated with 'interstitial' regions. In addition to "interstitial"

background ($B_{inter}$), "intrastitial" background ($B_{intra}$) exists within the region occupied by an amplified DNA colony. The combination of these two background signals dictates the achievable CNR, and subsequently directly impacts the optical instrument requirements, architecture costs, reagent costs, run-times, cost/genome, and ultimately the accuracy and data quality for cyclic array-based sequencing applications. The $B_{inter}$ background signal arises from a variety of sources; a few examples include auto-fluorescence from consumable flow cells, non-specific adsorption of detection molecules that yield spurious fluorescence signals that may obscure the signal from the ROI, the presence of non-specific DNA amplification products (e.g., those arising from primer dimers). In typical next generation sequencing (NGS) applications, this background signal in the current field-of-view (FOV) is averaged over time and subtracted. The signal arising from individual DNA colonies (i.e., (S)-$B_{inter}$ in the FOV) yields a discernable feature that can be classified. In some instances, the intrastitial background ($B_{intra}$) can contribute a confounding fluorescence signal that is not specific to the target of interest, but is present in the same ROI thus making it far more difficult to average and subtract.

The implementation of nucleic acid amplification on the low-binding substrates of the present disclosure may decrease the $B_{inter}$ background signal by reducing non-specific binding, may lead to improvements in specific nucleic acid amplification, and may lead to a decrease in non-specific amplification that can impact the background signal arising from both the interstitial and intrastitial regions. In some instances, the disclosed low-binding support surfaces, optionally used in combination with the disclosed hybridization buffer formulations, may lead to improvements in CNR by a factor of 2, 5, 10, 100, or 1000-fold over those achieved using conventional supports and hybridization, amplification, and/or sequencing protocols. Although described here in the context of using fluorescence imaging as the read-out or detection mode, the same principles apply to the use of the disclosed low non-specific binding supports and nucleic acid hybridization and amplification formulations for other detection modes as well, including both optical and non-optical detection modes.

The disclosed low-binding supports, optionally used in combination with the disclosed hybridization and/or amplification protocols, yield solid-phase reactions that exhibit: (i) negligible non-specific binding of protein and other reaction components (thus minimizing substrate background), (ii) negligible non-specific nucleic acid amplification product, and (iii) provide tunable nucleic acid amplification reactions.

In some embodiments, fluorescence images of the disclosed low background surfaces when used in nucleic acid hybridization or amplification applications to create polonies of hybridized or clonally-amplified nucleic acid molecules (e.g., that have been directly or indirectly labeled with a fluorophore) exhibit contrast-to-noise ratios (CNRs) of at least 10, 20, 30, 40, 50, 60, 70, 80, 90, 100, 110, 120, 130, 140, 150, 160, 170, 180, 190, 20, 210, 220, 230, 240, 250, or greater than 250.

In some embodiments, a fluorescence image of the surface exhibits a contrast-to-noise ratio (CNR) of at least 20 when a sample nucleic acid molecule or complementary sequences thereof are labeled with a Cyanine dye-3 (Cy3) fluorophore, and when the fluorescence image is acquired using an inverted fluorescence microscope (e.g., Olympus IX83) with a 20×0.75 NA objective, a 532 nm light source, a bandpass and dichroic mirror filter set optimized for 532 nm excitation and Cy3 fluorescence emission, and a camera (e.g., Andor sCMOS, Zyla 4.2) under non-signal saturating conditions while the surface is immersed in a buffer (e.g., 25 mM ACES, pH 7.4 buffer).

Sequencing Polymerases

In some aspects, the present disclosure provides methods for sequencing nucleic acid molecules, where any of the sequencing methods described herein employ at least one type of sequencing polymerase and a plurality of nucleotides, or employ at least one type of sequencing polymerase and a plurality of nucleotides and a plurality of multivalent molecules. In some embodiments, the sequencing polymerase(s) is/are capable of incorporating a complementary nucleotide opposite a nucleotide in a concatemer template molecule. In some embodiments, the sequencing polymerase(s) is/are capable of binding a complementary nucleotide unit of a multivalent molecule opposite a nucleotide in a concatemer template molecule. In some embodiments, the plurality of sequencing polymerases comprises recombinant mutant polymerases.

Examples of suitable polymerases for use in sequencing with nucleotides and/or multivalent molecules include but are not limited to: Klenow DNA polymerase; *Thermus aquaticus* DNA polymerase I (Taq polymerase); KlenTaq polymerase; Candidatus altiarchaeales archaeon; Candidatus Hadarchaeum Yellowstonense; Hadesarchaea archaeon; Euryarchaeota archaeon; Thermoplasmata archaeon; *Thermococcus* polymerases such as *Thermococcus litoralis*, bacteriophage T7 DNA polymerase; human alpha, delta and epsilon DNA polymerases; bacteriophage polymerases such as T4, RB69 and phi29 bacteriophage DNA polymerases; *Pyrococcus furiosus* DNA polymerase (Pfu polymerase); *Bacillus subtilis* DNA polymerase III; *E. coli* DNA polymerase III alpha and epsilon; 9 degree N polymerase; reverse transcriptases such as HIV type M or O reverse transcriptases; avian myeloblastosis virus reverse transcriptase; Moloney Murine Leukemia Virus (MMLV) reverse transcriptase; or telomerase. Further non-limiting examples of DNA polymerases include those from various Archaea genera, such as, *Aeropyrum, Archaeglobus, Desulfurococcus, Pyrobaculum, Pyrococcus, Pyrolobus, Pyrodictium, Staphylothermus, Stetteria, Sulfolobus, Thermococcus,* and *Vulcanisaeta* and the like or variants thereof, including such polymerases as are known in the art such as 9 degrees N, VENT, DEEP VENT, THERMINATOR, Pfu, KOD, Pfx, Tgo and RB69 polymerases.

Nucleotides

In some aspects, the present disclosure provides methods for sequencing nucleic acid molecules using nucleotides, wherein at least one nucleotide in the plurality of nucleotides comprise a base, sugar and at least one phosphate group. In some embodiments, at least one nucleotide in the plurality comprises an aromatic base, a five carbon sugar (e.g., ribose or deoxyribose), and one or more phosphate groups (e.g., 1-10 phosphate groups). The plurality of nucleotides can comprise at least one type of nucleotide selected from the group consisting of dATP, dGTP, dCTP, dTTP and dUTP. The plurality of nucleotides can comprise at a mixture of any combination of two or more types of nucleotides selected from the group consisting of dATP, dGTP, dCTP, dTTP and/or dUTP. In some embodiments, at least one nucleotide in the plurality is not a nucleotide analog. In some embodiments, at least one nucleotide in the plurality comprises a nucleotide analog.

In some embodiments, in any of the methods for sequencing nucleic acid molecules described herein, at least one nucleotide in the plurality of nucleotides comprise a chain of one, two or three phosphorus atoms where the chain is typically attached to the 5' carbon of the sugar moiety via an ester or phosphoramide linkage. In some embodiments, at least one nucleotide in the plurality is an analog having a phosphorus chain in which the phosphorus atoms are linked together with intervening O, S, NH, methylene or ethylene. In some embodiments, the phosphorus atoms in the chain include substituted side groups including 0, S or $BH_3$. In some embodiments, the chain includes phosphate groups substituted with analogs including phosphoramidate, phosphorothioate, phosphordithioate, and O-methylphosphoroamidite groups.

In some embodiments, in any of the methods for sequencing nucleic acid molecules described herein, at least one nucleotide in the plurality of nucleotides comprises a terminator nucleotide analog having a chain terminating moiety (e.g., blocking moiety) at the sugar 2' position, at the sugar 3' position, or at the sugar 2' and 3' position. In some embodiments, the chain terminating moiety can inhibit polymerase-catalyzed incorporation of a subsequent nucleotide unit or free nucleotide in a nascent strand during a primer extension reaction. In some embodiments, the chain terminating moiety is attached to the 3' sugar hydroxyl position where the sugar comprises a ribose or deoxyribose sugar moiety. In some embodiments, the chain terminating moiety is removable/cleavable from the 3' sugar hydroxyl position to generate a nucleotide having a 3'OH sugar group which is extendible with a subsequent nucleotide in a polymerase-catalyzed nucleotide incorporation reaction. In some embodiments, the chain terminating moiety comprises an alkyl group, alkenyl group, alkynyl group, allyl group, aryl group, benzyl group, azide group, amine group, amide group, keto group, isocyanate group, phosphate group, thio group, disulfide group, carbonate group, urea group, acetal group, or silyl group. In some embodiments, the chain terminating moiety is cleavable/removable from the nucleotide, for example by reacting the chain terminating moiety with a chemical agent, pH change, light or heat. In some embodiments, the chain terminating moieties alkyl, alkenyl, alkynyl and allyl are cleavable with tetrakis(triphenylphosphine)palladium(0) $(Pd(PPh_3)_4)$ with piperidine, or with 2,3-Dichloro-5,6-dicyano-1,4-benzo-quinone (DDQ). In some embodiments, the chain terminating moieties aryl and benzyl are cleavable with H2 Pd/C. In some embodiments, the chain terminating moieties amine, amide, keto, isocyanate, phosphate, thio, disulfide are cleavable with phosphine or with a thiol group including beta-mercaptoethanol or dithiothritol (DTT). In some embodiments, the chain terminating moiety carbonate is cleavable with potassium carbonate $(K_2CO_3)$ in MeOH, with triethylamine in pyridine, or with Zn in acetic acid (AcOH). In some embodiments, the chain terminating moieties urea and silyl are cleavable with tetrabutylammonium fluoride, pyridine-HF, with ammonium fluoride, or with triethylamine trihydrofluoride.

In some embodiments, in any of the methods for sequencing nucleic acid molecules described herein, at least one nucleotide in the plurality of nucleotides comprises a terminator nucleotide analog having a chain terminating moiety (e.g., blocking moiety) at the sugar 2' position, at the sugar 3' position, or at the sugar 2' and 3' position. In some embodiments, the chain terminating moiety comprises an azide, azido or azidomethyl group. In some embodiments, the chain terminating moiety comprises a 3'-O-azido or 3'-O-azidomethyl group. In some embodiments, the chain terminating moieties azide, azido and azidomethyl group are cleavable/removable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP) or Tri (hydroxyproyl)phosphine (THPP). In some embodiments, the cleaving agent comprises 4-dimethylaminopyridine (4-DMAP).

In some embodiments, in any of the methods for sequencing nucleic acid molecules described herein, the nucleotide comprises a chain terminating moiety which is selected from the group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydral, 3'-aminomethyl, 3'-ethyl, 3'butyl, 3'-tert butyl, 3'-Fluorenyl-methyloxycarbonyl, 3' tert-Butyloxycarbonyl, 3'-O-alkyl hydroxylamino group, 3'-phosphorothioate, and 3-O-benzyl, or derivatives thereof.

In some embodiments, in any of the methods for sequencing nucleic acid molecules described herein, the plurality of nucleotides comprises a plurality of nucleotides labeled with detectable reporter moiety. The detectable reporter moiety comprises a fluorophore. In some embodiments, the fluorophore is attached to the nucleotide base. In some embodiments, the fluorophore is attached to the nucleotide base with a linker which is cleavable/removable from the base. In some embodiments, at least one of the nucleotides in the plurality is not labeled with a detectable reporter moiety. In some embodiments, a particular detectable reporter moiety (e.g., fluorophore) that is attached to the nucleotide can correspond to the nucleotide base (e.g., dATP, dGTP, dCTP, dTTP or dUTP) to permit detection and identification of the nucleotide base.

In some embodiments, in any of the methods for sequencing nucleic acid molecules described herein, the cleavable linker on the nucleotide base comprises a cleavable moiety comprising an alkyl group, alkenyl group, alkynyl group, allyl group, aryl group, benzyl group, azide group, amine group, amide group, keto group, isocyanate group, phosphate group, thio group, disulfide group, carbonate group, urea group, acetal group, or silyl group. In some embodiments, the cleavable linker on the base is cleavable/removable from the base by reacting the cleavable moiety with a chemical agent, pH change, light or heat. In some embodiments, the cleavable moieties alkyl, alkenyl, alkynyl and allyl are cleavable with tetrakis(triphenylphosphine)palladium(0) (Pd(PPh$_3$)$_4$) with piperidine, or with 2,3-Dichloro-5,6-dicyano-1,4-benzo-quinone (DDQ). In some embodiments, the cleavable moieties aryl and benzyl are cleavable with H2 Pd/C. In some embodiments, the cleavable moieties amine, amide, keto, isocyanate, phosphate, thio, disulfide are cleavable with phosphine or with a thiol group including beta-mercaptoethanol or dithiothritol (DTT). In some embodiments, the cleavable moiety carbonate is cleavable with potassium carbonate (K$_2$CO$_3$) in MeOH, with triethylamine in pyridine, or with Zn in acetic acid (AcOH). In some embodiments, the cleavable moieties urea and silyl are cleavable with tetrabutylammonium fluoride, pyridine-HF, with ammonium fluoride, or with triethylamine trihydrofluoride.

In some embodiments, in any of the methods for sequencing nucleic acid molecules described herein, the cleavable linker on the nucleotide base comprises cleavable moiety including an azide, azido or azidomethyl group. In some embodiments, the cleavable moieties azide, azido and azidomethyl group are cleavable/removable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP) or Tri(hydroxyproyl)phosphine (THPP). In some embodiments, the cleaving agent comprises 4-dimethylaminopyridine (4-DMAP).

In some embodiments, in any of the methods for sequencing nucleic acid molecules described herein, the chain terminating moiety (e.g., at the sugar 2' and/or sugar 3' position) and the cleavable linker on the nucleotide base have the same or different cleavable moieties. In some embodiments, the chain terminating moiety (e.g., at the sugar 2' and/or sugar 3' position) and the detectable reporter moiety linked to the base are chemically cleavable/removable with the same chemical agent. In some embodiments, the chain terminating moiety (e.g., at the sugar 2' and/or sugar 3' position) and the detectable reporter moiety linked to the base are chemically cleavable/removable with different chemical agents.

Multivalent Molecules

Figures 25, 26:
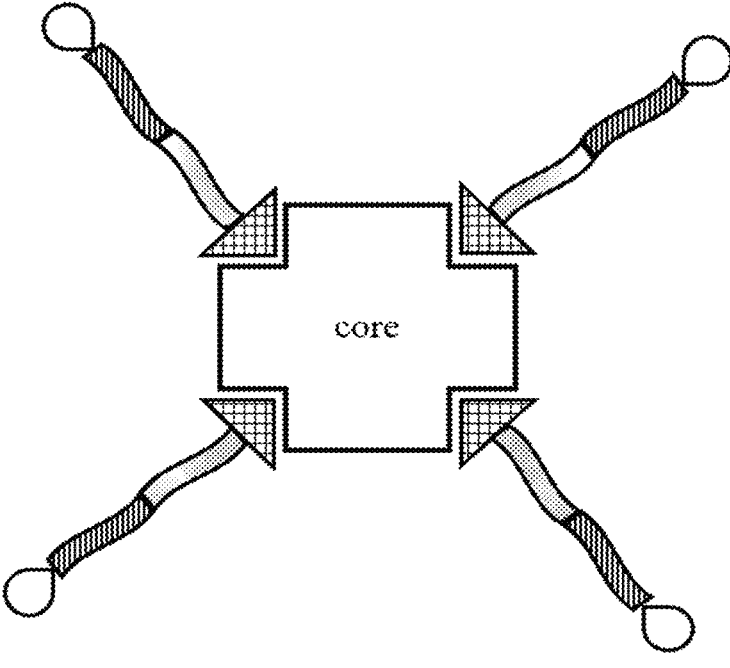
FIG. 25 shows a schematic of an exemplary multivalent molecule comprising a core attached to a plurality of nucleotide-arms, where the nucleotide arms comprise biotin, spacer, linker and a nucleotide unit.
FIG. 26 is a schematic of an exemplary nucleotide-arm comprising a core attachment moiety, spacer, linker, and nucleotide unit.
Figure 28:
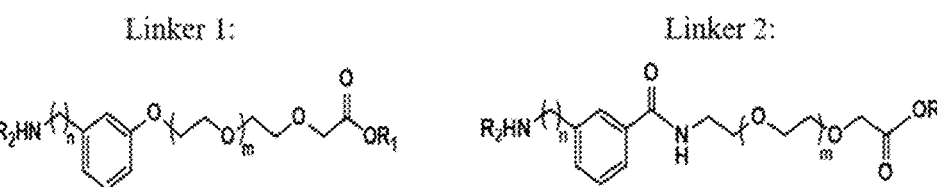
FIG. 28 shows the chemical structures of various exemplary linkers, including Linkers 1-9.
Figure 28:
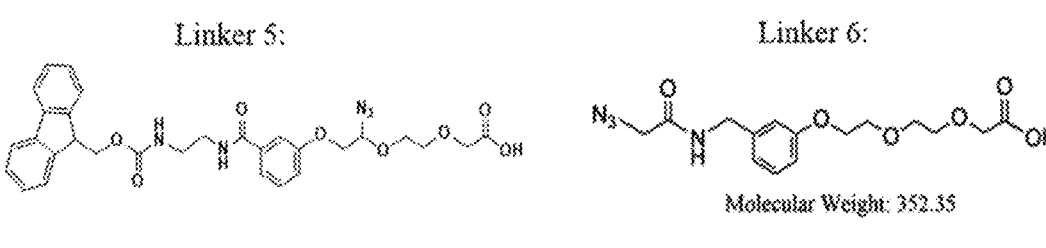
Figure 28:
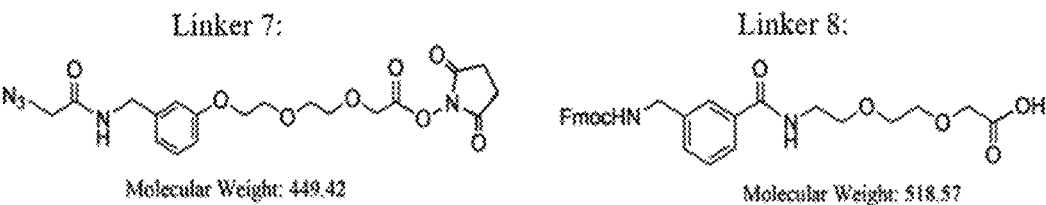
Figure 28:
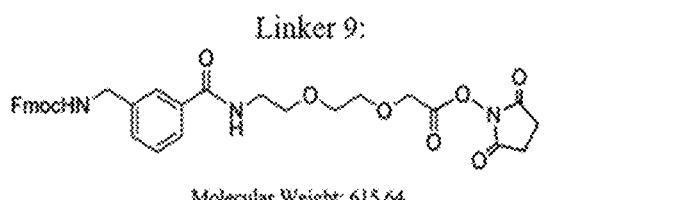
Figure 29:
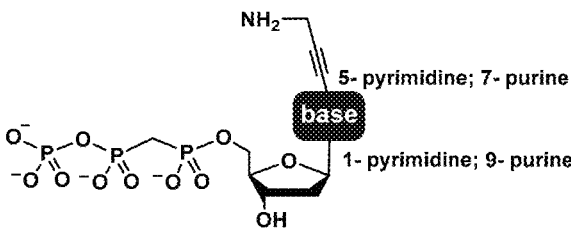
FIG. 29 shows the chemical structures of various exemplary linkers joined/attached to nucleotide units.

In some aspects, the present disclosure provides methods for sequencing nucleic acid molecules which employ multivalent molecules. In some embodiments, the multivalent molecule comprises a plurality of nucleotide arms attached to a core and having any configuration including a starburst, helter skelter, or bottle brush configuration (e.g., FIG. 22). In some embodiments, the multivalent molecule comprises: (1) a core; and (2) a plurality of nucleotide arms which comprise (i) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit. In some embodiments, the nucleotide unit comprises a base, sugar and at least one phosphate group, and the linker is attached to the nucleotide unit through the base. In some embodiments, the linker comprises an aliphatic chain or an oligo ethylene glycol chain where both linker chains having 2-6 subunits. In some embodiments, the linker also includes an aromatic moiety. An exemplary nucleotide arm is shown in FIG. 26. Exemplary multivalent molecules are shown in FIGS. 22-25. An exemplary spacer is shown in FIG. 27 (top) and exemplary linkers are shown in FIG. 27 (bottom) and FIG. 28. Exemplary nucleotides attached to a linker are shown in FIGS. 29-31. An exemplary biotinylated nucleotide arm is shown in FIG. 32.

In some embodiments, a multivalent molecule comprises a core attached to multiple nucleotide arms, and wherein the multiple nucleotide arms have the same type of nucleotide unit which is selected from the group consisting of dATP, dGTP, dCTP, dTTP and dUTP.

In some embodiments, a multivalent molecule comprises a core attached to multiple nucleotide arms, where each arm includes a nucleotide unit. The nucleotide unit comprises an aromatic base, a five carbon sugar (e.g., ribose or deoxyribose), and one or more phosphate groups (e.g., 1-10 phosphate groups). The plurality of multivalent molecules can comprise one type multivalent molecule having one type of nucleotide unit selected from the group consisting of dATP, dGTP, dCTP, dTTP, and dUTP. The plurality of multivalent molecules can comprise at a mixture of any combination of two or more types of multivalent molecules, where individual multivalent molecules in the mixture comprise nucleotide units selected from the group consisting of dATP, dGTP, dCTP, dTTP, and/or dUTP.

In some embodiments, the nucleotide unit comprises a chain of one, two or three phosphorus atoms where the chain is typically attached to the 5' carbon of the sugar moiety via an ester or phosphoramide linkage. In some embodiments, at least one nucleotide unit is a nucleotide analog having a phosphorus chain in which the phosphorus atoms are linked together with intervening O, S, NH, methylene or ethylene. In some embodiments, the phosphorus atoms in the chain include substituted side groups including 0, S or BH$_3$. In some embodiments, the chain includes phosphate groups substituted with analogs including phosphoramidate, phosphorothioate, phosphordithioate, and O-methylphosphoroamidite groups.

In some embodiments, the multivalent molecule comprises a core attached to multiple nucleotide arms, and wherein individual nucleotide arms comprise a nucleotide unit which is a nucleotide analog having a chain terminating moiety (e.g., blocking moiety) at the sugar 2' position, at the sugar 3' position, or at the sugar 2' and 3' position. In some embodiments, the nucleotide unit comprises a chain terminating moiety (e.g., blocking moiety) at the sugar 2' position, at the sugar 3' position, or at the sugar 2' and 3' position. In some embodiments, the chain terminating moiety can inhibit polymerase-catalyzed incorporation of a subsequent nucleotide unit or free nucleotide in a nascent strand during a primer extension reaction. In some embodiments, the chain terminating moiety is attached to the 3' sugar hydroxyl position where the sugar comprises a ribose or deoxyribose sugar moiety. In some embodiments, the chain terminating moiety is removable/cleavable from the 3' sugar hydroxyl position to generate a nucleotide having a 3'OH sugar group which is extendible with a subsequent nucleotide in a polymerase-catalyzed nucleotide incorporation reaction. In some embodiments, the chain terminating moiety comprises an alkyl group, alkenyl group, alkynyl group, allyl group, aryl group, benzyl group, azide group, amine group, amide group, keto group, isocyanate group, phosphate group, thio group, disulfide group, carbonate group, urea group, acetal group, or silyl group. In some embodiments, the chain terminating moiety is cleavable/removable from the nucleotide unit, for example by reacting the chain terminating moiety with a chemical agent, pH change, light or heat. In some embodiments, the chain terminating moieties alkyl, alkenyl, alkynyl and allyl are cleavable with tetrakis(triphenylphosphine)palladium(0) (Pd(PPh$_3$)$_4$) with piperidine, or with 2,3-Dichloro-5,6-dicyano-1,4-benzo-quinone (DDQ). In some embodiments, the chain terminating moieties aryl and benzyl are cleavable with H2 Pd/C. In some embodiments, the chain terminating moieties amine, amide, keto, isocyanate, phosphate, thio, disulfide are cleavable with phosphine or with a thiol group including beta-mercaptoethanol or dithiothritol (DTT). In some embodiments, the chain terminating moiety carbonate is cleavable with potassium carbonate (K$_2$CO$_3$) in MeOH, with triethylamine in pyridine, or with Zn in acetic acid (AcOH). In some embodiments, the chain terminating moieties urea and silyl are cleavable with tetrabutylammonium fluoride, pyridine-HF, with ammonium fluoride, or with triethylamine trihydrofluoride.

In some embodiments, the nucleotide unit comprises a chain terminating moiety (e.g., blocking moiety) at the sugar 2' position, at the sugar 3' position, or at the sugar 2' and 3' position. In some embodiments, the chain terminating moiety comprises an azide, azido or azidomethyl group. In some embodiments, the chain terminating moiety comprises a 3'-O-azido or 3'-O-azidomethyl group. In some embodiments, the chain terminating moieties azide, azido and azidomethyl group are cleavable/removable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP) or Tri(hydroxyproyl)phosphine (THPP). In some embodiments, the cleaving agent comprises 4-dimethylaminopyridine (4-DMAP).

In some embodiments, the nucleotide unit comprising a chain terminating moiety which is selected from the group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydral, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof.

In some embodiments, the multivalent molecule comprises a core attached to multiple nucleotide arms, wherein the nucleotide arms comprise a spacer, a linker, and nucleotide unit, and wherein the core, linker and/or nucleotide unit is labeled with detectable reporter moiety. In some embodiments, the detectable reporter moiety comprises a fluorophore. In some embodiments, a particular detectable reporter moiety (e.g., fluorophore) that is attached to the multivalent molecule can correspond to the base (e.g., dATP, dGTP, dCTP, dTTP, or dUTP) of the nucleotide unit to permit detection and identification of the nucleotide base.

In some embodiments, at least one nucleotide arm of a multivalent molecule has a nucleotide unit that is attached to a detectable reporter moiety. In some embodiments, the detectable reporter moiety is attached to the nucleotide base. In some embodiments, the detectable reporter moiety comprises a fluorophore. In some embodiments, a particular detectable reporter moiety (e.g., fluorophore) that is attached to the multivalent molecule can correspond to the base (e.g., dATP, dGTP, dCTP, dTTP or dUTP) of the nucleotide unit to permit detection and identification of the nucleotide base.

In some embodiments, the core of a multivalent molecule comprises an avidin-like or streptavidin-like moiety and the core attachment moiety comprises biotin. In some embodiments, the core comprises a streptavidin-type or avidin-type moiety which includes an avidin protein, as well as any derivatives, analogs and other non-native forms of avidin that can bind to at least one biotin moiety. Other forms of avidin moieties include native and recombinant avidin and streptavidin as well as derivatized molecules, e.g. non-glycosylated avidin and truncated streptavidins. For example, an avidin moiety may include de-glycosylated forms of avidin, bacterial streptavidin produced by *Streptomyces* (e.g., *Streptomyces avidinii*), as well as derivatized forms, for example, N-acyl avidins, e.g., N-acetyl, N-phthalyl and N-succinyl avidin, and the commercially-available products EXTRAVIDIN™, CAPTAVIDIN™, NEUTRAVIDIN™ and NEUTRALITE AVIDIN™.

In some embodiments, any of the methods for sequencing nucleic acid molecules described herein can include forming a binding complex, where the binding complex comprises (i) a polymerase, a nucleic acid concatemer molecule duplexed with a primer, and a nucleotide, or the binding complex comprises (ii) a polymerase, a nucleic acid concatemer molecule duplexed with a primer, and a nucleotide unit of a multivalent molecule. In some embodiments, the binding complex has a persistence time of greater than about 0.1, 0.2, 0.3, 0.4, 0.5, 0.6, 0.7, 0.8, 0.9 or 1 second. The binding complex has a persistence time of greater than about 0.1-0.25 seconds, or about 0.25-0.5 seconds, or about 0.5-0.75 seconds, or about 0.75-1 second, or about 1-2 seconds, or about 2-3 seconds, or about 3-4 second, or about 4-5 seconds, and/or wherein the method is or may be carried out at a temperature of at or above 15° C., at or above 20° C., at or above 25° C., at or above 35° C., at or above 37° C., at or above 42° C. at or above 55° C. at or above 60° C., or at or above 72° C., or at or above 80° C., or within a range defined by any of the foregoing. The binding complex (e.g., ternary complex) remains stable until subjected to a condition that causes dissociation of interactions between any of the polymerase, template molecule, primer and/or the nucleotide unit or the nucleotide. For example, a dissociating condition comprises contacting the binding complex with any one or any combination of a detergent, EDTA and/or water. In some embodiments, the present disclosure provides said method wherein the binding complex is deposited on, attached to, or hybridized to, a surface showing a contrast to noise ratio in the detecting step of greater than 20. In some embodiments, the present disclosure provides said method wherein the contacting is performed under a condition that stabilizes the binding complex when the nucleotide or nucleotide unit is complementary to a next base of the template nucleic acid, and destabilizes the binding complex when the nucleotide or nucleotide unit is not complementary to the next base of the template nucleic acid.

EXAMPLES

The following examples are meant to be illustrative and can be used to further understand embodiments of the present disclosure and should not be construed as limiting the scope of the present teachings in any way.

Example 1: Fragmenting Input DNA

Genomic DNA was fragmented using two different methods. Genomic DNA was fragmented using enzymatic FRAGMENTASE ULTRA™ (from New England Biolabs™). A range of input amounts of genomic DNA were tested, including 1 ng/μL to 1000 ng/μL. At the lowest range, as little as 1 ng of genomic DNA was tested. The fragmenting reaction included 7 μL of FRAGMENTASE™ reaction buffer, 2 μL of FRAGMENTASE™ enzyme, 26 μL genomic DNA. The fragmenting reaction was incubated at 37° C. for 15 minutes, and was heated killed at 65° C. for 30 minutes. The average fragmented DNA was approximately 250 bp. The fragmented DNA was treated with enzymatic end-repair and A-tailing reactions.

Genomic DNA was also fragmented by shearing using Covaris to achieve insert sizes of about 200, 250, 350 and 400 bp. The amount of input fragmented nucleic acids to prepare the linear library molecules included 50 ng, 100 ng, 500 ng and 1 ug.

Example 2: Preparing Library Molecules

The fragmented double-stranded DNA was ligated at both ends to Y-shaped adaptors. The Y-shaped adaptors each comprised a first oligonucleotide strand having a full-length or partial-length sequence of a universal sequence for a forward sequencing primer binding site (120), and a second oligonucleotide strand having a full-length or partial-length sequence of a universal sequence for a reverse sequencing primer binding site (130). Exemplary universal sequences for a forward sequencing primer binding site (120), and for universal sequences for a reverse sequencing primer binding site (130), are listed in Table 1. The resulting double-stranded library molecules (100) were heat denatured to generate a plurality of single stranded library molecules (100). Exemplary single stranded library molecules (100) are shown in FIGS. 1 and 3.

Example 3: Preparing Double-Stranded Splint Adaptors

The double-stranded splint adaptors comprised first splint strands (300) hybridized to second splint strands (400). An exemplary double-stranded splint adaptor is shown in FIG. 2. The double-stranded splint adaptors were denatured using NaOH at room temperature for 5 minutes, and then annealed at 37° C. for 5 minutes. Alternatively, the double-stranded splint adaptors were heat denatured and then annealed at 37° C. for 5 minutes.

The first splint strand comprised a first region (320), an internal region (310), and a second region (330). The first region (320) of the first splint strand can hybridize to the universal sequence for a forward sequencing primer binding site (120) of the single-stranded library molecule (100). The second region (330) of the first splint strand can hybridize to the universal sequence for a reverse sequencing primer binding site (130) of the single-stranded library molecule (100). Exemplary sequences for regions (320) and (330) of the first splint strand are listed in Table 2.

Example 4: Preparing Library-Splint Complexes

The single-stranded library molecules (100) were annealed to the double-stranded splint adaptors (200) (e.g., FIG. 3) in an annealing buffer containing 100 mM potassium acetate and 30 mM HEPES (pH 7.5), in a thermal cycler apparatus. The annealing program includes: 5 minutes at 95 degrees C., 5 minutes at 37 degrees C., and hold at 37 degrees C.

In a first embodiment of library-splint complexes, individual single stranded library molecules (100) comprised an insert region (110) comprising a human genomic sequence, a universal sequence for a forward sequencing primer binding site (120) having the sequence 5'-CGTGCTGGAT-TGGCTCACCAGACACCTTCCGACAT-3' (SEQ ID NO:51), and a universal sequence for a reverse sequencing primer binding site (130) having the sequence 5'-ATGTCG-GAAGGTGTGCAGGCTACCGCTTGTCAACT-3' (SEQ ID NO:4). The second splint strand (400) comprised at least three sub-regions, including first, second and third sub-regions. The first sub-region (411) comprised a universal binding sequence for an immobilized surface pinning primer having the sequence 3'-TGGGACTTTCATGCACG-5' (SEQ ID NO:24). The second sub-region (412) comprised a short random sequence (NNN) and one of four sample index sequences. The third sub-region (413) comprised a universal binding sequence for an immobilized surface capture primer having the sequence 3'-TAATGTACCTAGTC-CACTCCGA-5' (SEQ ID NO:19). Other exemplary sequences in the short splint strand (400) including the surface capture primer binding sequences, surface pinning primer binding sequences, and sample index sequences are listed in Table 3.

In a second embodiment of library-splint complexes, individual single stranded library molecules (100) comprised an insert region (110) comprising a human genomic sequence, a universal sequence for a forward sequencing primer binding site (120) having the sequence 5'-CGTGCTGGATTGGCTCACCAGACACCTTCCGA-CAT-3' (SEQ ID NO:1), and a universal sequence for a reverse sequencing primer binding site (130) having the sequence 5'-ATGTCGGAAGGTGTGCAGGC-TACCGCTTGTCAACT-3' (SEQ ID NO:4). The second splint strand (400) comprised at least three sub-regions, including first, second and third sub-regions. The first sub-region (411) comprised a universal binding sequence for an immobilized surface pinning primer having the sequence 3'-TGGGACTTTCATGCACGTAATGTAC-5' (SEQ ID NO:7). The second sub-region (412) comprised a universal binding sequence for an immobilized surface capture primer having the sequence 3'-CTAGTC-CACTCCGACGCTGCTGA-5' (SEQ ID NO:18). The third sub-region (413) comprised a short random sequence (NNN) and one of four sample index sequences. In this second embodiment, after a ligation reaction to generate covalently closed circular molecules (600), the short random sequence (NNN) and sample index sequence in sub-region (413) were joined to the universal sequence for a reverse sequencing primer binding site (130) in the covalently closed circular library molecules (600) (e.g., see Example 5 below). Other exemplary sequences for surface capture primer binding sequences, surface pinning primer binding sequences, and sample index sequences are listed in Table 3.

Example 5: Preparing Covalently Closed Circular Library Molecules

The annealing mixture from Example 4 was subjected to an enzymatic ligation and phosphorylation reaction by adding to the annealing mixture T7 DNA ligase and T4 polynucleotide kinase with a T4 DNA ligase reaction buffer. The enzymatic mixture was incubated in a thermal cycling apparatus with a heated lid set to 75 degrees C. The thermal cycling apparatus program included: 10 minutes at 37 degrees, 10 minutes at 65 degrees, and hold at 4 degrees. The ligation and phosphorylation reactions generated covalently closed circular library molecules (600) that were hybridized to first splint strands (300) (e.g., FIG. 4).

An enzymatic exonuclease digestion was conducted by adding to the ligation/phosphorylation reaction mixture T7 exonuclease and Thermolabile exonuclease. The exonuclease reaction mixture was incubated in a thermal cycling apparatus which was programmed: 10 minutes at 37 degrees C., 2 minutes at 80 degrees C., and hold at 4 degrees C.

The exonuclease reaction mixture was subjected to multiple cycles of clean-up using SPRI SELECT™ beads (from Beckman Coulter™).

The yield of the cleaned preparation of covalently closed circular library molecules (e.g., single stranded molecules) was quantified using Qubit or qPCR.

Example 6: Rolling Circle Amplification and Sequencing

The covalently closed circular library molecules from Example 5 was distributed onto a support that was passivated with a low non-specific binding coating in the presence of a high efficiency hybridization buffer and subjected to on-support rolling circle amplification to generate immobilized concatemers. The low non-specific binding coating included a plurality of immobilized surface capture primers and surface pinning primers. Exemplary surface capture and pinning primers are listed in Table 4.

Example 7: Sequencing Using Multivalent Molecules and Nucleotides

The concatemers were subjected to recursive two-stage sequencing reactions using fluorescently-labeled multivalent molecules in the first stage and un-labeled nucleotide analogs (e.g., 3' chain terminator blocking group) in the second stage.

The two-stage sequencing reaction was conducted on a flow cell having a plurality of concatemer template molecules immobilized thereon (e.g., immobilized polonies).

The first-stage sequencing reaction was conducted by hybridizing a plurality of a soluble sequencing primers to concatemer template molecules that were immobilized to a flow cell to form immobilized primer-concatemer duplexes. A plurality of a first sequencing polymerase was flowed onto the flow cell (e.g., contacting the immobilized primer-concatemer duplexes) and was incubated under a condition suitable to bind the sequencing polymerase to the duplexes to form complexed polymerases. A mixture of fluorescently labeled multivalent molecules (e.g., at different concentrations of about 20-100 nM) was flowed onto the flow cell in the presence of a buffer that includes a non-catalytic cation (e.g., strontium, barium and/or calcium) and was incubated under conditions suitable to bind complementary nucleotide units of the multivalent molecules to the complexed polymerases to form avidity complexes without polymerase-catalyzed incorporation of the nucleotide units. The fluorescently labeled multivalent molecules was labeled at their cores. The complexed polymerases were washed. An image (not shown) was obtained of the fluorescently labeled multivalent molecules that remain bound to the complexed polymerases. The first sequencing polymerases and multivalent molecules were removed, while retaining the sequencing primers hybridized to the immobilized concatemers (retained duplexes), by washing with a buffer comprising a detergent.

The first stage sequencing reaction was suitable for forming a plurality of avidity complexes on the concatemer template molecules (e.g., polonies). For example, the first stage sequencing reaction comprised: (a) binding a first nucleic acid primer, a first polymerase, and a first multivalent molecule to a first portion of a concatemer template molecule thereby forming a first binding complex, wherein a first nucleotide unit of the first multivalent molecule was bound to the first polymerase; and (b) binding a second nucleic acid primer, a second polymerase, and the first multivalent molecule to a second portion of the same concatemer template molecule thereby forming a second binding complex, wherein a second nucleotide unit of the first multivalent molecule was bound to the second polymerase, wherein the first and second binding complexes which included the same multivalent molecule to form a first avidity complex.

The second-stage sequencing reaction was conducted by contacting the retained duplexes with a plurality of second sequencing polymerases to form complexed polymerases. A mixture of non-labeled nucleotide analogs (e.g., 3'O-methylazido nucleotides) (e.g., at different concentrations of about 1-5 μM) was added to the complexed polymerases in the presence of a buffer that includes a catalytic cation (e.g., magnesium and/or manganese) and was incubated under conditions suitable to bind complementary nucleotides to the complexed polymerases and promote polymerase-catalyzed incorporation of the nucleotides to generate a nascent extended sequencing primer. The complexed polymerases were washed. No image was obtained. The incorporated non-labeled nucleotide analogs were reacted with a cleaving reagent that removes the 3' O-methylazido group and generated an extendible 3'OH group.

The second sequencing polymerases were removed, while retaining the nascent extended sequencing primers hybridized to the concatemers (retained duplexes), by washing with a buffer comprising a detergent. Recurring sequencing reactions were conducted by performing multiple cycles of first-stage and second-stage sequencing reactions to generate extended forward sequencing primer strands.

For immobilized concatemers generated from the first embodiment of library-splint complexes described in Example 4 above, the order of sequencing included: (1) sequencing the insert region (110) using forward sequencing primers to generate a plurality of forward insert extension products; (2) conducting a pairwise turn reaction; (3) sequencing the insert region (110) using reverse sequencing primers to generate a plurality of reverse insert extension products; and (4) sequencing the short random sequence (NNN) and a sample index sequence using reverse sequencing primers having the sequence 5'-ACCCT-GAAAGTACGTGC-3' (SEQ ID NO: 62) to generate a plurality of sample index extension products. The sequencing results are listed in Table A below.

TABLE A

| Circular library loading concentration | Raw reads (millions) | Pass filter rate | R1 Q30 | R2 Q30 | Index assignment rate |
|---|---|---|---|---|---|
| 9 pM | 883M | 96.2% | 99.0% | 97.7% | 95% |
| 9 pM | 750M | 95.3% | 94.8% | 91.5% | 94.4% |

For immobilized concatemers generated from the second embodiment of library-splint complexes described in Example 4 above, the order of sequencing included: (1) sequencing the short random sequence (NNN) and a sample index sequence using forward sequencing primers having the sequence 5'-ATGTCGGAAGGTGTGCAGGC-TACCGCTTGTCAACT-3' (SEQ ID NO:4) to generate a plurality of sample index extension products; (2) sequencing the insert region (110) using forward sequencing primers to generate a plurality of forward insert extension products; (3) conducting a pairwise turn reaction; and (4) sequencing the insert region (110) using reverse sequencing primers to generate a plurality of reverse insert extension products. The sequencing results are listed in Table B below.

TABLE B

| Circular library loading concentration | Raw reads (millions) | Pass filter reads (millions) | Pass filter rate | R1 Q30 | R2 Q30 |
|---|---|---|---|---|---|
| 12 pM | 1116M | 994.3 | 89.1% | 94.4% | 93.4% |
| 12 pM | 1126M | 991.6 | 88/0% | 94.3% | 92.9% |

INCORPORATION BY REFERENCE

Throughout this application various publications, patents, and/or patent applications are referenced. The disclosures of the publications, patents and/or patent applications are hereby incorporated by reference in their entireties into this application in order to more fully describe the state of the art to which this disclosure pertains.

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

What is claimed:

1. A method for forming a plurality of library-splint complexes (500) comprising:

a) providing a plurality of double-stranded splint adaptors (200), wherein individual double-stranded splint adaptors (200) in the plurality comprise a first splint strand (300) hybridized to all or a portion of a second splint strand (400), wherein the double-stranded splint adaptor includes a double-stranded region and two flanking single-stranded regions, wherein the first splint strand comprises a first region (320), an internal region (310) comprising a universal adaptor sequence for a surface capture primer binding site, and a second region (330), and wherein:

ii) the internal region of the first splint strand (310) is hybridized to all or a portion of the second splint strand (400), and (ii) the internal region (310) of the first splint strand (300) comprises at least three sub-regions comprising sub-region (311), sub-region (312) and sub-region (313), wherein the first splint strand, or both splint strands comprise sample index sequence comprising a 3-mer random sequence (NNN), and wherein sub-region (311), subregion (312) or subregion (313) comprise the sample index sequence of the first splint strand, and the sample index sequence of the first splint strand comprises an 18-carbon spacer and/or an 18-carbon spacer and at least one deoxyinosine; and b) hybridizing the plurality of double-stranded splint adaptors with a plurality of single-stranded nucleic acid library molecules (100), wherein individual single-stranded nucleic acid library molecules comprise a sequence of interest (110) flanked on a first side by a universal adaptor sequence for a forward sequencing primer binding site (120) and flanked on a second side by a universal adaptor sequence for a reverse sequencing primer binding site (130), wherein the first region of the first splint strand (320) hybridizes to the universal adaptor sequence for the forward sequencing primer binding site (120) and the second region of the first splint strand (330) hybridizes to the universal adaptor sequence for the reverse sequencing primer binding site (130), wherein the first splint strand (300) comprises one or more nucleotide sequences selected from the group consisting of SEQ ID NOS: 7-10 and 12-14, thereby circularizing the plurality of single-stranded nucleic acid library molecules to form a plurality of library-splint complexes (500), individual library-splint complexes having two nicks.

2. The method of claim 1, further comprising: (c) contacting the plurality of library-splint complexes (500) with a ligase to generate a plurality of covalently closed circular library molecules (600).

3. The method of claim 1, wherein the sub-region (311) comprises the universal adaptor sequence for a surface capture primer binding site, a universal adaptor sequence for a surface pinning primer binding site, the sample index sequence comprising the short random sequence (NNN) and/or a unique molecule index (UMI).

4. The method of claim 1, wherein the sub-region (312) comprises the universal adaptor sequence for a surface capture primer binding site, the sample index sequence comprising the short random sequence (NNN) and/or a unique molecule index (UMI).

5. The method of claim 1, wherein the sub-region (313) comprises the universal adaptor sequence for a surface capture primer binding site, a universal adaptor sequence for a surface pinning primer binding site, the sample index sequence comprising the short random sequence (NNN) and/or a unique molecule index (UMI).

6. The method of claim 2, further comprising:

i) distributing the plurality of covalently closed circular library molecules (600) onto a support having a plurality of the surface capture primers immobilized to the support, under a condition suitable for hybridizing individual covalently closed circular library molecules (600) to individual immobilized surface capture primers thereby immobilizing the plurality of covalently closed circular library molecules (600) to the support.

7. The method of claim 6, wherein the support further comprises a plurality of surface pinning primers immobilized to the support.

8. The method of claim 6, further comprising:

ii) contacting the plurality of covalently closed circular library molecules (600) immobilized to the support with a plurality of strand-displacing polymerases and a plurality of nucleotides, under a condition suitable to conduct a rolling circle amplification reaction on the support using the plurality of surface capture primers as immobilized amplification primers and the plurality of covalently closed circular library molecules (600) as template molecules, thereby generating a plurality of nucleic acid concatemer molecules immobilized to the surface capture primers.

9. The method of claim 8, further comprising:

iii) sequencing the plurality of nucleic acid concatemer molecules immobilized to the surface capture primers, wherein the sequencing comprises (i) sequencing the sample index sequence and (ii) sequencing the sequence of interest (110).

10. The method of claim 8, further comprising:

iii) sequencing the plurality of nucleic acid concatemer molecules immobilized to the surface capture primers, wherein the sequencing comprises (A) sequencing one or more short random sequences (NNN), (B) sequencing one or more sample index sequences, and (C) sequencing the sequence of interest (110).

11. The method of claim 3, wherein the internal region (310) of the first splint strand (300) comprises one sample index sequence.

12. The method of claim 1, wherein the single-stranded nucleic acid library molecule (100) comprises one or more nucleotide sequences selected from the group consisting of SEQ ID NOS: 1-6 and 43-44.

13. The method of claim 1, wherein the second splint strand (400) comprises one or more nucleotide sequences selected from the group consisting of SEQ ID NOS: 18-26, 45-47, 49, 5'-CATGTAAT-3', 5'-GTAGGAGCCNNN-3', 5'-CCGCTGCTANNN-3', 5'-AACAACAAGNNN-3', 5'-GGTGGTCTANNN-3', 5'-TTGGCCAACNNN-3', 5'-CAGGAGTGCNNN-3', and 5'-ATCACACTANNN-3'.

14. The method of claim 1, wherein the first splint strand (300) is a universal long splint strand comprising:
  i) at least one sub-region only partially hybridized to the second splint strand (400), and/or
  iii) a sub-region comprising a spacer sequence.

15. The method of claim 1, wherein the first splint strand (300) and the second splint strand (400) each comprise one or more sub-regions, and wherein the second splint strand comprises a sub-region that does not hybridize to the first splint strand, thereby providing a duplex formed by hybridization of the first splint strand to the second splint strand comprising a loop of the sub-region of the second splint strand.

16. A method for forming a plurality of library-splint complexes (500) comprising:
  a) providing a plurality of double-stranded splint adaptors (200), wherein individual double-stranded splint adaptors (200) in the plurality comprise a first splint strand (300) hybridized to all or a portion of a second splint strand (400),
    wherein the double-stranded splint adaptor includes a double-stranded region and two flanking single-stranded regions, wherein the first splint strand comprises a first region (320), an internal region (310) comprising a universal adaptor sequence for a surface capture primer binding site, and a second region (330),
    wherein the first splint strand, the second splint strand, or both splint strands comprise a sample index sequence comprising a 3-mer random sequence (NNN), and
    wherein the first splint strand (300) and the second splint strand (400) each comprise one or more sub-regions, and wherein the second splint strand comprises a sub-region that does not hybridize to the first splint strand, thereby providing a duplex formed by hybridization of the first splint strand to the second splint strand comprising a loop of the sub-region of the second splint strand; and
  b) hybridizing the plurality of double-stranded splint adaptors with a plurality of single-stranded nucleic acid library molecules (100), wherein individual single-stranded nucleic acid library molecules comprise a sequence of interest (110) flanked on a first side by a universal adaptor sequence for a forward sequencing primer binding site (120) and flanked on a second side by a universal adaptor sequence for a reverse sequencing primer binding site (130), wherein the first region of the first splint strand (320) hybridizes to the universal adaptor sequence for the forward sequencing primer binding site (120) and the second region of the first splint strand (330) hybridizes to the universal adaptor sequence for the reverse sequencing primer binding site (130), wherein the first splint strand (300) comprises one or more nucleotide sequences selected from the group consisting of SEQ ID NOS: 7-10 and 12-14,
    thereby circularizing the plurality of single-stranded nucleic acid library molecules to form a plurality of library-splint complexes (500), individual library-splint complexes (500) having two nicks.

17. The method of claim 16, further comprising: (c) contacting the plurality of library-splint complexes (500)

with a ligase to generate a plurality of covalently closed circular library molecules (600).

18. The method of claim 16, wherein the internal region (310) of the first splint strand (300) comprises at least three sub-regions.

19. The method of claim 18, wherein the at least three sub-regions comprise sub-region (311), sub-region (312) and sub-region (313).

20. The method of claim 19, wherein the sub-region (311) comprises the universal adaptor sequence for a surface capture primer binding site, a universal adaptor sequence for a surface pinning primer binding site, the sample index sequence comprising the short random sequence (NNN) and/or a unique molecule index (UMI).

21. The method of claim 19, wherein the sub-region (312) comprises the universal adaptor sequence for a surface capture primer binding site, the sample index sequence comprising the short random sequence (NNN) and/or a unique molecule index (UMI).

22. The method of claim 19, wherein the sub-region (313) comprises the universal adaptor sequence for a surface capture primer binding site, a universal adaptor sequence for a surface pinning primer binding site, the sample index sequence comprising the short random sequence (NNN) and/or a unique molecule index (UMI).

23. The method of claim 17, further comprising:
  i) distributing the plurality of covalently closed circular library molecules (600) onto a support having a plurality of the surface capture primers immobilized to the support, under a condition suitable for hybridizing individual covalently closed circular library molecules (600) to individual immobilized surface capture primers thereby immobilizing the plurality of covalently closed circular library molecules (600) to the support.

24. The method of claim 23, wherein the support further comprises a plurality of surface pinning primers immobilized to the support.

25. The method of claim 23, further comprising:
  ii) contacting the plurality of covalently closed circular library molecules (600) immobilized to the support with a plurality of strand-displacing polymerases and a plurality of nucleotides, under a condition suitable to conduct a rolling circle amplification reaction on the support using the plurality of surface capture primers as immobilized amplification primers and the plurality of covalently closed circular library molecules (600) as template molecules,
  thereby generating a plurality of nucleic acid concatemer molecules immobilized to the surface capture primers.

26. The method of claim 25, further comprising:
  iii) sequencing the plurality of nucleic acid concatemer molecules immobilized to the surface capture primers, wherein the sequencing comprises (i) sequencing the sample index sequence and (ii) sequencing the sequence of interest (110).

27. The method of claim 25, further comprising:
  iii) sequencing the plurality of nucleic acid concatemer molecules immobilized to the surface capture primers, wherein the sequencing comprises (A) sequencing one or more short random sequences (NNN), (B) sequencing one or more sample index sequences, and (C) sequencing the sequence of interest (110).

28. The method of claim 16, wherein the internal region (310) of the first splint strand (300) comprises one sample index sequence.

29. The method of claim 16, wherein the single-stranded nucleic acid library molecule (100) comprises one or more nucleotide sequences selected from the group consisting of SEQ ID NOS: 1-6 and 43-44.

30. The method of claim 16, wherein the second splint strand (400) comprises one or more nucleotide sequences selected from the group consisting of SEQ ID NOS: 18-26, 45-47, 49, 5'-CATGTAAT-3', 5'-GTAGGAGCCNNN-3', 5'-CCGCTGCTANNN-3', 5'-AACAACAAGNNN-3', 5'-GGTGGTCTANNN-3', 5'-TTGGCCAACNNN-3', 5'-CAGGAGTGCNNN-3', and 5'-ATCACACTANNN-3'.

* * * * *

SEQUENCE LISTING

```
Sequence total quantity: 74
SEQ ID NO: 1              moltype = DNA  length = 35
FEATURE                   Location/Qualifiers
source                    1..35
                          mol_type = other DNA
                          organism = synthetic construct
SEQUENCE: 1
cgtgctggat tggctcacca gacaccttcc gacat                           35

SEQ ID NO: 2              moltype = DNA  length = 33
FEATURE                   Location/Qualifiers
source                    1..33
                          mol_type = other DNA
                          organism = synthetic construct
SEQUENCE: 2
acactctttc cctacacgac gctcttccga tct                             33

SEQ ID NO: 3              moltype = DNA  length = 33
FEATURE                   Location/Qualifiers
source                    1..33
```

-continued

```
                        mol_type = other DNA
                        organism = synthetic construct
SEQUENCE: 3
tcgtcggcag cgtcagatgt gtataagaga cag                                           33

SEQ ID NO: 4           moltype = DNA   length = 35
FEATURE                Location/Qualifiers
source                 1..35
                        mol_type = other DNA
                        organism = synthetic construct
SEQUENCE: 4
atgtcggaag gtgtgcaggc taccgcttgt caact                                         35

SEQ ID NO: 5           moltype = DNA   length = 34
FEATURE                Location/Qualifiers
source                 1..34
                        mol_type = other DNA
                        organism = synthetic construct
SEQUENCE: 5
agatcggaag agcacacgtc tgaactccag tcac                                          34

SEQ ID NO: 6           moltype = DNA   length = 34
FEATURE                Location/Qualifiers
source                 1..34
                        mol_type = other DNA
                        organism = synthetic construct
SEQUENCE: 6
ctgtctctta tacacatctc cgagcccacg agac                                          34

SEQ ID NO: 7           moltype = DNA   length = 35
FEATURE                Location/Qualifiers
source                 1..35
                        mol_type = other DNA
                        organism = synthetic construct
SEQUENCE: 7
atgtcggaag gtgtctggtg agccaatcca gcacg                                         35

SEQ ID NO: 8           moltype = DNA   length = 18
FEATURE                Location/Qualifiers
source                 1..18
                        mol_type = other DNA
                        organism = synthetic construct
SEQUENCE: 8
gtgagccaat ccagcacg                                                            18

SEQ ID NO: 9           moltype = DNA   length = 33
FEATURE                Location/Qualifiers
source                 1..33
                        mol_type = other DNA
                        organism = synthetic construct
SEQUENCE: 9
agatcggaag agcgtcgtgt agggaaagag tgt                                           33

SEQ ID NO: 10          moltype = DNA   length = 33
FEATURE                Location/Qualifiers
source                 1..33
                        mol_type = other DNA
                        organism = synthetic construct
SEQUENCE: 10
ctgtctctta tacacatctg acgctgccga cga                                           33

SEQ ID NO: 11          moltype = DNA   length = 35
FEATURE                Location/Qualifiers
source                 1..35
                        mol_type = other DNA
                        organism = synthetic construct
SEQUENCE: 11
atgtcggaag gtgtgcaggc taccgcttgt caact                                         35

SEQ ID NO: 12          moltype = DNA   length = 18
FEATURE                Location/Qualifiers
source                 1..18
                        mol_type = other DNA
                        organism = synthetic construct
SEQUENCE: 12
agttgacaag cggtagcc                                                            18

SEQ ID NO: 13          moltype = DNA   length = 34
FEATURE                Location/Qualifiers
```

-continued

```
source                   1..34
                         mol_type = other DNA
                         organism = synthetic construct
SEQUENCE: 13
gtgactggag ttcagacgtg tgctcttccg atct                                    34

SEQ ID NO: 14          moltype = DNA   length = 34
FEATURE                Location/Qualifiers
source                 1..34
                       mol_type = other DNA
                       organism = synthetic construct
SEQUENCE: 14
gtctcgtggg ctcggagatg tgtataagag acag                                    34

SEQ ID NO: 15          moltype =   length =
SEQUENCE: 15
000

SEQ ID NO: 16          moltype =   length =
SEQUENCE: 16
000

SEQ ID NO: 17          moltype =   length =
SEQUENCE: 17
000

SEQ ID NO: 18          moltype = DNA   length = 23
FEATURE                Location/Qualifiers
source                 1..23
                       mol_type = other DNA
                       organism = synthetic construct
SEQUENCE: 18
agtcgtcgca gcctcacctg atc                                                23

SEQ ID NO: 19          moltype = DNA   length = 22
FEATURE                Location/Qualifiers
source                 1..22
                       mol_type = other DNA
                       organism = synthetic construct
SEQUENCE: 19
agcctcacct gatccatgta at                                                 22

SEQ ID NO: 20          moltype = DNA   length = 31
FEATURE                Location/Qualifiers
source                 1..31
                       mol_type = other DNA
                       organism = synthetic construct
SEQUENCE: 20
agtcgtcgca gcctcacctg atccatgtaa t                                       31

SEQ ID NO: 21          moltype = DNA   length = 15
FEATURE                Location/Qualifiers
source                 1..15
                       mol_type = other DNA
                       organism = synthetic construct
SEQUENCE: 21
agtcgtcgca gcctc                                                         15

SEQ ID NO: 22          moltype = DNA   length = 24
FEATURE                Location/Qualifiers
source                 1..24
                       mol_type = other DNA
                       organism = synthetic construct
SEQUENCE: 22
atctcgtatg ccgtcttctg cttg                                               24

SEQ ID NO: 23          moltype = DNA   length = 25
FEATURE                Location/Qualifiers
source                 1..25
                       mol_type = other DNA
                       organism = synthetic construct
SEQUENCE: 23
catgtaatgc acgtactttc agggt                                              25

SEQ ID NO: 24          moltype = DNA   length = 17
FEATURE                Location/Qualifiers
source                 1..17
                       mol_type = other DNA
                       organism = synthetic construct
```

-continued

```
SEQUENCE: 24
gcacgtactt tcagggt                                                    17

SEQ ID NO: 25          moltype = DNA   length = 33
FEATURE                Location/Qualifiers
source                 1..33
                       mol_type = other DNA
                       organism = synthetic construct
SEQUENCE: 25
acctgatcca tgtaatgcac gtactttcag ggt                                  33

SEQ ID NO: 26          moltype = DNA   length = 24
FEATURE                Location/Qualifiers
source                 1..24
                       mol_type = other DNA
                       organism = synthetic construct
SEQUENCE: 26
aatgatacgg cgaccaccga gatc                                            24

SEQ ID NO: 27          moltype =   length =
SEQUENCE: 27
000

SEQ ID NO: 28          moltype =   length =
SEQUENCE: 28
000

SEQ ID NO: 29          moltype =   length =
SEQUENCE: 29
000

SEQ ID NO: 30          moltype =   length =
SEQUENCE: 30
000

SEQ ID NO: 31          moltype =   length =
SEQUENCE: 31
000

SEQ ID NO: 32          moltype =   length =
SEQUENCE: 32
000

SEQ ID NO: 33          moltype =   length =
SEQUENCE: 33
000

SEQ ID NO: 34          moltype = DNA   length = 23
FEATURE                Location/Qualifiers
source                 1..23
                       mol_type = other DNA
                       organism = synthetic construct
SEQUENCE: 34
gatcaggtga ggctgcgacg act                                             23

SEQ ID NO: 35          moltype = DNA   length = 22
FEATURE                Location/Qualifiers
source                 1..22
                       mol_type = other DNA
                       organism = synthetic construct
SEQUENCE: 35
attacatgga tcaggtgagg ct                                              22

SEQ ID NO: 36          moltype = DNA   length = 15
FEATURE                Location/Qualifiers
source                 1..15
                       mol_type = other DNA
                       organism = synthetic construct
SEQUENCE: 36
gaggctgcga cgact                                                      15

SEQ ID NO: 37          moltype = DNA   length = 21
FEATURE                Location/Qualifiers
source                 1..21
                       mol_type = other DNA
                       organism = synthetic construct
SEQUENCE: 37
caagcagaag acggcatacg a                                               21
```

-continued

```
SEQ ID NO: 38          moltype = DNA   length = 24
FEATURE                Location/Qualifiers
source                 1..24
                       mol_type = other DNA
                       organism = synthetic construct
SEQUENCE: 38
caagcagaag acggcatacg agat                                       24

SEQ ID NO: 39          moltype = DNA   length = 25
FEATURE                Location/Qualifiers
source                 1..25
                       mol_type = other DNA
                       organism = synthetic construct
SEQUENCE: 39
catgtaatgc acgtactttc agggt                                      25

SEQ ID NO: 40          moltype = DNA   length = 33
FEATURE                Location/Qualifiers
source                 1..33
                       mol_type = other DNA
                       organism = synthetic construct
SEQUENCE: 40
acctgatcca tgtaatgcac gtactttcag ggt                             33

SEQ ID NO: 41          moltype = DNA   length = 20
FEATURE                Location/Qualifiers
source                 1..20
                       mol_type = other DNA
                       organism = synthetic construct
SEQUENCE: 41
aatgatacgg cgaccaccga                                            20

SEQ ID NO: 42          moltype = DNA   length = 24
FEATURE                Location/Qualifiers
source                 1..24
                       mol_type = other DNA
                       organism = synthetic construct
SEQUENCE: 42
aatgatacgg cgaccaccga gatc                                       24

SEQ ID NO: 43          moltype = DNA   length = 30
FEATURE                Location/Qualifiers
source                 1..30
                       mol_type = other DNA
                       organism = synthetic construct
SEQUENCE: 43
atgtcggaag gtgtgcaggc taccgcttgt                                 30

SEQ ID NO: 44          moltype = DNA   length = 25
FEATURE                Location/Qualifiers
source                 1..25
                       mol_type = other DNA
                       organism = synthetic construct
SEQUENCE: 44
atgtcggaag gtgtgcaggc taccg                                      25

SEQ ID NO: 45          moltype = DNA   length = 25
FEATURE                Location/Qualifiers
source                 1..25
                       mol_type = other DNA
                       organism = synthetic construct
SEQUENCE: 45
cgcagcctca cctgatccat gtaat                                      25

SEQ ID NO: 46          moltype = DNA   length = 27
FEATURE                Location/Qualifiers
source                 1..27
                       mol_type = other DNA
                       organism = synthetic construct
SEQUENCE: 46
agcctcacct gatccatgta atcatgc                                    27

SEQ ID NO: 47          moltype = DNA   length = 25
FEATURE                Location/Qualifiers
source                 1..25
                       mol_type = other DNA
                       organism = synthetic construct
SEQUENCE: 47
catgtaatgc acgtactttc agggt                                      25
```

```
SEQ ID NO: 48              moltype =   length =
SEQUENCE: 48
000

SEQ ID NO: 49              moltype = DNA   length = 22
FEATURE                    Location/Qualifiers
source                     1..22
                           mol_type = other DNA
                           organism = synthetic construct
SEQUENCE: 49
cgttagcacg tactttcagg gt                                                 22

SEQ ID NO: 50              moltype = DNA   length = 25
FEATURE                    Location/Qualifiers
source                     1..25
                           mol_type = other DNA
                           organism = synthetic construct
SEQUENCE: 50
attacatgga tcaggtgagg ctgcg                                              25

SEQ ID NO: 51              moltype = DNA   length = 35
FEATURE                    Location/Qualifiers
source                     1..35
                           mol_type = other DNA
                           organism = synthetic construct
SEQUENCE: 51
cgtgctggat tggctcacca gacaccttcc gacat                                   35

SEQ ID NO: 52              moltype = DNA   length = 35
FEATURE                    Location/Qualifiers
source                     1..35
                           mol_type = other DNA
                           organism = synthetic construct
SEQUENCE: 52
agttgacaag cggtagcctg cacaccttcc gacat                                   35

SEQ ID NO: 53              moltype = DNA   length = 30
FEATURE                    Location/Qualifiers
source                     1..30
                           mol_type = other DNA
                           organism = synthetic construct
SEQUENCE: 53
acaagcggta gcctgcacac cttccgacat                                         30

SEQ ID NO: 54              moltype = DNA   length = 22
FEATURE                    Location/Qualifiers
source                     1..22
                           mol_type = other DNA
                           organism = synthetic construct
SEQUENCE: 54
agcctcacct gatccatgta at                                                 22

SEQ ID NO: 55              moltype = DNA   length = 27
FEATURE                    Location/Qualifiers
source                     1..27
                           mol_type = other DNA
                           organism = synthetic construct
SEQUENCE: 55
agcctcacct gatccatgta atcatgc                                            27

SEQ ID NO: 56              moltype = DNA   length = 23
FEATURE                    Location/Qualifiers
source                     1..23
                           mol_type = other DNA
                           organism = synthetic construct
SEQUENCE: 56
agtcgtcgca gcctcacctg atc                                                23

SEQ ID NO: 57              moltype = DNA   length = 31
FEATURE                    Location/Qualifiers
source                     1..31
                           mol_type = other DNA
                           organism = synthetic construct
SEQUENCE: 57
agtcgtcgca gcctcacctg atccatgtaa t                                       31

SEQ ID NO: 58              moltype = DNA   length = 36
FEATURE                    Location/Qualifiers
```

-continued

```
source                  1..36
                        mol_type = other DNA
                        organism = synthetic construct
SEQUENCE: 58
agtcgtcgca gcctcacctg atccatgtaa tcgtga                                         36

SEQ ID NO: 59          moltype = DNA   length = 36
FEATURE                Location/Qualifiers
source                  1..36
                        mol_type = other DNA
                        organism = synthetic construct
SEQUENCE: 59
agtcgtcgca gcctcacctg atccatgtaa tcatgc                                         36

SEQ ID NO: 60          moltype = DNA   length = 35
FEATURE                Location/Qualifiers
source                  1..35
                        mol_type = other DNA
                        organism = synthetic construct
SEQUENCE: 60
atgtcggaag gtgtgcaggc taccgcttgt caact                                          35

SEQ ID NO: 61          moltype = DNA   length = 25
FEATURE                Location/Qualifiers
source                  1..25
                        mol_type = other DNA
                        organism = synthetic construct
SEQUENCE: 61
accctgaaag tacgtgcatt acatg                                                     25

SEQ ID NO: 62          moltype = DNA   length = 17
FEATURE                Location/Qualifiers
source                  1..17
                        mol_type = other DNA
                        organism = synthetic construct
SEQUENCE: 62
accctgaaag tacgtgc                                                              17

SEQ ID NO: 63          moltype = DNA   length = 22
FEATURE                Location/Qualifiers
source                  1..22
                        mol_type = other DNA
                        organism = synthetic construct
SEQUENCE: 63
accctgaaag tacgtgctaa cg                                                        22

SEQ ID NO: 64          moltype = DNA   length = 33
FEATURE                Location/Qualifiers
source                  1..33
                        mol_type = other DNA
                        organism = synthetic construct
SEQUENCE: 64
accctgaaag tacgtgcatt acatggatca ggt                                            33

SEQ ID NO: 65          moltype = DNA   length = 68
FEATURE                Location/Qualifiers
source                  1..68
                        mol_type = other DNA
                        organism = synthetic construct
misc_feature           32..34
                        note = any nucleotide
misc_feature           35..43
                        note = sample index sequence
SEQUENCE: 65
agtcgtcgca gcctcacctg atccatgtaa tnnnnnnnnn nnncatgtaa tgcacgtact    60
ttcagggt                                                            68

SEQ ID NO: 66          moltype = DNA   length = 102
FEATURE                Location/Qualifiers
source                  1..102
                        mol_type = other DNA
                        organism = synthetic construct
misc_feature           42..50
                        note = sample index sequence
misc_feature           51..53
                        note = any nucleotide
SEQUENCE: 66
gtgagccaat ccagcacccc tgaaagtacg tgcattacat gnnnnnnnnn nnnattacat    60
ggatcaggtg aggctgcgac gactagttga caagcggtag cc                      102
```

```
SEQ ID NO: 67              moltype = DNA   length = 100
FEATURE                    Location/Qualifiers
source                     1..100
                           mol_type = other DNA
                           organism = synthetic construct
misc_feature               42..51
                           note = sample index sequence
SEQUENCE: 67
gtgagccaat ccagcacccc tgaaagtacg tgcattacat gnnnnnnnnn nattacatgg   60
atcaggtgag gctgcgacga ctagttgaca agcggtagcc                        100

SEQ ID NO: 68              moltype = DNA   length = 102
FEATURE                    Location/Qualifiers
source                     1..102
                           mol_type = other DNA
                           organism = synthetic construct
modified_base              42..53
                           mod_base = i
SEQUENCE: 68
gtgagccaat ccagcacccc tgaaagtacg tgcattacat gnnnnnnnnn nnnattacat   60
ggatcaggtg aggctgcgac gactagttga caagcggtag cc                     102

SEQ ID NO: 69              moltype = DNA   length = 91
FEATURE                    Location/Qualifiers
source                     1..91
                           mol_type = other DNA
                           organism = synthetic construct
misc_feature               42
                           note = Spacer18
SEQUENCE: 69
gtgagccaat ccagcacccc tgaaagtacg tgcattacat gnattacatg gatcaggtga   60
ggctgcgacg actagttgac aagcggtagc c                                  91

SEQ ID NO: 70              moltype = DNA   length = 94
FEATURE                    Location/Qualifiers
source                     1..94
                           mol_type = other DNA
                           organism = synthetic construct
misc_feature               42
                           note = SPACER18
misc_feature               43..45
                           note = any nucleotide
SEQUENCE: 70
gtgagccaat ccagcacccc tgaaagtacg tgcattacat gnnnnattac atggatcagg   60
tgaggctgcg acgactagtt gacaagcggt agcc                               94

SEQ ID NO: 71              moltype = DNA   length = 90
FEATURE                    Location/Qualifiers
source                     1..90
                           mol_type = other DNA
                           organism = synthetic construct
SEQUENCE: 71
gtgagccaat ccagcacccc tgaaagtacg tgcattacat gattacatgg atcaggtgag   60
gctgcgacga ctagttgaca agcggtagcc                                    90

SEQ ID NO: 72              moltype = DNA   length = 31
FEATURE                    Location/Qualifiers
source                     1..31
                           mol_type = other DNA
                           organism = synthetic construct
SEQUENCE: 72
agtcgtcgca gcctcacctg atccatgtaa t                                  31

SEQ ID NO: 73              moltype = DNA   length = 25
FEATURE                    Location/Qualifiers
source                     1..25
                           mol_type = other DNA
                           organism = synthetic construct
SEQUENCE: 73
catgtaatgc acgtactttc agggt                                         25

SEQ ID NO: 74              moltype = DNA   length = 92
FEATURE                    Location/Qualifiers
source                     1..92
                           mol_type = other DNA
                           organism = synthetic construct
```

-continued

```
SEQUENCE: 74
gtgagccaat ccagcacgac cctgaaagta cgtgcattac atgattacat ggatcaggtg   60
aggctgcgac gactagttga caagcggtag cc                                 92
```